United States Patent
Vasiljeva et al.

(10) Patent No.: US 11,867,695 B2
(45) Date of Patent: Jan. 9, 2024

(54) COMPOSITIONS AND METHODS FOR DETECTING PROTEASE ACTIVITY IN BIOLOGICAL SYSTEMS

(71) Applicant: CytomX Therapeutics, Inc., South San Francisco, CA (US)

(72) Inventors: Olga Vasiljeva, Cupertino, CA (US); Elizabeth-Edna Mary Menendez, San Mateo, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 178 days.

(21) Appl. No.: 17/246,167

(22) Filed: Apr. 30, 2021

(65) Prior Publication Data

US 2021/0382053 A1 Dec. 9, 2021

Related U.S. Application Data

(63) Continuation of application No. 16/277,497, filed on Feb. 15, 2019, now Pat. No. 11,035,859, which is a
(Continued)

(51) Int. Cl.
*G01N 33/573* (2006.01)
*A61K 49/00* (2006.01)
(Continued)

(52) U.S. Cl.
CPC ....... *G01N 33/573* (2013.01); *A61K 47/6849* (2017.08); *A61K 47/6855* (2017.08);
(Continued)

(58) Field of Classification Search
CPC ............. G01N 33/573; G01N 33/5735; G01N 33/57484; G01N 2333/95; A61K 47/6849; A61K 47/6855; A61K 47/6889; A61K 49/0021; A61K 49/0058; A61P 35/00; C07K 16/2863; C07K 16/2896; C07K 2319/50; C07K 2319/60
See application file for complete search history.

(56) References Cited

U.S. PATENT DOCUMENTS 7,465,790 B2 12/2008 Waldmann et al.
7,666,817 B2 2/2010 Daugherty et al.
(Continued)

FOREIGN PATENT DOCUMENTS

EP 1 523 503 B1 4/2009
EP 1 324 771 B1 6/2011
(Continued)

OTHER PUBLICATIONS

Yan et al., (Vet. Pathol. 40:227-236(2003). (Year: 2003).*
(Continued)

*Primary Examiner* — Jana A Hines
(74) *Attorney, Agent, or Firm* — CytomX Therapeutics, Inc.

(57) ABSTRACT

The invention relates generally to compositions and methods for detecting protease activity in a subject or a biological sample using activatable antibodies, and the use of these compositions and methods in a variety of diagnostic indications.

26 Claims, 22 Drawing Sheets

Specification includes a Sequence Listing.

Related U.S. Application Data continuation of application No. 14/147,324, filed on Jan. 3, 2014, now Pat. No. 10,261,083.

(60) Provisional application No. 61/897,659, filed on Oct. 30, 2013, provisional application No. 61/830,940, filed on Jun. 4, 2013, provisional application No. 61/763,237, filed on Feb. 11, 2013, provisional application No. 61/755,810, filed on Jan. 23, 2013, provisional application No. 61/749,486, filed on Jan. 7, 2013, provisional application No. 61/749,529, filed on Jan. 7, 2013, provisional application No. 61/749,212, filed on Jan. 4, 2013, provisional application No. 61/749,220, filed on Jan. 4, 2013.

(51) Int. Cl.
  C07K 16/28 (2006.01)
  G01N 33/574 (2006.01)
  A61K 47/68 (2017.01)

(52) U.S. Cl.
  CPC ...... *A61K 47/6889* (2017.08); *A61K 49/0021* (2013.01); *A61K 49/0058* (2013.01); *C07K 16/2863* (2013.01); *C07K 16/2896* (2013.01); *G01N 33/57484* (2013.01); *C07K 2319/50* (2013.01); *C07K 2319/60* (2013.01); *G01N 2333/95* (2013.01)

(56) References Cited

U.S. PATENT DOCUMENTS

| | | |
|---|---|---|
| 8,293,685 B2 | 10/2012 | Daugherty et al. |
| 8,513,390 B2 | 8/2013 | Stagliano et al. |
| 8,518,404 B2 | 8/2013 | Daugherty et al. |
| 8,529,898 B2 | 9/2013 | Daugherty et al. |
| 8,541,203 B2 | 9/2013 | Daugherty et al. |
| 8,563,269 B2 | 10/2013 | Stagliano et al. |
| 8,809,504 B2 | 8/2014 | Lauermann |
| 9,169,321 B2 | 10/2015 | Daugherty et al. |
| 9,453,078 B2 | 9/2016 | Stagliano et al. |
| 9,545,442 B2 | 1/2017 | Lowman et al. |
| 9,889,211 B2 | 2/2018 | Lowman et al. |
| 10,261,083 B2 | 4/2019 | Vasiljeva et al. |
| 11,035,859 B2 | 6/2021 | Vasiljeva et al. |
| 2004/0109855 A1 | 6/2004 | Waldmann et al. |
| 2009/0304719 A1 | 12/2009 | Daugherty et al. |
| 2010/0150939 A1 | 6/2010 | Blanchetot et al. |
| 2010/0189651 A1 | 7/2010 | Stagliano et al. |
| 2010/0189727 A1 | 7/2010 | Rodeck et al. |
| 2011/0178279 A1 | 7/2011 | Williams et al. |
| 2012/0149061 A1 | 6/2012 | Stagliano et al. |
| 2012/0207756 A1 | 8/2012 | Stagliano et al. |
| 2012/0237512 A1 | 9/2012 | Daugherty et al. |
| 2012/0237977 A1 | 9/2012 | Daugherty et al. |
| 2012/0244154 A1 | 9/2012 | Daugherty et al. |
| 2013/0309230 A1 | 11/2013 | Stagliano et al. |
| 2014/0024810 A1 | 1/2014 | Stagliano et al. |
| 2014/0045195 A1 | 2/2014 | Daugherty et al. |
| 2016/0122425 A1 | 5/2016 | Daugherty et al. |
| 2016/0228546 A1 | 8/2016 | Stagliano et al. |
| 2017/0081397 A1 | 3/2017 | Stagliano et al. |

FOREIGN PATENT DOCUMENTS

| | | | |
|---|---|---|---|
| WO | WO 2001/91798 A2 | 12/2001 | |
| WO | WO 2002/30460 A2 | 4/2002 | |
| WO | WO 2004/009638 A1 | 1/2004 | |
| WO | WO 2007/105027 A1 | 9/2007 | |
| WO | WO 2009/025846 A2 | 2/2009 | |
| WO | WO-2009025846 A2 * | 2/2009 | ........... A61K 39/395 |
| WO | WO 2010/077643 A1 | 7/2010 | |
| WO | WO 2010/081173 A2 | 7/2010 | |
| WO | WO 2010/129609 A2 | 11/2010 | |
| WO | WO 2013/163631 A2 | 10/2013 | |
| WO | WO 2013/192550 A2 | 12/2013 | |

OTHER PUBLICATIONS

Ai et al., "Magnetite-Loaded Polymeric Micelles as Ultrasensitive Magnetic-Resonance Probes", Advanced Materials, 2005, 17(16):1949-1952.

Atanasijevic et al., "Calcium-sensitive MRI contrast agents based on superparamagnetic iron oxide nanoparticles and calmodulin," Proc Natl Acad Sci USA, 103.40(2006):14707-14712.

Bussolati G., "A modified Trastuzumad antibody for the immunohistochemical detection of HER-2 overexperssion in breast cancer", British Journal of Cancer, Apr. 11, 2005; 92(7):1261-1267.

Chen G. et al., "Targeting the epidermal growth factor receptor in non-small cell lung cancer cells: the effect of combining RNA interference with tyrosine kinase inhibitors or cetuximab", BMC Medicine, Mar. 21, 2012; 10:28.

Desnoyers L.R. "Tumor-specific activation of an EGFR-targeting probody ehnaces therapeutic index", Science Translational Medicine, vol. 5, No. 207, 2013, 24 pages.

Donaldson J. et al., "Design and development of masked therapeutic antibodies to limit off-target effects: application to anti-EGFR antibodies", Cancer Biology & Therapy, Nov. 2009; 8(22):2147-2152.

Doody J. et al., "Inhibitory activity of cetuximab on epidermal growth factor receptor mutations in non small cell lung cancers", Molecular Cancer Therapeutics, Oct. 2007; 6(10):2642-2651.

Erster O. et al., "Site-specific targeting of antibody activity in vivo mediated by disease-associated proteases", Journal of Controlled Release, Aug. 10, 2012 ; 161(3):804-812.

Fredericks, W.M. et al., "Metabolic mapping of proteinase activity with emphasis on in situ zymography of gelatinases: Review and protocols", *J. Histochem Cytochem*, Jun. 2004, 52(6):711-722.

Goodall et al. "Ubiquitous Elevation of Matrix Metalloproteinase-2 Expression in the Vasculature of Patients with Abdominal Aneurysms", Circulation, vol. 104, p. 304-309 (2001).

Hranec E. et al., "Activitiy of type IV collagenases (MMP-2 and MMP-9) in primary pulmonary carcinomas: a quantitative analysis", J Cancer Res Clin Oncol, Apr. 2002, 128(4):197-204.

Irving, B.A. (Feb. 2015) "Probodies Empower a New Generation of Antibody Immunotherapies,"CytomX Therapeutics Inc. presentation at Keystone Symposia™ on Molecular and Cellular Biology, Feb. 8-13, 2015; 25 pages.

Killen et al., "Specific killing of lymphocytes that cause experimental autoimmune myasthenia gravis by ricin toxin-acetylcholine receptor conjugates," The Journal of Immunology, (1984), 133(5):2549-2553.

Lindsey et al. "Matrix-Dependent Mechanism of Neutrophil-Mediated Release and Activation of Matrix Metalloproteinase 9 in Myocardial Ischemia/Reperfusion", Circulation, vol. 103, p. 2181-2187 (2001).

Lopez-Otin, C., "Emerging roles of proteases in tumour suppression", Nature Reviews, Oct. 2007; 7(10):800-8.

Mikhaylov, G., et al., "Ferri-liposomes as an MRI-visible drug-delivery system for targeting tumours and their microenvironment", Nature Nanotechnology 6, (2011), 594-602.

Mook O., et al., "In situ localization of gelatinolytic acitivity in the extracellular matrix of metastases of colon cancer in rat liver using quenched fluorogenic DQ-gelatin," Journal of Histochemistry & Cytochemistry, 51(2003):821-829.

Murthy R. et al., "Legumain expression in relation to clinicopathologic and biological variables in colorectal cancer," Clinical Cancer Research, 11 (2005): 2293-2299.

Nielsen B. et al. "Urokinase plasminogen activator is localized in stromal cells in ductal breast cancer," Laboratory Investigation, 81 (2001): 1485-1501.

Perez et al., "Magnetic relaxation switches capable of sensing molecular interactions", Nature Biotechnology 2002, 20, 816-820.

(56) References Cited

OTHER PUBLICATIONS

Snoek-Van Beurden, P. et al., "Zymographic techniques for the analysis of matrix metalloproteinases and their inhibitors" *Biotechniques Rapid Dispatches*, 2005, 38(1):73-83.

Tsai, W-C. et al., "Matriptase and Survivin Expression Associated with Tumor Progression and Malignant Potential in Breast Cancer of Chinese Women: Tissue Microarray Analysis of Immunostaining Scores with Clinicopathological Parameters", *Disease Markers*, 2008, 24(2):89-99.

Turk, B., "Targeting proteases: successes, failures and future prospects", Nature Review Drug Discovery, Sep. 2006; 5(9):785-799.

Vandooren J. et al., "Zymography methods for visualizing hydrolytic enzymes" Nature Methods, Mar. 2013; 10(3):211-220.

Yan S. et al., "In situ zymography: a molecular pathology technique to localize endogenous protease activity in tissue sections", Vet Pathol., May 2003; 40(3):227-236.

Zhao M. et al., "Magnetic sensors for protease assays", Angewandte Chemie, Int Ed Engl 2003; 42(12):1375-1378.

\* cited by examiner

* Broad Spectrum Protease Inhibitor Cocktail

* Broad Spectrum Protease Inhibitor Cocktail

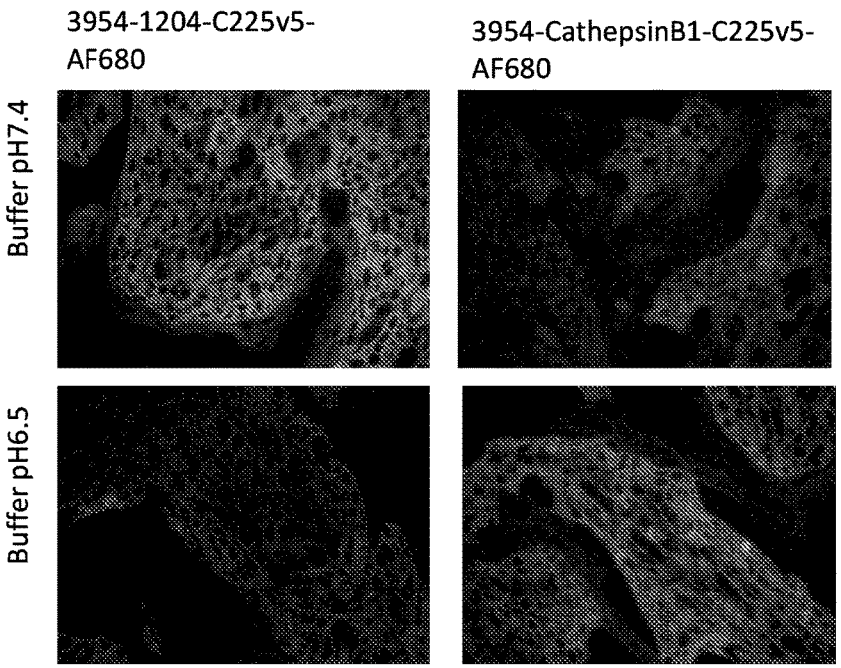

* Broad Spectrum Protease Inhibitor Cocktail

| Patient # | EGFR | MT-SP1 | Cetuximab | 3954-1204-C225 | Cancer Type |
|---|---|---|---|---|---|
| 5594 | +++ | ++ | +++ | ~90% | Esophageal |

FIGURE 18
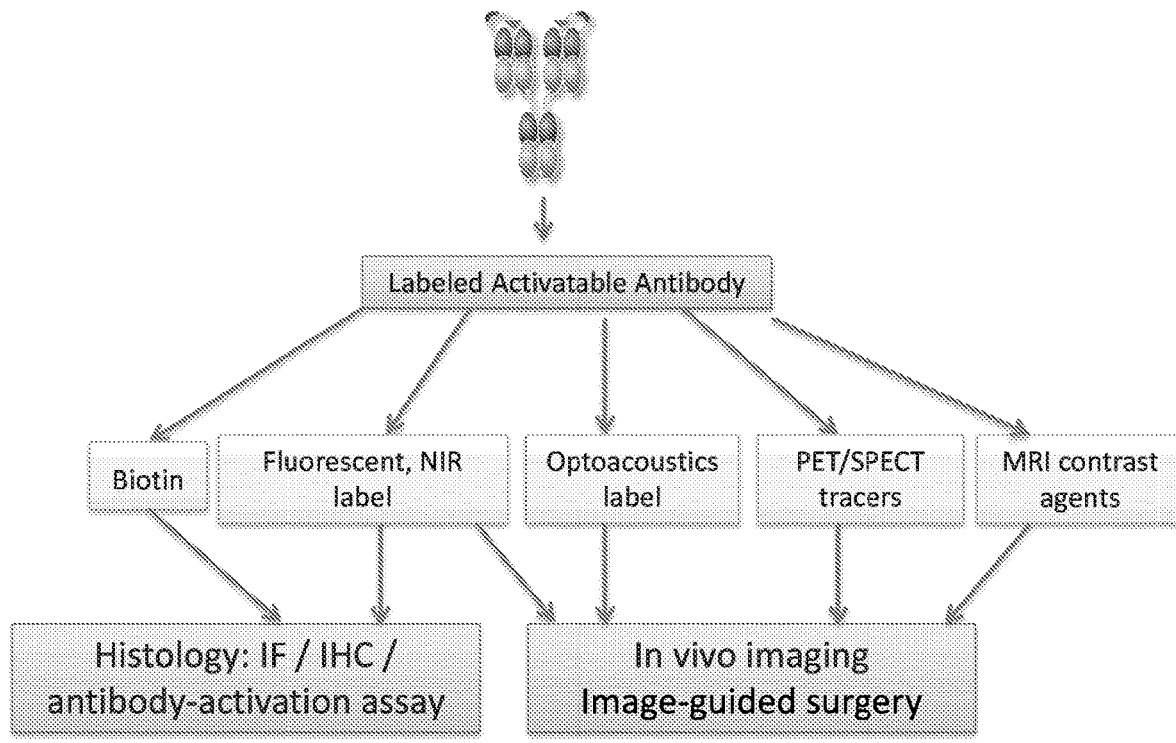
FIGURE 19A 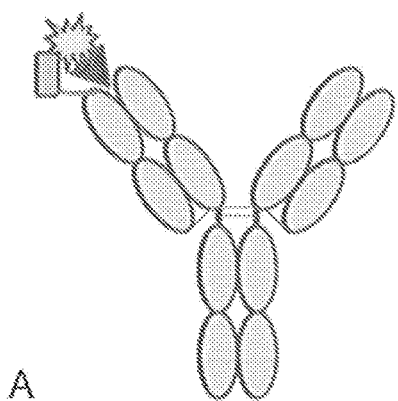 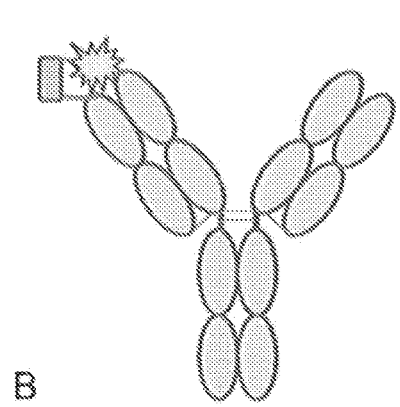 FIGURE 19B
A　　　　　　　　　　　　　　　B FIGURE 22 Subject #1

Subject #2

*ex vivo*: 120h

Tumor to Background Ratio (T/N)
*in vivo*: 96h

| Patient | 4D11 IHC | 4D11 + BSPI | 5342-1204-4D11 In Situ Imaging | 5342-1204-4D11 + BSPI |
|---|---|---|---|---|
| MM00015 | +++ | +++ | +++ | +/- |
| MM00102 | +++ | +++ | ++ | +/- |

COMPOSITIONS AND METHODS FOR DETECTING PROTEASE ACTIVITY IN BIOLOGICAL SYSTEMS

RELATED APPLICATIONS

This application is a Continuation Application of U.S. application Ser. No. 16/277,497, filed Feb. 15, 2019, now U.S. Pat. No. 11,035,859, issued Jun. 15, 2021, which is a Continuation Application of U.S application Ser. No. 14/147,324, filed Jan. 3, 2014, now U.S. Pat. No. 10,261, 083, issued Apr. 16, 2019, which claims the benefit of U.S. Provisional Application No. 61/749,220, filed Jan. 4, 2013; U.S. Provisional Application No. 61/749,212, filed Jan. 4, 2013; U.S. Provisional Application No. 61/749,529, filed Jan. 7, 2013; U.S. Provisional Application No. 61/749,486, filed Jan. 7, 2013; U.S. Provisional Application No. 61/755, 810, filed Jan. 23, 2013; U.S. Provisional Application No. 61/763,237, filed Feb. 11, 2013; U.S. Provisional Application No. 61/830,940, filed Jun. 4, 2013; and U.S. Provisional Application No. 61/897,659, filed Oct. 30, 2013, each of which is incorporated herein by reference in its entirety.

INCORPORATION-BY-REFERENCE OF SEQUENCE LISTING

The contents of the file named "CYTM_024 CO2US_SeqList_ST25", which was created on Apr. 8, 2021, and is 174 KB in size are hereby incorporated by reference in their entirety.

FIELD OF THE INVENTION

The invention relates generally to compositions and methods for detecting protease activity in a subject or a biological sample using activatable antibodies, and the use of these compositions and methods in a variety of diagnostic indications.

BACKGROUND OF THE INVENTION

Aberrant protease activity has been implicated in various disorders. Accordingly, there exists a need for methods that can reliably detect specific protease activity in biological samples.

SUMMARY OF THE INVENTION

The present invention provides methods and compositions for detecting specific protease activity in biological samples using activatable antibodies. These compositions and methods can be used in a variety of diagnostic indications, e.g., in vivo, in vitro, in situ, or ex vivo.

The compositions and methods described herein provide a potent new technology that enables the detection of specific protease activity in a subject or biological sample, e.g., a cell or tissue sample, through the use of protease-activated antibody technology. Imaging of activatable antibodies represents a unique approach to characterize protease activity in subjects and biological samples. This technology enables validation of proteolytic activation of an activatable antibody and binding of the activated antibody to a target in cells and tissues expressing proteases capable of cleaving the activatable antibody. The results allow the determination of whether a cell or tissue has protease activity of a specificity and concentration sufficient to activate an activatable antibody that binds a desired target in that cell or tissue.

An activatable antibody of the disclosure contains a masking moiety that blocks the antigen-binding site of the antibody. The masking moiety is joined to the antibody via a protease substrate-containing linker referred to herein as a cleavable moiety (CM). Through selection of a CM that is cleaved by specific protease(s), a portfolio of activatable antibodies for the screening of activity of proteases with different specificities has been developed. Compositions and methods disclosed herein have been applied to the in vivo and ex vivo screening of xenograft tumor-bearing mice and to the in situ screening of human patient tumor tissues, revealing the presence of proteolytic activity. Protease inhibitors inhibited such activity in tumor tissues. Compositions and methods disclosed herein support the use of activatable antibodies as therapeutics for treating diseases characterized by aberrant, typically increased, protease activity. Compositions and methods disclosed herein also are useful to identify or otherwise refine, e.g., stratify, a patient population suitable for treatment with an activatable antibody of the disclosure. In some embodiments, a subject tests positive for both the target bound by the activated antibody and a protease that cleaves the substrate in the cleavable moiety (CM) of the activatable antibody being tested. Such a patient is identified as a suitable candidate for treatment with such an activatable antibody comprising such a CM, because the target and protease are co-localized in a tissue thereby effecting activation of and binding by the antibody. In some embodiments, a subject that tests positive for both the target and protease using such activatable antibody is administered such activatable antibody as therapy.

The invention provides methods of using activatable antibodies that bind a target in a variety of diagnostic and/or prophylactic indications, as well as kits for use in these methods. The target is, for example, any of the targets listed in Table 1, or any combination thereof. For example, the invention provides methods of detecting presence or absence of a cleaving agent and a target in a subject or a sample by (i) contacting a subject or biological sample with an activatable antibody, and (ii) measuring a level of activated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target, or both the cleaving agent and the target are absent and/or not sufficiently present at a detectable level in the subject or biological sample at a detectable level. In some embodiments, the biological sample comprises more than one tissue type. In some embodiments, the biological sample is a tissue microarray. In some embodiments, the biological sample is a frozen tissue microarray.

Such an activatable antibody includes a masking moiety (MM), a cleavable moiety (CM) that is cleaved by the cleaving agent, and an antibody or an antigen binding fragment thereof (AB) that specifically binds the target. In some embodiments, the activatable antibody in an uncleaved (i.e., non-activated) state comprises a structural arrangement from N-terminus to C-terminus as follows: MM-CM-AB or AB-CM-MM. In some embodiments, the MM is a peptide that inhibits binding of the AB to the target, and wherein the MM does not have an amino acid sequence of a naturally occurring binding partner of the AB. In some embodiments, the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is a conjugated activatable antibody, i.e., the activatable antibody is conjugated to an agent. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent and a target of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present at a detectable level in the subject or biological sample. In some embodiments, the biological sample comprises more than one tissue type. In some embodiments, the biological sample is a tissue microarray. In some embodiments, the biological sample is a frozen tissue microarray.

The invention also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present at a detectable level in the subject or biological sample. Such an activatable antibody includes a masking moiety (MM), a cleavable moiety (CM) that is cleaved by the cleaving agent, and an antibody or antigen binding fragment thereof (AB) that specifically binds the target. In some embodiments, the activatable antibody in an uncleaved (i.e., non-activated) state comprises a structural arrangement from N-terminus to C-terminus as follows: MM-CM-AB or AB-CM-MM. In some embodiments, the MM is a peptide that inhibits binding of the AB to the target, and wherein the MM does not have an amino acid sequence of a naturally occurring binding partner of the AB. In some embodiments, the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is a conjugated activatable antibody. In some embodiments, the activatable antibody is not conjugated to an agent. In some embodiments, the detectable label is attached to the masking moiety.

In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label. In some embodiments, the biological sample comprises more than one tissue type. In some embodiments, the biological sample is a tissue microarray. In some embodiments, the biological sample is a frozen tissue microarray.

The invention also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present at a detectable level in the subject or biological sample. In some embodiments, the biological sample comprises more than one tissue type. In some embodiments, the biological sample is a tissue microarray. In some embodiments, the biological sample is a frozen tissue microarray.

The invention provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present at a detectable level in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a cleavable moiety (CM) that is cleaved by the cleaving agent, and an antibody or antigen binding fragment thereof (AB) that specifically binds the target. In some embodiments, the activatable antibody in an uncleaved (i.e., non-activated) state comprises a structural arrangement from N-terminus to C-terminus as follows: MM-CM-AB or AB-CM-MM. In some embodiments, the MM is a peptide that inhibits binding of the AB to the target, and wherein the MM does not have an amino acid sequence of a naturally occurring binding partner of the AB. In some embodiments, the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is a conjugated activatable antibody. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label. In some embodiments, the biological sample comprises more than one tissue type. In some embodiments, the biological sample is a tissue microarray. In some embodiments, the biological sample is a frozen tissue microarray.

The invention also provides kits for use in methods of detecting presence or absence of a cleaving agent and a target of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present at a detectable level in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The invention also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM; and (ii) measuring a level of detectable label in the subject or biological sample, wherein a detectable level of the detectable label in the subject or biological sample indicates that the cleaving agent is absent and/or not sufficiently present at a detectable level in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a cleavable moiety (CM) that is cleaved by the cleaving agent, and an antibody or antigen binding fragment thereof (AB) that specifically binds the target. In some embodiments, the activatable antibody in an uncleaved (i.e., non-activated) state comprises a structural arrangement from N-terminus to C-terminus as follows: MM-CM-AB or AB-CM-MM. In some embodiments, the MM is a peptide that inhibits binding of the AB to the target, and wherein the MM does not have an amino acid sequence of a naturally occurring binding partner of the AB. In some embodiments, the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is a conjugated activatable antibody. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label. In some embodiments, the biological sample comprises more than one tissue type. In some embodiments, the biological sample is a tissue microarray. In some embodiments, the biological sample is a frozen tissue microarray.

The invention also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of the detectable label in the subject or biological sample indicates that the cleaving agent, the target, or both the cleaving agent and the target are absent and/or not sufficiently present at a detectable level in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. In some embodiments, the biological sample comprises more than one tissue type. In some embodiments, the biological sample is a tissue microarray. In some embodiments, the biological sample is a frozen tissue microarray.

In some embodiments of these methods and/or kits, the target is selected from the group of targets listed in Table 1. In some embodiments, the AB is or is derived from an antibody selected from the group of antibodies listed in Table 2. In some embodiments, the antigen binding fragment thereof is selected from the group consisting of a Fab fragment, a F(ab')2 fragment, a scFv, and a scAb. In some embodiments, the AB has an equilibrium dissociation constant of about 100 nM or less for binding to the target. In some embodiments, the MM has an equilibrium dissociation constant for binding to the AB that is greater than the equilibrium dissociation constant of the AB to the target. In some embodiments, the MM does not interfere or compete with the AB of the activatable antibody in a cleaved state for binding to the target. In some embodiments, the MM is a polypeptide of no more than 40 amino acids in length. In some embodiments, the MM polypeptide sequence is different from that of the target and the MM polypeptide sequence is no more than 50% identical to any natural binding partner of the AB. In some embodiments, the MM does not include more than 25% amino acid sequence identity to the target. In some embodiments, the MM does not include more than 10% amino acid sequence identity to the target. In some embodiments, the CM is a substrate for a protease selected from the group of proteases listed in Table 3. In some embodiments, the CM is a polypeptide of up to 15 amino acids in length. In some embodiments, the protease is co-localized with the target in a tissue, and the protease cleaves the CM in the activatable antibody when the activatable antibody is exposed to the protease. In some embodiments, the activatable antibody includes a linking peptide between the MM and the CM. In some embodiments, the activatable antibody includes a linking peptide between the CM and the AB. In some embodiments, the activatable antibody includes a first linking peptide (LP1) and a second linking peptide (LP2), and the activatable antibody in an uncleaved state has the structural arrangement from N-terminus to C-terminus as follows: MM-LP1-CM-LP2-AB or AB-LP2-CM-LP 1-MM. In some embodiments, the two linking peptides need not be identical to each other. In some embodiments, at least one of LP1 or LP2 includes an amino acid sequence selected from the group consisting of $(GS)_n$, $(GGS)_n$, $(GSGGS)_n$ (SEQ ID NO: 33) and $(GGGS)_n$ (SEQ ID NO: 34), where n is an integer of at least one. In some embodiments, at least one of LP1 or LP2 includes an amino acid sequence selected from the group consisting of GGSG (SEQ ID NO: 35), GGSGG (SEQ ID NO: 36), GSGSG (SEQ ID NO: 37), GSGGG (SEQ ID NO: 38), GGGSG (SEQ ID NO: 39), and GSSSG (SEQ ID NO: 40). In some embodiments, the activatable antibody in an uncleaved state includes a spacer, wherein the spacer is joined directly to the MM and has the structural arrangement from N-terminus to C-terminus of spacer-MM-CM-AB. In some embodiments, the activatable antibody in an uncleaved state includes a spacer, wherein the spacer is joined directly to the MM and has the structural arrangement from N-terminus to C-terminus of AB-CM-MM-spacer.

In some embodiments of these methods and/or kits, the biological sample comprises more than one tissue type. In some embodiments of these methods and/or kits, the biological sample is a tissue microarray. In some embodiments of these methods and/or kits, the biological sample is a frozen tissue microarray.

In some embodiments of these methods and/or kits, the activatable antibody includes a detectable label. In some embodiments of these methods and/or kits, the detectable label includes an imaging agent, a contrasting agent, an enzyme, a fluorescent label, a chromophore, a dye, one or more metal ions, or a ligand-based label. In some embodiments of these methods and/or kits, the imaging agent comprises a radioisotope. In some embodiments of these methods, the radioisotope is indium or technetium. In some embodiments of these methods, the radioisotope is or is derived from iodine. In some embodiments of these methods, the radioisotope is $^{125}I$ or $^{133}I$. In some embodiments of these methods and/or kits, the contrasting agent comprises iodine, gadolinium or iron oxide. In some embodiments of these methods and/or kits, the enzyme comprises horseradish peroxidase, alkaline phosphatase, or β-galactosidase. In some embodiments of these methods and/or kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and/or kits, the luminescent label comprises an N-methylacrydium derivative. In some embodiments of these methods and/or kits, the label comprises an Alexa Fluor® label, such as Alex Fluor® 680 or Alexa Fluor® 750. In some embodiments of these methods and/or kits, the ligand-based label comprises biotin, avidin, streptavidin or one or more haptens. In some embodiments of these methods and/or kits, the detectable label is a bioluminescent label. In some embodiments of these methods and/or kits, the bioluminescent label is D-luciferin. In some embodiments of these methods and/or kits, the bioluminescent label is conjugated to the activatable antibody via a releasable linker. In some embodiments of these methods and/or kits, the releasable linker is a disulfide bond.

In some embodiments of these methods and/or kits, the detectable label is conjugated to at least a portion of the activatable antibody. For example, in some embodiments of these methods and/or kits, the detectable label is conjugated to the AB. In some embodiments of these methods and/or kits, the detectable label is conjugated to at least the MM. In some embodiments of these methods and/or kits where the detectable label is conjugated to at least the MM, the detectable label conjugated to the MM is biotin. Such constructs are useful for a variety of imaging techniques, including by way of non-limiting example, magnetic resonance (MR) imaging. In these embodiments, the activatable antibody having the biotinylated MM is administered to a subject in conjunction with avidin and/or streptavidin-coated magnetic nanoparticles prior to MR imaging. In some embodiments, the magnetic nanoparticles are coated with anti-biotin antibodies. In some embodiments of these methods and/or kits, the activatable antibody having a biotinylated MM and the coated magnetic nanoparticles are administered simultaneously. In some embodiments of these methods and/or kits, the activatable antibody having a biotinylated MM and the coated magnetic nanoparticles are administered sequentially. These kits and methods are useful for monitoring activation of an activatable antibody.

In some embodiments of these methods and/or kits, the subject is a mammal. In some embodiments of these methods and/or kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods and/or kits, the method and/or kit is used to identify or otherwise refine, e.g., stratify, a patient population suitable for treatment with an activatable antibody of the disclosure. For example, in any of the methods provided herein, patients that test positive for both the target and a protease that cleaves the substrate in the cleavable moiety (CM) of the activatable antibody being tested in these methods are identified as suitable candidates for treatment with such an activatable antibody comprising such a CM. Likewise, in any of the methods provided herein, patients that test negative for either or both of the target and the protease that cleaves the substrate in the CM in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM that is cleaved by the patient at the site of disease).

The invention also provides kits for use in methods of identifying or otherwise refining a patient population, where the kits include at least (i) an activatable antibody and/or conjugated activatable antibody described herein for use in contacting a subject or biological sample, (ii) means for detecting the level of activated activatable antibody and/or conjugated activatable antibody in the subject or biological sample, wherein a detectable level of activated activatable antibody in the sample indicates that the sample is positive for the presence of the target and a cleaving agent that cleaves the substrate in the cleavable moiety (CM) of the activatable antibody and/or conjugated activatable antibody and (iii) means for identifying and selecting one or more subjects that test positive for the presence of the target and the cleaving agent thereby identifying or refining a patient population. In some embodiments, the kit also includes instructions for administering a therapeutically effective amount of such an activatable antibody and/or conjugated activatable antibody described herein to the one or more subjects in the patient population that test positive for the presence of the target and the cleaving agent. In some embodiments, the kit also includes instructions for administering a therapeutically effective amount of such an activatable antibody and/or conjugated activatable antibody described herein to the one or more subjects in the patient population that did not test positive for the presence of both the target and the cleaving agent. In some embodiments, the kit also includes instructions for administering a therapeutically effective amount of another anti-target therapeutic agent described herein to the one or more subjects in the patient population that did not test positive for the presence of both the target and the cleaving agent. In some embodiments, the activatable antibody comprises a detectable label. In some embodiments, the detectable label comprises an imaging agent, a contrasting agent, an enzyme, a fluorescent label, a chromophore, a dye, a radioisotope, one or more metal ions, or a ligand-based label. In some embodiments, the disorder is cancer. In some embodiments, the disorder is an autoimmune disease and/or an inflammatory disorder. In some embodiments, the biological sample comprises more than one tissue type. In some embodiments, the biological sample is a tissue microarray. In some embodiments, the biological sample is a frozen tissue microarray.

In some embodiments of these methods, the target is selected from the group of targets listed in Table 1. In some embodiments, the AB is or is derived from an antibody selected from the group of antibodies listed in Table 2. In some embodiments, the antigen binding fragment thereof is selected from the group consisting of a Fab fragment, a F(ab')$_2$ fragment, a scFv, and a scAb. In some embodiments, the AB has an equilibrium dissociation constant of about 100 nM or less for binding to the target. In some embodiments, the MM has an equilibrium dissociation constant for binding to the AB that is greater than the equilibrium dissociation constant of the AB to the target. In some embodiments, the MM does not interfere or compete with the AB of the activatable antibody in a cleaved state for binding to the target. In some embodiments, the MM is a polypeptide of no more than 40 amino acids in length. In some embodiments, the MM polypeptide sequence is different from that of the target, and the MM polypeptide sequence is no more than 50% identical to any natural binding partner of the AB. In some embodiments, the MM does not include more than 25% amino acid sequence identity to the target. In some embodiments, the MM does not include more than 10% amino acid sequence identity to the target. In some embodiments, the CM is a substrate for a protease selected from the group of proteases listed in Table 3. In some embodiments, the CM is a polypeptide of up to 15 amino acids in length. In some embodiments, the protease is co-localized with the target in a tissue, and the protease cleaves the CM in the activatable antibody when the activatable antibody is exposed to the protease. In some embodiments, the activatable antibody includes a linking peptide between the MM and the CM. In some embodiments, the activatable antibody includes a linking peptide between the CM and the AB. In some embodiments, the activatable antibody includes a first linking peptide (LP1) and a second linking peptide (LP2), and the activatable antibody in an uncleaved state has the structural arrangement from N-terminus to C-terminus as follows: MM-LP1-CM-LP2-AB or AB-LP2-CM-LP1-MM. In some embodiments, the two linking peptides need not be identical to each other. In some embodiments, at least one of LP1 or LP2 includes an amino acid sequence selected from the group consisting of $(GS)_n$, $(GGS)_n$, $(GSGGS)_n$ (SEQ ID NO: 33) and $(GGGS)_n$ (SEQ ID NO: 34), where n is an integer of at least one. In some embodiments, at least one of LP1 or LP2 includes an amino acid sequence selected from the group consisting of GGSG (SEQ ID NO: 35), GGSGG (SEQ ID NO: 36), GSGSG (SEQ ID NO: 37), GSGGG (SEQ ID NO: 38), GGGSG (SEQ ID NO: 39), and GSSSG (SEQ ID NO: 40). In some embodiments, the activatable antibody in an uncleaved state includes a spacer, wherein the spacer is joined directly to the MM and has the structural arrangement from N-terminus to C-terminus of spacer-MM-CM-AB. In some embodiments, the activatable antibody in an uncleaved state includes a spacer, wherein the spacer is joined directly to the MM and has the structural arrangement from N-terminus to C-terminus of AB-CM-MM-spacer.

In some embodiments of these methods, the cleaving agent is a protease that is co-localized in the subject or biological sample with the target, and the CM is a polypeptide that functions as a substrate for the protease, wherein the protease cleaves the CM in the activatable antibody when the activatable antibody is exposed to the protease. In some embodiments, the CM is a substrate for a protease selected from the group of proteases listed in Table 3. In some embodiments of these methods, the CM is a polypeptide of up to 15 amino acids in length. In some embodiments of these methods, the CM is coupled to the N-terminus of the AB. In some embodiments of these methods, the CM is coupled to the C-terminus of the AB. In some embodiments of these methods, the CM is coupled to the N-terminus of a variable light (VL) chain of the AB. In some embodiments of these methods, the CM is coupled to the N-terminus of a variable heavy (VH) chain of the AB.

In some embodiments of these methods, the cleaving agent is an enzyme. In some embodiments of these methods, the cleaving agent is a reducing agent. In some embodiments of these methods, the cleaving agent is photolysis.

In some embodiments of these methods, the cleaving agent is an enzyme and the CM is a substrate for the enzyme. In some embodiments of these methods, the enzyme is a protease disclosed herein. In some embodiments of these methods, the protease is one of the proteases disclosed herein. In some embodiments of these methods, the protease is selected from the group consisting of uPA, legumain, MT-SP1, ADAM17, BMP-1, TMPRSS3, TMPRSS4, MMP-9, MMP-12, MMP-13, and MMP-14. In some embodiments, the enzyme comprises uPA. In some embodiments, the enzyme comprises legumain. In some embodiments, the enzyme comprises MT-SP1. In some embodiments, the enzyme comprises a matrix metalloprotease (MMP). In some embodiments, the MMP is selected from the group consisting of MMP-9, MMP-12, MMP-13, and MMP-14. In some embodiments, the protease is not active or is significantly less active in tissues that do not significantly express the target. In some embodiments, the protease is not active or is significantly less active in healthy, e.g., non-diseased tissues.

The invention also provides methods of using conjugated activatable antibodies (also referred to herein as activatable antibody conjugates) in a variety of diagnostic indications. For example, the invention provides methods of detecting presence or absence of a cleaving agent and a target of interest in a subject or a sample by (i) contacting a subject or biological sample with an activatable antibody and/or conjugated activatable antibody and (ii) measuring a level of antibody and/or conjugated activatable antibody in the subject or biological sample, wherein a detectable level of activated antibody and/or conjugated activatable antibody in the subject or biological sample indicates that the cleaving agent and the target are present in the subject or biological sample and wherein no detectable level of activated antibody and/or conjugated activatable antibody in the subject or biological sample indicates that the cleaving agent, the target or both the cleaving agent and the target are absent and/or not sufficiently present at a detectable level in the subject or biological sample. In some embodiments, the biological sample comprises more than one tissue type. In some embodiments, the biological sample is a tissue microarray. In some embodiments, the biological sample is a frozen tissue microarray.

The invention also provides methods of detecting presence or absence of a cleaving agent in a subject or a sample by (i) contacting a subject or biological sample with an activatable antibody and/or conjugated activatable antibody in the presence of the target, and (ii) measuring a level of activated antibody and/or conjugated activatable antibody in the subject or biological sample, wherein a detectable level of activated antibody and/or conjugated activatable antibody in the subject or biological sample indicates that the cleaving agent is present in the subject or biological sample and wherein no detectable level of antibody and/or conjugated activatable antibody in the subject or biological sample indicates that the cleaving agent is absent and/or not sufficiently present at a detectable level in the subject or biological sample. In some embodiments, the biological sample comprises more than one tissue type. In some embodiments, the biological sample is a tissue microarray. In some embodiments, the biological sample is a frozen tissue microarray.

The invention also provides methods of detecting presence or absence of a cleaving agent in a subject or a sample by (i) contacting a subject or biological sample with an activatable antibody and/or conjugated activatable antibody; and (ii) measuring a level of detectable label in the subject or biological sample, wherein a detectable level of the detectable label in the subject or biological sample indicates that the cleaving agent is absent and/or not sufficiently present at a detectable level in the subject or biological sample, and wherein no detectable level of the detectable label in the subject or biological sample indicates that the cleaving agent is present in the subject or biological sample. In some embodiments, the biological sample comprises more than one tissue type. In some embodiments, the biological sample is a tissue microarray. In some embodiments, the biological sample is a frozen tissue microarray.

The invention also provides methods of detecting presence or absence of a cleaving agent and a target in a subject or a sample by (i) contacting a subject or biological sample with an activatable antibody and/or conjugated activatable antibody; and (ii) measuring a level of detectable label in the subject or biological sample, wherein a detectable level of the detectable label in the subject or biological sample indicates that the cleaving agent and/or target is absent and/or not sufficiently present at a detectable level in the subject or biological sample, and wherein a reduced detectable level of the detectable label in the subject or biological sample indicates that the cleaving agent and the target is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. In some embodiments, the biological sample comprises more than one tissue type. In some embodiments, the biological sample is a tissue microarray. In some embodiments, the biological sample is a frozen tissue microarray.

In some embodiments of these methods, the activatable antibody and/or conjugated activatable antibody includes a detectable label selected from the group consisting of an imaging agent, a contrasting agent, an enzyme, a fluorescent label, a chromophore, a dye, one or more metal ions, and a ligand-based label. In some embodiments of these methods, the imaging agent comprises a radioisotope. In some embodiments of these methods, the radioisotope is indium or technetium. In some embodiments of these methods, the contrasting agent comprises iodine, gadolinium or iron oxide. In some embodiments of these methods, the enzyme comprises horseradish peroxidase, alkaline phosphatase, or β-galactosidase. In some embodiments of these methods, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods, the luminescent label comprises an N-methylacrydium derivative. In some embodiments of these methods, the label comprises an Alexa Fluor® label, such as Alex Fluor® 680 or Alexa Fluor® 750. In some embodiments of these methods, the ligand-based label comprises biotin, avidin, streptavidin or one or more haptens.

In some embodiments of these methods, the subject is a mammal. In some embodiments of these methods, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods, the method is used to identify or otherwise refine a patient population suitable for treatment with an activatable antibody and/or conjugated activatable antibody of the disclosure. For example, patients that test positive for both the target and a protease that cleaves the substrate in the cleavable moiety (CM) of the activatable antibody and/or conjugated activatable antibody being tested in these methods are identified as suitable candidates for treatment with such antibody and/or such a conjugated activatable antibody comprising such a CM. Likewise, patients that test negative for either or both of the target and the protease that cleaves the substrate in the CM in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM that is cleaved by the patient at the site of disease).

In some embodiments, the activatable antibody binds the target in an activated state and includes (i) an antibody or an antigen binding fragment thereof (AB) that specifically binds to the target; (ii) a cleavable moiety (CM) coupled to the AB, wherein the CM is a polypeptide that functions as a substrate for a protease; and (iii) a masking moiety (MM) that inhibits the binding of the AB of the activatable antibody in an uncleaved state to the target, wherein the MM is coupled to the AB via the CM.

In some embodiments, the activatable antibody and/or conjugated activatable antibody has the structural arrangement from N-terminus to C-terminus as follows in the uncleaved state: MM-CM-AB or AB-CM-MM.

In some embodiments, the activatable antibody and/or conjugated activatable antibody includes a linking peptide between the MM and the CM.

In some embodiments, the activatable antibody and/or conjugated activatable antibody includes a linking peptide between the CM and the AB.

In some embodiments, the activatable antibody and/or conjugated activatable antibody includes a first linking peptide (LP1) and a second linking peptide (LP2), and wherein the activatable antibody and/or conjugated activatable antibody has the structural arrangement from N-terminus to C-terminus as follows in the uncleaved state: MM-LP1-CM-LP2-AB or AB-LP2-CM-LP1-MM. In some embodiments, the two linking peptides need not be identical to each other.

In some embodiments, the activatable antibody and/or conjugated activatable antibody includes an antibody or antigen-binding fragment thereof that specifically binds the target. In some embodiments, the antibody or immunologically active fragment thereof that binds the target is a monoclonal antibody, domain antibody, single chain, Fab fragment, a F(ab')$_2$ fragment, a scFv, a scAb, a dAb, a single domain heavy chain antibody, and a single domain light chain antibody. In some embodiments, such an antibody or immunologically active fragment thereof that binds the target is a mouse, chimeric, humanized or fully human monoclonal antibody.

In some embodiments, the antibody or an antigen binding fragment thereof (AB) specifically binds to a target selected from those shown Table 1.

In some embodiments, the antibody or an antigen binding fragment thereof (AB) is or is derived from an antibody selected from those shown in Table 2.

In some embodiments, the AB has an equilibrium dissociation constant of about 100 nM or less for binding to the target.

In some embodiments, the MM has an equilibrium dissociation constant for binding to the AB that is greater than the equilibrium dissociation constant of the AB to the target. In some embodiments, the MM has an equilibrium dissociation constant for binding to the AB that is no more than the equilibrium dissociation constant of the AB to the target. In some embodiments, the MM does not interfere or compete with the AB of the activatable antibody in a cleaved state for binding to the target.

In some embodiments, the MM is a polypeptide of about 2 to 40 amino acids in length, for example, no more than 40 amino acids long.

In some embodiments, the MM polypeptide sequence is different from that of the target, and the MM polypeptide sequence is no more than 50% identical to any natural binding partner of the AB.

In some embodiments, the MM does not include more than 25% amino acid sequence identity to the target. In some embodiments, the MM does not include more than 10% amino acid sequence identity to the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 20-fold greater than the equilibrium dissociation constant of an unmodified AB binding to the target, and whereas the AB of the activatable antibody in the cleaved state binds the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 40-fold greater than the equilibrium dissociation constant of an unmodified AB binding to the target, and whereas the AB of the activatable antibody in the cleaved state binds the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 50-fold greater than the equilibrium dissociation constant of an unmodified AB binding to the target, and whereas the AB of the activatable antibody in the cleaved state binds the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 100-fold greater than the equilibrium dissociation constant of an unmodified AB binding to the target, and whereas the AB of the activatable antibody in the cleaved state binds the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 200-fold greater than the equilibrium dissociation constant of an unmodified AB binding to the target, and whereas the AB of the activatable antibody in the cleaved state binds the target.

In some embodiments, the coupling of the MM reduces the ability of the AB to bind the target such that the dissociation constant ($K_d$) of the AB when coupled to the MM towards the target is at least 20 times greater than the $K_d$ of the AB when not coupled to the MM towards the target. In some embodiments, the coupling of the MM reduces the ability of the AB to bind the target such that the dissociation constant ($K_d$) of the AB when coupled to the MM towards the target is at least 40 times greater than the IQ of the AB when not coupled to the MM towards the target. In some embodiments, the coupling of the MM reduces the ability of the AB to bind the target such that the dissociation constant ($K_d$) of the AB when coupled to the MM towards the target is at least 50 times greater than the IQ of the AB when not coupled to the MM towards the target. In some embodiments, the coupling of the MM reduces the ability of the AB to bind the target such that the $K_d$ of the AB when coupled to the MM towards the target is at least 100 times greater than the $K_d$ of the AB when not coupled to the MM towards the target. In some embodiments, the coupling of the MM reduces the ability of the AB to bind the target such that the $K_d$ of the AB when coupled to the MM towards the target is at least 1000 times greater than the $K_d$ of the AB when not coupled to the MM towards the target. In some embodiments, the coupling of the MM reduces the ability of the AB to bind the target such that the $K_d$ of the AB when coupled to the MM towards the target is at least 10,000 times greater than the $K_d$ of the AB when not coupled to the MM towards the target.

In some embodiments, the MM includes the amino acid sequence CISPRGCPDGPYVMY (SEQ ID NO: 12).

In some embodiments, in the presence of the target, the MM reduces the ability of the AB to bind the target by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the protease is co-localized with the target in a tissue, and the protease cleaves the CM in the activatable antibody when the activatable antibody is exposed to the protease. In some embodiments, the protease is not active or is significantly less active in tissues that do not significantly express the target. In some embodiments, the protease is not active or is significantly less active in healthy, e.g., non-diseased tissues.

In some embodiments, the CM is a polypeptide of up to 15 amino acids in length.

In some embodiments, the CM is a substrate for a protease selected from the group consisting of those shown in Table 3. In some embodiments, the CM is a substrate for a protease selected from the group consisting of uPA (urokinase plasminogen activator), legumain and MT-SP1 (matriptase). In some embodiments, the protease comprises uPA. In some embodiments, the protease comprises legumain. In some embodiments, the protease comprises MT-SP1.

In some embodiments, the CM is a substrate for at least two proteases. In some embodiments, each protease is selected from the group consisting of those shown in Table 3. In some embodiments, the CM is a substrate for at least two proteases, wherein one of the proteases is selected from the group consisting of uPA, legumain and MT-SP1 and the other protease is selected from the group consisting of those shown in Table 3. In some embodiments, the CM is a substrate for at least two proteases selected from the group consisting of uPA, legumain and MT-SP1.

In some embodiments, the CM includes the amino acid sequence LSGRSDNH (SEQ ID NO: 14).

In some embodiments, the activatable antibody and/or conjugated activatable antibody includes at least a first CM and a second CM. In some embodiments, at least one of the first CM and the second CM is a polypeptide that functions as a substrate for a protease selected from the group consisting of uPA, legumain, and MT-SP1. In some embodiments, at least one of the first CM and the second CM comprises the amino acid sequence LSGRSDNH (SEQ ID NO: 14). In some embodiments, the first CM is cleaved by a first cleaving agent selected from the group consisting of uPA, legumain, and MT-SP1 in a target tissue and the second CM is cleaved by a second cleaving agent in a target tissue. In some embodiments, the first cleaving agent and the second cleaving agent are the same enzyme selected from the group consisting of uPA, legumain, and MT-SP1, and the first CM and the second CM are different substrates for the enzyme. In some embodiments, the first cleaving agent and the second cleaving agent are different enzymes. In some embodiments, the first cleaving agent and the second cleaving agent are co-localized in the target tissue. In some embodiments, the first CM and the second CM are cleaved by at least one cleaving agent in the target tissue.

In some embodiments, the activatable antibody and/or conjugated activatable antibody includes at least a first CM and a second CM. In some embodiments, at least one of the first CM and the second CM is a polypeptide that functions as a substrate for a protease selected from the group consisting of uPA, legumain, and MT-SP1. In some embodiments, at least one of the first CM and the second CM comprises the amino acid sequence LSGRSDNH (SEQ ID NO: 14). In some embodiments, the first CM is cleaved by a first cleaving agent selected from the group consisting of uPA, legumain, and MT-SP1 in a target tissue and the second CM is cleaved by a second cleaving agent in a target tissue. In some embodiments, the first cleaving agent and the second cleaving agent are the same enzyme selected from the group consisting of uPA, legumain, and MT-SP1, and the first CM and the second CM are different substrates for the enzyme. In some embodiments, the first cleaving agent and the second cleaving agent are different enzymes. In some embodiments, the first cleaving agent and the second cleaving agent are co-localized in the target tissue. In some embodiments, the first CM and the second CM are cleaved by at least one cleaving agent in the target tissue.

In some embodiments, at least one of LP1 or LP2 includes an amino acid sequence selected from the group consisting of $(GS)_n$, $(GGS)_n$, $(GSGGS)_n$ (SEQ ID NO: 33) and $(GGGS)_n$ (SEQ ID NO: 34), where n is an integer of at least one. In some embodiments, at least one of LP1 or LP2 includes an amino acid sequence selected from the group consisting of GGSG (SEQ ID NO: 35), GGSGG (SEQ ID NO: 36), GSGSG (SEQ ID NO: 37), GSGGG (SEQ ID NO: 38), GGGSG (SEQ ID NO: 39), and GSSSG (SEQ ID NO: 40). In some embodiments, LP1 includes the amino acid sequence GSSGGSGGSGGSG (SEQ ID NO: 13). In some embodiments, LP2 includes the amino acid sequence GSSGT (SEQ ID NO: 15) or GSSG (SEQ ID NO: 41).

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the agent is conjugated to the AB via a linker. In some embodiments, the linker is a cleavable linker. In some embodiments, the linker is selected from the group consisting of the linkers shown in Tables 5 and 6.

In some embodiments, the activatable antibody and/or conjugated activatable antibody also include a signal peptide. In some embodiments, the signal peptide is conjugated to the activatable antibody and/or conjugated activatable antibody via a spacer. In some embodiments, the spacer is conjugated to the activatable antibody and/or conjugated activatable antibody in the absence of a signal peptide. In some embodiments, the spacer is joined directly to the MM of the activatable antibody and/or conjugated activatable antibody. In some embodiments, the spacer includes at least the amino acid sequence QGQSGQ (SEQ ID NO: 11). In some embodiments, an activatable antibody and/or conjugated activatable antibody includes a spacer of sequence QGQSGQ (SEQ ID NO: 11) joined directly to a MM sequence disclosed herein in the structural arrangement from N-terminus to C-terminus of spacer-MM-CM-AB. In some embodiments, an activatable antibody and/or conjugated activatable antibody includes a spacer joined directly to a MM sequence disclosed herein in the structural arrangement from N-terminus to C-terminus of spacer-MM-CM-AB. In some embodiments, the activatable antibody in an uncleaved state includes a spacer, wherein the spacer is joined directly to the MM and has the structural arrangement from N-terminus to C-terminus of AB-CM-MM-spacer.

In some embodiments, the activatable antibody and/or conjugated activatable antibody is monospecific. In some embodiments, the activatable antibody and/or conjugated activatable antibody is multispecific, e.g., by way of non-limiting example, bispecific or trifunctional. In some embodiments, the activatable antibody and/or conjugated activatable antibody is formulated as part of a pro-Bispecific T Cell Engager (BITE) molecule. In some embodiments, the activatable antibody is formulated as part of a pro-Chimeric Antigen Receptor (CAR) modified T cell or other engineered receptor.

In some embodiments, the target is selected from the group of targets listed in Table 1. In some embodiments, the AB is or is derived from an antibody selected from the group of antibodies listed in Table 2. In some embodiments, the antigen binding fragment thereof is selected from the group consisting of a Fab fragment, a F(ab')$_2$ fragment, a scFv, and a scAb. In some embodiments, the AB has an equilibrium dissociation constant of about 100 nM or less for binding to the target. In some embodiments, the MM has an equilibrium dissociation constant for binding to the AB that is greater than the equilibrium dissociation constant of the AB to the target. In some embodiments, the MM does not interfere or compete with the AB of the activatable antibody in a cleaved state for binding to the target. In some embodiments, the MM is a polypeptide of no more than 40 amino acids in length. In some embodiments, the MM polypeptide sequence is different from that of the target and wherein the MM polypeptide sequence is no more than 50% identical to any natural binding partner of the AB. In some embodiments, the MM does not include more than 25% amino acid sequence identity to the target. In some embodiments, the MM does not include more than 10% amino acid sequence identity to the target. In some embodiments, the CM is a substrate for a protease selected from the group of proteases listed in Table 3. In some embodiments, the CM is a polypeptide of up to 15 amino acids in length. In some embodiments, the protease is co-localized with the target in a tissue, and wherein the protease cleaves the CM in the activatable antibody when the activatable antibody is exposed to the protease. In some embodiments, the activatable antibody includes a linking peptide between the MM and the CM. In some embodiments, the activatable antibody includes a linking peptide between the CM and the AB. In some embodiments, the activatable antibody includes a first linking peptide (LP1) and a second linking peptide (LP2), and wherein the activatable antibody in an uncleaved state has the structural arrangement from N-terminus to C-terminus as follows: MM-LP1-CM-LP2-AB or AB-LP2-CM-LP1-MM. In some embodiments, the two linking peptides need not be identical to each other. In some embodiments, at least one of LP1 or LP2 includes an amino acid sequence selected from the group consisting of $(GS)_n$, $(GGS)_n$, $(GSGGS)_n$ (SEQ ID NO: 33) and $(GGGS)_n$ (SEQ ID NO: 34), where n is an integer of at least one. In some embodiments, at least one of LP1 or LP2 includes an amino acid sequence selected from the group consisting of GGSG (SEQ ID NO: 35), GGSGG (SEQ ID NO: 36), GSGSG (SEQ ID NO: 37), GSGGG (SEQ ID NO: 38), GGGSG (SEQ ID NO: 39), and GSSSG (SEQ ID NO: 40). In some embodiments, the activatable antibody in an uncleaved state includes a spacer, wherein the spacer is joined directly to the MM and has the structural arrangement from N-terminus to C-terminus of spacer-MM-CM-AB. In some embodiments, the activatable antibody in an uncleaved state includes a spacer, wherein the spacer is joined directly to the MM and has the structural arrangement from N-terminus to C-terminus of AB-CM-MM-spacer.

In some embodiments, a method or kit is used to identify or otherwise refine a patient population suitable for treatment with an activatable antibody and/or conjugated activatable antibody of the disclosure, followed by treatment by administering that activatable antibody and/or conjugated activatable antibody to a subject in need thereof. For example, patients that test positive for both the target and a protease that cleaves the substrate in the cleavable moiety (CM) of the activatable antibody and/or conjugated activatable antibody being tested in these methods are identified as suitable candidates for treatment with such antibody and/or such a conjugated activatable antibody comprising such a CM, and the patient is then administered a therapeutically effective amount of the activatable antibody and/or conjugated activatable antibody that was tested. Likewise, patients that test negative for either or both of the target and the protease that cleaves the substrate in the CM in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM that is cleaved by the patient at the site of disease). In some embodiments, the patient is then administered a therapeutically effective amount of the activatable antibody and/or conjugated for which the patient tested positive.

In some embodiments, the activatable antibody binds the target in an activated state and includes (i) an antibody or an antigen binding fragment thereof (AB) that specifically binds to the target; (ii) a cleavable moiety (CM) coupled to the AB, wherein the CM is a polypeptide that functions as a substrate for a protease; and (iii) a masking moiety (MM) that inhibits the binding of the AB of the activatable antibody in an uncleaved state to the target, wherein the MM is coupled to the AB via the CM.

In some embodiments, the activatable antibody and/or conjugated activatable antibody has the structural arrangement from N-terminus to C-terminus as follows in the uncleaved state: MM-CM-AB or AB-CM-MM.

In some embodiments, the activatable antibody and/or conjugated activatable antibody includes a linking peptide between the MM and the CM.

In some embodiments, the activatable antibody and/or conjugated activatable antibody includes a linking peptide between the CM and the AB.

In some embodiments, the activatable antibody and/or conjugated activatable antibody includes a first linking peptide (LP1) and a second linking peptide (LP2), and wherein the activatable antibody and/or conjugated activatable antibody has the structural arrangement from N-terminus to C-terminus as follows in the uncleaved state: MM-LP1-CM-LP2-AB or AB-LP2-CM-LP1-MM. In some embodiments, the two linking peptides need not be identical to each other.

In some embodiments, the antibody or an antigen binding fragment thereof (AB) specifically binds to a target selected from those shown Table 1.

In some embodiments, the antibody or an antigen binding fragment thereof (AB) is or is derived from an antibody selected from those shown in Table 2.

In some embodiments, the AB has an equilibrium dissociation constant of about 100 nM or less for binding to the target.

In some embodiments, the activatable antibody and/or conjugated activatable antibody includes an antibody or antigen-binding fragment thereof that specifically binds the target. In some embodiments, the antibody or immunologically active fragment thereof that binds the target is a monoclonal antibody, domain antibody, single chain, Fab fragment, a F(ab')$_2$ fragment, a scFv, a scAb, a dAb, a single domain heavy chain antibody, and a single domain light chain antibody. In some embodiments, such an antibody or immunologically active fragment thereof that binds the target is a mouse, chimeric, humanized or fully human monoclonal antibody.

In some embodiments, the MM has an equilibrium dissociation constant for binding to the AB that is greater than the equilibrium dissociation constant of the AB to the target. In some embodiments, the MM has an equilibrium dissociation constant for binding to the AB that is no more than the equilibrium dissociation constant of the AB to the target. In some embodiments, the MM does not interfere or compete with the AB of the activatable antibody in a cleaved state for binding to the target.

In some embodiments, the MM is a polypeptide of about 2 to 40 amino acids in length, for example, no more than 40 amino acids long.

In some embodiments, the MM polypeptide sequence is different from that of the target, and the MM polypeptide sequence is no more than 50% identical to any natural binding partner of the AB.

In some embodiments, the MM does not include more than 25% amino acid sequence identity to the target. In some embodiments, the MM does not include more than 10% amino acid sequence identity to the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 20-fold greater than the equilibrium dissociation constant of an unmodified AB binding to the target, and whereas the AB of the activatable antibody in the cleaved state binds the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 40-fold greater than the equilibrium dissociation constant of an unmodified AB binding to the target, and whereas the AB of the activatable antibody in the cleaved state binds the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 50-fold greater than the equilibrium dissociation constant of an unmodified AB binding to the target, and whereas the AB of the activatable antibody in the cleaved state binds the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 100-fold greater than the equilibrium dissociation constant of an unmodified AB binding to the target, and whereas the AB of the activatable antibody in the cleaved state binds the target.

In some embodiments, the MM is positioned in the activatable antibody and/or conjugated activatable antibody such that in the uncleaved state, binding of the activatable antibody and/or conjugated activatable antibody to the target is reduced to occur with an equilibrium dissociation constant that is at least 200-fold greater than the equilibrium dissociation constant of an unmodified AB binding to the target, and whereas the AB of the activatable antibody in the cleaved state binds the target.

In some embodiments, the coupling of the MM reduces the ability of the AB to bind the target such that the dissociation constant ($K_d$) of the AB when coupled to the MM towards the target is at least 20 times greater than the $K_d$ of the AB when not coupled to the MM towards the target. In some embodiments, the coupling of the MM reduces the ability of the AB to bind the target such that the dissociation constant ($K_d$) of the AB when coupled to the MM towards the target is at least 40 times greater than the IQ of the AB when not coupled to the MM towards the target. In some embodiments, the coupling of the MM reduces the ability of the AB to bind the target such that the dissociation constant ($K_d$) of the AB when coupled to the MM towards the target is at least 50 times greater than the IQ of the AB when not coupled to the MM towards the target. In some embodiments, the coupling of the MM reduces the ability of the AB to bind the target such that the $K_d$ of the AB when coupled to the MM towards the target is at least 100 times greater than the $K_d$ of the AB when not coupled to the MM towards the target. In some embodiments, the coupling of the MM reduces the ability of the AB to bind the target such that the $K_d$ of the AB when coupled to the MM towards the target is at least 1000 times greater than the $K_d$ of the AB when not coupled to the MM towards the target. In some embodiments, the coupling of the MM reduces the ability of the AB to bind the target such that the $K_d$ of the AB when coupled to the MM towards the target is at least 10,000 times greater than the $K_d$ of the AB when not coupled to the MM towards the target.

In some embodiments, in the presence of the target, the MM reduces the ability of the AB to bind the target by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the protease is co-localized with the target in a tissue, and the protease cleaves the CM in the activatable antibody when the activatable antibody is exposed to the protease. In some embodiments, the protease is not active or is significantly less active in tissues that do not significantly express the target. In some embodiments, the protease is not active or is significantly less active in healthy, e.g., non-diseased tissues.

In some embodiments, the CM is a polypeptide of up to 15 amino acids in length.

In some embodiments, the CM is a substrate for a protease selected from the group consisting of those shown in Table 3. In some embodiments, the CM is a substrate for a protease selected from the group consisting of uPA (urokinase plasminogen activator), legumain and MT-SP1 (matriptase). In some embodiments, the protease comprises uPA. In some embodiments, the protease comprises legumain. In some embodiments, the protease comprises MT-SP1.

In some embodiments, the CM is a substrate for at least two proteases. In some embodiments, each protease is selected from the group consisting of those shown in Table 3. In some embodiments, the CM is a substrate for at least two proteases, wherein one of the proteases is selected from the group consisting of uPA, legumain and MT-SP1 and the other protease is selected from the group consisting of those shown in Table 3. In some embodiments, the CM is a substrate for at least two proteases selected from the group consisting of uPA, legumain and MT-SP1.

In some embodiments, the CM includes the amino acid sequence LSGRSDNH (SEQ ID NO: 14).

In some embodiments, the activatable antibody and/or conjugated activatable antibody includes at least a first CM and a second CM. In some embodiments, at least one of the first CM and the second CM is a polypeptide that functions as a substrate for a protease selected from the group consisting of uPA, legumain, and MT-SP1. In some embodiments, at least one of the first CM and the second CM comprises the amino acid sequence LSGRSDNH (SEQ ID NO: 14). In some embodiments, the first CM is cleaved by a first cleaving agent selected from the group consisting of uPA, legumain, and MT-SP1 in a target tissue and the second CM is cleaved by a second cleaving agent in a target tissue. In some embodiments, the first cleaving agent and the second cleaving agent are the same enzyme selected from the group consisting of uPA, legumain, and MT-SP1, and the first CM and the second CM are different substrates for the enzyme. In some embodiments, the first cleaving agent and the second cleaving agent are different enzymes. In some embodiments, the first cleaving agent and the second cleaving agent are co-localized in the target tissue. In some embodiments, the first CM and the second CM are cleaved by at least one cleaving agent in the target tissue.

In some embodiments, at least one of LP1 or LP2 includes an amino acid sequence selected from the group consisting of $(GS)_n$, $(GGS)_n$, $(GSGGS)_n$ (SEQ ID NO: 33) and $(GGGS)_n$ (SEQ ID NO: 34), where n is an integer of at least one. In some embodiments, at least one of LP1 or LP2 includes an amino acid sequence selected from the group consisting of GGSG (SEQ ID NO: 35), GGSGG (SEQ ID NO: 36), GSGSG (SEQ ID NO: 37), GSGGG (SEQ ID NO: 38), GGGSG (SEQ ID NO: 39), and GSSSG (SEQ ID NO: 40). In some embodiments, LP1 includes the amino acid sequence GSSGGSGGSGGSG (SEQ ID NO: 13). In some embodiments, LP2 includes the amino acid sequence GSSGT (SEQ ID NO: 15) or GSSG (SEQ ID NO: 41).

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the agent is conjugated to the AB via a linker. In some embodiments, the linker is a cleavable linker. In some embodiments, the linker is selected from the group consisting of the linkers shown in Tables 5 and 6.

In some embodiments, the activatable antibody and/or conjugated activatable antibody also include a signal peptide. In some embodiments, the signal peptide is conjugated to the activatable antibody and/or conjugated activatable antibody via a spacer. In some embodiments, the spacer is conjugated to the activatable antibody and/or conjugated activatable antibody in the absence of a signal peptide. In some embodiments, the spacer is joined directly to the MM of the activatable antibody and/or conjugated activatable antibody. In some embodiments, the spacer includes at least the amino acid sequence QGQSGQ (SEQ ID NO: 11). In some embodiments, an activatable antibody and/or conjugated activatable antibody includes a spacer of sequence QGQSGQ (SEQ ID NO: 11) joined directly to a MM sequence disclosed herein in the structural arrangement from N-terminus to C-terminus of spacer-MM-CM-AB. In some embodiments, an activatable antibody and/or conjugated activatable antibody includes a spacer joined directly to a MM sequence disclosed herein in the structural arrangement from N-terminus to C-terminus of spacer-MM-CM-AB. In some embodiments, the activatable antibody in an uncleaved state includes a spacer, wherein the spacer is joined directly to the MM and has the structural arrangement from N-terminus to C-terminus of AB-CM-MM-spacer.

In some embodiments, the activatable antibody and/or conjugated activatable antibody is monospecific. In some embodiments, the activatable antibody and/or conjugated activatable antibody is multispecific, e.g., by way of non-limiting example, bispecific or trifunctional. In some embodiments, the activatable antibody and/or conjugated activatable antibody is formulated as part of a pro-Bispecific T Cell Engager (BITE) molecule. In some embodiments, the activatable antibody is formulated as part of a pro-Chimeric Antigen Receptor (CAR) modified T cell or other engineered receptor.

In some embodiments, the target is selected from the group of targets listed in Table 1. In some embodiments, the AB is or is derived from an antibody selected from the group of antibodies listed in Table 2. In some embodiments, the antigen binding fragment thereof is selected from the group consisting of a Fab fragment, a F(ab')$_2$ fragment, a scFv, and a scAb. In some embodiments, the AB has an equilibrium dissociation constant of about 100 nM or less for binding to the target. In some embodiments, the MM has an equilibrium dissociation constant for binding to the AB that is greater than the equilibrium dissociation constant of the AB to the target. In some embodiments, the MM does not interfere or compete with the AB of the activatable antibody in a cleaved state for binding to the target. In some embodiments, the MM is a polypeptide of no more than 40 amino acids in length. In some embodiments, the MM polypeptide sequence is different from that of the target and wherein the MM polypeptide sequence is no more than 50% identical to any natural binding partner of the AB. In some embodiments, the MM does not include more than 25% amino acid sequence identity to the target. In some embodiments, the MM does not include more than 10% amino acid sequence identity to the target. In some embodiments, the CM is a polypeptide of up to 15 amino acids in length. In some embodiments, the protease is co-localized with the target in a tissue, and wherein the protease cleaves the CM in the activatable antibody when the activatable antibody is exposed to the protease. In some embodiments, the activatable antibody includes a linking peptide between the MM and the CM. In some embodiments, the activatable antibody includes a linking peptide between the CM and the AB. In some embodiments, the activatable antibody includes a first linking peptide (LP1) and a second linking peptide (LP2), and wherein the activatable antibody in an uncleaved state has the structural arrangement from N-terminus to C-terminus as follows: MM-LP1-CM-LP2-AB or AB-LP2-CM-LP 1-MM. In some embodiments, the two linking peptides need not be identical to each other. In some embodiments, at least one of LP1 or LP2 includes an amino acid sequence selected from the group consisting of (GS)$_n$, (GGS)$_n$, (GSGGS)$_n$ (SEQ ID NO: 33) and (GGGS)$_n$ (SEQ ID NO: 34), where n is an integer of at least one. In some embodiments, at least one of LP1 or LP2 includes an amino acid sequence selected from the group consisting of GGSG (SEQ ID NO: 35), GGSGG (SEQ ID NO: 36), GSGSG (SEQ ID NO: 37), GSGGG (SEQ ID NO: 38), GGGSG (SEQ ID NO: 39), and GSSSG (SEQ ID NO: 40). In some embodiments, the activatable antibody in an uncleaved state includes a spacer, wherein the spacer is joined directly to the MM and has the structural arrangement from N-terminus to C-terminus of spacer-MM-CM-AB. In some embodiments, the activatable antibody in an uncleaved state includes a spacer, wherein the spacer is joined directly to the MM and has the structural arrangement from N-terminus to C-terminus of AB-CM-MM-spacer.

The invention also provides kits and/or methods for detecting activation of activatable antibodies and binding of activated, activatable antibodies to a target of interest using a construct referred to herein as the "hemi-activatable antibody" in which the activatable antibody includes a first antigen binding domain and a second antigen binding domain, where the first antigen binding domain is not masked and the second antigen binding domain is masked and contains a labeled linker that includes a protease-cleavable sequence. In these hemi-activatable antibodies, the non-masked arm binds a tissue target, e.g., a tissue receptor, thereby anchoring the hemi-activatable antibody to the tissue. If the protease is present in the tissue and cleaves the labeled linker, the mask and/or label will dissociate from the hemi-activatable antibody, and the label signal (e.g., fluorescence) will decrease. If the protease is not present at a detectable level in the tissue, the level of label signal (e.g., fluorescence) should remain unchanged or relatively unchanged.

In some embodiments, the hemi-activatable antibody is labeled and the label is used as a co-register for the amount of bound material on tissue.

In some embodiments, the labeled or un-labeled hemi-activatable antibody is used, where the first antigen binding domain is not masked and the second antigen binding domain is masked and contains a linker that includes a protease-cleavable embraced into the fluorophore-quencher pair. In these hemi-activatable antibodies, the non-masked arm binds a tissue target, e.g., a tissue receptor, thereby anchoring the hemi-activatable antibody to the tissue. If the protease is present in the tissue and cleaves the labeled linker, the quencher and/or label will dissociate, and the label signal (e.g., fluorescence) will increase. If the protease is not present at a detectable level in the tissue, the level of label signal (e.g., fluorescence) should remain unchanged or relatively unchanged.

The invention also provides kits and/or methods for monitoring activation of activatable antibodies, for monitoring distribution of activatable antibodies, and/or for monitoring accumulation of activatable antibodies in a subject. In these methods, the activatable antibody is conjugated to any of a variety of detectable markers, and the markers are detected using the corresponding instrumentation or other analytic means. In some embodiments of these methods and/or kits, the activatable antibody is conjugated to a label such as, by way of non-limiting example, biotin, a fluorescent label, PET/SPECT tracers, optoacoustics reagents and/or MRI contrast agents. Suitable examples of such labels are described herein. These labels are then detected using any of a variety of methods including, by way of non-limiting example, western blot analysis, histology, immunofluorescence (IF), immunohistochemistry (IHC), and/or in vivo and/or intraoperative imaging methods.

The invention also provides kits and/or methods for evaluating activation of activatable antibodies and binding of activated activatable antibodies in tumor models by in vivo imaging with a "cold" pretreatment step. These methods are advantageous because they enable in vivo evaluation of (i) protease activity in tumor or diseased tissues; (ii) cleavability and specificity of substrates; (iii) activation and binding of activatable antibodies; and (iv) comparison of different substrates not compromised by labeling.

In these kits and/or methods, an indirect measure of activatable antibody activation and binding is performed by pretreatment of mice with "cold" non-labeled activatable antibody followed by administration of labeled antibody. The difference of fluorescence intensity or any other imaging modality, e.g., PET, MRI, etc., between the mice treated with only labeled antibody (i.e., no "cold" pretreatment) and mice treated with "cold" activatable antibody indicates the amount of receptor occupied by activated activatable antibody, also referred to herein as the level of occupied receptor. The baseline of the signal is set by pre-treatment of the tumor model, e.g., mice, with "cold" antibody leading to complete receptor occupancy. In addition, this control is able to demonstrate the signal of potentially trapped labeled material due to Enhanced Permeability and Retention (EPR) effect.

The invention also provides methods for sectioning tissue samples such as bone marrow biopsy samples from multiple myeloma patients. In some embodiments, the tissue sample is any frozen tissue that binds to a support matrix. In some embodiments, the tissue sample is a fatty or soft tissue, such as a breast cancer or lymph node sample. In some embodiments, the tissue is from a solid tumor. In some embodiments the tissue sample is a multiple myeloma sample. In some embodiments the tissue sample is a bone marrow biopsy from a multiple myeloma patient. In some embodiments, the sectioning of the tissue sample from the patient is followed by staining. In some embodiments, the sectioning of the tissue sample from the multiple myeloma patient is followed by staining. In some embodiments, the sectioning of a bone marrow biopsy sample from the multiple myeloma patient is followed by staining. In these methods, a tissue sample is frozen, in some embodiments to at least −30° C. In some embodiments, the frozen tissue sample is then adhered to a chuck. After the chuck is placed in a chuck holder, a support matrix miscible with frozen sectioning, e.g., plastic or adhesive material, e.g., adhesive tape, is applied to the face of the block. In some embodiments, the support matrix is then manipulated, e.g., using a plastic roller or other such apparatus, to ensure even adhesion. While the edge of the support matrix is held in place, the block is slowly lowered to the blade, and the section is taken. The tissue can be sectioned at any suitable width, e.g., at less than 1 micron (um), at 1 micron, at 2 microns, at 3 microns, at 4 microns, at 5 microns, at 6 microns, at 7 microns, at 8 microns, at 9 microns, at 10 microns or at greater than 10 microns. In some embodiments, the tissue is sectioned using a tungsten carbide knife, e.g., a 16 cm tungsten carbide knife. The tissue sections are kept on the support matrix and kept frozen. In some embodiments, tissue sections adhered to a support matrix are stained directly on the support matrix, thus eliminating the need for tissue transfer, which could result in possible damage.

BRIEF DESCRIPTION OF THE DRAWINGS

FIG. 5 depicts a series of images showing the pH dependence of activatable antibody activation by tissue sections. Incubation of activatable antibodies 3954-1204-C225v5 and 3954-LS4-C225v5 (CM LS4 (amino acid sequence RRALAL, SEQ ID NO: 252) is a substrate for cathepsin B) in a buffer at pH 6.5 (optimal pH for cathepsin B, an intracellular protease) on H292 xenograft tumor tissue resulted in activation of 3954-LS4-C225v5 (lower right panel) but no significant activation of 3954-1204-C225v5 (lower left panel). In contrast, incubation of these activatable antibodies at physiological pH (pH 7.4) resulted in activation of 3954-1204-C225v5 (upper left panel) but no significant activation of 3954-LS4-C225v5.

FIG. 6 is a series of tables depicting that 3954-1204-C225v5 is activatable in a wide range of human tumor samples. Column 2 indicates the expression level of EGFR receptor, as detected by a commercially available anti-EGFR antibody, for the various human cancer tissue samples. Column 3 indicates the amount of active matriptase (MT-SP1), as detected by antibody A11, in the various human cancer tissue samples. Columns 4 and 5 represent an evaluation of in situ activation and binding of the EGFR activatable antibody (col. 5) as compared to cetuximab (Cetux) tissue staining (col. 4). The IHC staining that measures the amount of EGFR and A11 antibodies binding to the tissue sample was scored from − to 3+: −, no staining; 1+ (i.e., "+"), weak staining; 2+ (i.e., "++"), moderate staining; and 3+ (i.e., "+++"), strong staining. The in situ imaging staining scoring is based on comparison with cetuximab (parental) antibody staining and defined as follows: −, no staining; 1+ (i.e., "+"), weak staining as compared to parental antibody; 2+ (i.e., "++"), moderate staining as compared to parental antibody; and 3+ (i.e., "+++"), analogous staining to parental antibody.

FIG. 9, middle column of images, demonstrates co-localization of matriptase (MT-SP1) activity with EGFR expression.

FIG. 18 is an illustration depicting various embodiments of using activatable antibodies and conjugated activatable antibodies in various imaging methods for monitoring activatable antibody distribution, accumulation and/or activation.

FIGS. 19A-19D are a series of illustrations providing a schematic overview of the hemi-activatable antibodies provided herein. FIGS. 19A and 19C depict hemi-activatable antibody designs where one arm of activatable antibody contains labeled linker and another arm represents antigen binding site of parental antibody (or antibody against ubiquitously expressed target). FIG. 19B depicts a hemi-activatable antibody design where the linker of the activatable antibody contains the labeling agent that masks the antigen binding site of antibody. FIG. 19D depicts a hemi-activatable antibody design where one arm of activatable antibody contains labeled linker and a quenched probe (Q), and another arm represents antigen binding site of parental antibody.

DETAILED DESCRIPTION OF THE INVENTION

Figure 1:
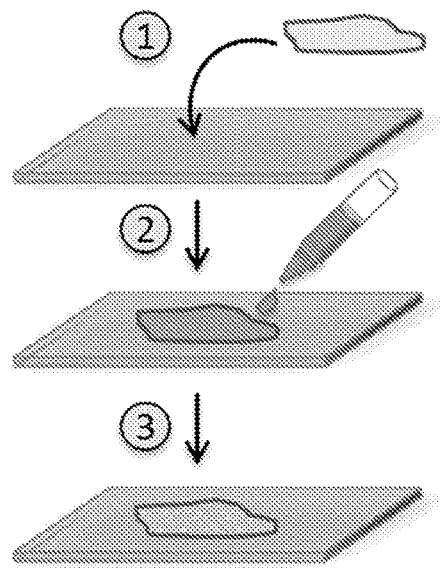
FIG. 1 is a schematic overview of a method of the disclosure, namely, in situ imaging of an activatable antibody of the disclosure: 1. A tissue section is laid over the slide. 2. The slide is covered with solution containing labeled activatable antibody and incubated. 3. After extensive washing, binding of the activatable antibody is visualized.

The present invention provides methods and compositions for detecting specific protease activity in biological samples using activatable antibodies. These compositions and methods can be used in a variety of diagnostic indications, e.g., in vivo, in vitro, in situ, or ex vivo.

The techniques provided herein enable detection of proteolytic activity in biological samples such as cell cultures or tissue sections. Using the techniques described herein, it is possible to quantify proteolytic activity based on the presence of a detectable label (e.g., a fluorescent label). These techniques are useful with any frozen cells or tissue derived from a disease site (e.g. tumor tissue) or healthy tissues.

Proteases are the enzymes that catalyze the hydrolytic cleavage of peptide bonds and can be divided into five distinct classes based on their catalytic mechanisms: serine, cysteine, aspartic, metallo or threonine proteases (C. Lopez-Otin, Nature Reviews 2007). Proteases are involved in numerous important physiological processes including protein turnover, blood coagulation, wound healing, digestion, fertilization, cell differentiation and growth, cell signaling, the immune response, and apoptosis. However, proteases can be very harmful if not strictly controlled. As such, inappropriate proteolysis can have a major role in cancer as well as cardiovascular, inflammatory, neurodegenerative, bacterial and viral and parasitic diseases. Because excessive proteolysis can be prevented by inhibition of the appropriate proteases, proteases are considered to be suitable targets for therapy (B. Turk, Nature Rev Drug Disc). Notably, the activity of proteases is tightly controlled through fundamental mechanisms including regulation of biosynthesis, activation of an inactive protease precursor, also known as pro-enzyme or zymogen, and by the binding of inhibitors and cofactors.

Several molecular techniques are available to identify and characterize proteases in cells and tissues. Most of those techniques are focused on the detection of mRNA or protein expression of proteases; however these techniques do not provide information on the activity of proteases, given the probability of the protease to be in its zymogen form or to be in the complex with protease inhibitor suppressing its activity. Therefore, development of reagents capable of protease activity detection in biological systems and, particularly, patient samples, is central to further the understanding of mechanism through which proteases are involved in homeostasis and disease development as well as help us to design better treatment strategies for clinical use.

Zymography is a technique enabling detection of functional proteases by use of reagents providing visualization of substrate degradation. Several types of zymography techniques are developed for the visualization of protease activity ex vivo that could be subdivided onto two categories: in gel zymography and in situ zymography (reviewed in Vandooren et al., 2013). The use of tissue homogenates for in gel zymography precludes the localization of enzyme activity on tissue and might potentially lead to modification of protease activity resulting from interaction of proteases or inhibitors that have may have been localized in distinct compartments of the intact cells or tissues (Hrabec, et al., J Cancer Res Clin Oncol 128:197-204, 2002). In contrast, in situ zymography techniques are based on the assessment of various protease activities in combination with their localization (Yan and Blomme, 2003). However, as compared to the in gel zymography where proteases could be identified by molecule weight, in in situ zymography interpretation of the data majorly relies on the specificity and selectivity of the substrates. Most of the reagents currently used for in situ zymography, such as DQ-collagen or DQ-casein, are based on the substrates that could be cleaved by many proteases that make interpretation of the data very speculative.

The methods described herein provide a novel and potent technology enabling selective detection of specific protease activity in biological samples, e.g., tissue samples, by the use of protease-activated antibody technology, referred to herein as activatable antibody imaging. In some embodiments, the method is activatable antibody in vivo imaging. In some embodiments, the method is activatable antibody ex vivo imaging. In some embodiments, the method is activatable antibody in situ imaging. In some embodiments, the method is activatable antibody in vitro imaging. These methods use activatable antibodies designed to incorporate different protease specific substrates to detect and localize specific protease activities in tissue sections.

Generally, the compositions and methods provided herein include an activatable antibodies include an antibody or antigen-binding fragment thereof (AB) that specifically binds a target, wherein the AB is coupled to a masking moiety (MM), such that coupling of the MM decreases the ability of the antibody or antigen-binding fragment thereof to bind the target. In some embodiments, the MM is coupled to the AB via a cleavable moiety (CM) that includes a substrate for a protease, for example, a protease that is co-localized with the target at a treatment site in a subject. Numerous studies have demonstrated the correlation of aberrant protease levels, e.g., uPA, legumain, MT-SP1, matrix metalloproteases (MMPs), in solid tumors. (See e.g., Murthy R V, et al. "Legumain expression in relation to clinicopathologic and biological variables in colorectal cancer." Clin Cancer Res. 11 (2005): 2293-2299; Nielsen B S, et al. "Urokinase plasminogen activator is localized in stromal cells in ductal breast cancer." Lab Invest 81 (2001): 1485-1501; Mook O R, et al. "In situ localization of gelatinolytic activity in the extracellular matrix of metastases of colon cancer in rat liver using quenched fluorogenic DQ-gelatin." J Histochem Cytochem. 51 (2003): 821-829).

The activatable antibodies provided herein include a substrate for a protease, which is useful in leveraging the protease activity in tumor cells for targeted antibody activation at the site of treatment and/or diagnosis. The substrate selection process is used to identify substrates that have a number of desirable characteristics. For example, the selected substrates are systemically stable (i.e., stable in the systemic circulation of a subject), are generally not susceptible to cleavage by circulating proteases such as plasmin, thrombin, tissue plasminogen activator (tPA), are non-toxic, are generally not susceptible to cleavage at potential sites of toxicity such as the skin by proteases such as ADAM 9, ADAM 10, ADAM 17 and/or kallikreins, such as KLK-5 and KLK-7, and are active at an intended site of treatment and/or diagnosis. In some embodiments, the identified substrates are selected for proteases that are overexpressed at an intended site of therapy and/or diagnosis but are not typically active at or in normal, healthy or otherwise non-diseased or damaged tissue, and then the selected substrates are subsequently counter-screened against proteases expressed in normal, e.g., non-diseased, tissue.

As a non-limiting example, the AB is a binding partner for any target listed in Table 1.

TABLE 1

| Exemplary Targets |
| --- |
| 1-92-LFA-3 |
| Anti-Lewis-Y |
| Apelin J receptor |
| APRIL |
| BAFF |
| C5 complement |
| C-242 |
| CD2 |
| CD3 |
| CD6 |
| CD9 |
| CD11a |
| CD19 |
| CD20 |
| CD22 |
| CD25 |
| CD28 |
| CD30 |
| CD33 |
| CD38 |
| CD40 |
| CD40L |
| CD41 |
| CD44 |
| CD47 |
| CD52 |
| CD56 |
| CD64 |
| CD70 |
| CD80 |
| CD81 |
| CD86 |
| CD95 |
| CD117 |
| CD132 (IL-2RG) |
| CD133 |
| CD137 |
| CD138 |
| CD166 |
| CD172A |
| CEACAM5 (CEA) |
| CEACAM6 (NCA-90) |
| CLAUDIN-3 |
| CLAUDIN-4 |
| cMet |
| Collagen |
| Cripto |
| CSFR |
| CSFR-1 |
| CTLA-4 |
| CTGF |
| CXCL10 |
| CXCL13 |
| CXCR1 |
| CXCR2 |
| CXCR4 |
| CYR61 |
| DL44 |
| DLL4 |
| DPP-4 |
| EGFR |
| Endothelin B receptor (ETBR) |
| EpCAM |
| EPHA2 |
| ERBB3 |
| F protein of RSV |
| FAP |
| FGF-2 |
| FGF8 |
| FGFR1 |
| FGFR2 |
| FGFR3 |
| FGFR4 |
| Folate receptor |
| G-CSF |
| G-CSFR |
| GLUT1 |
| GLUT4 |

TABLE 1-continued

| Exemplary Targets |
| --- |
| GM-CSF |
| GM-CSFR |
| GP IIb/IIIa receptors |
| Gp130 |
| GPIIB/IIIA |
| GPNMB |
| HER2/neu |
| HGF |
| hGH |
| Hyaluronidase |
| IFNalpha |
| IFNbeta |
| IFNgamma |
| IgE |
| IgE Receptor (FceRI) |
| IGF |
| IGF1R |
| IL1B |
| IL1R |
| IL2 |
| IL11 |
| IL12 |
| IL12p40 |
| IL-12R, IL-12Rbeta1 |
| IL13 |
| IL13R |
| IL15 |
| IL17 |
| IL18 |
| IL21 |
| IL23 |
| IL23R |
| IL27/IL27R (wsx1) |
| IL29 |
| IL-31R |
| IL31/IL31R |
| IL2R |
| IL4 |
| IL4R |
| IL6, IL6R |
| Insulin Receptor |
| Jagged Ligands |
| Jagged 1 |
| Jagged 2 |
| LIF-R |
| MRP4 |
| MUC1 |
| Mucin-16 |
| Na/K ATPase |
| Neutrophil elastase |
| NGF |
| Nicastrin |
| Notch Receptors |
| Notch 1 |
| Notch 2 |
| Notch 3 |
| Notch 4 |
| NOV |
| OSM-R |
| PAR2 |
| PDGF-AA |
| PDGF-BB |
| PDGFRalpha |
| PDGFRbeta |
| PD-1 |
| PD-L1, PD-L2 |
| Phosphatidyl-serine |
| P1GF |
| PSCA |
| PSMA |
| RAAG12 |
| RAGE |
| SLC44A4 |
| Sphingosine 1 Phosphate |
| TGFbeta |
| TLR2 |
| TLR4 |
| TLR6 |

TABLE 1-continued

Exemplary Targets

TLR7
TLR8
TLR9
TNFalpha
TNFR
TRAIL-R1
TRAIL-R2
Transferrin
Transferrin receptor
TRK-A
TRK-B
uPAR
VCAM-1
VEGF
VEGF-A
VEGF-B
VEGF-C
VEGF-D
VEGFR1
VEGFR2
VEGFR3
WISP-1
WISP-2
WISP-3
Alpha-4 integrin
Alpha-V integrin
alpha4beta1 integrin
alpha4beta7 integrin As a non-limiting example, the AB is or is derived from an antibody listed in Table 2.

TABLE 2

Exemplary sources for Abs

| Antibody Trade Name (antibody name) | Target |
|---|---|
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocerlizumab | CD20 |
| Arzerra ™ (ofatumumab) | CD20 |
| Obinutuzumab | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |

TABLE 2-continued

Exemplary sources for Abs

| Antibody Trade Name (antibody name) | Target |
|---|---|
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
|  | Notch, e.g., Notch 1 |
|  | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

In some embodiments, the AB binds Epidermal Growth Factor Receptor (EGFR). In some embodiments, the AB that binds EGFR includes one or more of the heavy chain and/or light chain sequences shown below.

C225v5 Antibody Heavy Chain Amino Acid Sequence
(SEQ ID NO: 2)
QVQLKQSGPGLVQPSQSLSITCTVSGFSLTNYGVHWVRQSPGKGLEWLG

VIWSGGNTDYNTPFTSRLSINKDNSKSQVFFKMNSLQSQDTAIYYCARA

LTYYDYEFAYWGQGTLVTVSAASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK*

C225v5 Antibody Light Chain Amino Acid Sequence:
(SEQ ID NO: 16)
QILLTQSPVILSVSPGERVSFSCRASQSIGTNIHWYQQRTNGSPRLLIK

YASESISGIPSRFSGSGSGTDFTLSINSVESEDIADYYCQQNNNWPTTF

GAGTKLELKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC*

C225v4 Antibody Heavy Chain Amino Acid Sequence:
(SEQ ID NO: 244)
QVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCARA

LTYYDYEFAYWGQGTLVTVSAASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK*

C225v6 Antibody Heavy Chain Amino Acid Sequence
(SEQ ID NO: 253)
QVQLKQSGPGLVQPSQSLSITCTVSGFSLTNYGVHWVRQSPGKGLEWLG

VIWSGGNTDYNTPFTSRLSINKDNSKSQVFFKMNSLQSQDTAIYYCARA

LTYYDYEFAYWGQGTLVTVSAASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYASTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK*

In some embodiments, the AB binds interleukin 6 receptor (IL-6R). In some embodiments, the AB that binds IL-6R includes one or more of the heavy chain and/or light chain sequences shown below.

Av1 Antibody Heavy Chain Amino Acid Sequence:
(SEQ ID NO: 254)
QVQLQESGPGLVRPSQTLSLTCTVSGYSITSDHAWSWVRQPPGRGLEWI

GYISYSGITTYNPSLKSRVTISRDNSKNTLYLQMNSLRAEDTAVYYCAR

SLARTTAMDYWGQGSLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK

Av1 Antibody Light Chain Amino Acid Sequence:
(SEQ ID NO: 255)
DIQMTQSPSSLSASVGDRVTITCRASQDISSYLNWYQQKPGKAPKLLIY

YTSRLHSGVPSRFSGSGSGTDFTFTISSLQPEDIATYYCQQGNTLPYTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In some embodiments, the AB binds a Jagged target, e.g., Jagged 1, Jagged 2 or both Jagged 1 and Jagged 2. In some embodiments, the AB that binds a Jagged target includes one or more of the heavy chain and/or light chain sequences shown below.

4D11 Light Chain sequence
(SEQ ID NO: 26)
DIQMTQSPSSLSASVGDRVTITCRASQSISSYLNWYQQKPGKAPKLLIY

AASSLQSGVPSRFSGSGSGTDFTLTISSLQPEDFATYYCQQTVVAPPLF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

4D11 Heavy Chain sequence
(SEQ ID NO: 28)
EVQLLESGGGLVQPGGSLRLSCAASGFTFSSYAMSWVRQAPGKGLEWVS

SIDPEGRQTYYADSVKGRFTISRDNSKNTLYLQMNSLRAEDTAVYYCAK

DIGGRSAFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK

4D11v2 Heavy Chain sequence
(SEQ ID NO: 256)
EVHLLESGGGLVQPGGSLRLSCAASGFTFSSYAMSWVRQAPGKGLEWVS

SIDPEGRQTYYADSVKGRFTISRDNSKNTLYLQMNSLRAEDTAVYYCAK

DIGGRSAFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK

4D11v2 Light Chain Sequence
(SEQ ID NO: 257)
DIQMTQSPSSLSASVGDRVTITCRASQSISSYLNWYQQKPGKAPKLLIY

AASSLQSGVPSRFSGSGSGTDFTLTISSLQPEDFATYYCQQTVVAPPLF

GQGTKVEIKRTVAAPSVFIFPPSDEQLKSGTASVVCLLNNFYPREAKVQ

WKVDNALQSGNSQESVTEQDSKDSTYSLSSTLTLXKADYEKHKVYACEV

THQGLSSPVTKSFNRGEC

In some embodiments, the AB that binds a Jagged target includes one or more of the variable heavy chain and/or variable light chain sequences shown below.

Variable Light Chain Amino Sequence Lc4
(SEQ ID NO: 258)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc4
(SEQ ID NO: 259)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc5
(SEQ ID NO: 260)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc5
(SEQ ID NO: 261)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYHGQFDYWGQGTLVTVSS

Variable Light Chain Amino Sequence Lc7
(SEQ ID NO: 262)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc7
(SEQ ID NO: 263)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc8
(SEQ ID NO: 264)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc8
(SEQ ID NO: 265)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKHIGRTNPFDYWGQGTLVTVSS

Variable Light Chain Amino Sequence Lc13
(SEQ ID NO: 266)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc13
(SEQ ID NO: 267)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc16
(SEQ ID NO: 268)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc16
(SEQ ID NO: 269)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYYGQFDYWGQGTLVTVSS

Variable Light Chain Amino Sequence Lc19
(SEQ ID NO: 270)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

-continued

Variable Heavy Chain Amino Sequence Hc19
(SEQ ID NO: 271)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc21
(SEQ ID NO: 272)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc21
(SEQ ID NO: 273)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc24
(SEQ ID NO: 274)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc24
(SEQ ID NO: 275)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYCAKSAAAFDYWGQGTLVTVSS

Variable Light Chain Amino Sequence Lc26
(SEQ ID NO: 276)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc26
(SEQ ID NO: 277)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc27
(SEQ ID NO: 278)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc27
(SEQ ID NO: 279)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFYGQFDYWGQGTLVTVSS

Variable Light Chain Amino Sequence Lc28
(SEQ ID NO: 280)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc28
(SEQ ID NO: 281)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc30
(SEQ ID NO: 282)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc30
(SEQ ID NO: 283)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYAKSAAAFDYWGQGTLVTVSS

-continued

Variable Light Chain Amino Sequence Lc31
(SEQ ID NO: 284)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc31
(SEQ ID NO: 285)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc32
(SEQ ID NO: 286)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc32
(SEQ ID NO: 287)
EVQLLESGGGLVQPGGSLRLSCAASGFTFSSYAMSWVRQAPGKGLEWVSSIDPEGWQTYYADSV

KGRFTISRDNSKNTLYLQMNSLRAEDTAVYYCAKSAAAFDYWGQGTLVTVSS

Variable Light Chain Amino Sequence Lc37
(SEQ ID NO: 288)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc37
(SEQ ID NO: 289)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPHNGQFDYWGQGTLVTVSS

Variable Light Chain Amino Sequence Lc39
(SEQ ID NO: 290)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc39
(SEQ ID NO: 291)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc40
(SEQ ID NO: 292)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Heavy Chain Amino Sequence Hc40
(SEQ ID NO: 293)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc47
(SEQ ID NO: 294)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc47
(SEQ ID NO: 295)
EVQLLESGGGLVQPGGSLRLSCAASGFTFSSYAMSWVRQAPGKGLEWVSSIDEMGWQTEYADSV

KGRFTISRDNSKNTLYLQMNSLRAEDTAVYYCAKSAAAFDYWGQGTLVTVSS

Variable 4B2 Light Chain
(SEQ ID NO: 296)
DIQMTQSPSSLSASVGDRVTITCRASQSISSYLNWYQQKPGKAPKLLIYAASSLQSGVPSRFSG

SGSGTDFTLTISSLQPEDFATYYCQQTLDAPPQFGQGTKVEIKR

-continued

Variable 4B2 Heavy Chain
(SEQ ID NO: 297)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKDIGGRSAFDYWGQGTLVTVSS Variable 4D11 Light Chain
(SEQ ID NO: 22)
DIQMTQSPSSLSASVGDRVTITCRASQSISSYLNWYQQKPGKAPKLLIYAASSLQSGVPSRFSG
SGSGTDFTLTISSLQPEDFATYYCQQTVVAPPLFGQGTKVEIKR Variable 4D11 Heavy Chain
(SEQ ID NO: 24)
EVQLLESGGGLVQPGGSLRLSCAASGFTFSSYAMSWVRQAPGKGLEWVSSIDPEGRQTYYADSV
KGRFTISRDNSKNTLYLQMNSLRAEDTAVYYCAKDIGGRSAFDYWGQGTLVTVSS Variable 4E7 Light Chain
(SEQ ID NO: 298)
DIQMTQSPSSLSASVGDRVTITCRASQSISSYLNWYQQKPGKAPKLLIYAASSLQSGVPSRFSG
SGSGTDFTLTISSLQPEDFATYYCQQSLVAPLTFGQGTKVEIKR Variable 4E7 Heavy Chain
(SEQ ID NO: 299)
EVQLLESGGGLVQPGGSLRLSCAASGFTFSSYAMSWVRQAPGKGLEWVSSIEEMGWQTKYADSV
KGRFTISRDNSKNTLYLQMNSLRAEDTAVYYCAKSAAAFDYWGQGTLVTVSS Variable 4E11 Light Chain
(SEQ ID NO: 300)
DIQMTQSPSSLSASVGDRVTITCRASQSISSYLNWYQQKPGKAPKLLIYAASSLQSGVPSRFSG
SGSGTDFTLTISSLQPEDFATYYCQQALDAPLMFGQGTKVEIKR Variable 4E11 Heavy Chain
(SEQ ID NO: 301)
EVQLLESGGGLVQPGGSLRLSCAASGFTFSSYAMSWVRQAPGKGLEWVSSIEPMGQLTEYADSV
KGRFTISRDNSKNTLYLQMNSLRAEDTAVYYCAKDIGGRSAFDYWGQGTLVTVSS Variable 6B7 Light Chain
(SEQ ID NO: 302)
DIQMTQSPSSLSASVGDRVTITCRASQSISSYLNWYQQKPGKAPKLLIYAASSLQSGVPSRFSG
SGSGTDFTLTISSLQPEDFATYYCQQALVAPLTFGQGTKVEIKR Variable 6B7 Heavy Chain
(SEQ ID NO: 303)
EVQLLESGGGLVQPGGSLRLSCAASGFTFSSYAMSWVRQAPGKGLEWVSSIDEMGWQTYYADSV
KGRFTISRDNSKNTLYLQMNSLRAEDTAVYYCAKSAAAFDYWGQGTLVTVSS Variable 6F8 Light Chain
(SEQ ID NO: 304)
DIQMTQSPSSLSASVGDRVTITCRASQSISSYLNWYQQKPGKAPKLLIYAASSLQSGVPSRFSG
SGSGTDFTLTISSLQPEDFATYYCQQALVAPLTFGQGTKVEIKR Variable 6F8 Heavy Chain
(SEQ ID NO: 305)
EVQLLESGGGLVQPGGSLRLSCAASGFTFSSYAMSWVRQAPGKGLEWVSSIDEMGWQTYYADSV
KGRFTISRDNSKNTLYLQMNSLRAEDTAVYYCAKSAAAFDYWGQGTLVTVSS By way of non-limiting example, the CM includes an amino acid sequence that is a substrate or is derived from a substrate that is cleaved by one or more of the following enzymes or proteases listed in Table 3.

TABLE 3

| Exemplary Enzymes/Proteases | | |
|---|---|---|
| ADAMS, ADAMTS, e.g. ADAM8 | Cysteine proteinases, e.g., Cruzipain | Serine proteases, e.g., activated protein C |

TABLE 3-continued

| Exemplary Enzymes/Proteases | | |
|---|---|---|
| ADAM9 | Legumain | Cathepsin A |
| ADAM10 | Otubain-2 | Cathepsin G |
| ADAM12 | KLKs, e.g., | Chymase |
| ADAM15 | KLK4 | coagulation factor |
| ADAM17/TACE | KLK5 | proteases (e.g., FVIIa, |
| ADAMDEC1 | KLK6 | FIXa, FXa, FXIa, |
| ADAMTS1 | KLK7 | FXIIa) |
| ADAMTS4 | KLK8 | Elastase |
| ADAMTS5 | KLK10 | Granzyme B |

TABLE 3-continued

Exemplary Enzymes/Proteases

| | | |
|---|---|---|
| Aspartate proteases, e.g., | KLK11 | Guanidinobenzoatase |
| BACE | KLK13 | HtrA1 |
| Renin | KLK14 | Human Neutrophil |
| Aspartic cathepsins, e.g., | Metallo proteinases, e.g., | Elastase |
| Cathepsin D | Meprin | Lactoferrin |
| Cathepsin E | Neprilysin | Marapsin |
| Caspases, e.g., | PSMA | NS3/4A |
| Caspase 1 | BMP-1 | PACE4 |
| Caspase 2 | MMPs, e.g., | Plasmin |
| Caspase 3 | MMP1 | PSA |
| Caspase 4 | MMP2 | tPA |
| Caspase 5 | MMP3 | Thrombin |
| Caspase 6 | MMP7 | Tryptase |
| Caspase 7 | MMP8 | uPA |
| Caspase 8 | MMP9 | Type II Transmembrane |
| Caspase 9 | MMP10 | Serine Proteases |
| Caspase 10 | MMP11 | (TTSPs), e.g., |
| Caspase 14 | MMP12 | DESC1 |
| Cysteine cathepsins, e.g., | MMP13 | DPP-4 |
| Cathepsin B | MMP14 | FAP |
| Cathepsin C | MMP15 | Hepsin |
| Cathepsin K | MMP16 | Matriptase-2 |
| Cathepsin L | MMP17 | MT-SP1/Matriptase |
| Cathepsin S | MMP19 | TMPRSS2 |
| Cathepsin V/L2 | MMP20 | TMPRSS3 |
| Cathepsin X/Z/P | MMP23 | TMPRSS4 |
| | MMP24 | |
| | MMP26 | |
| | MMP27 | |

The activatable antibodies provided herein include a masking moiety. In some embodiments, the masking moiety is an amino acid sequence that is coupled or otherwise attached to the activatable antibody and is positioned within the activatable antibody construct such that the masking moiety decreases the ability of the antibody to specifically bind the target. Suitable masking moieties are identified using any of a variety of known techniques. For example, peptide masking moieties are identified using the methods described in U.S. Pat. No. 8,293,685 by Daugherty et al., the contents of which are hereby incorporated by reference in their entirety.

In some embodiments, the masking moiety is selected for use with a specific antibody or antibody fragment. For example, suitable masking moieties for use with antibodies that bind EGFR include MMs that include the sequence CISPRG (SEQ ID NO: 43). By way of non-limiting examples, the MM can include a sequence such as CISPRGCG (SEQ ID NO: 44); CISPRGCPDGPYVMY (SEQ ID NO: 12); CISPRGCPDGPYVM (SEQ ID NO: 45), CISPRGCEPGTYVPT (SEQ ID NO: 46) and CISPRGCPGQIWHPP (SEQ ID NO: 47). Other suitable masking moieties include any of the EGFR-specific masks disclosed in PCT Publication No. WO 2010/081173, such as, by way of non-limiting example, GSHCLIPINMGAPSC (SEQ ID NO: 48); CISPRGCGGSSASQSGQGSHCLIPINMGAPSC (SEQ ID NO: 49); CNHHYFYTCGCISPRGCPG (SEQ ID NO: 50); ADHVFWGSYGCISPRGCPG (SEQ ID NO: 51); CHHVYWGHCGCISPRGCPG (SEQ ID NO: 52); CPHFTTTSCGCISPRGCPG (SEQ ID NO: 53); CNHHYHYYCGCISPRGCPG (SEQ ID NO: 54); CPHVSFGSCGCISPRGCPG (SEQ ID NO: 55); CPYYTLSYCGCISPRGCPG (SEQ ID NO: 56); CNHVYFGTCGCISPRGCPG (SEQ ID NO: 57); CNHFTLTTCGCISPRGCPG (SEQ ID NO: 58); CHHFTLTTCGCISPRGCPG (SEQ ID NO: 59); YNPCATPMCCISPRGCPG (SEQ ID NO: 60); CNHHYFYTCGCISPRGCG (SEQ ID NO: 61); CNHHYHYYCGCISPRGCG (SEQ ID NO: 62); CNHVYFGTCGCISPRGCG (SEQ ID NO: 63); CHHVYWGHCGCISPRGCG (SEQ ID NO: 64); CPHFTTTSCGCISPRGCG (SEQ ID NO: 65); CNHFTLTTCGCISPRGCG (SEQ ID NO: 66); CHHFTLTTCGCISPRGCG (SEQ ID NO: 67); CPYYTLSYCGCISPRGCG (SEQ ID NO: 68); CPHVSFGSCGCISPRGCG (SEQ ID NO: 69); ADHVFWGSYGCISPRGCG (SEQ ID NO: 70); YNPCATPMCCISPRGCG (SEQ ID NO: 71); CHHVYWGHCGCISPRGCG (SEQ ID NO: 72); C(N/P)H(HN/F)(Y/T)(F/W/T/L)(Y/G/T/S)(T/S/Y/H)CGCISPRGCG (SEQ ID NO: 73); CISPRGCGQPIPSVK (SEQ ID NO: 74); CISPRGCTQPYHVSR (SEQ ID NO: 75); and/or CISPRGCNAVSGLGS (SEQ ID NO: 76).

Suitable masking moieties for use with antibodies that bind a Jagged target, e.g., Jagged 1 and/or Jagged 2, include, by way of non-limiting example, masking moieties that include a sequence such as QGQSGQGQQQWCNIWINGGDCRGWNG (SEQ ID NO: 77); PWCMQRQDFLRCPQP (SEQ ID NO: 78); QLGLPAYMCTFECLR (SEQ ID NO: 79); CNLWVSGGDCGGLQG (SEQ ID NO: 80); SCSLWTSGSCLPHSP (SEQ ID NO: 81); YCLQLPHYMQAMCGR (SEQ ID NO: 82); CFLYSCTDVSYWNNT (SEQ ID NO: 83); PWCMQRQDYLRCPQP (SEQ ID NO: 84); CNLWISGGDCRGLAG (SEQ ID NO: 85); CNLWVSGGDCRGVQG (SEQ ID NO: 86); CNLWVSGGDCRGLRG (SEQ ID NO: 87); CNLWISGGDCRGLPG (SEQ ID NO: 88); CNLWVSGGDCRDAPW (SEQ ID NO: 89); CNLWVSGGDCRDLLG (SEQ ID NO: 90); CNLWVSGGDCRGLQG (SEQ ID NO: 91); CNLWLHGGDCRGWQG (SEQ ID NO: 92); CNIWLVGGDCRGWQG (SEQ ID NO: 93); CTTWFCGGDCGVMRG (SEQ ID NO: 94); CNIWGPSVDCGALLG (SEQ ID NO: 95); CNIWVNGGDCRSFEG (SEQ ID NO: 96); YCLNLPRYMQDMCWA (SEQ ID NO: 97); YCLALPHYMQADCAR (SEQ ID NO: 98); CFLYSCGDVSYWGSA (SEQ ID NO: 99); CYLYSCTDSAFWNNR (SEQ ID NO: 100); CYLYSCNDVSYWSNT (SEQ ID NO: 101); CFLYSCTDVSYW (SEQ ID NO: 102); CFLYSCTDVAYWNSA (SEQ ID NO: 103); CFLYSCTDVSYWGDT (SEQ ID NO: 104); CFLYSCTDVSYWGNS (SEQ ID NO: 105); CFLYSCTDVAYWNNT (SEQ ID NO: 106); CFLYSCGDVSYWGNPGLS (SEQ ID NO: 107); CFLYSCTDVAYWSGL (SEQ ID NO: 108); CYLYSCTDGSYWNST (SEQ ID NO: 109); CFLYSCSDVSYWGNI (SEQ ID NO: 110); CFLYSCTDVAYW (SEQ ID NO: 111); CFLYSCTDVSYWGST (SEQ ID NO: 112); CFLYSCTDVAYWGDT (SEQ ID NO: 113); GCNIWLNGGDCRGWVDPLQG (SEQ ID NO: 114); GCNIWLVGGDCRGWIGDTNG (SEQ ID NO: 115); GCNIWLVGGDCRGWIEDSNG (SEQ ID NO: 116); GCNIWANGGDCRGWIDNIDG (SEQ ID NO: 117); GCNIWLVGGDCRGWLGEAVG (SEQ ID NO: 118); GCNIWLVGGDCRGWLEEAVG (SEQ ID NO: 119); GGPALCNIWLNGGDCRGWSG (SEQ ID NO: 120); GAPVFCNIWLNGGDCRGWMG (SEQ ID NO: 121); GQQQWCNIWINGGDCRGWNG (SEQ ID NO: 122); GKSEFCNIWLNGGDCRGWIG (SEQ ID NO: 123); GTPGGCNIWANGGDCRGWEG (SEQ ID NO: 124); GASQYCNLWINGGDCRGWRG (SEQ ID NO: 125); GCNIWLVGGDCRPWVEGG (SEQ ID NO: 126); GCNIWAVGGDCRPFVDGG (SEQ ID NO: 127); GCNIWLNGGDCRAWVDTG (SEQ ID NO: 128); GCNIWIVGGDCRPFINDG (SEQ ID NO: 129);

GCNIWLNGGDCRPVVFGG (SEQ ID NO: 130); GCNIWLSGGDCRMFMNEG (SEQ ID NO: 131); GCNIWVNGGDCRSFVYSG (SEQ ID NO: 132); GCNIWLNGGDCRGWEASG (SEQ ID NO: 133); GCNI-WAHGGDCRGFIEPG (SEQ ID NO: 134); GCNIWLNGGDCRTFVASG (SEQ ID NO: 135); GCNI-WAHGGDCRGFIEPG (SEQ ID NO: 136); GFLENC-NIWLNGGDCRTG (SEQ ID NO: 137); GIYENC-NIWLNGGDCRMG (SEQ ID NO: 138); and/or GIPDNCNIWINGGDCRYG (SEQ ID NO: 139).

Suitable masking moieties for use with antibodies that bind an interleukin 6 target, e.g., interleukin 6 receptor (IL-6R), include, by way of non-limiting example, masking moieties that include a sequence such as QGQSGQYGSCSWNYVHIFMDC (SEQ ID NO: 140); QGQSGQGDFDIPFPAHWVPIT (SEQ ID NO: 141); QGQSGQMGVPAGCVWNYAHIFMDC (SEQ ID NO: 142); YRSCNWNYVSIFLDC (SEQ ID NO: 143); PGAF-DIPFPAHWVPNT (SEQ ID NO: 144); ESS-CVWNYVHIYMDC (SEQ ID NO: 145); YPGCKWNY-DRIFLDC (SEQ ID NO: 146); YRTCSWNYVGIFLDC (SEQ ID NO: 147); YGSCSWNYVHIFMDC (SEQ ID NO: 148); YGSCSWNYVHIFLDC (SEQ ID NO: 149); YGSCNWNYVHIFLDC (SEQ ID NO: 150); YTSCNWNYVHIFMDC (SEQ ID NO: 151); YPGCK-WNYDRIFLDC (SEQ ID NO: 152); WRSCNWNYAHI-FLDC (SEQ ID NO: 153); WSNCHWNYVHIFLDC (SEQ ID NO: 154); DRSCTWNYVRISYDC (SEQ ID NO: 155); SGSCKWDYVHIFLDC (SEQ ID NO: 156); SRSCIWNYAHIHLDC (SEQ ID NO: 157); SMSCYWQY-ERIFLDC (SEQ ID NO: 158); YRSCNWNYVSIFLDC (SEQ ID NO: 159); YGSCSWNYVHIFMDC (SEQ ID NO: 160); SGSCKWDYVHIFLDC (SEQ ID NO: 161); YKSCHWDYVHIFLDC (SEQ ID NO: 162); YGSCTWNYVHIFMEC (SEQ ID NO: 163); FSS-CNWNYVHIFLDC (SEQ ID NO: 164); WRSCNWNYA-HIFLDC (SEQ ID NO: 165); YGSCQWNYVHIFLDC (SEQ ID NO: 166); YRSCNWNYVHIFLDC (SEQ ID NO: 167); NMSCHWDYVHIFLDC (SEQ ID NO: 168); FGPCTWNYARISWDC (SEQ ID NO: 169); XXsCXWXYvhIfXdC (SEQ ID NO: 170); MGVPAGCVWNYAHIFMDC (SEQ ID NO: 171); RDTGGQCRWDYVHIFMDC (SEQ ID NO: 172); AGVPAGCTWNYVHIFMEC (SEQ ID NO: 173); VGVPNGCVWNYAHIFMEC (SEQ ID NO: 174); DGGPAGCSWNYVHIFMEC (SEQ ID NO: 175); AVGPAGCWWNYVHIFMEC (SEQ ID NO: 176); CTWNYVHIFMDCGEGEGP (SEQ ID NO: 177); GGVPEGCTWNYAHIFMEC (SEQ ID NO: 178); AEVPAGCWWNYVHIFMEC (SEQ ID NO: 179); AGVPAGCTWNYVHIFMEC (SEQ ID NO: 180); SGASGGCKWNYVHIFMDC (SEQ ID NO: 181); MGVPAGCVWNYAHIFMDC (SEQ ID NO: 182); TPGCRWNYVHIFMECEAL (SEQ ID NO: 183); VGVPNGCVWNYAHIFMEC (SEQ ID NO: 184); PGAF-DIPFPAHWVPNT (SEQ ID NO: 185); RGAC-DIPFPAHWIPNT (SEQ ID NO: 186); QGDF-DIPFPAHWVPIT (SEQ ID NO: 187); XGafDIPFPAHWvPnT (SEQ ID NO: 188); RGDGNDS-DIPFPAHWVPRT (SEQ ID NO: 189); SGVGRDR-DIPFPAHWVPRT (SEQ ID NO: 190); WAGGNDC-DIPFPAHWIPNT (SEQ ID NO: 191); WGDGMDVDIPFPAHWVPVT (SEQ ID NO: 192); AGSGNDSDIPFPAHWVPRT (SEQ ID NO: 193); ESRSG-YADIPFPAHWVPRT (SEQ ID NO: 194); and/or RECGRCGDIPFPAHWVPRT (SEQ ID NO: 195).

In some embodiments, the masking moiety is selected for use with any antibody or antibody fragment. For example, in some embodiments, the masking moiety is a non-binding steric moiety (NB) or a binding partner (BP) for a non-binding steric moiety, where the BP recruits or otherwise attracts the NB to the activatable antibody. For example, in some embodiments, the NB is a soluble, globular protein. In some embodiments, the NB is a protein that circulates in the bloodstream. In some embodiments, the NB is selected from the group consisting of albumin, fibrinogen, fibronectin, hemoglobin, transferrin, an immunoglobulin domain, and other serum proteins. In some embodiments, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides. In some embodiments, the activatable antibody has the structural arrangement from N-terminus to C-terminus as follows in the uncleaved state: NB-CM-AB, AB-CM-NB, BP-CM-AB or AB-CM-BP. In embodiments where the activatable antibody includes a BP and the activatable antibody is in the presence of the corresponding NB, the activatable antibody has a structural arrangement from N-terminus to C-terminus as follows in the uncleaved state: NB:BP-CM-AB or AB-CM-BP:NB, where ":" represents an interaction, e.g., binding, between the NB and BP. In some embodiments, the activatable antibody has the structural arrangement from N-terminus to C-terminus as follows in the uncleaved state: NB-LP1-CM-LP2-AB, AB-LP2-CM-LP 1-NB, BP-LP1-CM-LP2-AB or AB-LP2-CM-LP1-BP. In embodiments where the activatable antibody includes a BP and the activatable antibody is in the presence of the corresponding NB, the activatable antibody has a structural arrangement from N-terminus to C-terminus as follows in the uncleaved state: NB:BP-LP1-CM-LP2-AB or AB-LP2-CM-LP1-BP:NB, where ":" represents an interaction, e.g., binding, between the NB and BP.

The activatable antibodies provided herein include a cleavable moiety. In some embodiments, the cleavable moiety includes an amino acid sequence that is a substrate for a protease, usually an extracellular protease. Suitable substrates are identified using any of a variety of known techniques. For example, peptide substrates are identified using the methods described in U.S. Pat. No. 7,666,817 by Daugherty et al., the contents of which are hereby incorporated by reference in their entirety. (See also Boulware et al. "Evolutionary optimization of peptide substrates for proteases that exhibit rapid hydrolysis kinetics." Biotechnol Bioeng. 106.3 (2010): 339-46).

In some embodiments, the CM is selected for use with a specific protease. In some embodiments, the CM is a substrate for at least one protease selected from the group consisting of an ADAM 17, a BMP-1, a cysteine protease such as a cathepsin, a HtrA1, a legumain, a matriptase (MT-SP1), a matrix metalloprotease (MMP), a neutrophil elastase, a TMPRSS, such as TMPRSS3 or TMPRSS4, a thrombin, and a u-type plasminogen activator (uPA, also referred to as urokinase), In some embodiments, the CM is a substrate for an ADAM17. In some embodiments, the CM is a substrate for a BMP-1. In some embodiments, the CM is a substrate for a cathepsin. In some embodiments, the CM is a substrate for a cysteine protease. In some embodiments, the CM is a substrate for a HtrA1. In some embodiments, the CM is a substrate for a legumain. In some embodiments, the CM is a substrate for a MT-SP1. In some embodiments, the CM is a substrate for a MMP. In some embodiments, the CM is a substrate for a neutrophil elastase. In some embodiments, the CM is a substrate for a thrombin. In some embodiments, the CM is a substrate for a TMPRSS. In some embodiments, the CM is a substrate for TMPRSS3. In some embodiments, the CM is a substrate for TMPRSS4. In some embodiments, the CM is a substrate for uPA.

In some embodiments, the cleavable moiety is selected for use with a specific protease, for example a protease that is known to be co-localized with the target of the activatable antibody. For example, suitable cleavable moieties for use in the activatable antibodies of the disclosure are cleaved by at least a protease such as urokinase, legumain, at least one matrix metalloprotease (MMP), and/or MT-SP1 (matriptase) and include the sequence TGRGPSWV (SEQ ID NO: 196); SARGPSRW (SEQ ID NO: 197); TARGPSFK (SEQ ID NO: 198); LSGRSDNH (SEQ ID NO: 14); GGWHTGRN (SEQ ID NO: 199); HTGRSGAL (SEQ ID NO: 200); PLTGRSGG (SEQ ID NO: 201); AARGPAIH (SEQ ID NO: 202); RGPAFNPM (SEQ ID NO: 203); SSRGPAYL (SEQ ID NO: 204); RGPATPIM (SEQ ID NO: 205); RGPA (SEQ ID NO: 206); GGQPSGMWGW (SEQ ID NO: 207); FPRPLGITGL (SEQ ID NO: 208); VHMPLGFLGP (SEQ ID NO: 209); SPLTGRSG (SEQ ID NO: 210); SAGFSLPA (SEQ ID NO: 211); LAPLGLQRR (SEQ ID NO: 212); SGGPLGVR (SEQ ID NO: 213); and/or PLGL (SEQ ID NO: 214).

In some embodiments, the CM is a substrate for at least one matrix metalloprotease (MMP). Examples of MMPs include MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27. In some embodiments, the CM is a substrate for MMP9, MMP14, MMP1, MMP3, MMP13, MMP17, MMP11, and MMP19. In some embodiments the CM is a substrate for MMP9. In some embodiments, the CM is a substrate for MMP14. In some embodiments, the CM is a substrate for two or more MMPs. In some embodiments, the CM is a substrate for at least MMP9 and MMP14. In some embodiments, the CM comprises two or more substrates for the same MMP. In some embodiments, the CM comprises at least two or more MMP9 substrates. In some embodiments, the CM comprises at least two or more MMP14 substrates.

In some embodiments, the CM is a substrate for an MMP and includes the sequence ISSGLLSS (SEQ ID NO: 306); QNQALRMA (SEQ ID NO: 307); AQNLLGMV (SEQ ID NO: 308); STFPFGMF (SEQ ID NO: 309); PVGYTSSL (SEQ ID NO: 310); DWLYWPGI (SEQ ID NO: 311); MIAPVAYR (SEQ ID NO: 312); RPSPMWAY (SEQ ID NO: 313); WATPRPMR (SEQ ID NO: 314); FRLLDWQW (SEQ ID NO: 315); LKAAPRWA (SEQ ID NO: 316); GPSHLVLT (SEQ ID NO: 317); LPGGLSPW (SEQ ID NO: 318); MGLFSEAG (SEQ ID NO: 319); SPLPLRVP (SEQ ID NO: 320); RMHLRSLG (SEQ ID NO: 321); LAAPLGLL (SEQ ID NO: 322); AVGLLAPP (SEQ ID NO: 323); LLAPSHRA (SEQ ID NO: 324); PAGLWLDP (SEQ ID NO: 325); and/or ISSGLSS (SEQ ID NO: 326).

In some embodiments, activatable antibodies for use in the activatable antibodies of the disclosure may be made biosynthetically using recombinant DNA technology and expression in eukaryotic or prokaryotic species. The cDNAs encoding the masking moiety, linker sequence (which may include a cleavable moiety (CM), and antibody chain (heavy or light)) can be linked in an 5' to 3' (N- to C-terminal in the translated product) sequence to create the nucleic acid construct, which is expressed as the activatable antibody protein following a conventional antibody expression process. In some embodiments, the activatable antibody could be semi-synthetically produced by expressing a CM-antibody and then coupling the mask chemically at or near the N-terminus of the protein. In some embodiments, the activatable antibody could be produced by expressing an antibody and then coupling the mask and the CM chemically at or near the N-terminus of the protein such that the activatable antibody in the uncleaved state has the structural arrangement from N-terminus to C-terminus as follows: MM-CM-AB or AB-CM-MM.

The activatable antibodies described herein can also include an agent conjugated to the activatable antibody. In some embodiments, the conjugated agent is a therapeutic agent, such as an antineoplastic agent. In such embodiments, the agent is conjugated to a carbohydrate moiety of the activatable antibody, e.g., where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody. In some embodiments, the agent is conjugated to an amino group of the antibody or antigen-binding fragment of the activatable antibody. In some embodiments the agent is conjugated to a carboxylic acid group of the antibody or antigen-binding fragment of the activatable antibody. In some embodiments, the agent is a thiol-containing agent. In some embodiments, the agent is engineered to include one or more thiol groups.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, any of the cytotoxic agents listed in Table 4.

In some embodiments, the cytotoxic agent is a thiol-containing agent. In some embodiments, the cytotoxic agent is engineered to include one or more thiol groups. In some embodiments, the cytotoxic agent is a dolastatin or a derivative thereof (e.g. auristatin E, AFP, MMAF, MMAE, DMAF, DMAE). For example, the cytotoxic agent is monomethyl auristatin E (MMAE). In some embodiments, the cytotoxic agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

In some embodiments, the agent is a detectable moiety such as, for example, a label or other marker. For example, the agent is or includes a radiolabeled amino acid, one or more biotinyl moieties that can be detected by a marked anti-biotin antibody or avidin (e.g., anti-biotin antibody or streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene tri-aminepentaacetic acid (MX-DTPA) is an exemplary chelating agent for conjugation of radionuclide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Table 4 lists some of the exemplary pharmaceutical agents that may be employed in the herein described invention but in no way is meant to be an exhaustive list.

TABLE 4

| Exemplary Pharmaceutical Agents for Conjugation |
|---|
| CYTOTOXIC AGENTS |
| Auristatins |
| Auristatin E |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinolone |
| Dolastatins |
| Dolastatin derivatives |
| Dolastatin 16 DmJ |

TABLE 4-continued

| Exemplary Pharmaceutical Agents for Conjugation |
|---|
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10,11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Ampicillin |
| Sulfanilamide |
| Polymyxin |
| Chloramphenicol |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles (PBI) |
| Cibrostatin6 |
| Doxaliform |
| Anthracyclins analogues |
| Anthracyclins analogues |
| Cemadotin analogue (CemCH2-SH) |
| Pseudomonas toxin A (PE38) variant |
| Pseudomonas toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Neomycin |

TABLE 4-continued

Exemplary Pharmaceutical Agents for Conjugation

Kanamycin
Amikacin
Gentamicin
Tobramycin
Streptomycin B
Spectinomycin
Homoharringtonine
Pyrrolobenzodiazepine dimers (PBDs)
Functionalized pyrrolobenzodiazepenes
Calicheamicins
Podophyllotoxins
Taxanes
Vinca alkaloids

CONJUGATABLE DETECTION REAGENTS

Fluorescein and derivatives thereof
Fluorescein isothiocyanate (FITC)

RADIOISOTOPES $^{125}$I
$^{131}$I
$^{89}$Zr
$^{111}$In
$^{123}$I
$^{131}$I
$^{99m}$Tc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99m}$Tc (Technetium)

HEAVY METALS

Barium
Gold
Platinum

ANTI-MYCOPLASMALS

Tylosine
Spectinomycin

In some embodiments, in addition to the compositions and methods provided herein, the activatable antibody can also be coupled using any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents are useful in coupling protein molecules, such as the activatable antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133(5):2549-2553 (1984); Jansen et al., Immunological Reviews 62:185-216 (1982); and Vitetta et al., Science 238:1098 (1987).

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Suitable linkers include: (i) SMPT (4-succinimidyloxycarbonyl-alpha-methyl-alpha-(2-pridyl-dithio)-toluene (Pierce Chem. Co., Cat. (21558G); (ii) SPDP (succinimidyl-6 [3-(2-pyridyldithio) propionamido]hexanoate (Pierce Chem. Co., Cat #21651G); and (iii) Sulfo-LC-SPDP (sulfosuccinimidyl 6 [3-(2-pyridyldithio)-propianamide]hexanoate (Pierce Chem. Co. Cat. #2165-G.

The linkers described above contain components that have different attributes, thus leading to conjugates with differing physio-chemical properties. For example, the linker SMPT contains a sterically hindered disulfide bond, and can form conjugates with increased stability. Disulfide linkages, are in general, less stable than other linkages because the disulfide linkage is cleaved in vitro, resulting in less conjugate available.

The reagent EDC (1-ethyl-3-(3-dimethylaminopropyl) carbodiimide hydrochloride is useful to create a carboxamide starting with a carboxylic acid and a primary or secondary amine. Thus, EDC may be used to link lysine residues in an antibody with a carboxylic acid in a linker or toxin, or to link aspartate or glutamate residues in an antibody with an amine in a linker or toxin. Such conjugation reactions utilizing EDC may be enhanced by addition of NHS (N-hydroxysuccinimide) or sulfo-NHS (N-hydroxy-3-oxysulfonylsuccinimide). Addition of NHS or sulfo-NHS to such conjugation reactions may enhance the rate, completeness, selectivity, and/or reproducibility of the conjugation reactions.

In some embodiments, the linkers are cleavable. In some embodiments, the linkers are non-cleavable. In some embodiments, two or more linkers are present. The two or more linkers are all the same, e.g., cleavable or non-cleavable, or the two or more linkers are different, e.g., at least one cleavable and at least one non-cleavable.

In some embodiments, in addition to the compositions and methods provided herein, the activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the invention, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

Suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

Suitable linkers for attachment to neither oxidized nor reduced AB s include those having certain functional groups capable of reaction with the primary amino groups present in unmodified lysine residues in the AB. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

Suitable linkers for attachment to neither oxidized nor reduced AB s include those having certain functional groups capable of reaction with the carboxylic acid groups present in aspartate or glutamate residues in the AB, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In other embodiments the AB is first attached to the MM, CM and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

Alternatively, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers that are susceptible to cleavage by enzymes of the complement system, such as but not limited to urokinase, tissue plasminogen activator, trypsin, plasmin, or another enzyme having proteolytic activity may be used in one embodiment of the present invention. According to one method of the present invention, an agent is attached via a linker susceptible to cleavage by complement. The antibody is selected from a class that can activate complement. The antibody-agent conjugate, thus, activates the complement cascade and releases the agent at the target site. According to another method of the present invention, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 4.

Non-limiting examples of cleavable linker sequences are provided in Table 5.

TABLE 5

Exemplary Linker Sequences for Conjugation

| Types of Cleavable Sequences | Amino Acid Sequence |
| --- | --- |
| Plasmin cleavable sequences | |
| Pro-urokinase | PRFKIIGG (SEQ ID NO: 215) |
| | PRFRIIGG (SEQ ID NO: 216) |
| TGFβ | SSRHRRALD (SEQ ID NO: 217) |
| Plasminogen | RKSSIIIRMRDVVL (SEQ ID NO: 218) |
| Staphylokinase | SSSFDKGKYKKGDDA (SEQ ID NO: 219) |
| | SSSFDKGKYKRGDDA (SEQ ID NO: 220) |
| Factor Xa cleavable sequences | IEGR (SEQ ID NO: 221) |
| | IDGR (SEQ ID NO: 222) |
| | GGSIDGR (SEQ ID NO: 223) |
| MMP cleavable sequences | |
| Gelatinase A | PLGLWA (SEQ ID NO: 224) |
| Collagenase cleavable sequences | |
| Calf skin collagen (α1(I) chain) | GPQGIAGQ (SEQ ID NO: 225) |
| Calf skin collagen (α2(I) chain) | GPQGLLGA (SEQ ID NO: 226) |
| Bovine cartilage collagen (α1(II) chain) | GIAGQ (SEQ ID NO: 227) |
| Human liver collagen (α2(III) chain) | GPLGIAGI (SEQ ID NO: 228) |
| Human α$_2$M | GPEGLRVG (SEQ ID NO: 229) |
| Human PZP | YGAGLGVV (SEQ ID NO: 230) |
| | AGLGVVER (SEQ ID NO: 231) |
| | AGLGISST (SEQ ID NO: 232) |
| Rat α$_1$M | EPQALAMS (SEQ ID NO: 233) |
| | QALAMSAI (SEQ ID NO: 234) |
| Rat α$_2$M | AAYHLVSQ (SEQ ID NO: 235) |
| | MDAFLESS (SEQ ID NO: 236) |

TABLE 5-continued

Exemplary Linker Sequences for Conjugation

| Types of Cleavable Sequences | Amino Acid Sequence |
|---|---|
| Rat $\alpha_1 I_3$ (2J) | ESLPVVAV (SEQ ID NO: 237) |
| Rat $\alpha_1 I_3$ (27J) | SAPAVESE (SEQ ID NO: 238) |
| Human fibroblast collagenase | DVAQFVLT (SEQ ID NO: 239) |
| (autolytic cleavages) | VAQFVLTE (SEQ ID NO: 240) |
|  | AQFVLTEG (SEQ ID NO: 241) |
|  | PVQPIGPQ (SEQ ID NO: 242) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments the reducing agent that would modify a CM would also modify the linker of the conjugated activatable antibody.

Spacer Elements and Cleavable Elements: In still another embodiment, it may be necessary to construct the linker in such a way as to optimize the spacing between the agent and the AB of the activatable antibody. This may be accomplished by use of a linker of the general structure:

wherein

W is either —NH—CH$_2$— or —CH$_2$—;

Q is an amino acid, peptide; and n is an integer from 0 to 20.

In still other embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be effected by a particular mode of attachment or reaction. Any reaction providing a product of suitable stability and biological compatibility is acceptable.

Serum Complement and Selection of Linkers: According to one method of the present invention, when release of an agent is desired, an AB that is an antibody of a class that can activate complement is used. The resulting conjugate retains both the ability to bind antigen and activate the complement cascade. Thus, according to this embodiment of the present invention, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodiimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 4.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In other embodiments, the activatable antibody may be conjugated to one or more therapeutic agents and/or diagnostic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bissialyl ether. Other suitable linkers include cathepsin-labile substrates, particularly those that show optimal function at an acidic pH.

Exemplary hetero-bifunctional cross-linkers are referenced in Table 6.

TABLE 6

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines Sulfhydryls | Stable maleimide reactive group Enzyme-antibody conjugation Hapten-carrier protein conjugation | 11.6 Å |
| Sulfo-SMCC | Primary amines Sulfhydryls | Stable maleimide reactive group Water-soluble Enzyme-antibody conjugation | 11.6 Å |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment: In still other embodiments of the invention, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be

W—(CH$_2$)n-Q wherein
W is either —NH—CH$_2$— or —CH$_2$—;
Q is an amino acid, peptide; and
n is an integer from 0 to 20.

Non-Cleavable Conjugates: Alternatively, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

Definitions:

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo-or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')$_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; in some embodiments, the dissociation constant is ≤100 nM; in some embodiments, the dissociation constant is ≤10 nM.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a target, when the dissociation binding constant ($K_d$) is ≤1 µM as measured by assays such as radioligand binding assays or similar assays known to those skilled in the art. In some embodiments, the $K_d$ is 100 nM. In some embodiments, the $K_d$ is ≤10 nM. In some embodiments, the $K_d$ is ≤1 nM. In some embodiments, the $K_d$ is ≤100 pM to about 1 pM.

The compositions and methods provided herein enable the attachment of one or more agents to one or more cysteine residues in the AB without compromising the activity (e.g., the masking, activating or binding activity) of the activatable antibody.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein expressed from cDNA or recombinant RNA, or a protein of synthetic origin or some combination thereof, which by virtue of its origin, or source of derivation, the "isolated protein" (1) is not associated with proteins found in nature, (2) is free of other proteins from the same source, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism: in prokaryotes and eukaryotes, such control sequences generally include promoter, ribosomal binding site, and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length. In some embodiments, the oligonucleotides are 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phosphoranilladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland? Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction. Sequence regions on the DNA strand having the same sequence as the RNA and that are 5' to the 5' end of the RNA transcript are referred to as "upstream sequences". Sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity. In some embodiments, the two peptide sequences share at least 90 percent sequence identity. In some embodiments, the two peptide sequences share at least 95 percent sequence identity. In some embodiments, the two peptide sequences share at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present invention, providing that the variations in the amino acid sequence maintain at least 75% amino acid sequence identity to a reference sequence (e.g., the wild-type sequence). In some embodiments, the variations in the amino acid sequence maintain at least 80%, 90%, 95%, or 99% amino acid identity to the reference sequence. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or other properties of the resulting molecule, for example, in situations where the replacement does not involve an amino acid within a complementarity determining region (CDR) or other variable region. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. In some embodiments, amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

In some embodiments, the amino acid substitutions are those that: (1) decrease susceptibility to proteolysis, (2) decrease susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (e.g., conservative amino acid substitutions) may be made in the naturally-occurring sequence (e.g., in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 2, 3, 4, 5, 6, 7, 8, 9 or 10 amino acids long. In some embodiments, the fragment is an antibody fragment that is at least 14 amino acids long. In some embodiments, the fragment is a fragment of the AB that is least 20 amino acids long. In some embodiments, the fragment is a fragment of the AB that is at least 50 amino acids long. In some embodiments, the fragment is a fragment of the AB that is at least 70 amino acids long. The term "analog" as used herein refers to polypeptides that are comprised of a segment of at least 25 amino acids that has substantial identity to a portion of a deduced amino acid sequence and that has specific binding to a target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by a marked anti-biotin antibody or avidin (e.g., anti-biotin antibody or streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to decrease potential steric hindrance. The term "pharmaceutical agent or drug" as used herein refers to a chemical compound or composition capable of inducing a desired therapeutic effect when properly administered to a patient.

The term "drug" as used herein means an element, compound, agent, or molecular entity, including, e.g., a pharmaceutical, therapeutic, or pharmacologic compound. Drugs can be natural or synthetic or a combination thereof. A "therapeutic drug" is an agent that exerts a therapeutic (e.g., beneficial) effect on cancer cells or immune cells (e.g., activated immune cells), either alone or in combination with another agent (e.g., a prodrug converting enzyme in combination with a prodrug). Typically, therapeutic drugs useful in accordance with the methods and compositions described herein are those that exert a cytotoxic, cytostatic, or immunosuppressive effect. In certain embodiments, a drug is not a radioactive element. The drug can be a thiol-containing agent and/or the drug can be engineered to include one or more thiol groups.

"Cytotoxic agent," in reference to the effect of an agent on a cell, means killing of the cell. "Cytostatic agent" means an inhibition of cell proliferation.

The term "interchain disulfide bond," in the context of an antibody, refers to a disulfide bond between two heavy chains, or a heavy and a light chain.

The term "interchain thiol" refers to a thiol group of an antibody heavy or light chain that can participate in the formation of an interchain disulfide bond.

A protein is referred to as "fully-loaded" when all points of conjugation of a particular type and/or of similar reactivity are conjugated to drugs, resulting in a homogeneous population of protein-drug conjugate. A protein is referred to as "partially-loaded" when only some of the possible points of conjugation of a particular type and/or of a similar reactivity are conjugated to drugs, resulting in formation of a certain isomer or isomers of the protein-drug conjugate.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects. It is to be understood that the terms subject and patient are used interchangeably herein.

Use of Activatable Antibodies and/or Conjugated Activatable Antibodies

The activatable antibodies and/or conjugated activatable antibodies used in the kits and/or methods of the disclosure are specific for at least one target in a biological sample. The biological samples are, e.g., fresh cell samples, frozen cell samples, fresh tissue samples, and/or frozen tissue samples. In some embodiments, the samples are from a patient who is suffering from, is at risk for suffering from, or is suspected of suffering from a cancer or other neoplastic condition. In some embodiments, the samples are from a patient who is suffering from, is at risk for suffering from, or is suspected of suffering from inflammation and/or an inflammatory disorder. In some embodiments, the samples are from a patient who is suffering from, is at risk for suffering from, or is suspected of suffering from an autoimmune disease. In some embodiments, the samples are from a patient who is suffering from, is at risk for suffering from, or is suspected of suffering from a fibrotic disorder. In some embodiments, the samples are from a patient who is suffering from, is at risk for suffering from, or is suspected of suffering from hearing loss.

Activatable antibodies specific for Epidermal Growth Factor Receptor (EGFR) and/or conjugated activatable antibodies specific for EGFR are useful in methods and/or kits where the sample is or is derived from a patient who is suffering from, is at risk for suffering from, or is suspected of suffering from a cancer. In some embodiments, the cancer is a breast cancer, e.g., by way of non-limiting example, the breast cancer is a triple-negative breast cancer. In some embodiments, the cancer is a triple-negative breast cancer. In some embodiments, the cancer is colorectal cancer. In some embodiments, the cancer is gastric cancer. In some embodiments, the cancer is glioblastoma. In some embodiments, the cancer is a head and neck cancer, e.g., by way of non-limiting example, esophageal cancer. In some embodiments, the cancer is an esophageal cancer. In some embodiments, the cancer is a lung cancer, e.g., by way of non-limiting example, non-small cell lung cancer. In some embodiments, the cancer is a non-small cell lung cancer. In some embodiments, the cancer is ovarian/endometrial cancer. In some embodiments, the cancer is ovarian cancer. In some embodiments, the cancer is endometrial cancer. In some embodiments, the cancer is pancreatic cancer. In some embodiments, the cancer is prostate cancer. In some embodiments, the cancer is a renal cancer. In some embodiments, the cancer is a sarcoma, e.g., by way of non-limiting example, osteosarcoma. In some embodiments, the cancer is an osteosarcoma. In some embodiments, the cancer is a skin cancer, e.g., by way of non-limiting example, squamous cell cancer, basal cell carcinoma, and/or melanoma. In some embodiments, the cancer is a squamous cell cancer. In some embodiments, the cancer is a basal cell carcinoma. In some embodiments, the cancer is a melanoma.

Activatable antibodies and/or conjugated activatable antibodies specific for EGFR are useful in methods and/or kits where the sample is or is derived from a patient who is suffering from, is at risk for suffering from, or is suspected of suffering from an inflammatory disorder and/or an autoimmune disease. In some embodiments, the inflammatory and/or autoimmune disease is psoriasis.

Activatable antibodies and/or conjugated activatable antibodies specific for a Jagged target, e.g., Jagged 1 and/or Jagged 2 are useful in methods and/or kits where the sample is or is derived from a patient who is suffering from, is at risk for suffering from, or is suspected of suffering from a cancer. In some embodiments, the cancer is leukemia, including T-cell acute lymphoblastic leukemia (T-ALL) and chronic lymphocytic leukemia (CLL), lymphoblastic disease including multiple myeloma, and solid tumor, including lung, colorectal, prostate, pancreatic and breast, including triple negative breast cancer.

In some embodiments, the cancer is breast cancer, including by way of non-limiting example, ER/PR+ breast cancer, Her2+ breast cancer, triple-negative breast cancer. In some embodiments, the cancer is colorectal cancer. In some embodiments, the cancer is gastric cancer. In some embodiments, the cancer is glioblastoma. In some embodiments, the cancer is head and neck cancer. In some embodiments, the cancer is lung cancer, such as by way of non-limiting example, non-small cell lung cancer. In some embodiments, the cancer is multiple myeloma. In some embodiments, the cancer is ovarian cancer. In some embodiments, the cancer is pancreatic cancer. In some embodiments, the cancer is prostate cancer. In some embodiments, the cancer is sarcoma. In some embodiments, the cancer is renal cancer, such as by way of nonlimiting example, renal cell carcinoma. In some embodiments, the cancer is skin cancer, such as by way of nonlimiting example, squamous cell cancer, basal cell carcinoma, melanoma.

Activatable antibodies and/or conjugated activatable antibodies specific for a Jagged target, e.g., Jagged 1 and/or Jagged 2 are useful in methods and/or kits where the sample is or is derived from a patient who is suffering from, is at risk for suffering from, or is suspected of suffering from bone disease or metastasis in cancer, regardless of primary tumor origin.

Activatable antibodies and/or conjugated activatable antibodies specific for a Jagged target, e.g., Jagged 1 and/or Jagged 2 are useful in methods and/or kits where the sample is or is derived from a patient who is suffering from, is at risk for suffering from, or is suspected of suffering from a fibrotic disease. In some embodiments, the fibrotic disease is a fibrotic disease of the kidney, liver, lung, and skin. In some embodiments, the fibrotic disease is a fibrotic disorder, such as idiopathic pulmonary fibrosis (IPF). In some embodiments, the fibrotic disease is kidney fibrotic disease. In some embodiments, the fibrotic disease is liver fibrotic disease. In some embodiments, the fibrotic disease is peritoneal dialysis-induced fibrosis. In some embodiments, the fibrotic disease is scleroderma.

Activatable antibodies and/or conjugated activatable antibodies specific for a Jagged target, e.g., Jagged 1 and/or Jagged 2 are useful in methods and/or kits where the sample is or is derived from a patient who is suffering from, is at risk for suffering from, or is suspected of suffering from hearing loss.

Activatable antibodies and/or conjugated activatable antibodies specific for interleukin 6 receptor (IL-6R) are useful in methods and/or kits where the sample is or is derived from a patient who is suffering from, is at risk for suffering from, or is suspected of suffering from a cancer. In some embodiments, the cancer is breast cancer, including but not limited to, triple negative breast cancer (TNBC). In some embodiments, the cancer is Castleman's disease. In some embodiments, the cancer is hepatocellular carcinoma. In some embodiments, the cancer is lung cancer. In some embodiments, the cancer is multiple myeloma. In some embodiments, the cancer is ovarian cancer. In some embodiments, the cancer is prostate cancer.

Activatable antibodies and/or conjugated activatable antibodies specific for IL-6R are useful in methods and/or kits where the sample is or is derived from a patient who is suffering from, is at risk for suffering from, or is suspected of suffering from inflammation and/or an inflammatory disorder. In some embodiments, the disease or disorder is an autoimmune disease.

It will be appreciated that use of activatable antibodies and/or conjugated activatable antibodies in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments, therapies and/or diagnostics in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203 (1-2):1-60 (2000), Charman W N "Lipids, lipophilic drugs, and oral drug delivery-some emerging concepts." J Pharm Sci.89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Formulations of the invention, which include a conjugated activatable antibody, are used to diagnose, stage or otherwise analyze a disease or disorder associated with aberrant expression and/or activity of a target. For example, formulations of the invention are used to detect or otherwise analyze a cancer or other neoplastic condition.

In some embodiments, the formulations are used to detect or otherwise analyze a disease or disorder associated with aberrant expression and/or activity of EGFR. In some embodiments, the formulations are used to detect or otherwise analyze a disease or disorder associated with aberrant expression and/or activity of a Jagged target, e.g., Jagged 1 and/or Jagged 2. In some embodiments, the formulations are used to detect or otherwise analyze a disease or disorder associated with aberrant expression and/or activity of IL-6R.

Diagnosis, staging and/or other analysis is determined in association with any known method for diagnosing or treating the disease or disorder associated with aberrant target expression and/or activity.

Activatable antibodies and/or conjugated activatable antibodies can be used in the methods and/or kits of the disclosure in the form of compositions, including pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

One embodiment of an activatable antibody fragment is the smallest fragment that specifically binds to the binding domain of the target protein. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being detected or otherwise analyzed, e.g., those with complementary activities that do not adversely affect each other. Alternatively, or in addition, the composition can comprise an agent that enhances its function. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

In some embodiments, the activatable antibody contains a detectable label. An intact antibody, or a fragment thereof (e.g., Fab, scFv, or F(ab)$_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect a protein, polypeptide or peptide in a biological sample in vitro as well as in vivo. For example, in vitro techniques for detection of an analyte protein include enzyme linked immunosorbent assays (ELISAs), Western blots, immunoprecipitations, immunochemical staining, and immunofluorescence. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, CA, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Diagnostic Indications

Activatable antibodies and/or conjugated activatable antibodies are useful in the detection of a target in patient samples and accordingly are useful as diagnostics. For example, activatable antibodies and/or conjugated activatable antibodies are used in in vitro assays, e.g., ELISA, to detect target levels in a patient sample. In some embodiments, activatable antibodies and/or conjugated activatable antibodies are used in in situ assays, e.g., in situ imaging as disclosed herein, to detect target levels in a patient sample, e.g., a tissue. In some embodiments, activatable antibodies and/or conjugated activatable antibodies are used in ex vivo assays, such as those disclosed herein, to detect target levels in a patient or patient sample, e.g., an organ or a tissue. In some embodiments, activatable antibodies and/or conjugated activatable antibodies are used in in vivo assays, e.g., in vivo imaging as disclosed herein, to detect target levels in a patient. In any of these embodiments, the target is, for example, a target from those listed in Table 1, or any combination thereof.

In one embodiment, an activatable antibody and/or conjugated activatable antibodies is immobilized on a solid support (e.g., the well(s) of a microtiter plate). The immobilized activatable antibody and/or immobilized conjugated activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of the target in the test sample is determined by comparison with a standard curve developed from the standard samples.

It will be appreciated that based on the results obtained using the activatable antibodies and/or conjugated activatable antibodies in an in vitro diagnostic assay, it is possible to stage a disease in a subject based on expression levels of the target. For a given disease, a biological sample is taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies and/or conjugated activatable antibodies having an enzymatically cleavable CM can be used to detect the presence or absence of an enzyme that is capable of cleaving the CM. Such activatable antibodies and/or conjugated activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody and/or conjugated activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody and/or conjugated activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies and/or conjugated activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies and/or conjugated activatable antibodies can be used to detect the presence or absence of a cleaving agent in a sample. For example, where the activatable antibodies and/or conjugated activatable antibodies contain a CM susceptible to cleavage by an enzyme, the activatable antibodies and/or conjugated activatable antibodies can be used to detect (either qualitatively or quantitatively) the presence of an enzyme in the sample. In another example, where the activatable antibodies and/or conjugated activatable antibodies contain a CM susceptible to cleavage by a reducing agent, the activatable antibodies and/or conjugated activatable antibodies can be used to detect (either qualitatively or quantitatively) the presence of reducing conditions in a sample. To facilitate analysis in these methods, the activatable antibodies and/or conjugated activatable antibodies can be detectably labeled, and can be bound to a support (e.g., a solid support, such as a slide or bead). The detectable label can be positioned on a portion of the activatable antibody and/or conjugated activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies and/or conjugated activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies and/or conjugated activatable antibodies prior to contacting with the sample e.g., the presence of and/or an increase in detectable signal due to cleavage of the activatable antibody and/or conjugated activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies and/or conjugated activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody and/or conjugated activatable antibody is labeled with a detectable label. The detectable label may be a fluorescent dye, (e.g. Fluorescein Isothiocyanate (FITC), an Alexa Fluor® dye, Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g., horseradish peroxidase or alkaline phosphatase).

In some embodiments, the detectable label is a bioluminescent label. The bioluminescent label is conjugated to the activatable antibody via a releasable linker. In some embodiments, the releasable linker is a cleavable linker. In some embodiments, the releasable linker is a non-cleavable linker. Suitable cleavable linkers include any of the cleavable linkers described herein and others known to those skilled in the art. Suitable non-cleavable linkers include any of the cleavable linkers described herein and others known to those skilled in the art. In some embodiments, the releasable linker is a disulfide bond.

In some embodiments, the detectable label is a D-luciferin substrate. D-luciferin acts as a substrate in an ATP-dependent bioluminescent reaction catalyzed by luciferase. Thus, D-luciferin can be conjugated to an activatable antibody and will produce bioluminescence exclusively after activation of the activatable antibody, binding to the receptor and internalization. Thus, these embodiments of the conjugated activatable antibody do not require the use of a quencher molecule.

The D-luciferin is conjugated to the activatable antibody via a releasable linker. In some embodiments, the releasable linker is a cleavable linker. Suitable cleavable linkers include any of the cleavable linkers described herein. In some embodiments, the releasable linker is a disulfide bond.

In some embodiments, the detectable label is luciferase. Thus, the reaction will occur upon injection of D-luciferin substrate. This approach is advantageous because it does not require the presence of endogenous luciferase. Furthermore, the reaction will result in stronger signal—luciferase could activate hundreds of D-luciferin molecules, whereas one D-luciferin molecule will result in one reaction only.

The luciferase is conjugated to the activatable antibody and/or conjugated activatable antibody via a releasable linker. In some embodiments, the releasable linker is a cleavable linker. Suitable cleavable linkers include any of the cleavable linkers described herein. In some embodiments, the releasable linker is a disulfide bond.

Detection of the label in a sample that has been incubated with the labeled, activatable antibody indicates that the sample contains the target and contains a protease that is specific for the CM of the activatable antibody and/or conjugated activatable antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Figure 15:
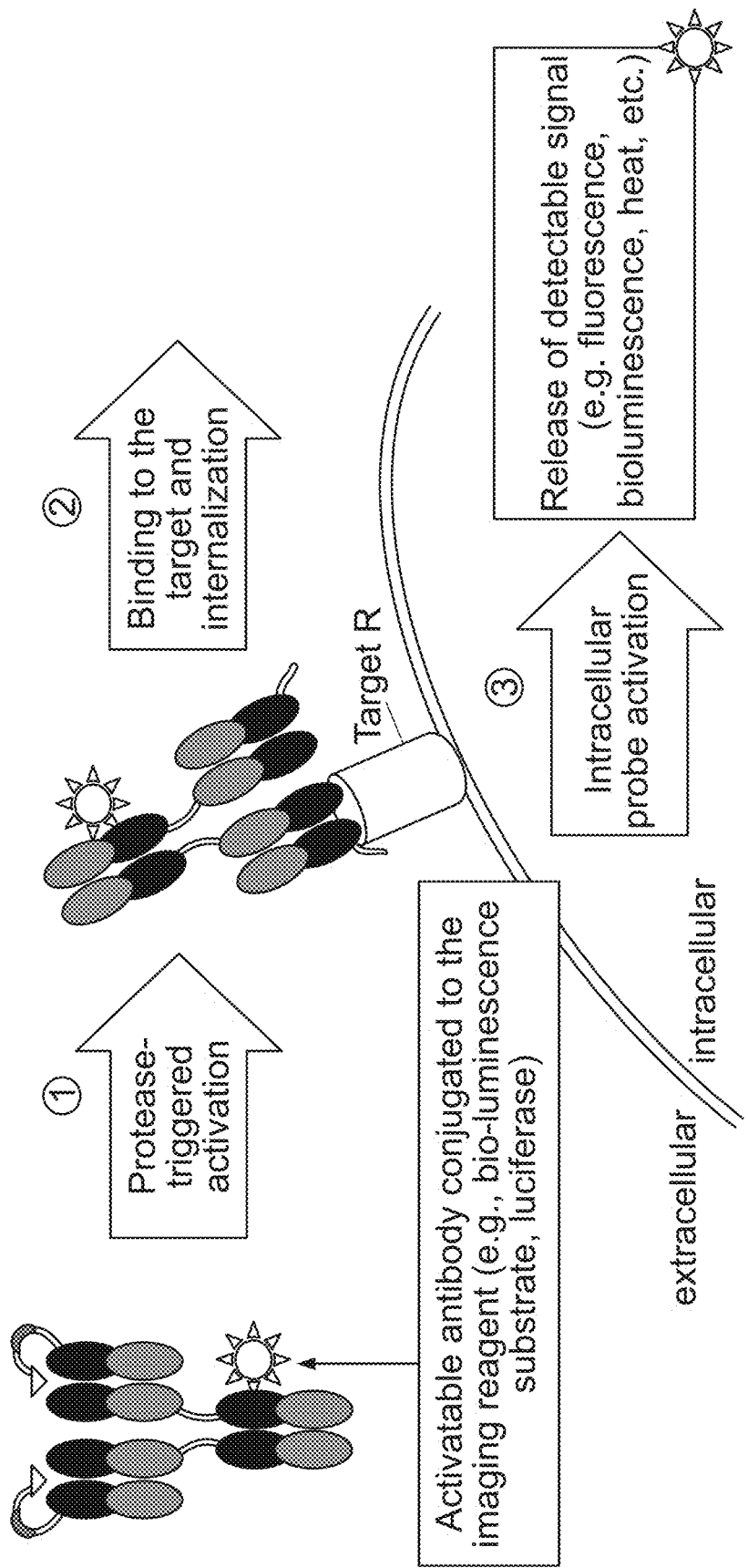
FIG. 15 is an illustration depicting exemplary internalization imaging approaches using an activatable antibody conjugated to an imaging reagent such that the activatable antibody is activated by a protease, the activated activatable antibody binds a target and internalizes, and then the imaging agent is activated intracellularly.
Figure 16:
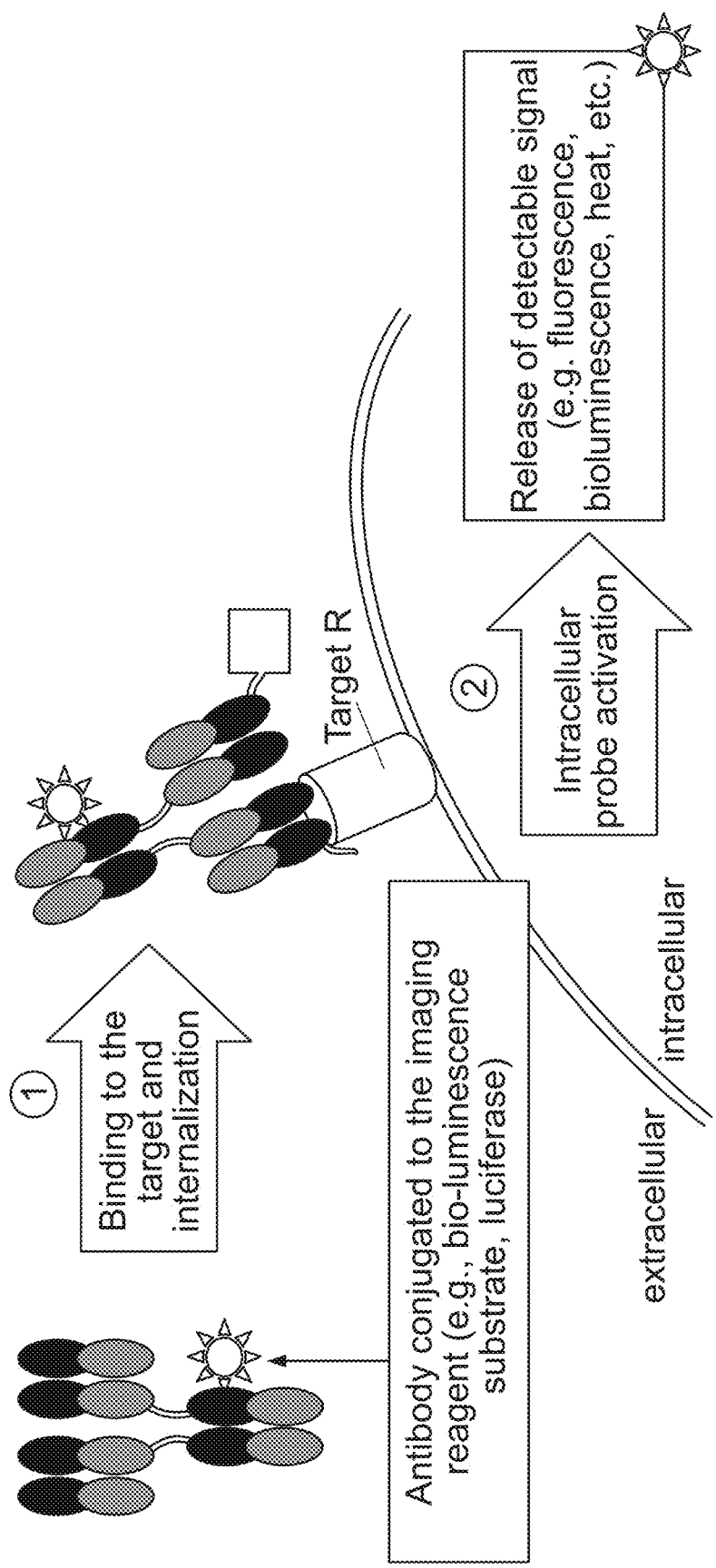
FIG. 16 is an illustration depicting internalization imaging approaches using an antibody conjugated to an imaging reagent, where the antibody binds a target and internalized, and then the imaging agent is activated intracellularly.

In embodiments where the conjugated activatable antibodies include a bioluminescent label, these conjugated activatable antibodies are useful for in vivo methods of monitoring activation of the conjugated activatable antibody. An exemplary embodiment of these in vivo imaging methods is shown in FIG. 15. In these methods, an activatable antibody is conjugated with one or more imaging reagents via a releasable, e.g., cleavable, linker After activation of the conjugated activatable antibody, receptor binding and internalization, the imaging reagent(s) is released. Each molecule of imaging agent that is released after entry generates a signal that can be measured allowing for real-time quantification of activatable antibody activation in vivo. Thus, the imaging reagent-conjugated activatable antibodies are useful as a marker for targeted delivery of the activatable antibody to a site of activation.

In some embodiments, the imaging reagent conjugated to the activatable antibody is D-luciferin. In these methods, an activatable antibody is conjugated with D-luciferin substrate via a releasable, e.g., cleavable, linker and exposed to cells that are stably transfected with luciferase. For example, the D-luciferin-conjugated activatable antibody is administered to a luciferase transgenic mouse or a xenograft mouse model that has been inoculated with a luciferase-transfected cell line. After activation of the conjugated activatable antibody, receptor binding and internalization, D-luciferin is released. Each molecule of free luciferin that is released after entry generates a photon that can be measured allowing for real-time quantification of activatable antibody activation in vivo. Thus, the D-luciferin-conjugated activatable antibodies are useful as a marker for targeted delivery of the activatable antibody to a site of activation.

Similar techniques are also useful for in vivo imaging where detection of the fluorescent signal in a subject, e.g., a mammal, including a human, indicates that the disease site contains the target and contains a protease that is specific for the CM of the activatable antibody. An example of such techniques is shown in Example 9 and in FIGS. 13A and 13B.

These techniques are also useful in kits and/or as reagents for the detection, identification or characterization of protease activity in a variety of cells, tissues, and organisms based on the protease-specific CM in the activatable antibody.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM Likewise, patients that test negative for either or both of the target and the protease that cleaves the substrate in the CM in the activatable antibody being tested using these methods might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

In some embodiments, in vivo imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM Likewise, patients that test negative might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

In some embodiments, in vivo imaging is used to monitor activation of the conjugated activatable antibody. For example, activation of a conjugated activatable antibody is monitored in vivo using magnetic resonance imaging (MRI).

Magnetic resonance imaging (MRI) is a diagnostic method that enables tissue differentiation on the basis of different relaxation times. Contrast agents alter the relaxation times and are used to enhance the visualization of properties correlated with patient anatomy and physiology. Two types of MR contrast agents are used to enhance the visualization of properties correlated with patient anatomy and physiology: T1 contrast agents that shorten the spin-lattice relaxation time of nearby protons, and T2 contrast agents that enhance spin-spin relaxation to reduce the signal of media-containing structures.

Currently, the most prominent T2 contrast agents are based on superparamagnetic iron oxide (SPIO) nanoparticles, which, in contrast to the T1 contrast agents, remain intravascular for a longer time, enabling a longer image-acquisition time window. Moreover, SPIO nanoparticles have been widely used for MRI in clinical practice for diagnostic applications (e.g., Feridex IV™ and Endorem™).

It is known that the contrast enhancement of nanoparticles depends on their size, surface properties, and the degree of aggregation. Notably, the enhancement of T2 relaxivity with a larger hydrodynamic diameter of the clusters formed by nanoparticles is a distinctive characteristic of superparamagnetic nanoparticles (see e.g., Ai et al., 2005. Magnetite-Loaded Polymeric Micelles as Ultrasensitive Magnetic-Resonance Probes Adv Mater 17(16):1949-1952; Atanasijevic et al., "Calcium-sensitive MRI contrast agents based on superparamagnetic iron oxide nanoparticles and calmodulin." Proc Natl Acad Sci U S A. 103.40(2006): 14707-12; Mikhaylov, G., et al. Ferri-liposomes as an MRI-visible drug-delivery system for targeting tumours and their microenvironment. Nat Nanotechnol 6, 594-602 (2011); Zhao M, Josephson L, Tang Y, Weissleder R. Magnetic sensors for protease assays. Angew Chem Int Ed Engl 2003; 42(12):1375-8). The proof of this concept was evidenced by a considerable increase in MRI relaxivity upon clustering of monodispersed SPIO particles inside the hydrophobic core of micelles, thus resulting in a high SPIO loading enabling ultra-sensitive MRI detection on a 1.5 T clinical MRI scanner (Ai et al., 2005).

Furthermore, this principle could be used for the development of SPIO-based MRI sensors that act as magnetic relaxation switches to detect molecular interactions in the reversible self-assembly of dispersed magnetic particles into stable nano-assemblies producing dramatic T2 contrast changes (Perez et al., 2002 Magnetic relaxation switches capable of sensing molecular interactions. Nat. Biotechnol. 20, 816-820; Atanasijevic et al., "Calcium-sensitive MRI contrast agents based on superparamagnetic iron oxide nanoparticles and calmodulin." Proc Natl Acad Sci USA. 103.40(2006):14707-12; Zhao M, Josephson L, Tang Y, Weissleder R. Magnetic sensors for protease assays. Angew Chem Int Ed Engl 2003; 42(12):1375-8). Similarly, a family of calcium indicators for functional MRI studies in vivo based on calcium-dependent protein-protein interactions have been developed by Atanasijevic et al., (Atanasijevic et al., 2006). The opposite approach was used in the work of Zhao et al., where the developed assay employs protease cleavable substrates, flanked by a biotinylated residue on each terminal that interact with avidin-magnetic nanoparticles thereby inducing a clustered state with high T2 relaxivity (Zhao et al., 2003). Thus, in the presence of proteases the substrate sequence will be cleaved between the two biotins resulting in monobiotinylated fragments that interact with avidin-magnetic nanoparticles without inducing aggregation.

Figure 17:
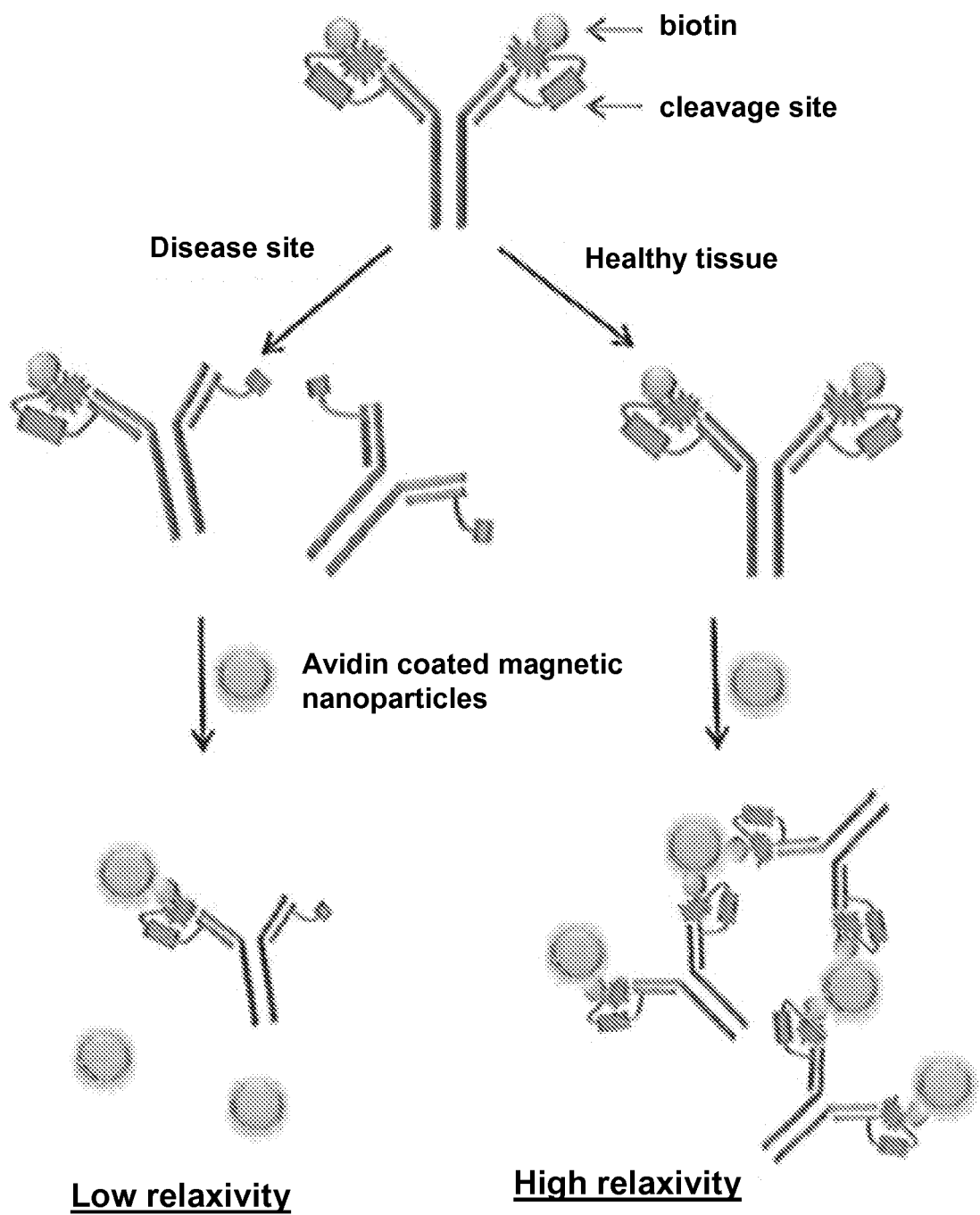
FIG. 17 is an illustration depicting an exemplary method of using a conjugated activatable antibody in magnetic resonance imaging techniques.
Figure 19C:
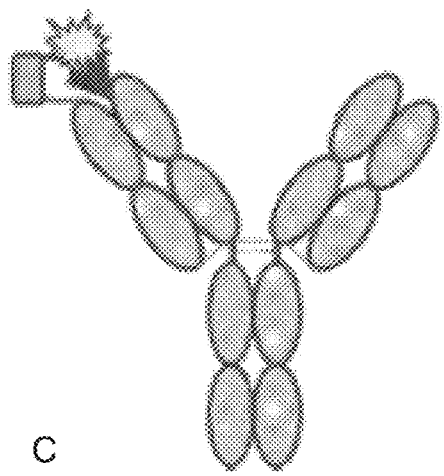
Figure 19D:
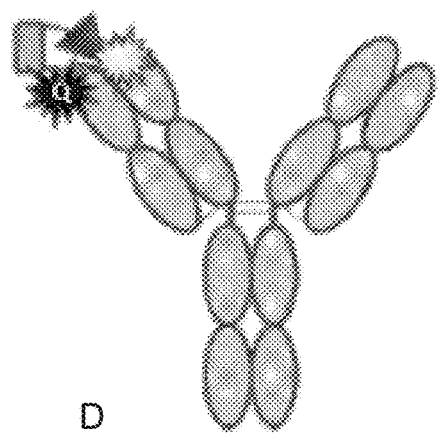

Thus, in some embodiments, the in vivo magnetic resonance (MR) imaging methods employ the effect of enhancement of T2 relaxivity of SPIO nanoparticles upon increase of hydrodynamic diameter of the clusters. An exemplary embodiment of these in vivo MR imaging methods shown in FIG. 17. In these methods, the masking moiety (MM) of an activatable antibody is biotinylated, as shown in FIG. 17, to produce a conjugated activatable antibody having a biotinylated MM, also referred to herein as a conjugated activatable antibody-based magnetic sensor. The conjugated activatable antibody having a biotinylated MM is then administered into a subject, and avidin coated-magnetic nanoparticles and/or streptavidin coated-magnetic nanoparticles are also injected into the subject at a time prior to the MR imaging. In some embodiments, the magnetic nanoparticles are coated with anti-biotin, which may be labeled. In some embodiments, the conjugated activatable antibody having a biotinylated MM and the coated magnetic nanoparticles are administered simultaneously. For example, the conjugated activatable antibody having a biotinylated MM and the coated magnetic nanoparticles can be formulated in a single composition or administered as two or more separate compositions. In some embodiments, the conjugated activatable antibody having a biotinylated MM and the coated magnetic nanoparticles are administered sequentially.

In these in vivo MR imaging methods, the immediate MR imaging after administration of the conjugated activatable antibody having a biotinylated MM provides a high MR contrast image (high relaxivity) that decreases upon activation of the conjugated activatable antibody having a biotinylated MM, which results in low MRI contrast. Thus, these in vivo MR imaging methods provide a non-invasive means for monitoring activation of the conjugated activatable antibody having a biotinylated MM in vivo.

In some embodiments, conjugated activatable antibodies are used in methods for the in vivo monitoring of various characteristics of the conjugated activatable antibody, such as, by way of non-limiting example, the distribution, accumulation, and/or activation of the conjugated activatable antibody. Several exemplary embodiments of these methods are shown in FIG. 18.

In the embodiments shown in FIG. 18, the "labeled" activatable antibody," also referred to herein as conjugated activatable antibody, can be detected using an antibody against the activatable antibody and/or against some portion of the activatable antibody, such as, for example, an antibody that binds to the antibody or antigen binding fragment thereof (AB), an antibody that binds to the masking moiety (MM), and/or an antibody that binds to the cleavable moiety (CM).

In the embodiments shown in FIG. 18, the labeled activatable antibody is an activatable antibody that is labeled by or conjugated with an imaging agent such as, e.g., a fluorescent marker, near infrared (NIR) label, PET/SPECT tracers, MRI contrast agents, and as such, the labeled activatable antibody can be detected using the corresponding instrumentation or other art-recognized means for detection. In some embodiments, the activatable antibody or some portion thereof, e.g., MM, CM, AB and/or combinations thereof, is biotinylated, which would allow the labeled activatable antibody to be captured from biological samples. In some embodiments, the biotinylated activatable antibody is used as a label with avidin and/or streptavidin for detection methods such as histological staining or western blot.

Figure 20:
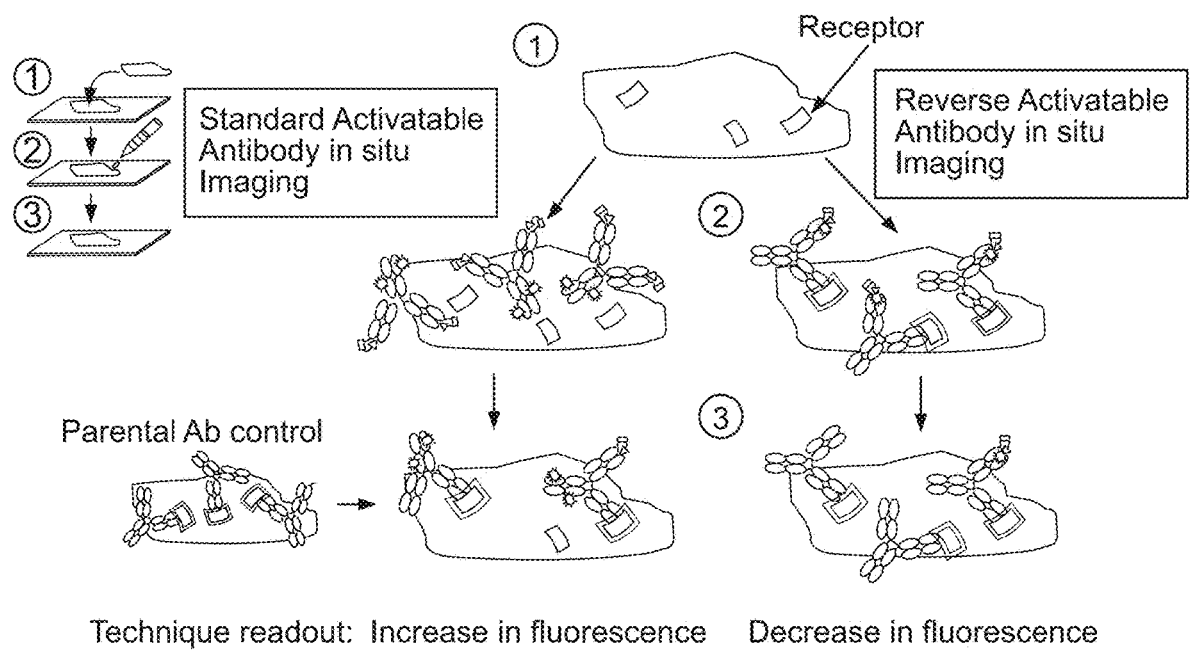
FIG. 20 is an illustration comparing the standard activatable antibody in situ imaging techniques of FIG. 1 with the in situ imaging methods referred to herein as "reverse" in situ imaging.

In some embodiments, the activatable antibody is a hemi-activatable antibody construct that includes a first antigen binding domain and a second antigen binding domain, where the first antigen binding domain is not masked and the second antigen binding domain is masked and contains a labeled linker, as shown in FIGS. 19A-19D. To promote efficient heterodimer formation, masking peptide and other moieties including linkers, probes, detectable labels and so on, are fused to the heavy chain. The hemi-activatable antibodies are useful in methods for validating activation of an activatable antibody and confirmation of binding by the activated antibody to a target in a biological sample. Such methods are referred to herein as "reverse" in situ imaging techniques, where the standard, i.e., non-reverse in situ imaging technique is shown in FIG. 1. A schematic representation of these reverse in situ imaging techniques is shown in FIG. 20. These methods are useful for the screening of diseased tissues and for selection of and refining of a patient population that is responsive to treatment with a given activatable antibody. These methods are also useful in methods for profiling of protease activity in biological samples and systems.

The reverse in situ imaging methods provided herein enable the characterization of the protease and target expression on the same tissue section through detection of the labeled linker cleavage. As such, the non-masked antibody arm of the hemi-activatable antibody will bind to the tissue receptor, thus anchoring the hemi-activatable antibody construct to the tissue. In case of substrate cleavage, the linker with mask and/or label will dissociate from the antigen binding site resulting in the decrease of the labeling (e.g. fluorescence) signal. In case of the absence of protease activity capable of the substrate cleavage, no difference in the detection signal (e.g. fluorescence) will be recorded. The binding of parental antibody is assessed by the detection of hemi-activatable antibody, using a labeled antibody construct or secondary reagent (e.g., anti-human IgG antibodies).

Hemi-activatable antibodies can be made using any of the methods provided herein or otherwise known in the art.

In some embodiments, these reverse in situ imaging methods include one or more of the following steps. First, frozen sections are laid over glass slides. The solution containing hemi-activatable antibody with labeled activatable antibody linker (e.g. fluorescent tag) is applied on the tissue and incubated. After incubation (time, concentration and buffer could vary: e.g., 1 hr., room temperature) the tissue is extensively washed to remove non-bind material and cleaved linker and the signal of residual label is validated by the respective method. In case of fluorescently labeled material proteolytic cleavage of activatable antibody linker could be detected by fluorescent microscopy as decrease of fluorescence. This technique can be combined with immunohistochemistry to enable co-detection of antibody binding enabling normalization of the signal to the parental antibody on the same tissue section. A comparison of these in situ imaging techniques as compared to the technique shown in FIG. 1 is shown in FIG. 20.

Additionally, these methods can be adapted for use with cell cultures or fresh tissues incubation. Alternatively, these methods could be performed in the presence of selective protease inhibitors. For example, an identification of proteases activating activatable antibody could be performed. The latter method modification will enable in situ characterization of the specificity and selectivity of various substrate sequences.

These methods provide a number of advantages, including by way of non-limiting examples, the ability to detect parental antibody binding and activation of an activatable antibody in the same tissue sample/section, which can improve the quantification of activation of the activatable antibody.

The invention will be further described in the following examples, which do not limit the scope of the invention described in the claims.

EXAMPLES

Example 1 Development and Characterization of Activatable Antibody In Situ Imaging The examples provided herein use an anti-EGFR activatable antibody, referred to herein as activatable antibody 3954-1204-C225v5 (also referred to herein as 3954-1204-C225v5 activatable antibody or 3954-1204-C225v5) that includes an EGFR-binding sequence, a masking moiety (MM), and a cleavable moiety (CM) that is a substrate for a protease. These examples also use a masked anti-EGFR antibody construct referred to herein as masked antibody 3954-NSUB-C225v5 (also referred to herein as 3954-NSUB-C225v5 masked antibody or 3954-NSUB-C225v5) that includes a non-cleavable moiety located between the MM and the EGFR-binding sequence. It is to be understood that while the examples provided herein use these anti-EGFR activatable antibody constructs, these methods are applicable to any activatable antibody.

Anti-EGFR activatable antibody constructs: The 3954-1204-C225v5 activatable anti-EGFR antibody construct includes the following heavy and light chain sequences:

3954-1204-C225v5 Activatable Antibody
Heavy Chain Nucleotide Sequence:
[C225v5 (SEQ ID NO: 1)]
(SEQ ID NO: 1)
[caggtgcagctgaaacagagcggccggggcctggtgcagccgagccaga gcctgagcattacctgcaccgtgagcggctttagcctgaccaactatggc gtgcattgggtgcgccagagcccgggcaaaggcctggaatggctggcgt gatttggagcggcggcaacaccgattataacaccccgtttaccagccgcc tgagcattaacaaagataacagcaaaagccaggtgttttttaaaatgaac agcctgcaaagccaggataccgcgatttattattgcgcgcgcgcgctgac ctattatgattatgaatttgcgtattggggccagggcaccctggtgaccg tgagcgcggctagcaccaagggcccatcggtcttccccctggcaccctcc tccaagagcacctctgggggcacagcggccctgggctgcctggtcaagga ctacttccccgaaccggtgacggtgtcgtggaactcaggcgccctgacca gcggcgtgcacaccttcccggctgtcctacagtcctcaggactctactcc ctcagcagcgtggtgaccgtgccctccagcagcttgggcacccagaccta catctgcaacgtgaatcacaagcccagcaacaccaaggtggacaagaaag ttgagcccaaatcttgtgacaaaactcacacatgcccaccgtgcccagca cctgaactcctggggggaccgtcagtcttcctcttccccccaaaacccaa ggacaccctcatgatctcccggacccctgaggtcacatgcgtggtggtgg acgtgagccacgaagaccctgaggtcaagttcaactggtacgtggacggc gtggaggtgcataatgccaagacaaagccgcgggaggagcagtacaacag cacgtaccgtgtggtcagcgtcctcaccgtcctgcaccaggactggctga atggcaaggagtacaagtgcaaggtctccaacaaagccctcccagccccc atcgagaaaaccatctccaaagccaaagggcagccccgagaaccacaggt gtacaccctgcccccatcccgggatgaactgaccaagaaccaggtcagcc tgacctgcctggtcaaaggcttctatcccagcgacatcgccgtggagtgg gagagcaatgggcagccggagaacaactacaagaccacgcctcccgtgct ggactccgacggctccttcttcctctacagcaagctcaccgtggacaaga gcaggtggcagcaggggaacgtcttctcatgctccgtgatgcatgaggct ctgcacaaccactacacgcagaagagcctctccctgtctccgggtaaatg a]

3954-1204-C225v5 Activatable Antibody
Heavy Chain Amino Acid Sequence:
[C225v5 (SEQ ID NO: 2)]
(SEQ ID NO: 2)
[QVQLKQSGPGLVQPSQSLSITCTVSGFSLTNYGVHWVRQSPGKGLEWLG

VIWSGGNTDYNTPFTSRLSINKDNSKSQVFFKMNSLQSQDTAIYYCARAL

TYYDYEFAYWGQGTLVTVSAASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

K*]

3954-1204-C225v5 Activatable Antibody
Light Chain Nucleotide Sequence:
[Spacer (SEQ ID NO: 5)] [Mask (SEQ ID NO: 6)][Linker 1 (SEQ ID NO: 7)][1204 Substrate (SEQ ID NO: 8)][Linker 2 (SEQ ID NO: 9)][C225 (SEQ ID NO: 10)]
(SEQ ID NO: 3)
[caaggccagtctggccag][tgcatctcacctgtggttgtccggacgg cccatacgtcatgtac][ggctcgagcggtggcagcggtggctctggtgg atccggt][ctgagcggccgttccgataatcat]

[ggcagtagcggtacc][cagatottgotgacccagagccggtgattct gagcgtgagcccgggcgaacgtgtgagctttagctgccgcgcgagccaga gcattggcaccaacattcattggtatcagcagcgcaccaacggcagcccg cgcctgctgattaaatatgcgagcgaaagcattagcggcattccgagccg ctttagcggcagcggcagcggcaccgattttaccctgagcattaacagcg tggaaagcgaagatattgcggattattattgccagcagaacaacaactgg ccgaccacctttggcgcgggcaccaaactggaactgaaacgtacggtggc tgcaccatctgtcttcatcttcccgccatctgatgagcagttgaaatctg gaactgcctctgttgtgtgcctgctgaataacttctatcccagagaggcc aaagtacagtggaaggtggataacgccctccaatcgggtaactcccagga gagtgtcacagagcaggacagcaaggacagcacctacagcctcagcagca ccctgacgctgagcaaagcagactacgagaaacacaaagtctacgcctgc gaagtcacccatcagggcctgagctcgcccgtcacaaagagcttcaacag gggagagtgttag]

3954-1204-C225v5 Activatable Antibody
Light Chain Nucleotide Sequence:
[Spacer (SEQ ID NO: 11)1[Mask (SEQ ID
NO: 12)1[Linker 1 (SEQ ID NO: 13)1[1204
Substrate (SEQ ID NO: 14)1[Linker 2
(SEQ ID NO: 15)1[C225 (SEQ ID NO: 16)]
(SEQ ID NO: 4)
[QGQGQ][CISPRGCPDGPYVMY][GSSGGSGGSGGSG][LSGRSDNH][

GSSGT][QILLIQSPVILSVSPGERVSFSCRASQSIGTNIHWYQQRTNGS

PRLLIKYASESISGIPSRFSGSGSGTDFTLSINSVESEDIADYYCQQNNN

WPTTFGAGTKLELKRTVAAPSVFIFPPSDEQLKSGTASVVCLLNNFYPRE

AKVQWKVDNALQSGNSQESVTEQDSKDSTYSLSSTLTLSKADYEKHKVYA

CEVTHQGLSSPVTKSFNRGEC*]

The 3954-NSUB-C225v5 masked anti-EGFR antibody construct includes the same heavy chain as the 3954-1204-C225v5 activatable anti-EGFR antibody shown above. The 3954-NSUB-C225v5 masked anti-EGFR antibody construct includes the following light chain sequence:

3954-1204-C225v5 Activatable Antibody
Light Chain Nucleotide Sequence:
[Spacer (SEQ ID NO: 5)][Mask (SEQ ID
NO: 6)][Linker 1-Noncleavable Substrate-
Linker 2 (SEQ ID NO: 19)][C225 (SEQ ID
NO: 10)]
(SEQ ID NO: 17)
[caaggccagtctggccag][tgcatctcacctgtggttgtccggacgg cccatacgtcatgtac][ggctcgagcggtggcagcggtggctctggtgg ctcaggtggaggctcgggcggtgggagcggcggttct][cagatottgct gacccagagccggtgattctgagcgtgagccgggcgaacgtgtgagct tagctgccgcgcgagccagagcattggcaccaacattcattggtatcag cagcgcaccaacggcagcccgcgcctgctgattaaatatgcgagcgaaag cattagcggcattccgagccgctttagcggcagcggcagcggcaccgatt ttaccctgagcattaacagcgtggaaagcgaagatattgcggattattat tgccagcagaacaacaactggccgaccacctttggcgcgggcaccaaact ggaactgaaacgtacggtggctgcaccatctgtcttcatcttcccgccat ctgatgagcagttgaaatctggaactgcctctgttgtgtgcctgctgaat aacttctatcccagagaggccaaagtacagtggaaggtggataacgccct ccaatcgggtaactcccaggagagtgtcacagagcaggacagcaaggaca gcacctacagcctcagcagcaccctgacgctgagcaaagcagactacgag aaacacaaagtctacgcctgcgaagtcacccatcagggcctgagctcgcc cgtcacaaagagcttcaacaggggagagtgttag]

3954-NSUB-C225v5 Masked Antibody Light
Chain Amino Acid Sequence: [Spacer (SEQ
ID NO: 11)][Mask (SEQ ID NO: 12)][Linker
1-Noncleavable Substrate-Linker 2 (SEQ
ID NO: 20)][C225 (SEQ ID NO: 16)]
(SEQ ID NO: 18)
[QGQSGQ][CISPRGCPDGPYVMY][GSSGGSGGSGGSGGGSGGSGGS]

[QILLTQSPVILSVSPGERVSFSCRASQSIGTNIHWYQQRTNGSPRLLIK

YASESISGIPSRFSGSGSGTDFTLSINSVESEDIADYYCQQNNNWPTTFG

AGTKLELKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC*]

The cleavable moiety (CM) used in the 3954-1204-c225v5 activatable anti-EGFR antibody can be cleaved by two serine proteases known to be upregulated in a variety of human carcinomas: urokinase-type plasminogen activator (uPA) and membrane type serine protease 1 (MT-SP1/matriptase); this CM can also be cleaved by legumain. The 3954-NSUB-c225v5 masked anti-EGFR antibody was used as a negative control, as it contains a non-cleavable substrate sequence resulting in a protease-resistant activatable antibody.

The unique feature of an activatable antibody to bind the target cell receptor exclusively after activation by a selected protease led to the creation of a novel and potent technique enabling detection of protease activity in biological systems, referred to herein as in situ imaging of activatable antibodies. This technique is based on the use of a labeled activatable antibody that can be selectively accumulated at the site of protease activity. A simple protocol was developed to apply this technique to methods of imaging protease activity in various tissue sections. This protocol includes three major steps: (1) frozen (or fresh) tissue sections are placed on the glass slide and briefly rinsed with PBS; (2) solution containing labeled activatable antibody (e.g., with a fluorescent dye Alexa Fluor® 680) is incubated on the tissue section in the dark; and (3) tissue sample is extensively washed with PBS, or other suitable buffer, and the binding of activated (i.e., cleaved) activatable antibody is visualized by fluorescent microscopy (FIG. 1). In some embodiments, step (1) includes a further rinse in PBS-Tween (PBS-T). In some embodiments, step (3) includes washing in PBS-T followed by PBS. In some embodiments, step (1) includes a further rinse in PBS-T, and step (3) includes washing in PBS-T followed by PBS.

Example 2 Characterization of Protease Activity in H292 Xenograft Tumor Tissues

Figure 2A:
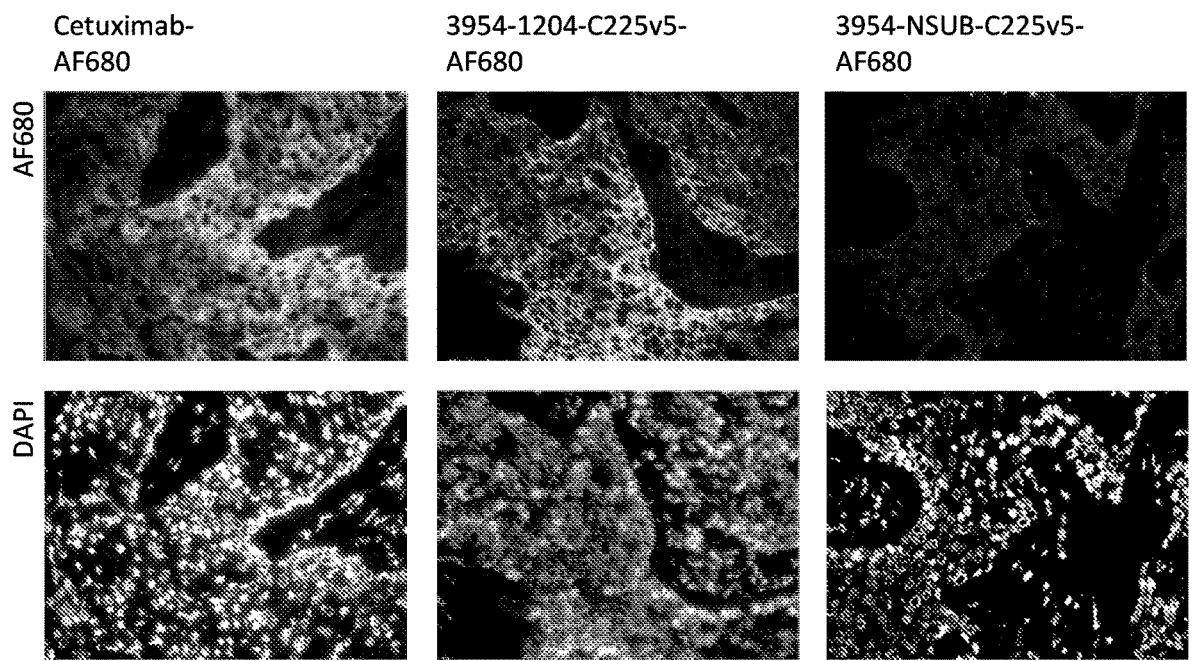
FIGS. 2A and 2B are a series of images depicting proof of principle for activatable antibody in situ imaging using non-small cell lung cancer H292 xenograft tumor tissues. These illustrations depict the ability of non-small cell lung cancer H292 xenograft tumor tissues to activate and bind anti-EGFR activatable antibody 3954-1204-C225v5. Such activation is inhibited by proteinase inhibitors or by excess unlabeled (i.e., "cold") antibody. As expected, masked antibody 3954-NSUB-C225v5, which has a GS-rich linker instead of a cleavable moiety, was not activated by NSCLC tissue samples.
Figure 2B:
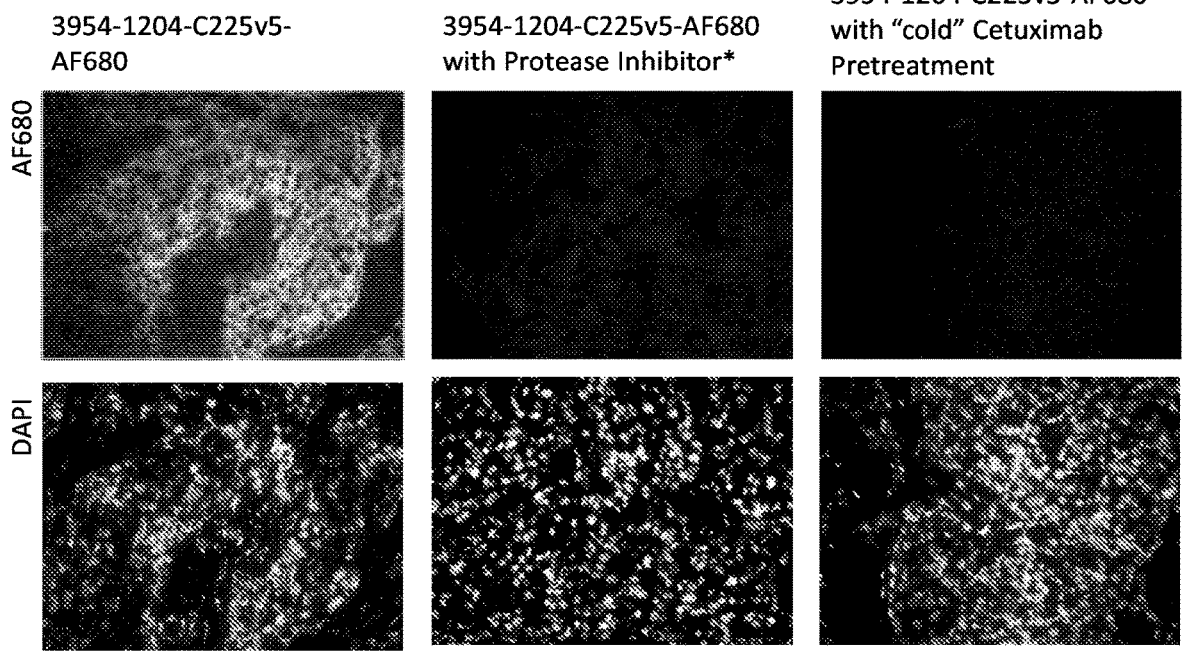

EGFR is highly expressed in H292 human non-small cell lung cancer cells, and efficacy of Cetuximab in this xenograft tumor model has been determined by multiple studies (see e.g., Doody et al., Mol Cancer Ther Oct. 2007 6; 2642; Chen et al., BMC Medicine 2012, 10:28). Accordingly, H292 tumor tissue samples were selected to validate the activatable antibody in situ imaging approach. The studies, the results of which are shown in FIGS. 2A and 2B, used the 3954-1204-c225v5 activatable anti-EGFR antibody, with the parental antibody (cetuximab) and 3954-NSUB-c225v5 (i.e., non-cleavable masked antibody), as positive and negative controls, respectively. H292 xenograft frozen tumor tissue sections were placed on the glass slide, rinsed two times with PBS-T followed by PBS, followed by 30 min pretreatment of tissue with broad spectrum protease inhibitors cocktail or buffer only. Alexa Fluor-680® labeled 3954-1204-c225v5 and Alexa Fluor-680® labeled 3954-NSUB-c225v5 were applied on the tissue and incubated for one hour in the dark (to prevent bleaching of fluorescence). After incubation with 1 µg/ml of the incubated tumor sections were rinsed three times with PBS-T followed by PBS and counterstained with nuclear marker DAPI for 1 minute. Fluorescence microscopy analysis revealed a positive staining of 3954-1204-c225v5 that was abolished by the pretreatment of tissue section with protease inhibitors, indicating that the binding of 3954-1204-c225v5 to the tissue sample is a result of the proteolytic event. Positive staining of 3954-1204-c225v5 was also abolished when the tissue was pretreated with an excess of unlabeled ("cold") cetuximab. Furthermore, incubation of H292 tissue revealed positive staining for Cetuximab antibody that was not affected by pretreatment of tissue with protease inhibitors, but was abolished when the tissue was pretreated with unlabeled cetuximab. As expected, no signal was detected for the non-cleavable 3954-NSUB-c225v5 detected on the tissue pretreated or not with protease inhibitors or unlabeled cetuximab.

Figure 3:
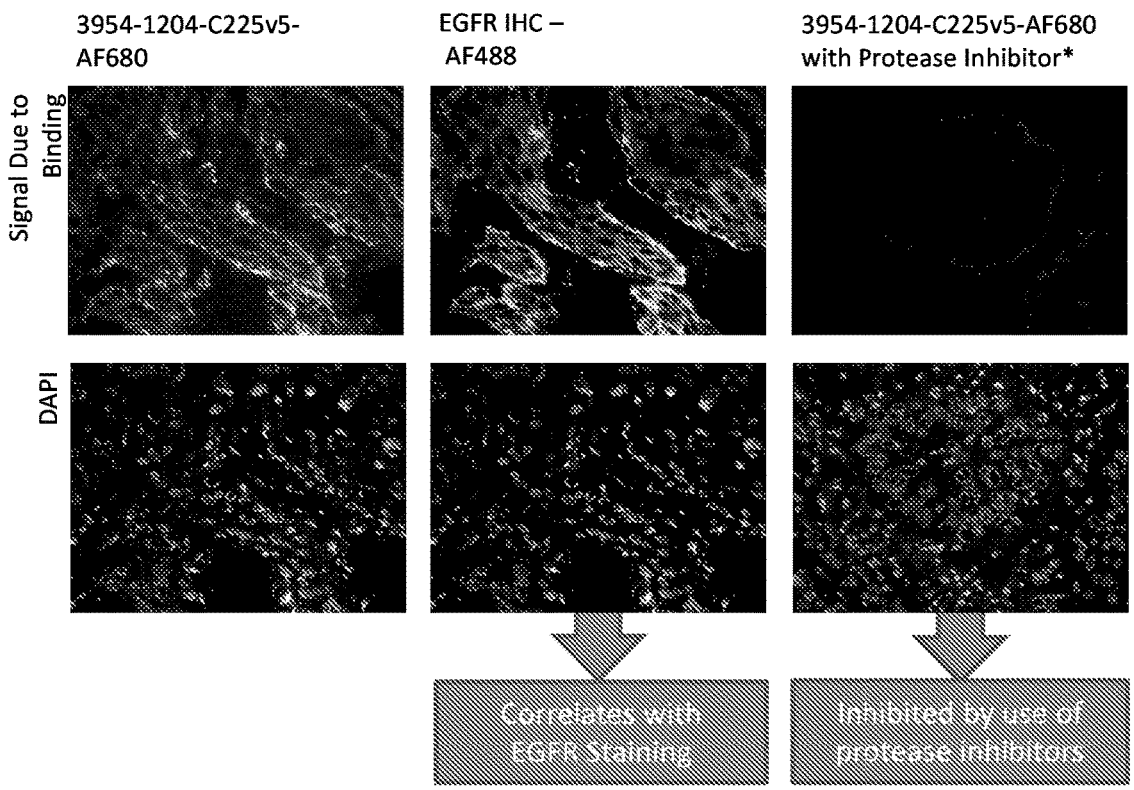
FIG. 3 is a series of images showing the ability of anti-EGFR activatable antibody 3954-1204-C225v5 to be activated and to bind frozen human cancer tissues using an in situ imaging method of the disclosure. The tissue image in the left panel of the top row demonstrates that anti-EGFR activatable antibody 3954-1204-C225v5 was activated by tissue-derived proteolytic cleavage of the anti-EGFR activatable antibody to yield C225v5 antibody that bound to the EGFR target in the tissue. The identical pattern of tissue staining was detected by exposing a commercially available anti-EGFR antibody to the tissue, as shown in the middle panel of the top row. The image in the right panel of the top row demonstrates that the fluorescent signal shown in left panel was inhibited by pre-treatment of the tissue with a 1:100 dilution of broad spectrum inhibitor cocktail set III and 50 mM EDTA. The bottom row represents DAPI nuclear staining

Example 3 Screening of Patient Tumor Samples using Activatable Antibody In Situ Imaging Frozen colorectal cancer patient tumor samples were used in the technique described above in Example 2 to evaluate the applicability of activatable antibody in situ imaging to validate protease activity on human tissues. First, dual staining for 3954-1204-c225v5 in situ imaging and EGFR immunohistochemistry (IHC) was performed to confirm co-localization of the fluorescent signal (FIG. 3). Furthermore, pretreatment of tumor tissue with broad spectrum protease inhibitors (PI) completely abolished binding of 3954-1204-c225v5 (FIG. 3), indicating the successful inhibition of protease activity, which is required for 3954-1204-c225v5 activation.

Figure 4:
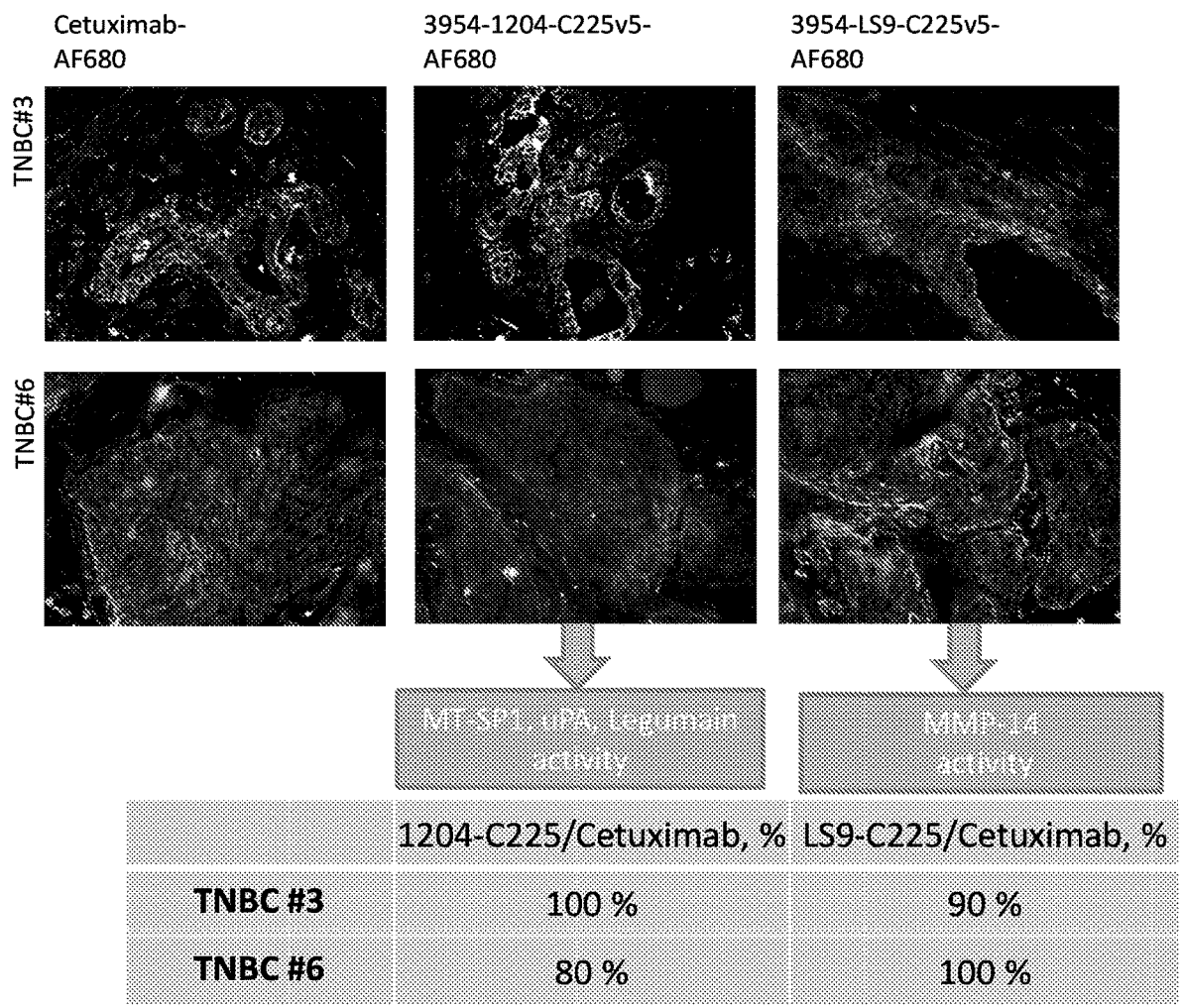
FIG. 4 is a series of images depicting the activation of activatable antibodies 3954-1204-C225v5 (middle panels) and 3954-LS9-C225v5 (right panels) by tumor tissues of triple negative breast cancer (TNBC). CM 1204 (amino acid sequence LSGRSDNH, SEQ ID NO: 14) is a substrate for MT-SP1, uPA and legumain; and a known cleavable moiety referred to herein as CM LS9 (amino acid sequence SLAPLGLQRR, SEQ ID NO: 251), which is a substrate for MMP-14. Protease activity was quantified as percent of activatable antibody activation and tissue binding compared to cetuximab staining efficiency (left panels).

Next, the heterogeneity of protease activity between different tumor tissues was investigated. These studies screened two triple negative breast cancer (TNBC) patient tumor samples with activatable antibodies capable of activation by uPA (3954-1204-C225v5) and MMP-14 (3954-LS9-C225v5). Notably, as shown in FIG. 4, whereas a differential rate of 3954-1204-C225v5 activation was detected in samples containing the substrate that is cleaved by uPA, Mt-SP1, and legumain, a high level of MMP activity was demonstrated for both tumor tissues. The results on the ability of human triple negative breast cancer patients' tissue samples to activate and bind anti-EGFR activatable antibodies are summarized in Table 7.

TABLE 7

In situ imaging of 3954-1204-C225v5 and 3954-LS9-C225v5 activatable antibodies in human triple negative breast cancer patients' tumor tissues.

| Patient # | Stage | Her-2 neu | ER | PR | Cetuximab | 1204-c225, % | LS9-c225, % |
|---|---|---|---|---|---|---|---|
| 1 | IIIA | 0 | negative | negative | + | 45 | 40 |
| 2 | IIIB | 0 | | | + | 15 | 50 |
| 3 | IIA | | | | ++ | 100 | 95 |
| 4 | IIA | | | | +++ | 45 | 85 |
| 5 | IIA | | | | − | — | — |
| 6 | IIIA | | | | ++ | 80 | 100 |
| 7 | IIA | 1 | | | ++ | 50 | 100 |
| 8 | IIA | 0 | | | ++ | 0 | 85 |
| 9 | IIA | 1+ | | | + | 50 | 100 |
| 10 | IIA | 0 | | | ++ | 45 | 30 |

*Cetuximab staining scored from − to 3+ that measures the amount of antibody binding: −, no staining; 1+, weak staining; 2+, moderate staining; and 3+, strong staining.
**Protease activity was quantified as percent of activatable antibody staining intensity compared to Cetuximab staining.

Such an in situ imaging technique enables detection of proteolytic activity in biological samples such as cell cultures or tissue sections. Using this technique, it is possible to quantify proteolytic activity based on the presence of a detectable label (e.g., a fluorescent label). These techniques are useful with any frozen cells or tissue derived from a disease site (e.g. tumor tissue) or healthy tissues. These techniques are also useful with fresh cells and tissues.

Example 4. In Situ Imaging of Anti-EGFR Activatable Antibodies

The present Example describes the use of in situ imaging of the activation and binding of an anti-EGFR activatable antibody of the disclosure. The results indicate that anti-EGFR activatable antibodies of the disclosure can be activated by proteases expressed by a tissue and bind EGFR targets on that tissue.

In situ imaging of activatable antibodies represents a unique approach to characterize protease activity in cells and tissues. This technology enables validation of activatable antibody activation and binding to a target in histological sections of cells and tissues expressing proteases capable of cleaving the activatable antibody. A schematic of such an in situ approach is presented in FIG. 1.

In situ imaging of the activation and binding of an anti-EGFR activatable antibody (also referred to herein as in situ imaging) by a cell or tissue capable of cleaving the activatable antibody at a site co-localized with the target recognized by the activated antibody was conducted as follows: Frozen tissue sections were laid over glass slides. A solution containing labeled anti-EGFR activatable antibodies (labeled, e.g., with a fluorescent tag) was applied on the tissue and incubated, e.g., for 1 hour at room temperature (about 22-24° C.) in an incubation buffer of 50 mM Tris-HCl buffer pH 7.4, containing 150 mM NaCl, 100 μM $ZnCl_2$, 5 mM $CaCl_2$ and 0.05% Tween 20; activatable antibody at a concentration of about 1 m/ml. The conditions of such an incubation can be adjusted to be conducive to the cleavage agent in the tissue section by, for example, varying the pH of the solution (e.g., within a range of about pH 7 to about pH 8.5), the temperature of the incubation (e.g., within a range of about 20° C. to about 40° C., e.g., room temperature or 37° C.), the incubation time (e.g., within a range of about 15 minutes to about 150 minutes, and/or the activatable antibody concentrations (e.g., within a range of about 0.05 μg/ml to about 10 m/ml). The tissue was then extensively washed to remove non-bound material and detectable label was measured. For example, when a fluorescent tag was used, the tissue was submitted to fluorescent microscopy. Detection of activated antibody on the tissue indicated that the tissue expressed proteases that cleaved the activatable antibody and also expressed EGFR targets to which the activated antibody bound.

FIG. 6 demonstrates that 3954-1204-C225v5 is activatable in a wide range of human tumor samples. Column 2 indicates the expression level of EGFR receptor, as detected by an EGFR antibody (monoclonal rabbit anti-EGFR antibody, Cell Signaling), for the various human cancer tissue samples. Column 3 indicates the amount of active matriptase (MT-SP1), as detected by antibody A11, in the various human cancer tissue samples. Columns 4 and 5 represent an evaluation of in situ activation and binding of the EGFR activatable antibody (col. 5) as compared to cetuximab (Cetux) tissue staining (col. 4). The staining that measures the amount of EGFR, A11 and cetuximab antibodies binding to the tissue sample was scored from – to 3+: –, no staining; 1+ (i.e., "+"), weak staining; 2+ (i.e., "++"), moderate staining; and 3+ (i.e., "+++"), strong staining. The activatable antibody in situ imaging staining scoring is based on comparison with cetuximab antibody staining and defined as follows: –, no staining; 1+ (i.e., "+"), weak staining as compared to parental antibody; 2+ (i.e., "++"), moderate staining as compared to parental antibody; and 3+ (i.e., "+++"), analogous staining to parental antibody. As shown in FIG. 6, high levels of active matriptase have been observed in 8 of 9 samples from colorectal cancer (CRC) tumors, and high levels of active matriptase have been observed in samples from 5 of 10 lung cancer (NSCLC) tumors. No active matriptase was observed in samples from adjacent healthy lung tissue.

These data suggest the utility of in situ imaging in methods of effectively and efficiently identifying or otherwise refining a patient population suitable for treatment with an anti-EGFR activatable antibody of the disclosure, such as activatable antibody 3954-1204-C225v5. For example, patients that test positive for both the target (e.g., EGFR) and the protease that cleaves the substrate in the cleavable moiety (CM) of the anti-EGFR activatable antibody (e.g., MT-SP1) using these in situ imaging techniques could be identified as suitable candidates for treatment with the anti-EGFR activatable antibody being tested Likewise, patients that test negative for either or both of the target (e.g., EGFR) and the protease that cleaves the substrate in the CM (e.g., MT-SP1) using these in situ imaging techniques might be identified as suitable candidates for another form of therapy. In some embodiments, such patients can be tested with other anti-EGFR activatable antibodies until a suitable anti-EGFR activatable antibody for treatment is identified (e.g., an anti-EGFR activatable antibody comprising a CM that is cleaved by the patient at the site of disease).

Example 5. In Situ Imaging of Anti-EGFR Activatable Antibodies

The present Example describes the use of an in situ imaging approach to screen a patient's tissue samples for the activation and binding of an anti-EGFR activatable antibody. The results indicate that anti-EGFR activatable antibodies of the disclosure can be activated by proteases expressed by a cancer patient's tissue and bind to EGFR receptor on that tissue.

Figure 7:
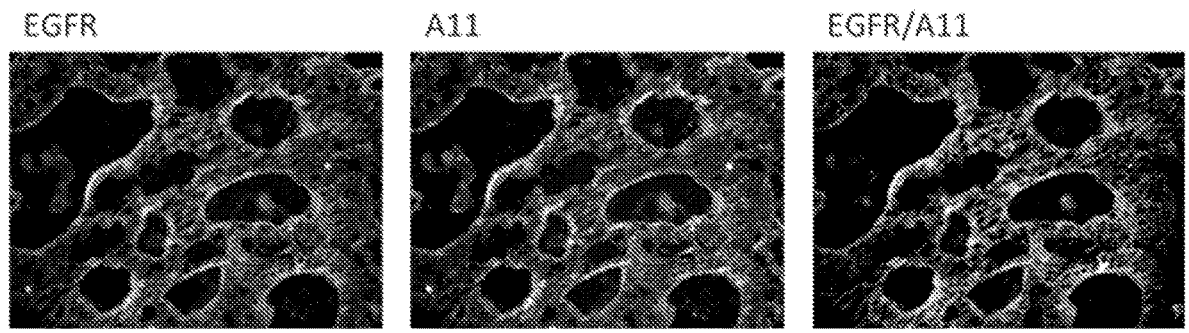
FIG. 7 is an illustration depicting the co-localization of EGFR and A11 in human colorectal cancer liver metastasis tissue samples.
Figure 8:
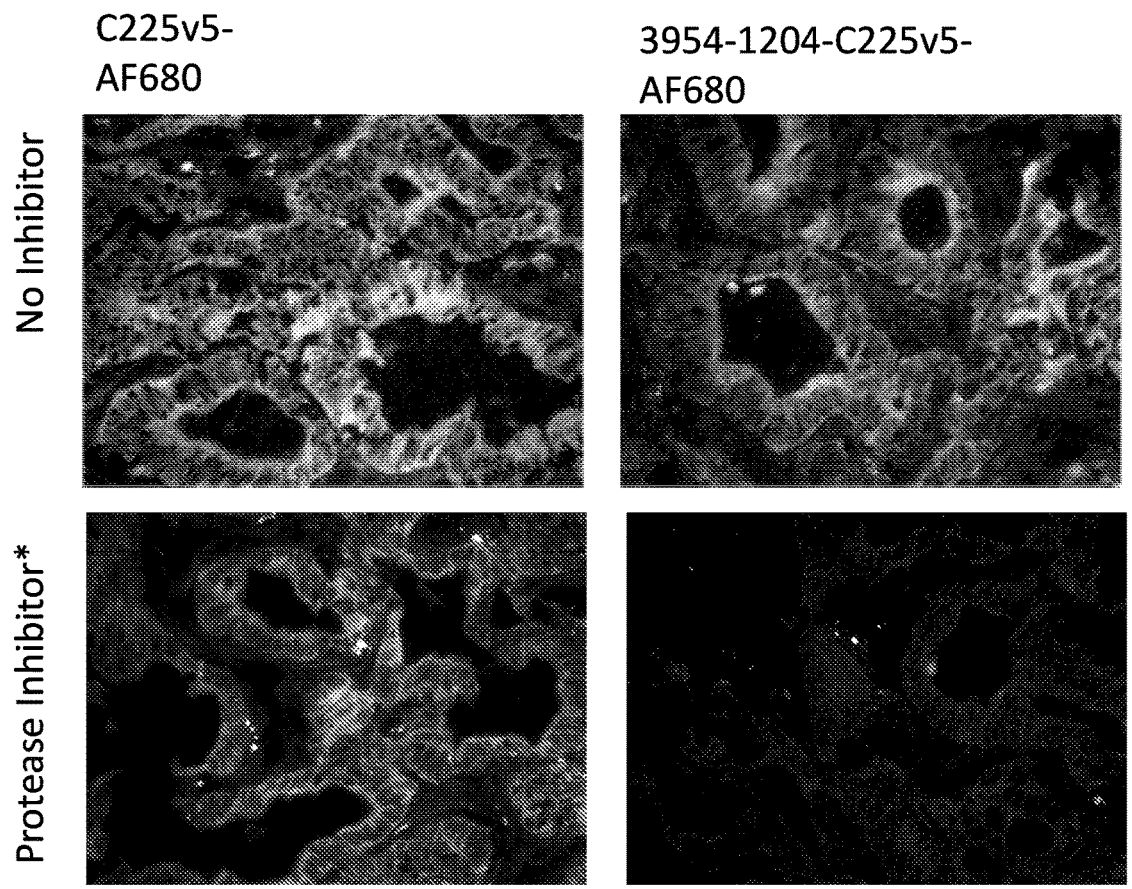
FIG. 8 is an illustration depicting the ability of human colorectal cancer liver metastasis tissues to activate and bind anti-EGFR activatable antibodies.
Figure 12:
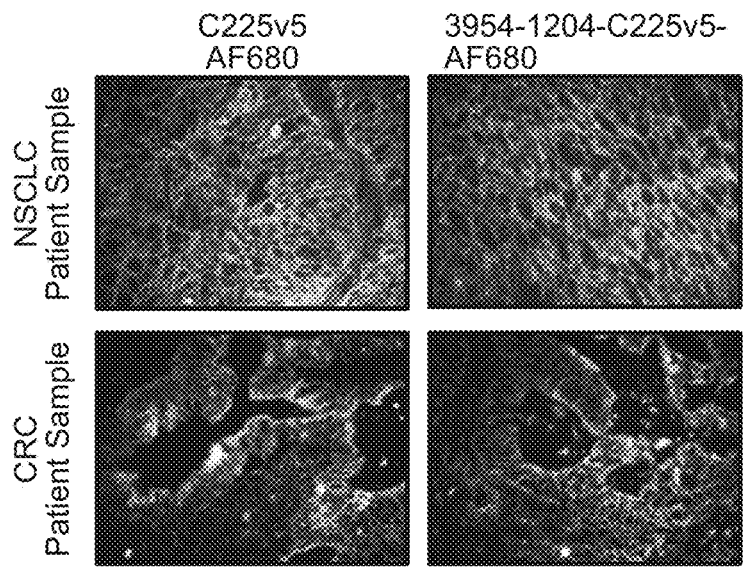
FIG. 12 depicts a series of images that demonstrate in situ imaging of antibody C225v5 and activation of activatable antibody 3954-1204-C225v5 on non-small cell lung cancer (NSCLC) and colorectal cancer (CRC) human tissue samples.

Human colorectal cancer, non-small cell lung cancer (NSCLC) and liver metastasis tissue samples, provided by the Cooperative Human Tissue Network which is funded by the National Cancer Institute, were profiled for EGFR and MT-SP1 expression by treating frozen tissue with labeled EGFR and A11 antibodies at 1 μg/ml and 5 μg/ml concentrations, respectively for 1 hour (FIG. 7 and Tables 8-11). Furthermore, the ability of anti-EGFR activatable antibody 3954-1204-C225V5 to be activated and to bind human tumor or liver metastasis tissues was evaluated using in situ imaging (FIG. 7 and Tables 8-11). The activatable antibody was labeled with Alexa Fluor® 680 (Invitrogen) as described above. The resultant activatable antibody 3954-1204-C225V5-AF680 (also referred to as 1204-C225v5 or 1204-C225) was incubated with frozen patient tissue samples according to the protocol of in situ imaging described herein. FIG. 8 illustrates the ability of colorectal cancer liver metastasis tissues to activate and bind anti-EGFR activatable antibodies. FIG. 12 illustrates the ability of colorectal cancer and NSCLC tissues to activate and bind anti-EGFR activatable antibodies. The results on the ability of cancer patient's tissue samples to activate and bind anti-EGFR activatable antibodies are summarized in the Tables 8-11. The IHC staining that measures the amount of EGFR and A11 antibodies binding to the tissue sample was scored from – to 3+: –, no staining; 1+ (i.e., "+"), weak staining; 2+ (i.e., "++"), moderate staining; and 3+ (i.e., "+++"), strong staining. The in situ imaging staining scoring is based on comparison with cetuximab antibody staining and defined as follows: –, no staining; 1+ (i.e., "+"), weak staining as compared to parental antibody; 2+ (i.e., "++"), moderate staining as compared to parental antibody; and 3+ (i.e., "+++"), analogous staining to parental antibody.

TABLE 8

Screening for EGFR and MT-SP1 expression and in situ imaging of 3954-1204-C225 activatable antibody in human colorectal cancer patients tumor tissues.

| Patient # | IHC* EGFR | IHC* MT-SP1 | in situ imaging** Cetuximab | in situ imaging** Activatable Antibody | Tumor type | Stage | Grade | AJCC 7th edition | Treatment |
|---|---|---|---|---|---|---|---|---|---|
| 5577 | +++ | +++ | ++ | ++ | Ademo-carcinoma | N/A | G2 Moderately Differentiated | N/A | UNKNOWN |
| 5579 | +++ | − | ++ | ++ | Ademo-carcinoma | N/A | G3 Poorly Differentiated | (pT4, pN2, PM1) | UNKNOWN |
| 5638 | ++ | + | ++ | ++ | Ademo-carcinoma | Stage IIA | G2 Moderately Differentiated | (pT3, pN0, pMn/a) | UNKNOWN |
| 5640 | ++ | ++ | ++ | +++ | Ademo-carcinoma | Stage IIA | G2 Moderately Differentiated | IIA (pT3, pN0, pMn/a) | UNKNOWN |
| 5642 | ++ | + | +++ | + | Ademo-carcinoma | Stage IIA | G3 Poorly Differentiated | II (pT3, pN0, pMn/a) | UNKNOWN |
| 5650 | ++ | + | ++ | ++ | Ademo-carcinoma | Stage IIIB | G2 Moderately Differentiated | IIIB (pT3, pN0, pMn/a) | UNKNOWN |
| 5652 | +++ | +++ | +++ | ++ | Ademo-carcinoma | Stage IIA | G2 Moderately Differentiated | (pT3, pN0, pMn/a) | UNKNOWN |
| 5656 | +++ | ++ | +++ | +++ | Ademo-carcinoma | Stage IIB | G2 Moderately Differentiated | pT3c/d, pN1, pMn/a) | UNKNOWN |
| 5658 | + | ++ | ++ | +++ | Ademo-carcinoma | Stage IIIB | G3 Poorly Differentiated | (pT3, pN1, pMn/a) | UNKNOWN |
| 5660 | +++ | +++ | ++ | +++ | Ademo-carcinoma | Stage I | G2 Moderately Differentiated | (pT2, pN0, pMn/a) | UNKNOWN |
| 5662 | − | − | − | − | Ademo-carcinoma | Stage IIA | G2 Moderately Differentiated | (pT3, pN0, pMn/a) | UNKNOWN |
| 5663 | + | − | + | − | Ademo-carcinoma | Stage IIA | G3 Poorly Differentiated | (pT3, pN0, pMn/a) | UNKNOWN |
| 5665 | ++ | + | ++ | ++ | Ademo-carcinoma | N/A | N/A | (pT4, pN1, pMn/a) | UNKNOWN |

*The IHC staining scored from − to 3+ that measures the amount of antibody binding: −, no staining; 1+, weak staining; 2+, moderate staining; and 3+, strong staining.
**The in situ imaging staining scoring is based on comparison with parental antibody staining: −, no staining; 1+, weak staining as compared to parental antibody; 2+, moderate staining as compared to parental antibody; and 3+, analogous staining to parental antibody.

TABLE 9

Screening for EGFR and MT-SP1 expression and in situ imaging of 3954-1204-C225 activatable antibody in human colorectal cancer liver metastasis tissues.

| Patient # | IHC* EGFR | IHC* MT-SP1 | in situ imaging** Cetuximab | in situ imaging** Activatable Antibody w/1204 | Tumor type | Stage | Grade | AJCC 7th ed. | Treatment |
|---|---|---|---|---|---|---|---|---|---|
| 10398 | ++ | ++ | ++ | + | Metastatic Adeno-carcinoma | N/A | N/A | N/A | N/A |
| 10404 | +++ | ++ | +++ | +++ | Metastatic Adeno-carcinoma | Stage IV | N/A | N/A | Yes - N/A |
| 10444 | +++ | + | ++ | +++ | Metastatic Adeno-carcinoma | Stage IV | N/A | N/A | Yes - N/A |
| 10465 | ++ | ++ | ++ | ++ | Metastatic Adeno-carcinoma | Stage IV | N/A | N/A | Yes - N/A |
| 10470 | ++ | ++ | ++ | ++ | Metastatic Adeno-carcinoma | Stage IV | N/A | N/A | FOLFIRI Avastin |
| 10484 | − | ++ | − | − | Metastatic Adeno-carcinoma | Stage IV | N/A | N/A | FOLFOX |
| 10498 | ++/+ | ++ | ++ | +++ | Metastatic Adeno-carcinoma | N/A | N/A | N/A | Chemo-FOLFIRI Radiation-Pelvic XRT |
| 10510 | ++ | +++ | + | +++ | Metastatic Adeno-carcinoma | Stage IV | N/A | N/A | Chemo- 5FU Leucovorin Radiation-Pelvic XRT |

TABLE 9-continued

Screening for EGFR and MT-SP1 expression and in situ imaging of 3954-1204-C225 activatable antibody in human colorectal cancer liver metastasis tissues.

| | IHC* | | in situ imaging** | | | | | | |
|---|---|---|---|---|---|---|---|---|---|
| | | | | Activatable | | | | | |
| Patient # | EGFR | MT-SP1 | Cetux-imab | Antibody w/1204 | Tumor type | Stage | Grade | AJCC 7th ed. | Treatment |
| 10515 | + | ++ | + | +/− | Metastatic Adenocarcinoma | N/A | N/A | N/A | FOLFIRI Avastin |
| 10517 | ++ | + | ++/+ | +++/++ | Metastatic Adenocarcinoma | Stage IV | N/A | N/A | FOLFOX |
| 10519 | ++ | + | ++ | +++ | Metastatic Adenocarcinoma | | G2, Moderately Differentiated | N/A | Folfox (Previous) CPT11, Leucovorin, 5FU (Current) |

*The IHC staining scored from − to 3+ that measures the amount of antibody binding: −, no staining; 1+, weak staining; 2+, moderate staining; and 3+, strong staining.
**The in situ imaging staining scoring is based on comparison with parental antibody staining: −, no staining; 1+, weak staining as compared to parental antibody; 2+, moderate staining as compared to parental antibody; and 3+, analogous staining to parental antibody.

TABLE 10

Screening for EGFR and MT-SP1 expression and in situ imaging of 3954-1204-C225 activatable antibody in human NSCLC patients tissues.

| | IHC* | | in situ imaging** | | | | | | |
|---|---|---|---|---|---|---|---|---|---|
| Patient # | EGFR | MT-SP1 | Cetux-imab | Activatable Antibody | Tumor type | Stage | Grade | AJCC 7th edition | Treatment |
| 5648 | − | − | − | − | Adenocarcinoma | Stage I | G2 Moderately differentiated | IB (pT2, pN0 (0/12), pM n/a) | UNKNOWN |
| 5608 | − | +++ | − | − | Adenocarcinoma | Stage I | G2 Moderately differentiated | IB (pT2, pN0(0/12), pM n/a) | NONE |
| 5624 | − | − | − | − | Squamous Cell Carcinoma | Stage I | G2 Moderately differentiated | IB (pT2a, pN0, pMn/a) | NONE |
| 5613 | + | − | ++ | + | Squamous Cell Carcinoma | Stage I | G3 Poorly differentiated | IB (pT2a, pN0, M n/a) | NONE |
| 5614 | +++ | ++ | +++ | ++ | Squamous Cell Carcinoma | Stage I | G3 Poorly differentiated | IB (pT2, pN0(0/12), pM n/a) | NONE |
| 5633 | + | +/− | + | + | Adenocarcinoma | Stage I | G2 Moderately differentiated | IA (pT1b, pN0, pMn/a) | YES - N/A |
| 5636 | + | + | + | + | Large Cell Carcinoma | Stage I | G3 Poorly differentiated | IA (pT1a, pN0, pMn/a) | NONE |
| 5630 | + | + | + | − | Squamous Cell Carcinoma | Stage I | G2 Moderately differentiated | IB (pT2a, pN0, pMn/a) | NONE |
| 5618 | +++ | + | +++ | +++ | Squamous Cell Carcinoma | Stage I | G2 Moderately differentiated | IB (pT2, pN0, pMn/a) | NONE |
| 5619 | + | +/− | ++ | + | Adenocarcinoma | Stage II | G2 Moderately differentiated | IIB (pT2, pN1, pM n/a) | NONE |
| 5627 | ++ | − | ++ | +++ | Squamous Cell Carcinoma | Stage II | G2 Moderately differentiated | IIB (pT2b, pN1, pM n/a) | NONE |
| 5629 | +++ | − | +++ | ++ | Adenocarcinoma | Stage II | G2 Moderately differentiated | IIB (pT2b, pN1, pMn/a) | NONE |
| 5646 | +/− | + | + | + | Large Cell Neuro-Endocrine Carcinoma | Stage II | G3 Poorly differentiated | IIB (pT2, pN1, pMX) | NONE |

TABLE 10-continued

Screening for EGFR and MT-SP1 expression and in situ imaging of 3954-1204-C225 activatable antibody in human NSCLC patients tissues.

| Patient # | IHC* EGFR | IHC* MT-SP1 | in situ imaging** Cetuximab | in situ imaging** Activatable Antibody | Tumor type | Stage | Grade | AJCC 7th edition | Treatment |
|---|---|---|---|---|---|---|---|---|---|
| 5654 | +/− | ++ | − | − | Large Cell Neuro-Endocrine Carcinoma | Stage II | G3 Poorly differentiated | IIA (pT2, pN0, pMn/a) | NONE |
| 5607 | − | + | − | − | Adeno-carcinoma | Stage III | G3 Poorly differentiated | IIIA (pT2, pN0, pMn/a) | NONE |
| 5610 | − | − | − | − | Squamous Cell Carcinoma | Stage III | G2 Moderately differentiated | IIIA (pT3, pN1) | NONE |
| 5615 | + | − | ++ | + | Squamous Cell Carcinoma | Stage III | G3 Poorly differentiated | IIIA (pT3, pN1, M n/a) | NONE |
| 5620 | +/− | − | − | − | Large Cell Basaloid Carcinoma | Stage III | G3 Poorly differentiated | IIIA (pT3, pN1, pMn/a) | NONE |
| 5621 | +++ | ++ | +++ | ++ | Squamous Cell Carcinoma | Stage III | G2 Moderately differentiated | IIIA (pT4, pN0, M n/a) | NONE |
| 5625 | +++ | ++ | +++ | ++ | Squamous Cell Carcinoma | Stage III | G2 Moderately differentiated | IIIA (pT4, pN2, pM n/a) | YES - N/A |

*The IHC staining scored from − to 3+ that measures the amount of antibody binding: −, no staining; 1+, weak staining; 2+, moderate staining; and 3+, strong staining.
**The in situ imaging staining scoring is based on comparison with parental antibody staining: −, no staining; 1+, weak staining as compared to parental antibody; 2+, moderate staining as compared to parental antibody; and 3+, analogous staining to parental antibody.

TABLE 11

Screening for EGFR and MT-SP1 expression and in situ imaging of 3954-1204-C225 activatable antibody in human colorectal cancer patients' tumor tissues.

| Specimen Number | Stage | Grade | Cetuximab* | PB1** |
|---|---|---|---|---|
| HF-0101-10 | Stage I | G2 Moderately Differentiated | ++ | +++ |
| HF-0101-38 | Stage I | G2, Moderately Differentiated | ++/+ | +++ |
| HF-0101-30 | Stage I | G2, Moderately Differentiated | ++ | ++ |
| HF-0101-31 | Stage I | G2, Moderately Differentiated | +++ | + |
| HF-0101-32 | Stage I | G2, Moderately Differentiated | ++ | ++ |
| HF-0101-33 | Stage I | G2, Moderately Differentiated | ++ | ++ |
| HF-0101-34 | Stage II | G2, Moderately Differentiated | ++ | ++ |
| HF-0101-24 | Stage IIA | G2, Moderately Differentiated | − | − |
| HF-0101-03 | Stage IIA | G2 Moderately Differentiated | ++ | ++ |
| HF-0101-04 | Stage IIA | G2 Moderately Differentiated | ++ | +++ |
| HF-0101-05 | Stage IIA | G3 Poorly Differentiated | +++ | + |
| HF-0101-11 | Stage IIA | G2 Moderately Differentiated | − | − |
| HF-0101-12 | Stage IIA | G3 Poorly Differentiated | + | − |
| HF-0101-07 | Stage IIA | G2 Moderately Differentiated | +++ | ++ |
| HF-0101-37 | Stage IIA | G2, Moderately Differentiated | ++ | +++ |
| HF-0101-18 | Stage IIA | G2, Moderately Differentiated | ++ | ++ |
| HF-0101-28 | Stage IIA | G2, Moderately Differentiated | ++ | ++ |
| HF-0101-29 | Stage IIA | G2, Moderately Differentiated | ++ | +++ |
| HF-0101-08 | Stage IIB | G2 Moderately Differentiated | +++ | +++ |
| HF-0101-22 | Stage IIB | G2, Moderately Differentiated | +++ | ++ |
| HF-0101-36 | Stage IIB | G2, Moderately Differentiated | +++ | ++ |
| HF-0101-19 | Stage IIIB | G2, Moderately Differentiated | +/− | +++ |
| HF-0101-25 | Stage IIIB | G2, Moderately Differentiated | ++ | ++ |
| HF-0101-26 | Stage IIIB | G2, Moderately Differentiated | + | ++ |
| HF-0101-09 | Stage IIIB | G3 Poorly Differentiated | ++ | +++ |
| HF-0101-06 | Stage IIIB | G2 Moderately Differentiated | ++ | ++ |

TABLE 11-continued

Screening for EGFR and MT-SP1 expression and in situ imaging of 3954-1204-C225 activatable antibody in human colorectal cancer patients' tumor tissues.

| Specimen Number | Stage | Grade | Cetuximab* | PB1** |
|---|---|---|---|---|
| HF-0101-14 | Stage IIIB | G2, Moderately Differentiated | ++ | ++ |
| HF-0101-15 | Stage IIIB | G2, Moderately Differentiated | +++ | ++ |
| HF-0101-17 | Stage IIIB | G2, Moderately Differentiated | +++ | +++ |
| HF-0101-20 | Stage IIIC | G2, Moderately Differentiated | ++ | +++ |

Cetuximab staining scored from − to 3+ that measures the amount of antibody binding: −, no staining; 1+, weak staining; 2+, moderate staining; and 3+, strong staining.
**PB1 staining scoring is based on comparison with parental antibody (Cetuximab)staining: −, no staining; 1+, weak staining as compared to parental antibody; 2+, moderate staining as compared to parental antibody; and 3+, analogous staining to parental antibody.

Example 6. Quantification of In Situ Imaging of Anti-EGFR Activatable Antibodies The present Example describes in situ imaging of the activation and binding of an anti-EGFR activatable antibody to biological tissues ex vivo in combination with anti-EGFR antibody IHC and A11 antibody IHC. The use of commercially available anti-EGFR antibody IHC allows one to normalize the staining of parental antibody (e.g. cetuximab) and anti-EGFR activatable antibody to the quantity of EGFR expression in a tissue. Co-staining with EGFR antibodies also enables qualitative quantification of in situ imaging of anti-EGFR activatable antibodies relative to the cetuximab staining normalized to EGFR expression. Quantification of the fluorescent signal can be performed using bioanalytical software for research imaging, such as MetaMorph. The staining of tissue with antibody that specifically recognizes the active site of MT-SP1 (antibody A11) can also be performed to monitor the activity of MT-SP1, an enzyme that proteolytically cleaves the substrate of activatable antibodies 3954-1204-C225v4, 3954-1204-C225v5, and 3954-1204-C225v6.

Quantification of in situ imaging of anti-EGFR activatable antibody cleavage by a cell or tissue performed in combination with EGFR IHC was conducted as follows: Frozen tissue sections were laid over glass slides and rinsed in PBS followed by PBS-T. A solution containing labeled anti-EGFR activatable antibodies (labeled, e.g., with a fluorescent tag) was applied on the tissue and incubated, e.g., for 1 hour at room temperature in an incubation buffer of 50 mM Tris-HCl buffer pH 7.4, containing 150 mM NaCl, 100 µM ZnCl$_2$, 5 mM CaCl$_2$ and 0.05% Tween 20; activatable antibody at a concentration of about 1µm/ml. The tissue was then rinsed in PBS-T to remove non-bound material, and endogenous IgG was blocked with 3% BSA. Sections were incubated with commercially available anti-Rabbit, anti-EGFR antibodies and labeled A11 antibodies (labeled, e.g., with a fluorescent tag), e.g., for 1 hour at room temperature. After rinsing, secondary antibody Anti-Rabbit IgG labeled with a fluorescent tag was applied and incubated on the sections e.g., for 30 minutes at room temperature at a concentration of 5 µg/ml to amplify the primary antibody. Sections were rinsed in PBS-T followed by PBS, counterstained with DAPI, and detectable label was measured. For example, when a fluorescent tag was used, the tissue was submitted to fluorescent microscopy. The ability of anti-EGFR activatable antibody to be activated and to bind to the receptor in situ was quantified by the following equation:

$$PbA = \frac{(Ab\ EGFR - Pb\ \text{in situ imaging})}{(Pb\ EGFR - Ab\ \text{in situ imaging})} \cdot 100\%,$$

which can also be written as:

$$PbA = \frac{(Pb\ \text{in situ imaging}/Pb\ EGFR)}{(Ab\ \text{in situ imaging}/Ab\ EGFR)} \cdot 100^*$$

where PbA=% of anti-EGFR activatable antibody activation and binding as compared to parental antibody (e.g. cetuximab), Ab EGFR=staining intensity of EGFR IHC on the section with cetuximab binding, Pb EGFR=staining intensity of EGFR IHC on the section with anti-EGFR activatable antibody in situ imaging, Ab in situ imaging=intensity of cetuximab binding, Pb in situ imaging=intensity of anti-EGFR activatable antibody binding.

Figure 9:
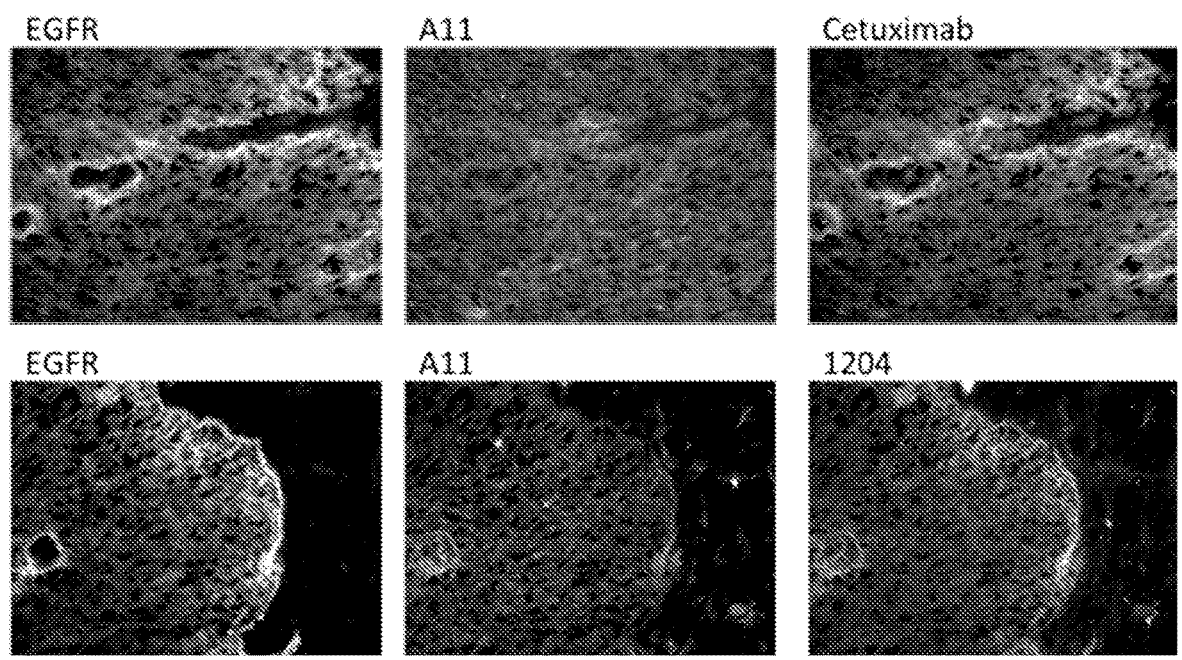
FIG. 9 is a series of images showing the triple staining of in situ imaging, EGFR IHC and A11 IHC. The upper row of images demonstrates the staining performed on a single tissue slice, demonstrating (left to right): EGFR expression, activity of matriptase (MT-SP1) and binding of cetuximab under in situ imaging conditions. The lower row of images demonstrates the staining performed on a single tissue slice, demonstrating (left to right): EGFR expression, activity of matriptase (MT-SP1) and in situ imaging of anti-EGFR activatable antibody 3954-1204-C225v5. The right column of images in FIG. 9 compares binding of cetuximab (upper image) and of anti-EGFR activatable antibody activated by tissue-derived proteolytic cleavage (lower image) under in situ imaging conditions. A similar pattern of tissue staining was detected by exposing a commercially available anti-EGFR antibody to the tissue, as shown in FIG. 9, left column of images.

Human esophageal and pancreatic cancer tissue samples were profiled for EGFR and MT-SP1 expression; the ability of anti-EGFR activatable antibody 3954-1204-C225v5 to be activated and to bind human tumor was evaluated using in situ imaging. The activatable antibody was labeled with Alexa Fluor® 680 (Invitrogen) as described above. The resultant activatable antibody 3954-1204-C225v5-AF680 was incubated with frozen patient tissue samples according to the protocol of in situ imaging described herein. Furthermore, EGFR and Alexa Fluor® 750 labeled A11 antibodies were used by treating frozen tissue with at 1 µg/ml and 5 µg/ml concentrations, respectively for 1 hour. FIG. 9 illustrates the ability of esophageal cancer tissues to activate and bind anti-EGFR activatable antibodies. The results on the ability of esophageal and pancreatic cancer patients' tissue samples to activate and bind anti-EGFR activatable antibodies are summarized in Table 12. The IHC staining that measures the amount of Cetuximab, EGFR and A11 antibodies binding to the tissue sample was scored from − to 3+: −, no staining; 1+ (i.e., "+"), weak staining; 2+ (i.e., "++"), moderate staining; and 3+ (i.e., "+++"), strong staining. The in situ imaging of anti-EGFR activatable antibodies staining was quantified based on comparison with cetuximab antibody staining normalized to EGFR staining and calculated by the equation described above.

TABLE 12

Screening for EGFR and MT-SP1 expression and in situ imaging of 3954-1204-C225 activatable antibody in human esophageal and pancreatic cancer patients tumor tissues.

| | IHC | | in situ imaging | | |
|---|---|---|---|---|---|
| Patient # | EGFR | MT-SP1 | Cetuximab | 3954-1204-C225 | Disease Diagnosis |
| 5586 | ++ | ++ | ++ | ~55% | Esophageal cancer |
| 5594 | +++ | ++ | +++ | ~90% | Esophageal cancer |

TABLE 12-continued

Screening for EGFR and MT-SP1 expression and in situ imaging of 3954-1204-C225 activatable antibody in human esophageal and pancreatic cancer patients tumor tissues.

| | IHC | | in situ imaging | | |
|---|---|---|---|---|---|
| Patient # | EGFR | MT-SP1 | Cetuximab | 3954-1204-C225 | Disease Diagnosis |
| 5595 | ++ | ++ | +++ | ~80% | Esophageal cancer |
| 5606 | +++ | +++ | +++ | ~100% | Esophageal cancer |
| 5641 | +++ | ++ | ++ | ~90% | Esophageal cancer |
| 5587 | ++ | +++ | ++ | ~100% | Pancreatic cancer |
| 5617 | + | + | + | ~80% | Pancreatic cancer |
| 5623 | ++ | ++ | ++ | ~75% | Pancreatic cancer |
| 13007 | ++ | ++ | ++ | ~100% | Pancreatic cancer |
| 13011 | − | + | − | — | Pancreatic cancer |

*The IHC and Cetuximab staining scored from − to 3+ that measures the amount of antibody binding: −, no staining; 1+, weak staining; 2+, moderate staining; and 3+, strong staining.
**The 3954-1204-C225 in situ imaging scoring is based on comparison with parental antibody staining normalized to the EGFR IHC staining and identified as % of activation: −, no activation; 100% activation resulting in staining analogous to staining to parental antibody.

FIG. 9 is a series of images showing the triple staining of in situ imaging, EGFR IHC and A11 IHC. The upper row of images demonstrates the staining performed on a single tissue slice, demonstrating (left to right): EGFR expression, activity of matriptase (MT-SP1) and binding of cetuximab under in situ imaging conditions. The lower row of images demonstrates the staining performed on a single tissue slice, demonstrating (left to right): EGFR expression, activity of matriptase (MT-SP1) and in situ imaging of anti-EGFR activatable antibody 3954-1204-C225v5 (1204). The right column of images in FIG. 9 compares binding of cetuximab (upper image) and of anti-EGFR activatable antibody activated by tissue-derived proteolytic cleavage (lower image) under in situ imaging conditions. The identical pattern of tissue staining was detected by exposing a commercially available anti-EGFR antibody to the tissue, as shown in FIG. 9, left column of images. FIG. 9, middle column of images, demonstrates co-localization of matriptase (MT-SP1) activity with EGFR expression. As used herein, the term "co-localization" is not intended to imply any overlay or other overlap of the EGFR and/or A11 staining, and the term "co-localization" is used to indicate the presence of MT-SP1 activity in EGFR-expressing patient tissue. Overall, these data demonstrate about 90% activation of anti-EGFR antibody 3954-1204-C255v5 by the human esophageal cancer tissue sample.

Example 7. In Situ Imaging of Anti-Jagged Activatable Antibodies

The present Example describes the use of in situ imaging of the activation and binding of an anti-Jagged activatable antibody of the disclosure.

The examples provided herein use an anti-Jagged activatable antibody, referred to herein as activatable antibody 5342-1204-4D11 (also referred to herein as 5342-1204-4D11 activatable antibody or 5342-1204-4D11) that includes an antibody or antigen binding fragment thereof (AB) that specifically binds both Jagged 1 and Jagged 2, a masking moiety (MM), and a cleavable moiety (CM) that is a substrate for a protease. The examples provided herein use an anti-Jagged activatable antibody, referred to herein as activatable antibody 5342-PLGL-4D11 (also referred to herein as 5342-PLGL-4D11 activatable antibody or 5342-PLGL-4D11) that includes an antibody or antigen binding fragment thereof (AB) that specifically binds both Jagged 1 and Jagged 2, a masking moiety (MM), and a cleavable moiety (CM) that is a substrate for a protease and includes the sequence PLGL. The examples provided herein use an anti-Jagged antibody, referred to herein as 4D11 that includes an antibody or antigen binding fragment thereof (AB) that specifically binds both Jagged 1 and Jagged 2. It is to be understood that while the examples provided herein use these anti-Jagged activatable antibody constructs, these methods are applicable to any activatable antibody.

Anti-Jagged Antibody Constructs and Anti-Jagged Activatable Antibody Constructs:

The 4D11 anti-Jagged antibody includes the following heavy and light chain sequences:

```
4D11 Light Chain Variable Region Nucleotide Sequence
                                                       (SEQ ID NO: 21)
GACATCCAGATGACCCAGTCTCCATCCTCCCTGTCTGCATCTGTAGGAGACAGAGTCACCATCA

CTTGCCGGGCAAGTCAGAGCATTAGCAGCTATTTAAATTGGTATCAGCAGAAACCAGGGAAAGC

CCCTAAGCTCCTGATCTATGCGGCATCCAGTTTGCAAAGTGGGGTCCCATCAAGGTTCAGTGGC

AGTGGATCTGGGACAGATTTCACTCTCACCATCAGCAGTCTGCAACCTGAAGATTTTGCAACTT

ACTACTGTCAACAGACGGTTGTGGCGCCTCCGTTATTCGGCCAAGGGACCAAGGTGGAAATCAA

ACGT

4D11 Light Chain Variable Region Amino Acid Sequence
                                                       (SEQ ID NO: 22)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKR

4D11 Heavy Chain Variable Region Nucleotide Sequence
                                                       (SEQ ID NO: 23)
GAGGTGCAGCTGTTGGAGTCTGGGGGAGGCTTGGTACAGCCTGGGGGGTCCCTGAGACTCTCCT

GTGCAGCCTCTGGATTCACCTTTAGCAGCTATGCCATGAGCTGGGTCCGCCAGGCTCCAGGGAA

GGGGCTGGAGTGGGTGTCAAGTATTGACCCGGAAGGTCGGCAGACATATTACGCAGACTCCGTG

AAGGGCCGGTTCACCATCTCCAGAGACAATTCCAAGAACACGCTGTATCTGCAAATGAACAGCC
```

-continued

TGAGAGCCGAGGACACGGCCGTATATTACTGTGCGAAAGACATCGGCGGCAGGTCGGCCTTTGA

CTACTGGGGCCAGGGAACCCTGGTCACCGTCTCCTCA

4D11 Heavy Chain Variable Region Amino Acid Sequence
(SEQ ID NO: 24)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSS

4D11 Light Chain Nucleotide Sequence
(SEQ ID NO: 25)
GACATCCAGATGACCCAGTCTCCATCCTCCCTGTCTGCATCTGTAGGAGACAGAGTCACCATCA

CTTGCCGGGCAAGTCAGAGCATTAGCAGCTATTTAAATTGGTATCAGCAGAAACCAGGGAAAGC

CCCTAAGCTCCTGATCTATGCGGCATCCAGTTTGCAAAGTGGGGTCCCATCAAGGTTCAGTGGC

AGTGGATCTGGGACAGATTTCACTCTCACCATCAGCAGTCTGCAACCTGAAGATTTTGCAACTT

ACTACTGTCAACAGACGGTTGTGGCGCCTCCGTTATTCGGCCAAGGGACCAAGGTGGAAATCAA

ACGTACGGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGGGAGAGT

GT

4D11 Light Chain Amino Acid Sequence
(SEQ ID NO: 26)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

4D11 Heavy Chain Nucleotide Sequence
(SEQ ID NO: 27)
GAGGTGCAGCTGTTGGAGTCTGGGGGAGGCTTGGTACAGCCTGGGGGGTCCCTGAGACTCTCCT

GTGCAGCCTCTGGATTCACCTTTAGCAGCTATGCCATGAGCTGGGTCCGCCAGGCTCCAGGGAA

GGGGCTGGAGTGGGTGTCAAGTATTGAAGAGATGGGTTGGCAGACAAAGTACGCAGACTCCGTG

AAGGGCCGGTTCACCATCTCCAGAGACAATTCCAAGAACACGCTGTATCTGCAAATGAACAGCC

TGAGAGCCGAGGACACGGCCGTATATTACTGTGCGAAATCGGCTGCTGCTTTTGACTACTGGGG

CCAGGGAACCCTGGTCACCGTCTCCTCAGCTAGCACCAAGGGCCCATCGGTCTTCCCCCTGGCA

CCCTCCTCCAAGAGCACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTGCACACCTTCCCGGC

TGTCCTACAGTCCTCAGGACTCTACTCCCTCAGCAGCGTGGTGACCGTGCCCTCCAGCAGCTTG

GGCACCCAGACCTACATCTGCAACGTGAATCACAAGCCCAGCAACACCAAGGTGGACAAGAAAG

TTGAGCCCAAATCTTGTGACAAAACTCACACATGCCCACCGTGCCCAGCACCTGAACTCCTGGG

GGGACCGTCAGTCTTCCTCTTCCCCCCAAAACCCAAGGACACCCTCATGATCTCCCGGACCCCT

GAGGTCACATGCGTGGTGGTGGACGTGAGCCACGAAGACCCTGAGGTCAAGTTCAACTGGTACG

TGGACGGCGTGGAGGTGCATAATGCCAAGACAAAGCCGCGGGAGGAGCAGTACAACAGCACGTA

CCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGC

CCCGAGAACCACAGGTGTACACCCTGCCCCCATCCCGGGAGGAGATGACCAAGAACCAGGTCAG

CCTGACCTGCCTGGTCAAAGGCTTCTATCCCAGCGACATCGCCGTGGAGTGGGAGAGCAATGGG

```
CAGCCGGAGAACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTCCGGGTAAA
```

4D11 Heavy Chain Amino Acid Sequence
(SEQ ID NO: 28)

```
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K
```

The 5342-1204-4D11 activatable anti-Jagged antibody construct includes the heavy chain sequences of the 4D11 antibody shown above in SEQ ID NO: 28 and the following light chain sequences:

5342-1204-4D11 Light Chain Nucleotide Sequence
(SEQ ID NO: 29)
```
CAAGGCCAGTCTGGCCAGTGCAATATTTGGCTCGTAGGTGGTGATTGCAG

GGGCTGGCAGGGGGGCTCGAGCGGTGGCAGCGGTGGCTCTGGTGGTCTGA

GCGGCCGTTCCGATAATCATGGCGGCGGTTCTGACATCCAGATGACCCAG

TCTCCATCCTCCCTGTCTGCATCTGTAGGAGACAGAGTCACCATCACTTG

CCGGGCAAGTCAGAGCATTAGCAGCTATTTAAATTGGTATCAGCAGAAAC

CAGGGAAAGCCCCTAAGCTCCTGATCTATGCGGCATCCAGTTTGCAAAGT

GGGGTCCCATCAAGGTTCAGTGGCAGTGGATCTGGGACAGATTTCACTCT

CACCATCAGCAGTCTGCAACCTGAAGATTTTGCAACTTACTACTGTCAAC

AGACGGTTGTGGCGCCTCCGTTATTCGGCCAAGGGACCAAGGTGGAAATC

AAACGTACGGTGGCTGCACCATCTGTCTTCATCTTCCCGCCATCTGATGA

GCAGTTGAAATCTGGAACTGCCTCTGTTGTGTGCCTGCTGAATAACTTCT

ATCCCAGAGAGGCCAAAGTACAGTGGAAGGTGGATAACGCCCTCCAATCG

GGTAACTCCCAGGAGAGTGTCACAGAGCAGGACAGCAAGGACAGCACCTA

CAGCCTCAGCAGCACCCTGACGCTGAGCAAAGCAGACTACGAGAAACACA

AAGTCTACGCCTGCGAAGTCACCCATCAGGGCCTGAGCTCGCCCGTCACA

AAGAGCTTCAACAGGGGAGAGTGT
```

5342-1204-4D11 Light Chain Amino Acid Sequence
(SEQ ID NO: 30)
```
QGQSGQCNIWLVGGDCRGWQGGSSGGSGGSGGLSGRSDNHGGGSDIQMTQ

SPSSLSASVGDRVTITCRASQSISSYLNWYQQKPGKAPKLLIYAASSLQS

GVPSRFSGSGSGTDFTLTISSLQPEXFATYYCQQTVVAPPLFGQGTKVEI

KRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVT

KSFNRGEC
```

The 5342-PLGL-4D11 activatable anti-Jagged antibody construct includes the heavy chain sequences of the 4D11 antibody shown above and the following light chain sequences:

5342-PLGL-4D11 Light Chain Nucleotide Sequence
(SEQ ID NO: 31)
```
CAAGGCCAGTCTGGCCAGTGCAATATTTGGCTCGTAGGTGGTGATTGCAG

GGGCTGGCAGGGGGCTCGAGCGGTGGCAGCGGTGGCTCTGGTGGCTCAG

GTGGAGGCTCGCCACTGGGCCTGGGCGGTTCTGACATCCAGATGACCCAG

TCTCCATCCTCCCTGTCTGCATCTGTAGGAGACAGAGTCACCATCACTTG

CCGGGCAAGTCAGAGCATTAGCAGCTATTTAAATTGGTATCAGCAGAAAC

CAGGGAAAGCCCCTAAGCTCCTGATCTATGCGGCATCCAGTTTGCAAAGT

GGGGTCCCATCAAGGTTCAGTGGCAGTGGATCTGGGACAGATTTCACTCT

CACCATCAGCAGTCTGCAACCTGAAGATTTTGCAACTTACTACTGTCAAC

AGACGGTTGTGGCGCCTCCGTTATTCGGCCAAGGGACCAAGGTGGAAATC

AAACGTACGGTGGCTGCACCATCTGTCTTCATCTTCCCGCCATCTGATGA

GCAGTTGAAATCTGGAACTGCCTCTGTTGTGTGCCTGCTGAATAACTTCT

ATCCCAGAGAGGCCAAAGTACAGTGGAAGGTGGATAACGCCCTCCAATCG

GGTAACTCCCAGGAGAGTGTCACAGAGCAGGACAGCAAGGACAGCACCTA

CAGCCTCAGCAGCACCCTGACGCTGAGCAAAGCAGACTACGAGAAACACA

AAGTCTACGCCTGCGAAGTCACCCATCAGGGCCTGAGCTCGCCCGTCACA

AAGAGCTTCAACAGGGGAGAGTGT
```

5342-PLGL-4D11 Light Chain Amino Acid Sequence
(SEQ ID NO: 32)
```
QGQSGQCNIWLVGGDCRGWQGGSSGGSGGSGGSGGGSPLGLGGSDIQMTQ

SPSSLSASVGDRVTITCRASQSISSYLNWYQQKPGKAPKLLIYAASSLQS

GVPSRFSGSGSGTDFTLTISSLQPEDFATYYCQQTVVAPPLFGQGTKVEI

KRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVT

KSFNRGEC
```

In situ imaging of activatable antibodies represents a unique approach to characterize protease activity in cells and tissue. This technology enables validation of activatable antibody activation and binding to a target in histological sections of cells and tissues expressing proteases capable of cleaving the activatable antibody. A schematic of such an in situ approach is presented in FIG. 1.

In situ imaging of the activation and binding of an anti-Jagged activatable antibody (also referred to herein as in situ imaging) by a cell or tissue capable of cleaving the activatable antibody at a site co-localized with the target recognized by the activated antibody was conducted as follows: Frozen tissue sections were laid over glass slides. A solution containing labeled anti-Jagged activatable antibodies (labeled, e.g., with a fluorescent tag) was applied on the tissue and incubated, e.g., for 1 hour at room temperature (about 22-24° C.) in an incubation buffer of 50 mM Tris-HCl buffer pH 7.4, containing 150 mM NaCl, 100 µM $ZnCl_2$, 5 mM $CaCl_2$ and 0.05% Tween 20; activatable antibody at a concentration of about 1 µg/ml. The tissue was then extensively washed to remove non-bound material and detectable label was measured. For example, when a fluorescent tag was used, the tissue was submitted to fluorescent microscopy. Detection of activated antibody on the tissue indicated that the tissue expressed proteases that cleaved the activatable antibody and also expressed Jagged targets to which the activated antibody bound.

The abilities of anti-Jagged activatable antibodies 5342-1204-4D11 and 5342-PLGL-4D11 to be activated and to bind BxPC3 xenograft tumor tissue were evaluated using in situ imaging. The activatable antibodies were labeled with Alexa Fluor® 680 (Invitrogen) to produce labeled activatable antibodies 5342-1204-4D11-AF680 and 5342-PLGL-4D11-AF680, also referred to herein as 1204-4D11-AF680 and PLGL-4D11-AF680, respectively. Also tested was labeled anti-Jagged parental antibody 4D11-AF680. Each of 4D11-AF680, 1204-4D11-AF680 and PLGL-4D11-AF680 was incubated with a frozen BxPC3 xenograft tumor tissue sample as described above. The results are shown on FIG. 10, panels A, B, and C, respectively. The red fluorescent tissue images demonstrate binding of 4D11 antibody and of 4D 11 antibodies activated by tissue-derived proteolytic cleavage of the respectively activatable antibodies to Jagged. Panels D, E, and F represent the fluorescent images obtained after incubation of 4D11-AF680, 1204-4D11-AF680 and PLGL-4D11-AF680 with frozen BxPC3 xenograft tumor tissue pre-treated with a 1:100 dilution of broad spectrum protease inhibitor cocktail set III (Catalog No. 539134, EMD Millipore) and 50 micromolar (µM) Galardin (Catalog No. 364205, Calbiochem Millipore). Reduced red fluorescence in panels E and F indicates that the binding of activatable antibodies 1204-4D11-AF680 and PLGL-4D11-AF680 seen in panels B and C was effected by cleavage of the activatable antibodies by tissue-derived proteases; the protease inhibitor cocktail inhibited such proteolysis. Blue staining represents DAPI nuclear staining Binding of anti-Jagged parental antibody 4D11 or of anti-Jagged activatable antibodies 5342-1204-4D11 and 5342-PLGL-4D11 to frozen BxPC3 xenograft tumor tissue was inhibited by pre-treating such tissue with unlabeled anti-Jagged parental antibody 4D11 or by pre-treating such tissue with Jagged 1, Jagged 2, or a combination thereof.

Figure 11:
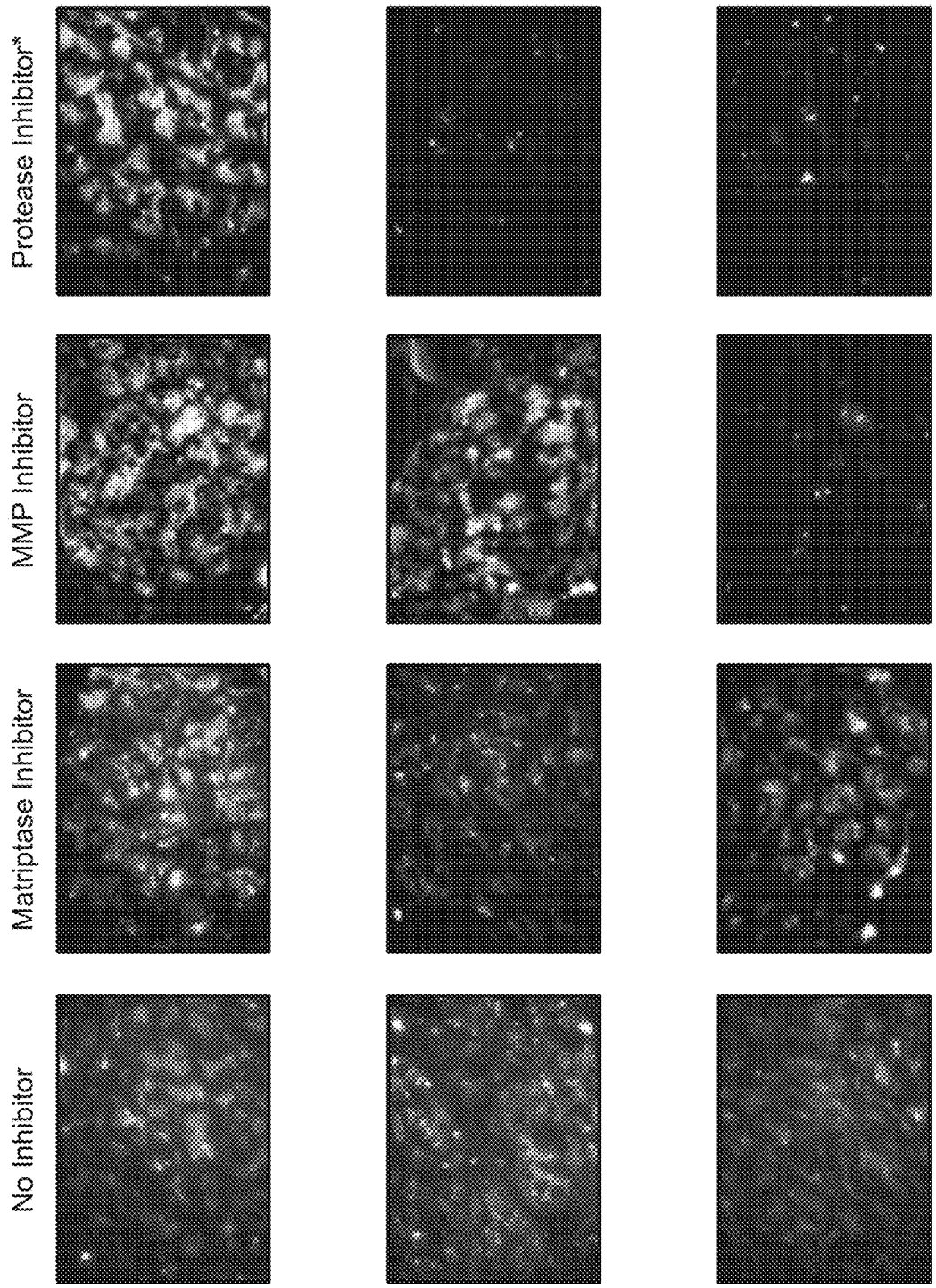
FIG. 11 is a series of images depicting activation of anti-Jagged activatable antibodies 5342-1204-4D11 and 5342-PLGL-4D11 as demonstrated by in situ imaging of human pancreatic cancer tissue. Each of 4D11-AF680 (4D11) (column 1, row 1), 5342-1204-4D11-AF680 (1204) (col. 1, row 2) and 5342-PLGL-4D11-AF680 (PLGL) (col. 1, row 3) was incubated with a frozen tissue sample isolated from a human patient with pancreatic cancer. The panels in Columns 2, 3, and 4, respectively, represent the fluorescent images obtained after incubation of 4D11-AF680, 5342-1204-4D11-AF680 and 5342-PLGL-4D11-AF680 with frozen pancreatic cancer patient tissue pre-treated antibody A11, an antibody that specifically binds to the active site of the MT-SP1 protease, also known as matriptase; (col. 2); with an MMP inhibitor (FIG. 11, col. 3); or with a broad spectrum protease inhibitor cocktail (col. 4).

Activation of anti-Jagged activatable antibodies 5342-1204-4D11 and 5342-PLGL-4D11 were also evaluated by in situ imaging of human pancreatic cancer tissue. Each of 4D11-AF680 4D11), 1204-4D11-AF680 (1204) and PLGL-4D11-AF680 (PLGL) was incubated with a frozen tissue sample isolated from a human patient with pancreatic cancer. The results are shown on FIG. 11, panels in column 1, rows 1, 2, and 3, respectively. The panels in Columns 2, 3, and 4, respectively, represent the fluorescent images obtained after incubation of 4D11-AF680, 1204-4D11-AF680 and PLGL-4D11-AF680 with frozen pancreatic cancer patient tissue pre-treated with 10 µg/ml of antibody A11 (A11 is an antibody that specifically binds to the active site of the MT-SP1 protease, also known as matriptase) (FIG. 11, column 2) with 50 µM of broad spectrum MMP inhibitor Galardin (Calbiochem, Millipore) (FIG. 11, column 3) or with a 1:100 dilution of broad spectrum protease inhibitor cocktail set III (Cat. No. 539134, EMD Millipore) and 50 µM Galardin (FIG. 11, column 4). Blue staining represents DAPI nuclear staining. The results suggest that the pancreatic tissue sample produces active matriptase and metalloprotease, the presence of which effects cleavage of respective activatable antibody cleavable moieties, thereby releasing the masking moiety and enabling stable binding of the activated antibody to Jagged targets on the tissue.

Example 8 In situ Imaging of Anti-Jagged Activatable Antibodies

The present Example describes the use of in situ imaging to screen pancreatic cancer xenograft tumor tissue and human pancreatic cancer tissue for the activation and binding of an anti-Jagged activatable antibody. The results indicate that anti-Jagged activatable antibodies of the disclosure can be activated by proteases expressed by such tissues and bind Jagged targets on such tissues.

BxPC3 tumor samples and human pancreatic cancer tissue samples were profiled for Jagged and MT-SP1 expression by 1 hour treatment of frozen tissue with labeled anti-Jagged antibody 4D11 and anti-matriptase A11 antibody at 1 µg/ml and 5 µg/ml concentrations, respectively. The results are shown in Table 13, columns 2 and 3, respectively.

Figure 10:
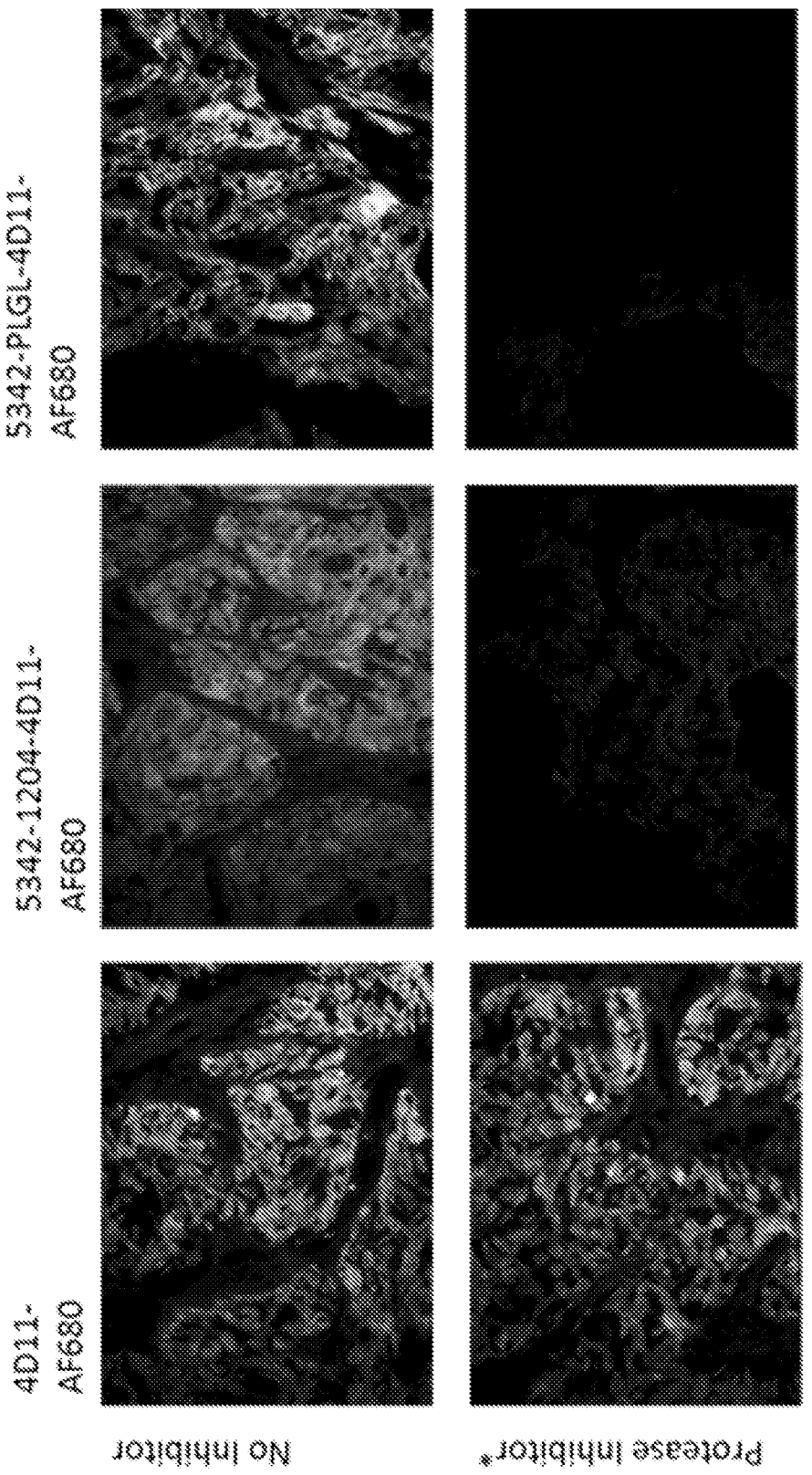
FIG. 10 is a series of images depicting the abilities of anti-Jagged activatable antibodies referred to herein as 5342-1204-4D11 and 5342-PLGL-4D11 to be activated and to bind BxPC3 xenograft tumor tissue as demonstrated using in situ imaging; CM PLGL (amino acid sequence PLGL, SEQ ID NO: 214) is a pan-MMP substrate. The activatable antibodies were labeled with Alexa Fluor® 680 to produce labeled activatable antibodies 5342-1204-4D11-AF680 and 5342-PLGL-4D11-AF680. Also tested was labeled anti-Jagged parental antibody 4D11-AF680. Each of 4D11-AF680 (Panel A), 5342-1204-4D11-AF680 (Panel B) and 5342-PLGL-4D11-AF680 (Panel C) was incubated with a frozen BxPC3 xenograft tumor tissue sample. Panels D, E, and F represent the fluorescent images obtained after incubation of 4D11-AF680, 5342-1204-4D11-AF680 and 5342-PLGL-4D11-AF680 with frozen BxPC3 xenograft tumor tissue pre-treated with a broad spectrum protease inhibitor cocktail.

In addition, the abilities of anti-Jagged activatable antibodies 5342-1204-4D11 and 5342-PLGL-4D11 to be activated and to bind BxPC3 xenograft and human pancreatic cancer tissues were evaluated using in situ imaging. The activatable antibodies were labeled with Alexa Fluor® 680 (Invitrogen) as described above (Example 7). These labeled activatable antibodies, i.e., 5342-1204-4D11-AF680 (also referred to herein as 1204-4D11-AF680) and 5342-PLGL-4D11-AF680 (also referred to herein as PLGL-4D11-AF680), were incubated with frozen BxPC3 xenograft tissue or with human pancreatic cancer tissue samples isolated from four patients according to the protocol of in situ imaging described above (Example 7). Table 13 summarizes the results demonstrating the ability of BxPC3 tumor and pancreatic cancer patients' tissue samples to activate and bind activated anti-Jagged activatable antibodies. In Table 13, the IHC staining that measured the amount of anti-Jagged antibody 4D11 or anti-matriptase antibody A11 binding to the tissue samples (columns 2 and 3) was scored from – to 3+: –, no staining; 1+, weak staining; 2+, moderate staining; and 3+, strong staining. The in situ imaging staining (columns 4 and 5) scoring is based on comparison with 4D11 antibody staining and defined as follows: –, no staining; 1+, weak staining as compared to parental antibody; 2+, moderate staining as compared to parental antibody; and 3+, analogous staining to parental antibody. The BxPC3 results are also shown in FIG. 10.

TABLE 13

Screening for Jagged and MT-SP1 expression and in situ imaging of anti-Jagged activatable antibodies in BxPC3 xenograft and human pancreatic cancer tissues.

| | IHC | | in situ imaging | |
|---|---|---|---|---|
| Specimen # | 4D11 | A11 | 4D11-1204-AF680 | 4D11-PLGL-AF680 |
| BxPC3 | ++ | ++ | +++ | +++ |
| 5587 | ++ | + | ++ | +++ |
| 5617 | +++ | ++ | +++ | ++ |
| 5623 | +++ | ++ | ++ | + |
| 5631 | ++ | − | ++ | + |

Example 9 In vivo and Ex Vivo Imaging of Anti-EGFR Activatable Antibodies

The examples provided herein use an anti-EGFR activatable antibody, referred to herein as activatable antibody 3954-1204-C225v4 (also referred to herein as 3954-1204-C225v4 activatable antibody or 3954-1204-C225v4) that includes an EGFR-binding sequence, a masking moiety (MM), and a cleavable moiety (CM) that is a substrate for a protease. These examples also use a masked anti-EGFR antibody construct referred to herein as masked antibody 3954-NSUB-C225v4 (also referred to herein as 3954-NSUB-C225v4 masked antibody or 3954-NSUB-C225v4) that includes a non-cleavable moiety located between the MM and the EGFR-binding sequence. It is to be understood that while the examples provided herein use these anti-EGFR activatable antibody constructs, these methods are applicable to any activatable antibody.

The 3954-1204-C225v4 activatable anti-EGFR antibody construct includes the following heavy and light chain sequences:

```
3954-1204-C225v4 Activatable Antibody
Heavy Chain Nucleotide Sequence:
[C225v4 (SEQ ID NO: 243)]
                                          (SEQ ID NO: 243)
[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacacccccgtttac cagccgcctgagcattaacaaagataacagcaaaagccaggtgttttttaaaatgaacagcctg caaagcaacgataccgcgatttattattgcgcgcgcgcgctgacctattatgattatgaatttg cgtattggggccagggcaccctggtgaccgtgagcgcggctagcaccaagggcccatcggtctt cccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagccctcccagccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]
```

```
3954-1204-C225v4 Activatable Antibody
Heavy Chain Amino Acid Sequence:
[C225v4 (SEQ ID NO: 244)]
                                          (SEQ ID NO: 244)
[QVQLKQSGPGLVQPSQSLSITCTVSGFSLTNYGVHWVRQSPGKGLEWLGVIWSGGNTDYNTPF

TSRLSINKDNSKSQVFFKMNSLQSNDTAIYYCARALTYYDYEFAYWGQGTLVTVSAASTKGPSV
```

-continued

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

3954-1204-C225v4 Activatable Antibody
Light Chain Nucleotide Sequence:
[Spacer (SEQ ID NO: 5)][Mask (SEQ ID
NO: 6)][Linker 1 (SEQ ID NO: 7)][1204
Substrate (SEQ ID NO: 8)][Linker 2 (SEQ
ID NO: 9)][C225v4 (SEQ ID NO: 247)]

(SEQ ID NO: 245)
[caaggccagtctggccag][tgcatctcacctcgtggttgtccggacggcccatacgtcatgt ac][*ggctcgagcggtggcagcggtggctctggtggatccggt*][ctgagcggccgttccgata atcat][*ggcagtagcggtacc*][cagatcttgctgacccagagccggtgattctgagcgtga gcccgggcgaacgtgtgagctttagctgccgcgcgagccagagcattggcaccaacattcattg gtatcagcagcgcaccaacggcagcccgcgcctgctgattaaatatgcgagcgaaagcattagc ggcattccgagccgctttagcggcagcggcagcggcaccgattttaccctgagcattaacagcg tggaaagcgaagatattgcggattattattgccagcagaacaacaactggccgaccacctttgg cgcgggcaccaaactggaactgaaacgtacggtggctgcaccatctgtcttcatcttcccgcca tctgatgagcagttgaaatctggaactgcctctgttgtgtgcctgctgaataacttctatccca gagaggccaaagtacagtggaaggtggataacgccctccaatcgggtaactcccaggagagtgt cacagagcaggacagcaaggacagcacctacagcctcagcagcaccctgacgctgagcaaagca gactacgagaaacacaaagtctacgcctgcgaagtcacccatcagggcctgagctcgcccgtca caaagagcttcaacaggggagagtgttag]

3954-1204-C225v4 Activatable Antibody
Light Chain Amino Acid Sequence:
[Spacer (SEQ ID NO: 11)][Mask (SEQ ID
NO: 12)][Linker 1 (SEQ ID NO: 13)][1204
Substrate (SEQ ID NO: 14)][Linker 2 (SEQ
ID NO: 15)][C225v4 (SEQ ID NO: 248)]

(SEQ ID NO: 246)
[QGQSGQ][CISPRGCPDGPYVMY][*GSSGGSGGSGGSG*][LSGRSDNH][*GSSGT*][QILLIQ

SPVILSVSPGERVSFSCRASQSIGTNIHWYQQRTNGSPRLLIKYASESISGIPSRFSGSGSGTD

FTLSINSVESEDIADYYCQQNNNWPTTFGAGTKLELKRTVAAPSVFIFPPSDEQLKSGTASVVC

LLNNFYPREAKVQWKVDNALQSGNSQESVTEQDSKDSTYSLSSTLTLSKADYEKHKVYACEVTH

QGLSSPVTKSFNRGEC*]

The 3954-NSUB-C225v4 masked anti-EGFR antibody construct includes the same heavy chain as the 3954-1204-C225v4 activatable anti-EGFR antibody shown above. The 3954-NSUB-C225v4 masked anti-EGFR antibody construct includes the following light chain sequence:

3954-NSUB-C225v4 Masked Antibody Light
Chain Nucleotide Sequence: [Spacer
(SEQ ID NO: 5)][Mask (SEQ ID NO: 6)]
[Linker 1-Noncleavable Substrate-Linker
2 (SEQ ID NO: 19)][C225 (SEQ ID NO: 247)]
[caaggccagtctggccag][tgcatctcacctcgtggttgtccggacgg cccatacgtcatgtac][*ggctcgagcggtggcagcggtggctctggtgg*

-continued
*ctcaggtggaggctcgggcggtgggagcggcggttct*][cagatcttgct gacccagagccggtgattctgagcgtgagcccgggcgaacgtgtgagct ttagctgccgcgcgagccagagcattggcaccaacattcattggtatcag cagcgcaccaacggcagcccgcgcctgctgattaaatatgcgagcgaaag cattagcggcattccgagccgctttagcggcagcggcagcggcaccgatt ttaccctgagcattaacagcgtggaaagcgaagatattgcggattattat tgccagcagaacaacaactggccgaccacctttggcgcgggcaccaaact ggaactgaaacgtacggtggctgcaccatctgtcttcatcttcccgccat -continued ctgatgagcagttgaaatctggaactgcctctgttgtgtgcctgctgaat aacttctatcccagagaggccaaagtacagtggaaggtggataacgccct ccaatcgggtaactcccaggagagtgtcacagagcaggacagcaaggaca gcacctacagcctcagcagcacctgacgctgagcaaagcagactacgag aaacacaaagtctacgcctgcgaagtcacccatcagggcctgagctcgcc cgtcacaaagagcttcaacaggggagagtgttag]

3954-NSUB-C225v4 Masked Antibody Light
Chain Amino Acid Sequence: [Spacer
(SEQ ID NO: 11)][Mask (SEQ ID NO: 12)]
[Linker 1-Noncleavable Substrate-Linker
2 (SEQ ID NO: 20)1[C225v4 (SEQ ID NO: 248)]
(SEQ ID NO: 250)
[QGQSGQ][CISPRGCPDGPYVMY][GSSGGSGGSGGSGGGSGGGSGGS]

[QILLTQSPVILSVSPGERVSFSCRASQSIGTNIHWYQQRTNGSPRLLIK

YASESISGIPSRFSGSGSGTDFTLSINSVESEDIADYYCQQNNNWPTTFG

AGTKLELKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC*]

The masking moiety (MM) used in the 3954-1204-c225v4 activatable anti-EGFR antibody can be cleaved by two serine proteases known to be upregulated in a variety of human carcinomas: urokinase-type plasminogen activator (uPA) and membrane type serine protease 1 (MT-SP1/matriptase). The 3954-NSUB-c225v4 masked anti-EGFR antibody was used as a negative control, as it contains a non-cleavable substrate sequence resulting in a protease-resistant activatable antibody.

Figure 13A:
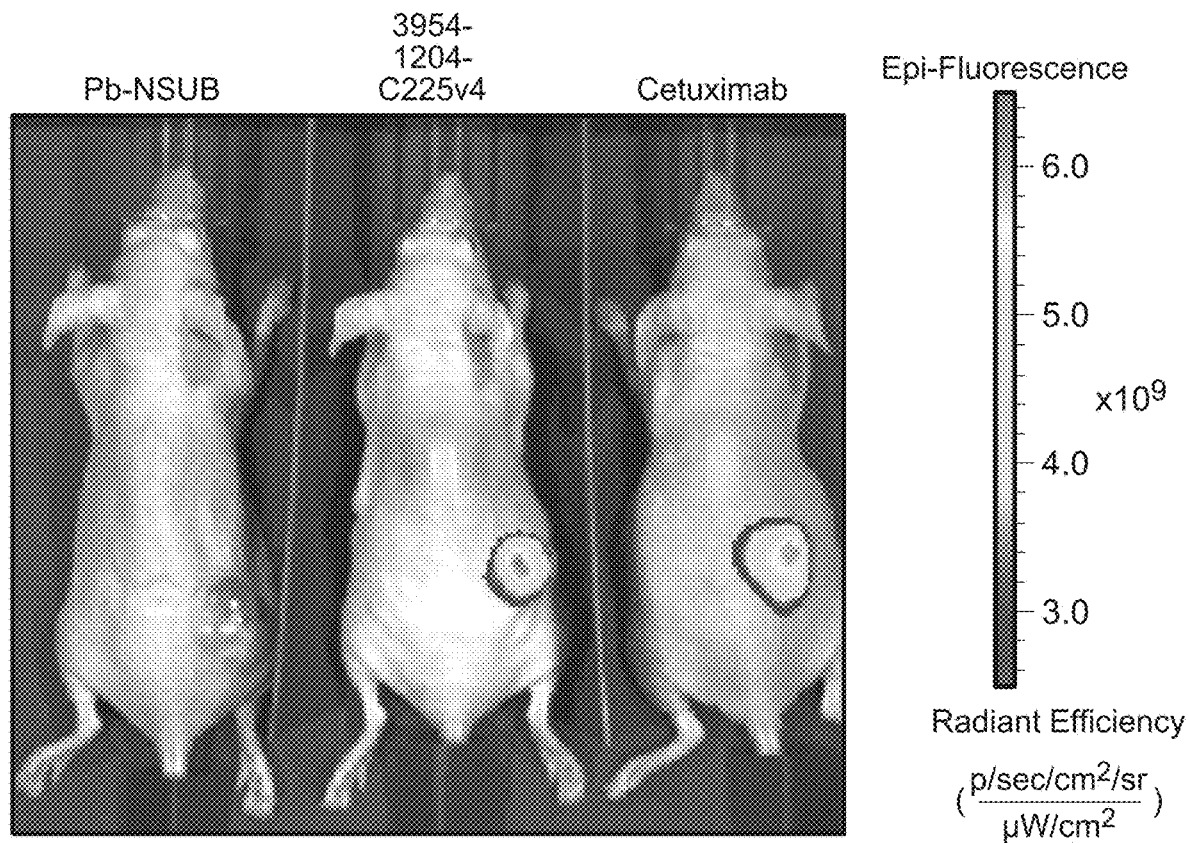
FIGS. 13A and 13B are a series of photographs that depict optical imaging of H292 xenograft tumor bearing mice injected intraperitoneally with a masked anti-EGFR antibody construct referred to herein as masked antibody 3954-NSUB-C225v4, the activatable anti-EGFR antibody construct referred to herein as 3954-1204-C225v4 or cetuximab (i.e., unmodified cetuximab). The mice were imaged using an IVIS Spectrum/CT imaging system (Caliper Life-Sciences) (FIG. 13A). Necropsy was used to evaluate bio-distribution ex vivo (FIG. 13B). These photographs demonstrate that the 3954-1204-C225v4 activatable antibody localizes to the tumor site in the H292 xenograft mouse model.
Figure 13B:
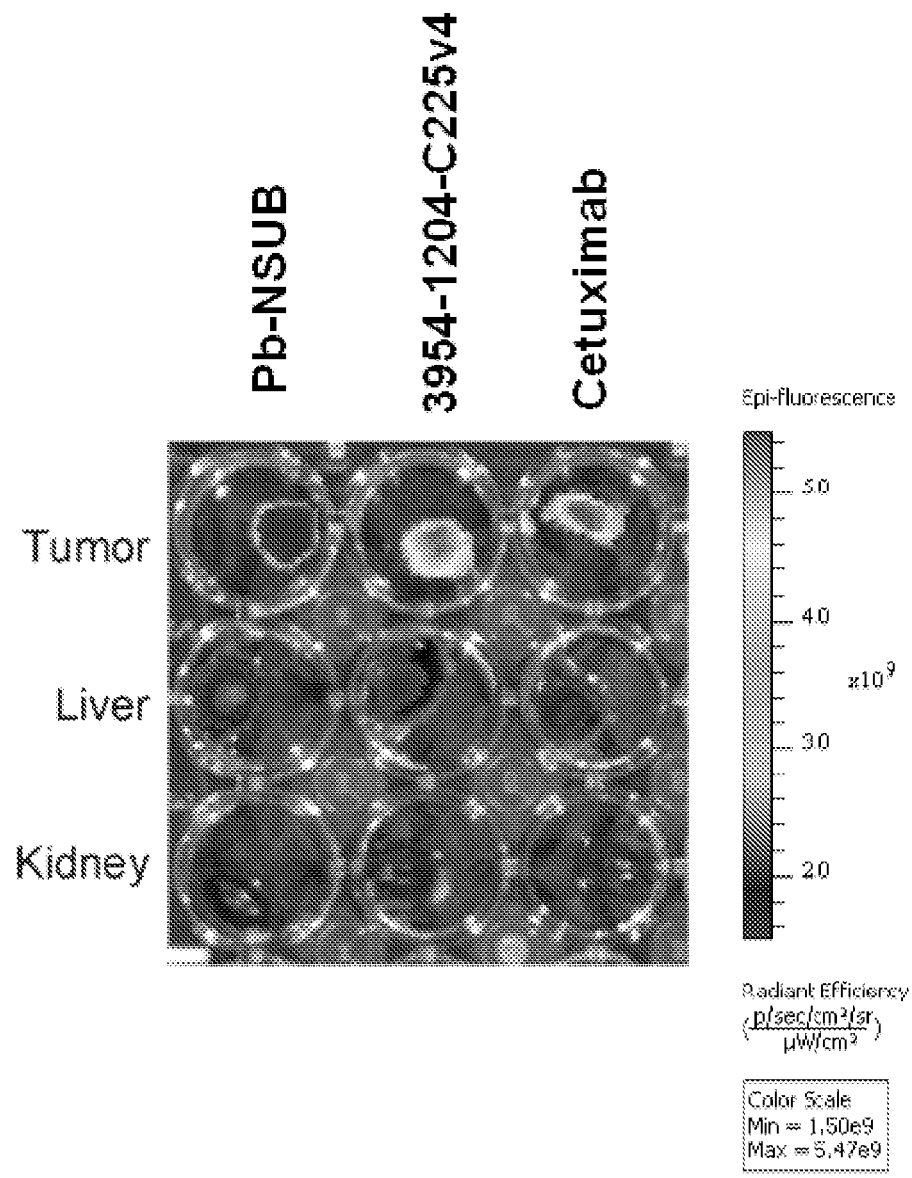

Evaluation of activatable anti-EGFR antibody distribution in vivo by optical imaging. HT29 xenograft tumor bearing mice were injected intraperitoneally with 12.5 mg/kg Alexa Fluor 750 conjugated activatable anti-EGFR antibodies. One hour before imaging the mice were injected intravenously with quenched PEGylated Cy5.5 substrate probes (2 nmol). The mice were imaged 24 h after activatable anti-EGFR antibody injection using an IVIS Spectrum/CT imaging system (Caliper LifeSciences). During the procedure, the mice were kept under gaseous anesthesia (5% isofluorane) at 37° C. Imaging at 750 nm was used to evaluate accumulation levels of the activatable anti-EGFR antibody 3954-1204-C225v4 and the non-cleavable masked anti-EGFR antibody 3954-NSUB-C225v4, as distribution of the labeled activatable anti-EGFR antibody construct at this wavelength is an indication of antibody activation and EGFR receptor binding. Imaging at 680 nm was used to evaluate the level of substrate cleavage by monitoring probe activation kinetics in tumor tissue. Finally, necropsy was used to evaluate biodistribution ex vivo. The results are shown in FIGS. 13A and 13B.

Example 10. In Situ Imaging of Non-Labeled Anti-EGFR Activatable Antibodies

The present Example describes the use of in situ imaging of non-labeled anti-EGFR activatable antibodies containing substrates that are cleaved by single protease. Cleavage was detected using a secondary antibody that specifically binds to the AB portion of the activatable antibody. The results indicate the ability to evaluate the activation and binding of non-labeled activatable antibodies.

Figure 14:
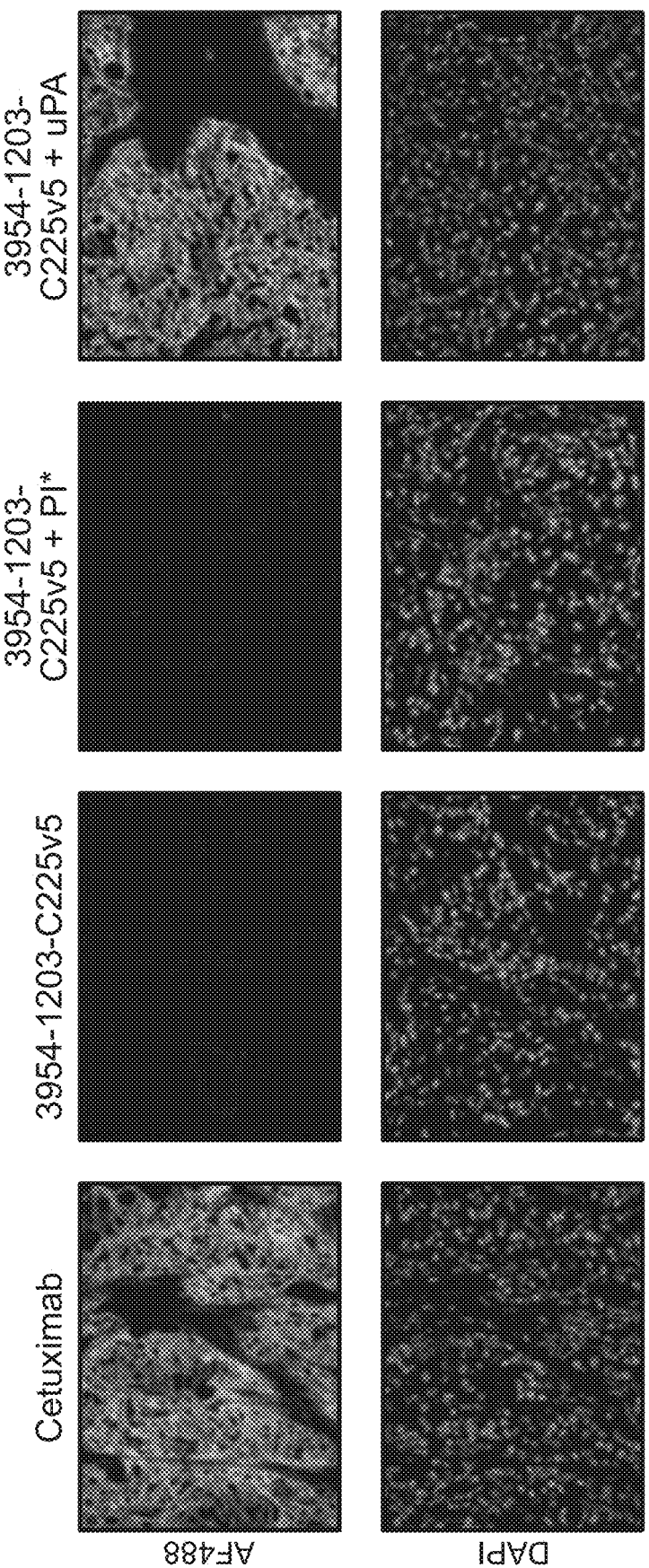
FIG. 14 is a series of images depicting the feasibility of conducting in situ imaging using non-labeled (i.e., unlabeled) activatable antibodies and a secondary reagent that comprises a detectable label and that specifically binds the AB of the activatable antibody.

In situ imaging of the activation and binding of a non-labeled anti-EGFR activatable antibody 3954-1203-C225v5 containing substrate 1203 (amino acid sequence TGRGPSWV, SEQ ID NO:196; cleavable by uPA) on H292 xenograft tumor tissue was conducted as follows: Frozen tissue sections were laid over glass slides. A solution containing non-labeled anti-EGFR activatable antibodies was applied on the tissue and incubated, e.g., for 1 hour at room temperature (about 22-24° C.) in an incubation buffer of 50 mM Tris-HCl buffer pH 7.4, containing 150 mM NaCl, 100 µM $ZnCl_2$, 5 mM $CaCl_2$ and 0.05% Tween 20; activatable antibody at a concentration of about 1µm/ml. The conditions of such an incubation can be adjusted to be conducive to the cleavage agent in the tissue section by, for example, varying the pH of the solution (e.g., within a range of about pH 7 to about pH 8.5), the temperature of the incubation (e.g., within a range of about 20° C. to about 40° C., e.g., room temperature or 37° C.), the incubation time (e.g., within a range of about 15 minutes to about 150 minutes, and/or the activatable antibody concentrations (e.g., within a range of about 0.05 µg/ml to about 10 µg/ml). The tissue was then extensively washed to remove non-bound material. The presence of activated antibody on the tissue was detected using a secondary anti-human IgG antibody labeled with FITC. The conditions of that detection can be adjusted to the detecting reagent and detection modality (e.g., fluorescently labeled). For example, when a fluorescent tag was used, the tissue was submitted to fluorescent microscopy. As shown in FIG. 14, anti-EGFR activatable antibody 3954-1203-C225v5 demonstrated undetectable staining using labeled anti-human IgG as compared to non-labeled cetuximab control, suggesting that the H292 xenograft tumor sample expressed very low levels, if any, uPA. In contrast, addition of recombinant uPA to the tissue during the in situ imaging procedure of activatable antibody 3954-12103-C255v5 demonstrated positive staining, similar to that of cetuximab, indicating that it is possible to conduct in situ imaging with non-labeled activatable antibodies and a secondary reagent that specifically binds to the activatable antibody, such as a labeled antibody.

Example 11. In Situ Imaging Using Tissue Microarrays

Figure 21:
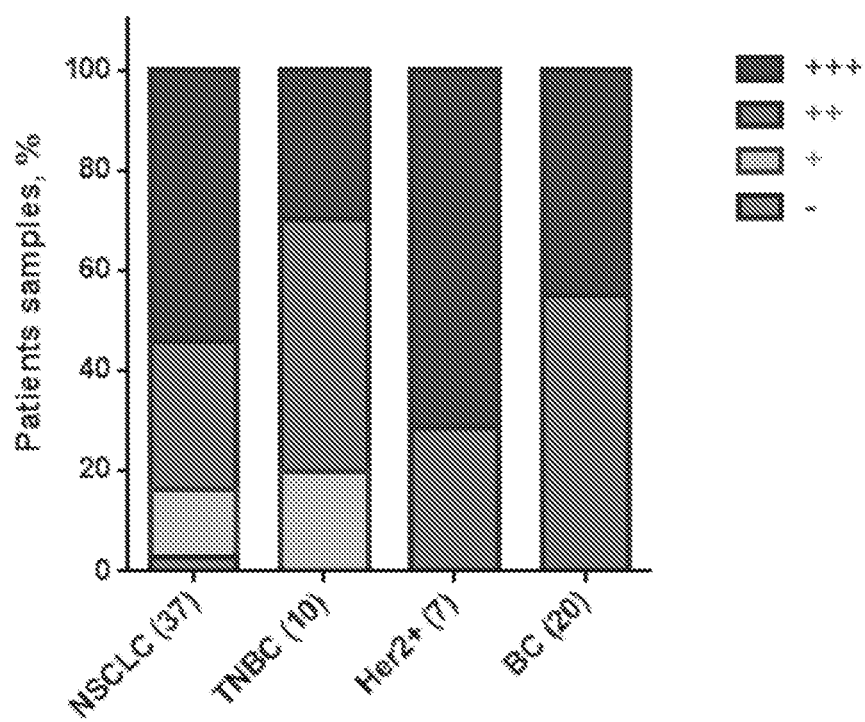
FIG. 21 is a graph depicting the level of activation rate observed in tissue microarray (TMA) samples from non-small cell lung cancer (NSCLC) and a breast cancer (BC) patent tumor samples. The in situ imaging staining scoring is based on comparison with 4D11 (parental) antibody staining and defined as follows: –, no staining; 1+ (i.e., "+"), weak staining as compared to parental antibody; 2+ (i.e., "++"), moderate staining as compared to parental antibody; and 3+ (i.e., "+++"), analogous staining to parental antibody.

The present Example describes using activatable antibodies to detect expression and/or activation in tissue microarrays (TMAs). The anti-Jagged antibody 4D11 was used with a non-small cell lung cancer (NSCLC) TMA and a breast cancer (BC) TMA. Most of the NSCLC and BC patient tumor samples were positive for Jagged expression. The same NSCLC and BC TMAs were contacted with the activatable anti-Jagged antibody referred to herein as 5342-1204-4D11. 97% of NSCLC and 100% of BC patient tumor samples were positive for binding and activation of 5342-1204-4D11 activatable anti-Jagged antibody. Furthermore, more than 80% of the tumor samples were characterized by a high activation rate (++or +++) as shown in FIG. 21. The same NSCLC and BC TMAs were contacted with the A11 antibody, which binds to the protease MT-SP1. 77% of the NSCLC and 98% of the BC patient tumor samples were positive for MT-SP1 activity. 8 NSCLC tumors lacked MT-SP1 activity, but demonstrated binding and activation of the 5342-1204-4D11 activatable anti-Jagged antibody, which suggests the participation of proteases in the activation of the 5342-1204-4D11 activatable anti-Jagged antibody.

Example 12. In Situ Imaging of Fine Needle Aspirate Samples

The present Example describes using in situ imaging on fine needle aspirate samples from a H292 xenograft study. Briefly, the following aspiration method was used: the nodule was immobilized post-sacrifice with forceps. A 23 gauge needle, which is closest to the gauge used in the clinic (e.g., 22-25), was used in a back and forth motion with slight suction applied for approximately 20 seconds. The needle was emptied into a small vial and immediately frozen on dry ice. Xenografts were collected after aspiration procedure, labeled to match aspirate sample and frozen immediately after extraction.

Figure 22:
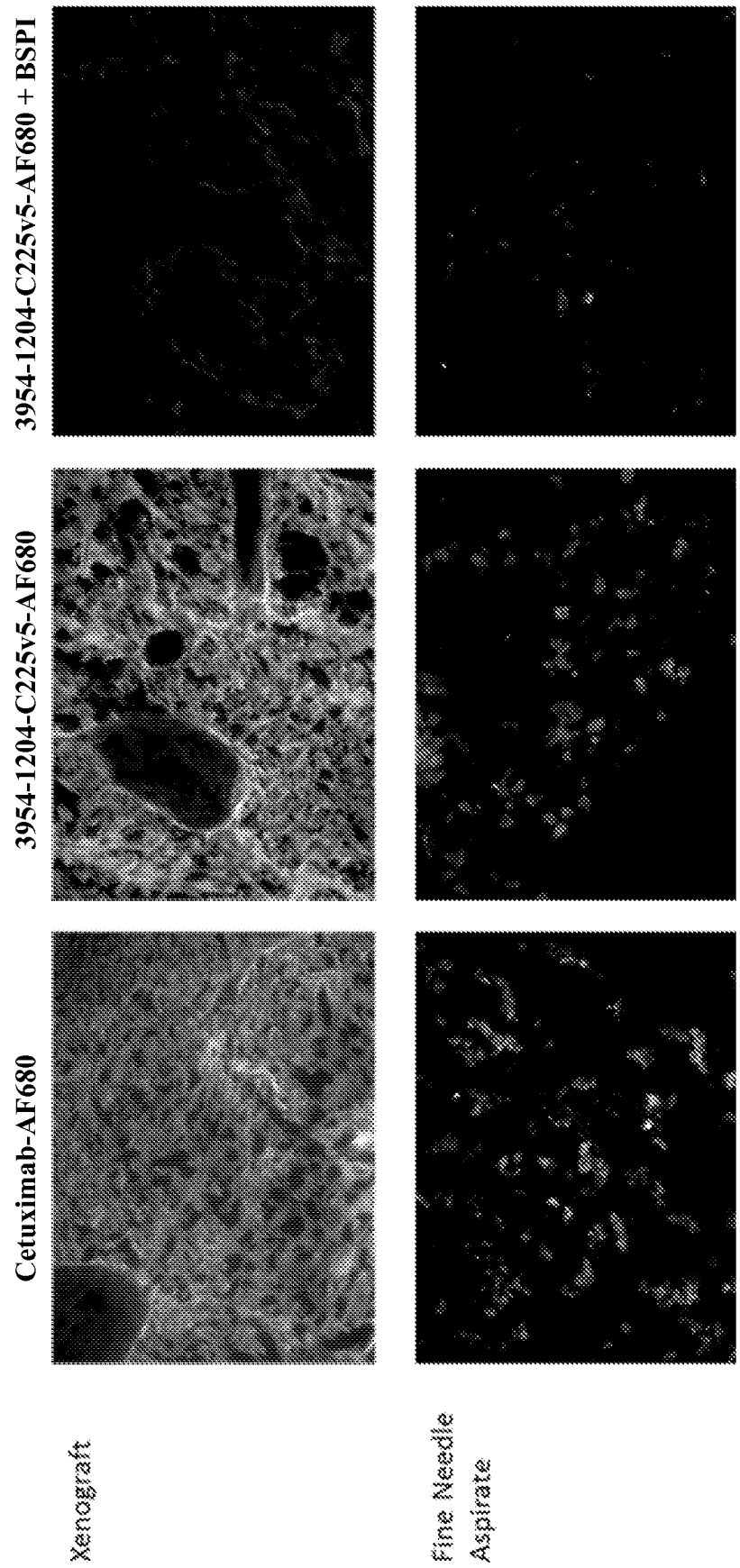
FIGS. 22 and 23 are illustrations depicting staining in fine needle aspirate (FNA) samples that were contacted with a labeled parental anti-EGFR antibody (cetuximab-AF680), a labeled anti-EGFR activatable antibody (3954-1204-C225v5-AF680) or a labeled anti-EGFR activatable antibody (3954-1204-C225v5-AF680) in the presence of a broad spectrum protease inhibitor (BSPI). The results from two subjects are shown in FIGS. 22 and 23, respectively.
Figure 23:
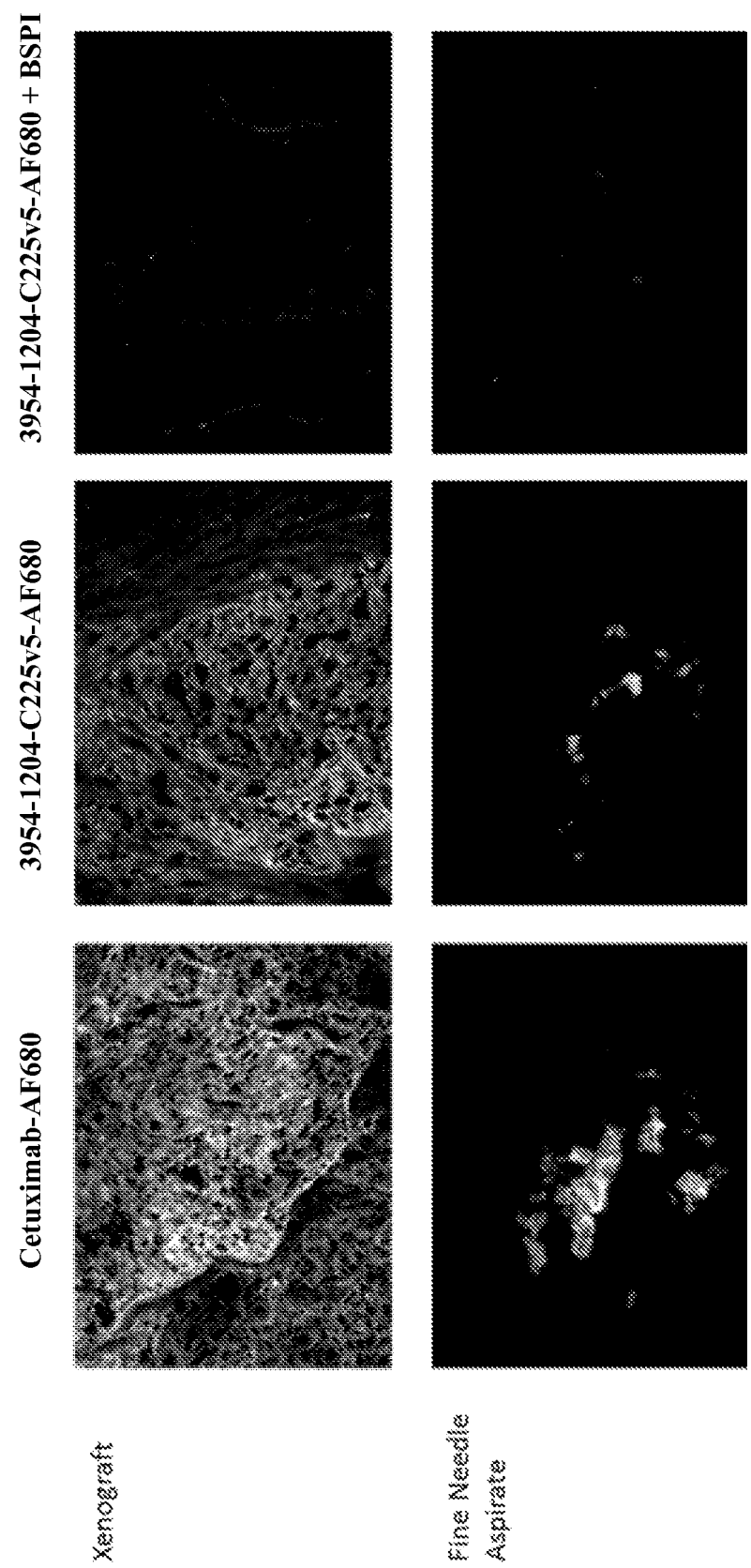

The fine needle aspirate (FNA) samples were then contacted with a labeled parental anti-EGFR antibody (cetuximab-AF680), a labeled anti-EGFR activatable antibody (3954-1204-C225v5-AF680) or a labeled anti-EGFR activatable antibody (3954-1204-C225v5-AF680) in the presence of a broad spectrum protease inhibitor (BSPI) (Broad Spectrum Protease Inhibitor Set III, EDTA Free, Catalog No. 539134, Calbiochem, Millipore, Billerica, MA) and 50 μM of broad spectrum MMP inhibitor Galardin, Catalog No. 364205 (Calbiochem, Millipore). The results from two subjects are shown in FIGS. 22 and 23. Staining for both the parental antibody and the activatable antibody was seen in all three samples.

Thus, these results demonstrate that in FNA samples that contain a sufficient number of cells, the in situ imaging techniques provided herein are useful in any of the diagnostic methods described herein.

Example 13. In vivo Imaging of Anti-Jagged Antibodies and Activatable Anti-Jagged Antibodies with Cold Competition in Cancer Cell Lines The studies provided herein use the anti-Jagged antibody 4D11 and the activatable anti-Jagged antibody 5342-1204-4D11. The anti-Jagged antibody and activatable anti-Jagged antibody were tested using BxPC3 cells, a human primary pancreatic adenocarcinoma cancer cell line.

The studies described herein were designed to evaluate the anti-Jagged antibody 4D11 and the anti-Jagged activatable antibody 5342-1204-4D11 accumulation in BxPC3 xenograft tumors by in vivo imaging with "cold" 4D11 pretreatment control. An overview of the groups used in the first set of studies is shown below in Table 14:

TABLE 14

Study Groups (n = 3)

| Group | Count | Pretreatment "cold"/Treatment | Dose (mg/kg) | Route |
|---|---|---|---|---|
| 1 | 3 | PBS/4D11-AF750 | —/10 | IP/IP |
| 2 | 3 | 4D11/4D11-AF750 | 20/10 | IP/IP |
| 3 | 3 | 5342-1204-4D11/ 4D11-AF750 | 20/10 | IP/IP |

Figure 24A:
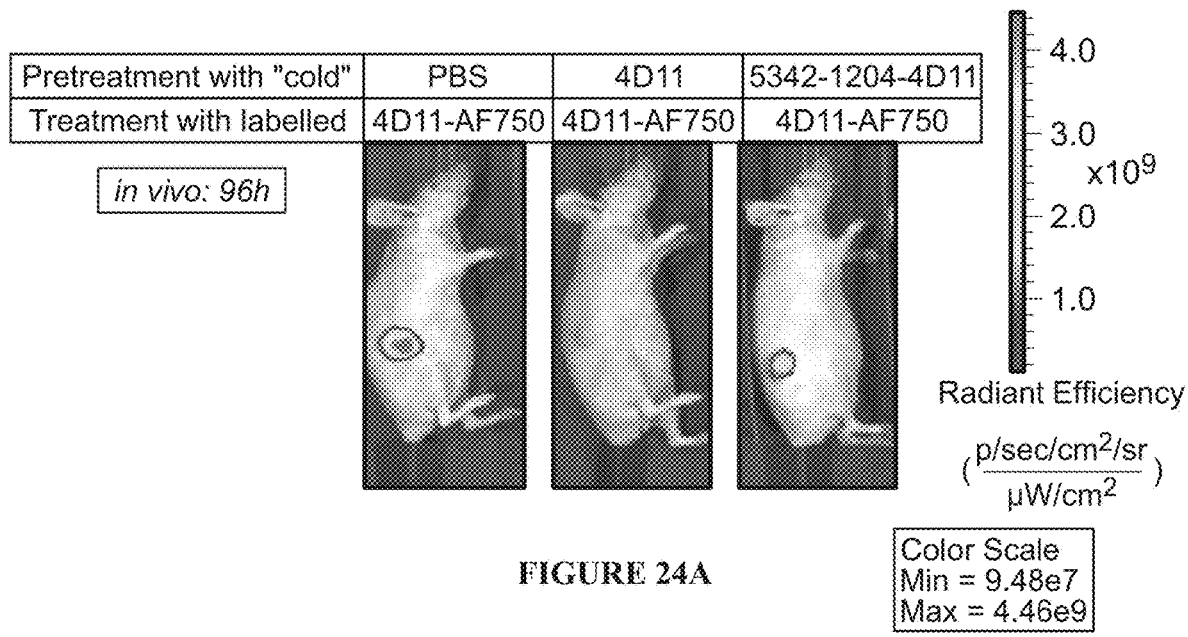
FIGS. 24A, 24B, and 24C are a series of photographs and graphs depicting the correlation between the level of activatable anti-Jagged antibody (5342-1204-4D11) accumulation detected using in vivo and ex vivo imaging of receptor occupancy.

Activation of the anti-Jagged activatable antibody 5342-1204-4D11 was estimated by imaging of receptor occupancy (FIG. 24A).

Figure 24B:
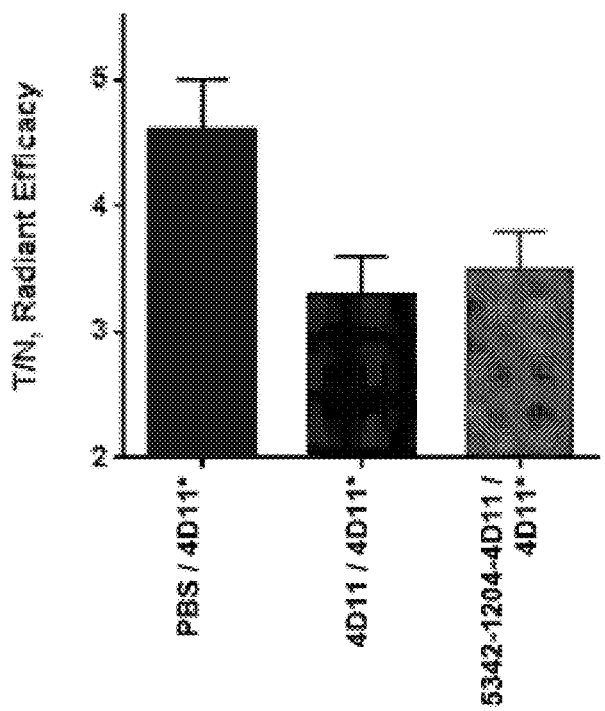
Figure 24C:
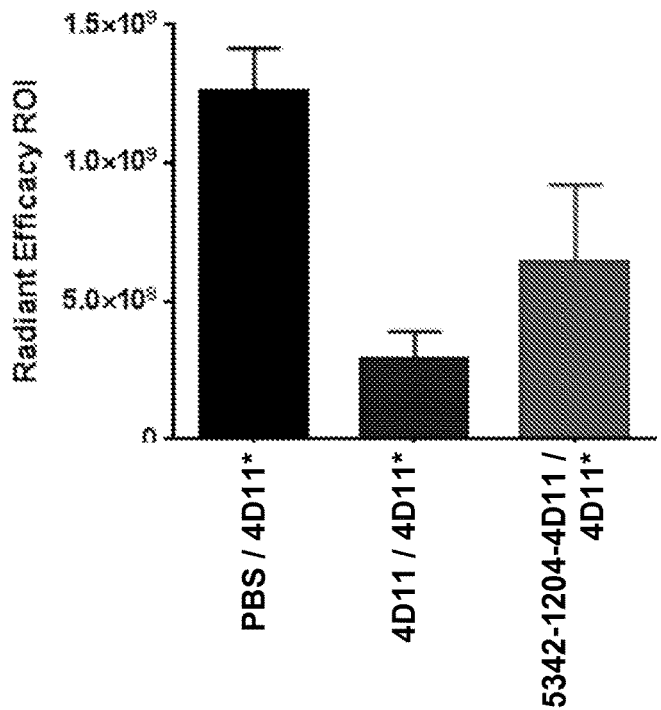

As seen in FIGS. 24A and 24B, in vivo imaging results (FIG. 24B) correlated with ex vivo imaging results (FIG. 24C).

Example 14. In Vivo Imaging of Activatable Anti-EGFR Antibodies with Cold Competition in Cancer Cell Lines The studies provided herein use the activatable anti-EGFR antibody 3954-1204-C225v5. The activatable anti-EGFR antibody was tested using H292 cells, a human non-small cell lung cancer cell line.

The studies described herein were designed to evaluate accumulation of the activatable anti-EGFR antibody 3954-1204-C225v5 in H292 xenograft tumors by in vivo imaging with "cold" C225v5 pretreatment control. An overview of the groups used in the first set of studies is shown below in Table 15:

TABLE 15

Study Groups (n = 3)

| Group | Count | Pretreatment "cold"/Treatment | Dose (mg/kg) | Route |
|---|---|---|---|---|
| 1 | 3 | PBS/C225v5-AF750 | —/10 | IP/IP |
| 2 | 3 | C225v5/C225v5-AF750 | 10/10 | IP/IP |
| 3 | 3 | 3954-1204-C225v5/ C225v5-AF750 | 10/10 | IP/IP |

Figure 25:
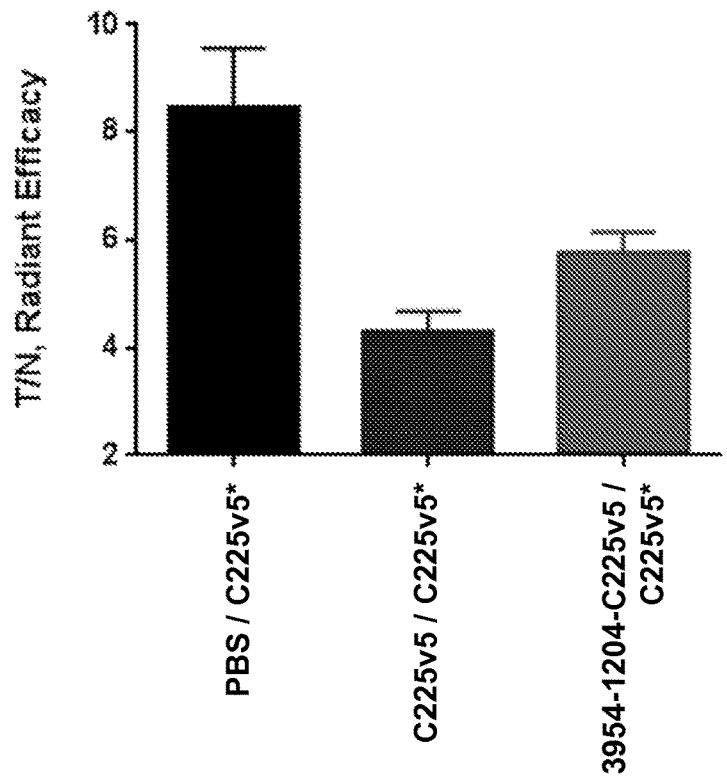
FIG. 25 is a graph depicting the estimated activation of the anti-EGFR activatable antibody 3954-1204-C225v5 using imaging of receptor occupancy.

Activation of the anti-EGFR activatable antibody 3954-1204-C225v5 was estimated by imaging of receptor occupancy (FIG. 25).

In vivo imaging of the anti-Jagged antibody 4D11 and the activatable anti-Jagged antibody 5342-1204-4D11 with "cold" competition in BxPC3 xenograft tumor model, and in vivo imaging of the activatable anti-EGFR antibody 3954-1204-C225v5 with "cold" competition in H292 xenograft tumor model have demonstrated that these methods are a viable method for detection of antibody binding. As such, these methods are useful in screening substrate cleavability in in vivo tumor models.

Example 15. Human Multiple Myeloma Bone Marrow Biopsy Sectioning Procedure

To develop a method to section and stain bone marrow and other tissues that are difficult to handle, several procedures were tested before a suitable protocol was established. Initially, the routine sectioning procedure of using a disposable blade was attempted. This was followed by evaluation of the 16 cm tungsten carbide knife as it has greater stability and reduced vibration when used on hard samples. Next, the use of adhesive tape was tried as follows: Tissue was placed onto adhesive tape and then sectioned; the tissue, adhered to the adhesive tape, was placed on a slide such that the tissue directly contacted the slide; various methods for tape removal and tissue section transfer to the slide were attempted without success; such methods included evaluating the effect of temperature and time allowed for tissue section adhesion to the slide. These failures led to the evaluation of leaving the tissue section on the adhesive tape throughout the staining procedure with no attempt made to transfer the sample to a slide, resulting in the successful protocol described below. It is to be appreciated that although the protocol below describes sectioning and staining of bone marrow tissues, such a method can also be used to section and stain other difficult tissues.

Bone marrow biopsy tissue isolated from patients with multiple myeloma was placed in a cryostat set at −30° C. and allowed to come to temperature before sectioning. After the tissue was adhered to the chuck and the chuck was inserted into the chuck holder, a piece of adhesive tape was applied to the face of the block. The adhesive tape was rolled on with a plastic roller to facilitate even adhesion. The bottom edge of the tape was held with forceps while the block was slowly lowered to the blade and the section was taken. The tissue was sectioned at 7 microns (um) utilizing a 16 cm tungsten carbide knife, and the tissue sections were kept on adhesive tape at −30° C. and stored long term at −80° C.

The resulting tissue sections were stained with respective immunofluorescence staining protocols, as described below, directly on the adhesive tape. Any suitable IHC protocol, including standard IHC protocol, can be used in these methods. The following immunofluorescence staining protocols were used in the studies described herein.

The ability of anti-Jagged activatable antibody 5342-1204-4D11 to be activated and to bind multiple myeloma tumor tissue was evaluated using in situ imaging. The activatable antibody was labeled with Alexa Fluor® 488 (Invitrogen) to produce labeled activatable antibody 5342-1204-4D11-AF488, also referred to herein as 1204-4D11-AF488. Also tested was labeled anti-Jagged parental antibody 4D11-AF488. To identify anti-Jagged activatable antibody 5342-1204-4D11-AF488 positive multiple myeloma cells, CD138 (eBiosciences), a malignant multiple myeloma plasma cell marker, was stained concurrently. Each of anti-Jagged antibody 4D11-AF488, anti-Jagged activatable antibody 5342-1204-4D11-AF488, and anti-Jagged activatable antibody 5342-1204-4D11-AF488 in the presence of a broad spectrum protease inhibitor (BPSI) was incubated with a frozen multiple myeloma tumor tissue sample in a cocktail with CD138 for 1 hour at room temperature (about 22-24° C.) in an incubation buffer of 50 mM Tris-HCl buffer pH 7.4, containing 150 mM NaCl, 100 µM $ZnCl_2$, 5 mM $CaCl_2$, 1% BSA and 0.05% Tween 20; activatable antibody at a concentration of about 2 µg/ml; CD138 at a concentration of 5 µg/ml. The tissue was then extensively washed to remove non-bound material. 4D11-AF488 and 1204-4D11-AF488 signals were amplified with rabbit anti-AF488. The rabbit anti-AF488 was incubated for 30 minutes at room temperature at a concentration of 5 µg/ml in 3% BSA. The tissue was then extensively washed to remove non-bound material. Detection of bound 4D11-AF488 and 1204-4D11-AF488 was accomplished with mouse anti-rabbit AF647 at 5 µg/ml in 3% BSA. Detection of CD138 was accomplished with anti-mouse IgG AF488 at 5 µg/ml in 3% BSA. The anti-rabbit IgG AF647 and anti-mouse IgG AF488 were applied as a cocktail and incubated for 30 minutes at room temperature.

Figure 26:
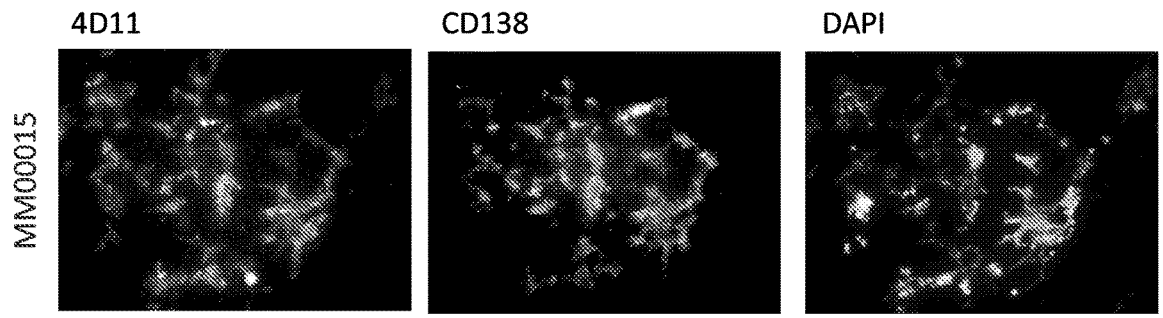
FIG. 26 is a photograph depicting co-localization of the anti-Jagged antibody 4D11 staining with CD138, a malignant multiple myeloma plasma cell marker in a multiple myeloma bone marrow biopsy patient sample (MM00015).
Figure 27:
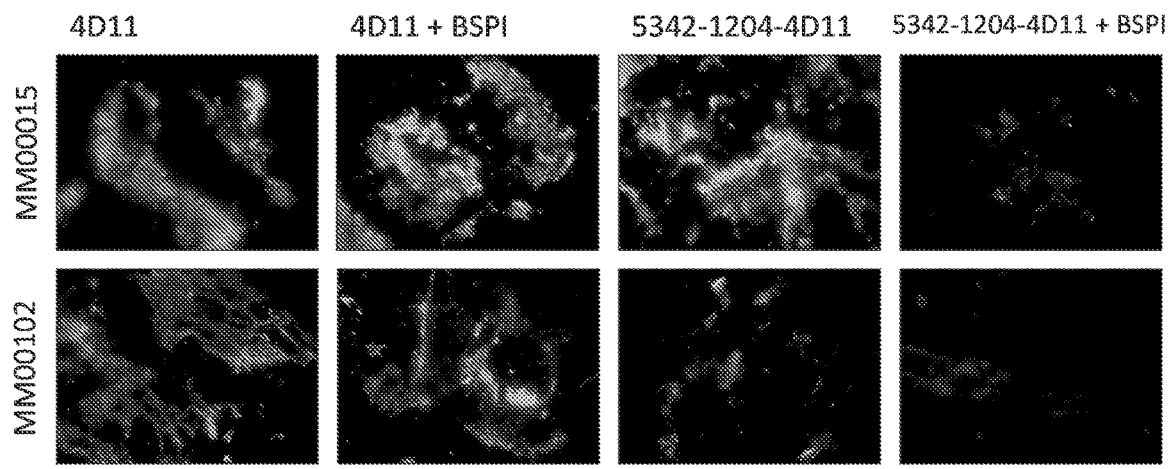
FIG. 27 is a photograph depicting the results of immunohistochemistry analysis of the anti-Jagged antibody 4D11, and in situ imaging analysis of the activatable anti-Jagged antibody 5342-1204-4D11 in two multiple myeloma bone marrow biopsy patient samples (MM00015 and MM00102).

Results are demonstrated in FIGS. 26 and 27. FIG. 26 indicates that the multiple myeloma bone marrow biopsy tissue expresses Jagged (as indicated by staining by anti-Jagged antibody 4D11) and CD138 (as indicated by staining by anti-CD138 antibody). FIG. 27 indicates that anti-Jagged activatable antibody 5342-1204-4D11 is activated by multiple myeloma bone marrow biopsy tissue and that such activation is inhibited in the presence of a broad spectrum protease inhibitor.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A method of treating a patient with an activatable antibody, the method comprising:
   (I) identifying a patient that is suitable for treatment with a second activatable antibody,
      wherein a patient that is identified as suitable for treatment with a second activatable antibody is positive for the presence of a co-localized cleaving agent and a target in a tissue sample from the patient, as determined by an in situ assay, wherein the cleaving agent is a protease, and wherein the in situ assay comprises:
      a) contacting the tissue sample with an uncleaved first activatable antibody, wherein the uncleaved first activatable antibody comprises:
         (i) an antibody or antigen binding fragment thereof (AB) that specifically binds to the target;
         (ii) a cleavable moiety (CM) coupled to the AB, wherein the CM is a polypeptide that functions as a substrate for the cleaving agent, whereby cleavage of the uncleaved first activatable antibody in the CM results in an activated first activatable antibody; and
         (iii) a masking moiety (MM) coupled to the AB via the CM, wherein the MM of the uncleaved first activatable antibody interferes with specific binding of the AB to the target,
      (b) measuring in situ the presence or absence of a detectable level of activated first activatable antibody in the tissue sample,
         wherein presence of a detectable level of activated first activatable antibody in the tissue sample from the patient indicates that the patient is positive for the presence of co-localized cleaving agent and target, and
         wherein absence of a detectable level of activated first activatable antibody in the tissue sample from the patient indicates that the patient is negative for the presence of co-localized cleaving agent and target, whereby the cleaving agent, the target, or both the cleaving agent and the target are absent or not co-localized at a detectable level in the tissue sample; and
   (II) administering to the patient identified in step (I), a therapeutically effective amount of the second activatable antibody,
      wherein the second activatable antibody comprises an AB that specifically binds to the same target, and a CM that functions as a substrate for the same cleaving agent, as the first activatable antibody in (a)(i) and (a)(ii), respectively, and wherein the second activatable antibody further comprises an MM, wherein the MM of the second activatable antibody interferes with specific binding of the AB to the target when the second activatable antibody is in an uncleaved state.

2. The method of claim 1, wherein the first activatable antibody comprises a detectable label.

3. The method of claim 2, wherein the detectable label comprises an imaging agent, a contrasting agent, an enzyme, a fluorescent label, a chromophore, a dye, a radioisotope, one or more metal ions, or a ligand-based label.

4. The method of claim 2, wherein the detectable label is a fluorescent dye.

5. The method of claim 1, wherein the in situ assay comprises a secondary reagent that specifically binds to the activated first activatable antibody, wherein the secondary reagent comprises a detectable label.

6. The method of claim 5, wherein the detectable label comprises an imaging agent, a contrasting agent, an enzyme, a fluorescent label, a chromophore, a dye, a radioisotope, one or more metal ions, or a ligand-based label.

7. The method of claim 5, wherein the detectable label is a fluorescent dye.

8. The method of claim 1, wherein the first activatable antibody and the second activatable antibody are the same.

9. The method of claim 1, wherein the first activatable antibody and the second activatable antibody are different.

10. The method of claim 1, wherein the tissue sample is a frozen tissue sample.

11. The method of claim 1, wherein the tissue sample is a tumor tissue sample.

12. The method of claim 1, wherein the patient is suffering from, is at risk of suffering from, or is suspected of suffering from a cancer.

13. The method of claim 1, wherein the patient is suffering from, is at risk of suffering from, or is suspected of suffering from an inflammatory disorder.

14. The method of claim 1, wherein the AB is an antibody selected from the group of antibodies consisting of: bevacizumab, ranibizumab, cetuximab, panitumumab, infliximab, adalimumab, natalizumab, basiliximab, eculizumab, efalizumab, tositumomab, ibritumomab tiuxetan, rituximab, ocrelizumab, ofatumumab, Obinutuzumab, daclizumab, brentuximab vedotin, gemtuzumab, gemtuzumab ozogamicin, alemtuzumab, abiciximab, omalizumab, trastuzumab, trastuzumab emtansine, palivizumab, ipilimumab, tremelimumab, Hu5c8, pertuzumab, ertumaxomab, abatacept, tanezumab, bavituximab, zalutumumab, mapatumumab, matuzumab, nimotuzumab, ICF62, mAb 528, CH806, MDX-447, edrecolomab, RAV12, huJ591, etanercept, alefacept, ankinra, GC1008, adecatumumab, figitumumab, tocilizumab, ustekinumab, denosumab, and an antigen binding fragment of said antibody selected from the group of antibodies.

15. The method of claim 1, wherein the AB is an antibody that binds to a target selected from the group consisting of: 1-92-LFA-3, Anti-Lewis-Y, Apelin J receptor, APRIL, BAFF, C5 complement, C-242, CD2, CD3, CD9, CD11a, CD19, CD20, CD22, CD25, CD28, CD30, CD33, CD40, CD40L, CD41, CD44, CD47, CD52, CD56, CD64, CD70, CD80, CD86, CD95, CD117, CD132, (IL-2RG), CD133, CD137, CD138, CD172A, CEACAMS (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLL4, DPP-4, EGFR, Endothelin B receptor (ETBR), EpCAM, EPHA2, ERBB3, F protein of RSV, FAP, FGF-2, FGF8, FGFR1, FGFR2, FGF43, FGFR4, Folate receptor, G-CSF, G-CSFR, GLUT1, GLUT4, GM-CSF, GM-CSFR, GP IIb/IIIa receptors, Gp130, GPNMB, HER2/neu, HGF, hGH, Hyaluronidase, IFNalpha, IFNbeta, IFNgamma, IgE, IgE Receptor (FcεRI), IGF, IGF1R, IL1B, IL-1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31r, IL2r, IL4, IL4R, IL6, IL6R, Insulin Receptor, Jagged Ligands, Jagged 1, Jagged 2, LIF-R, MRP4, MUC1, Mucin-16, Na/K ATPase, Neutrophil elastase, NGF, Nicastrin, Notch Receptors, Notch 1, Notch 2, Notch 3, Notch 4, NOV, OSM-R, PAR2, PDGF-AA, PDGF-BB, PDGFRalpha, PDGFRbeta, PD-1, PD-L1, PD-L2, Phosphatidyl-serine, P1GF, PSCA, PSMA, RAAG12, RAGE, SLC44A4, Sphingosine 1 Phosphate, TGFbeta, TLR2, TLR4, TL46, TLR7, TLR8, TLR9, TNFalpha, TNFR, TRAIL-R1, TRAIL-R2, Transferrin, Transferrin receptor, TRK-A, TRK-B, uPAR, VCAM-1, VEGF, VEGF-A, VEGF-B, VEGF-C, VEGF-D, VEGFR1, VEGFR2, VEGFR3, WISP-1, WISP-2, WISP-3, Alpha-4 integrin, Alpha-V integrin, and alpha4beta1 integrin, or an antigen binding fragment of said antibody that binds to a target selected from the group of targets.

16. The method of claim 1, wherein the antigen binding fragment thereof is selected from the group consisting of a Fab fragment, a F(ab')2 fragment, a scFv, and a scab.

17. The method of claim 1, wherein the MINI has an equilibrium dissociation constant for binding to the AB that is greater than the equilibrium dissociation constant of the AB to the target.

18. The method of claim 1, wherein the MINI does not interfere or compete with the AB of the activated activatable antibody for binding to the target.

19. The method of claim 1, wherein the CM is a substrate for a protease selected from the group consisting of an ADAMS, an ADAMTS, an aspartate protease, an aspartic cathepsin, a caspase, a cysteine cathpsin, a cysteine proteinase, a KLK, a metallo proteinase, an MMP, a serine protease, a coagulation factor protease, and a Type II Transmembrane Serine Protease.

20. The method of claim 1, wherein the CM is a substrate for a protease selected from the group consisting of ADAMS, ADAMS, ADAM12, ADAM15, ADAM17/TACE, ADAMDEC1, ADAMTS1, ADAMTS4, ADAMTS5, BACE, Renin, Cathepsin D, Cathepsin E, Caspase 1, Caspase 2, Caspase3, Caspase 4, Caspase 5, Caspase6, Caspase7, Caspase 8, Caspase 9, Caspase 10, Caspase 14, Cathepsin B, Cathepsin C, Cathepsin K, Cathepsin L, Cathepsin S, Cathepsin V/L2, Cathepsin X/Z/P, Cruzipain, Legumain, Otubain-2, KLK4, KLK5, KLK6, KLK7, KLK8, KLK10, KLK11, KLK13, KLK14, Meprin, Neprilysin, PSMA, BMP-1, MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, MMP27, activated protein C, Cathepsin A, Cathepsin G, Chymas, FVIIa, FIXa, FXa, FXI, FXIIa, elastase, granzyme B, Guanidinobenzoatase, HtrA1, human neutrophil elastase, lactoferrin, marapsin, NS3/4A, PACE4, Plasmin, PSA, tPA, thrombin, tryptase, uPA, DESC1, DPP-4, FAP, Hepsin, Matriptase-2, MT-SP1/Matriptase, TMPRSS2, TMPRSS3, and TMPRSS4.

21. The method of claim 1, wherein the second activatable antibody comprises a linking peptide between the MM and the CM.

22. The method of claim 1, wherein the second activatable antibody comprises a linking peptide between the CM and the AB.

23. The method of claim 1, wherein the first activatable antibody comprises a first linking peptide (LP1) between the MM and the CM.

24. The method of claim 1, wherein the second activatable antibody is conjugated to an agent.

25. The method of claim 24, wherein the agent is selected from the group consisting of a therapeutic agent, an antineoplastic agent, and a toxin or fragment thereof.

26. The method of claim 24, wherein the agent is a cytotoxic agent.

* * * * *

SEQUENCE LISTING

<160> NUMBER OF SEQ ID NOS: 326

<210> SEQ ID NO 1
<211> LENGTH: 1350
<212> TYPE: DNA
<213> ORGANISM: Artificial Sequence
<220> FEATURE:
<223> OTHER INFORMATION: 3954-1204-C225v5 Activatable Antibody Heavy
      Chain

<400> SEQUENCE: 1

```
caggtgcagc tgaaacagag cggcccgggc ctggtgcagc cgagccagag cctgagcatt         60
acctgcaccg tgagcggctt tagcctgacc aactatggcg tgcattgggt gcgccagagc        120
ccgggcaaag gcctggaatg gctgggcgtg atttggagcg gcggcaacac cgattataac        180
accccgttta ccagccgcct gagcattaac aaagataaca gcaaaagcca ggtgtttttt        240
aaaatgaaca gcctgcaaag ccaggatacc gcgatttatt attgcgcgcg cgcgctgacc        300
tattatgatt atgaatttgc gtattgggc cagggcaccc tggtgaccgt gagcgcggct        360
agcaccaagg gcccatcggt cttccccctg gcaccctcct ccaagagcac ctctggggc         420 acagcggccc tgggctgcct ggtcaaggac tacttccccg aaccggtgac ggtgtcgtgg        480
aactcaggcg ccctgaccag cggcgtgcac accttcccgg ctgtcctaca gtcctcagga        540
ctctactccc tcagcagcgt ggtgaccgtg ccctccagca gcttgggcac ccagacctac        600
atctgcaacg tgaatcacaa gcccagcaac accaaggtgg acaagaaagt tgagcccaaa        660
tcttgtgaca aaactcacac atgcccaccg tgcccagcac ctgaactcct ggggggaccg        720
```

-continued

```
tcagtcttcc tcttcccccc aaaacccaag gacaccctca tgatctcccg gaccectgag    780 gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020 gccaagggc agccccgaga ccacaggtg tacaccctgc ccccatcccg ggatgaactg      1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350
```

<210> SEQ ID NO 2
<211> LENGTH: 449
<212> TYPE: PRT
<213> ORGANISM: Artificial Sequence
<220> FEATURE:
<223> OTHER INFORMATION: 3954-1204-C225v5 Activatable Antibody Heavy
      Chain

<400> SEQUENCE: 2

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 3
<211> LENGTH: 786
<212> TYPE: DNA
<213> ORGANISM: Artificial Sequence
<220> FEATURE:
<223> OTHER INFORMATION: 3954-1204-C225v5 Activatable Antibody Light
      Chain

<400> SEQUENCE: 3

```
caaggccagt ctggccagtg catctcacct cgtggttgtc cggacggccc atacgtcatg      60
tacggctcga gcggtggcag cggtggctct ggtggatccg gtctgagcgg ccgttccgat     120
aatcatggca gtagcggtac ccagatcttg ctgacccaga gcccggtgat tctgagcgtg     180
agcccgggcg aacgtgtgag ctttagctgc cgcgcgagcc agagcattgg caccaacatt     240
cattggtatc agcagcgcac caacggcagc ccgcgcctgc tgattaaata tgcgagcgaa     300
agcattagcg gcattccgag ccgctttagc ggcagcggca gcggcaccga ttttaccctg     360
agcattaaca gcgtggaaag cgaagatatt gcggattatt attgccagca gaacaacaac     420
tggccgacca ccttttggcgc gggcaccaaa ctggaactga acgtacggt ggctgcacca     480 tctgtcttca tcttcccgcc atctgatgag cagttgaaat ctggaactgc ctctgttgtg     540
tgcctgctga ataacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                                786
```

<210> SEQ ID NO 4
<211> LENGTH: 261
<212> TYPE: PRT
<213> ORGANISM: Artificial Sequence
<220> FEATURE:
<223> OTHER INFORMATION: 3954-1204-C225v5 Activatable Antibody Light
      Chain

<400> SEQUENCE: 4

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Asp Asn His Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260
```

<210> SEQ ID NO 5
<211> LENGTH: 18
<212> TYPE: DNA
<213> ORGANISM: Artificial Sequence
<220> FEATURE:
<223> OTHER INFORMATION: 3954-1204-C225v5 Activatable Antibody Light
      Chain spacer

<400> SEQUENCE: 5
caaggccagt ctggccag                                                 18

<210> SEQ ID NO 6
<211> LENGTH: 45

```
<212> TYPE: DNA
<213> ORGANISM: Artificial Sequence
<220> FEATURE:
<223> OTHER INFORMATION: 3954-1204-C225v5 Activatable Antibody Light
      Chain mask

<400> SEQUENCE: 6
tgcatctcac ctcgtggttg tccggacggc ccatacgtca tgtac            45

<210> SEQ ID NO 7
<211> LENGTH: 39
<212> TYPE: DNA
<213> ORGANISM: Artificial Sequence
<220> FEATURE:
<223> OTHER INFORMATION: 3954-1204-C225v5 Activatable Antibody Light
      Chain linker 1

<400> SEQUENCE: 7
ggctcgagcg gtggcagcgg tggctctggt ggatccggt                   39

<210> SEQ ID NO 8
<211> LENGTH: 24
<212> TYPE: DNA
<213> ORGANISM: Artificial Sequence
<220> FEATURE:
<223> OTHER INFORMATION: 3954-1204-C225v5 Activatable Antibody Light
      Chain 1204 substrate

<400> SEQUENCE: 8
ctgagcggcc gttccgataa tcat                                   24

<210> SEQ ID NO 9
<211> LENGTH: 15
<212> TYPE: DNA
<213> ORGANISM: Artificial Sequence
<220> FEATURE:
<223> OTHER INFORMATION: 3954-1204-C225v5 Activatable Antibody Light
      Chain linker 2

<400> SEQUENCE: 9
ggcagtagcg gtacc                                             15

<210> SEQ ID NO 10
<211> LENGTH: 645
<212> TYPE: DNA
<213> ORGANISM: Artificial Sequence
<220> FEATURE:
<223> OTHER INFORMATION: C225v5 Antibody Light Chain

<400> SEQUENCE: 10
cagatcttgc tgacccagag cccggtgatt ctgagcgtga gcccgggcga acgtgtgagc     60
tttagctgcc gcgcgagcca gagcattggc accaacattc attggtatca gcagcgcacc    120
aacggcagcc cgcgcctgct gattaaatat gcgagcgaaa gcattagcgg cattccgagc    180
cgctttagcg gcagcggcag cggcaccgat tttaccctga gcattaacag cgtggaaagc    240
gaagatattg cggattatta ttgccagcag aacaacaact ggccgaccac ctttggcgcg    300
ggcaccaaac tggaactgaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
```
ctgagctcgc ccgtcacaaa gagcttcaac aggggagagt gttag 645

```
<210> SEQ ID NO 11
<211> LENGTH: 6
<212> TYPE: PRT
<213> ORGANISM: Artificial Sequence
<220> FEATURE:
<223> OTHER INFORMATION: 3954-1204-C225v5 Activatable Antibody Light
      Chain spacer

<400> SEQUENCE: 11

Gln Gly Gln Ser Gly Gln
1               5

<210> SEQ ID NO 12
<211> LENGTH: 15
<212> TYPE: PRT
<213> ORGANISM: Artificial Sequence
<220> FEATURE:
<223> OTHER INFORMATION: 3954-1204-C225v5 Activatable Antibody Light
      Chain mask

<400> SEQUENCE: 12

Cys Ile Ser Pro Arg Gly Cys Pro Asp Gly Pro Tyr Val Met Tyr
1               5                   10                  15

<210> SEQ ID NO 13
<211> LENGTH: 13
<212> TYPE: PRT
<213> ORGANISM: Artificial Sequence
<220> FEATURE:
<223> OTHER INFORMATION: 3954-1204-C225v5 Activatable Antibody Light
      Chain linker 1

<400> SEQUENCE: 13

Gly Ser Ser Gly Gly Ser Gly Gly Ser Gly Gly Ser Gly
1               5                   10

<210> SEQ ID NO 14
<211> LENGTH: 8
<212> TYPE: PRT
<213> ORGANISM: Artificial Sequence
<220> FEATURE:
<223> OTHER INFORMATION: 3954-1204-C225v5 Activatable Antibody Light
      Chain 1204 substrate

<400> SEQUENCE: 14

Leu Ser Gly Arg Ser Asp Asn His
1               5

<210> SEQ ID NO 15
<211> LENGTH: 5
<212> TYPE: PRT
<213> ORGANISM: Artificial Sequence
<220> FEATURE:
<223> OTHER INFORMATION: 3954-1204-C225v5 Activatable Antibody Light
      Chain linker 2

<400> SEQUENCE: 15

Gly Ser Ser Gly Thr
1               5

<210> SEQ ID NO 16
<211> LENGTH: 214
<212> TYPE: PRT
<213> ORGANISM: Artificial Sequence
<220> FEATURE:
<223> OTHER INFORMATION: C225v5 Antibody Light Chain
```

<400> SEQUENCE: 16

```
Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 17
<211> LENGTH: 777
<212> TYPE: DNA
<213> ORGANISM: Artificial Sequence
<220> FEATURE:
<223> OTHER INFORMATION: 3954-NSUB-C225v5 Masked Antibody Light Chain

<400> SEQUENCE: 17

```
caaggccagt ctggccagtg catctcacct cgtggttgtc cggacggccc atacgtcatg      60
tacggctcga gcggtggcag cggtggctct ggtggctcag gtggaggctc gggcggtggg     120
agcggcggtt ctcagatctt gctgacccag agcccggtga ttctgagcgt gagcccgggc     180
gaacgtgtga gctttagctg ccgcgcgagc cagagcattg gcaccaacat tcattggtat     240
cagcagcgca ccaacggcag cccgcgcctg ctgattaaat atgcgagcga aagcattagc     300
ggcattccga ccgctttag cggcagcggc agcggcaccg attttaccct gagcattaac     360
agcgtggaaa gcgaagatat tgcggattat tattgccagc agaacaacaa ctggccgacc     420
acctttggcg cgggcaccaa actggaactg aaacgtacgg tggctgcacc atctgtcttc     480
atcttcccgc catctgatga gcagttgaaa tctggaactg cctctgttgt gtgcctgctg     540
aataacttct atcccagaga ggccaaagta cagtggaagg tggataacgc cctccaatcg     600
ggtaactccc aggagagtgt cacagagcag gacagcaagg acagcaccta cagcctcagc     660
agcaccctga cgctgagcaa agcagactac gagaaacaca agtctacgc ctgcgaagtc     720
```
acccatcagg gcctgagctc gcccgtcaca aagagcttca acaggggaga gtgttag    777

<210> SEQ ID NO 18
<211> LENGTH: 258
<212> TYPE: PRT
<213> ORGANISM: Artificial Sequence
<220> FEATURE:
<223> OTHER INFORMATION: 3954-NSUB-C225v5 Masked Antibody Light Chain

<400> SEQUENCE: 18

```
Gln Gly Gln Ser Gly Gln Cys Ile Ser Pro Arg Gly Cys Pro Asp Gly
1               5                   10                  15
Pro Tyr Val Met Tyr Gly Ser Ser Gly Gly Ser Gly Gly Ser Gly Gly
            20                  25                  30
Ser Gly Gly Ser Gly Gly Gly Ser Gly Gly Ser Gln Ile Leu Leu
        35                  40                  45
Thr Gln Ser Pro Val Ile Leu Ser Val Ser Pro Gly Glu Arg Val Ser
    50                  55                  60
Phe Ser Cys Arg Ala Ser Gln Ser Ile Gly Thr Asn Ile His Trp Tyr
65                  70                  75                  80
Gln Gln Arg Thr Asn Gly Ser Pro Arg Leu Leu Ile Lys Tyr Ala Ser
                85                  90                  95
Glu Ser Ile Ser Gly Ile Pro Ser Arg Phe Ser Gly Ser Gly Ser Gly
            100                 105                 110
Thr Asp Phe Thr Leu Ser Ile Asn Ser Val Glu Ser Glu Asp Ile Ala
        115                 120                 125
Asp Tyr Tyr Cys Gln Gln Asn Asn Asn Trp Pro Thr Thr Phe Gly Ala
    130                 135                 140
Gly Thr Lys Leu Glu Leu Lys Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
            180                 185                 190
Lys Val Asp Asn Ala Leu Gln Ser Gly Asn Ser Gln Glu Ser Val Thr
        195                 200                 205
Glu Gln Asp Ser Lys Asp Ser Thr Tyr Ser Leu Ser Ser Thr Leu Thr
    210                 215                 220
Leu Ser Lys Ala Asp Tyr Glu Lys His Lys Val Tyr Ala Cys Glu Val
225                 230                 235                 240
Thr His Gln Gly Leu Ser Ser Pro Val Thr Lys Ser Phe Asn Arg Gly
                245                 250                 255
Glu Cys
```

<210> SEQ ID NO 19
<211> LENGTH: 69
<212> TYPE: DNA
<213> ORGANISM: Artificial Sequence
<220> FEATURE:
<223> OTHER INFORMATION: 3954-NSUB-C225v5 Masked Antibody Light Chain
      Linker 1-Noncleavable Substrate-Linker 2

<400> SEQUENCE: 19
ggctcgagcg gtggcagcgg tggctctggt ggctcaggtg gaggctcggg cggtgggagc    60
ggcggttct                                                            69

<210> SEQ ID NO 20

```
<211> LENGTH: 23
<212> TYPE: PRT
<213> ORGANISM: Artificial Sequence
<220> FEATURE:
<223> OTHER INFORMATION: 3954-NSUB-C225v5 Masked Antibody Light Chain
      Linker 1-Noncleavable Substrate-Linker 2

<400> SEQUENCE: 20

Gly Ser Ser Gly Gly Ser Gly Gly Ser Gly Gly Ser Gly Gly Gly Ser
1               5                   10                  15

Gly Gly Gly Ser Gly Gly Ser
            20

<210> SEQ ID NO 21
<211> LENGTH: 324
<212> TYPE: DNA
<213> ORGANISM: Artificial Sequence
<220> FEATURE:
<223> OTHER INFORMATION: 4D11 Light Chain Variable Region

<400> SEQUENCE: 21
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgcg gcatccagtt tgcaaagtgg ggtcccatca    180
aggttcagtg gcagtggatc tgggacagat ttcactctca ccatcagcag tctgcaacct    240
gaagattttg caacttacta ctgtcaacag acggttgtgg cgcctccgtt attcggccaa    300
gggaccaagg tggaaatcaa acgt                                           324

<210> SEQ ID NO 22
<211> LENGTH: 108
<212> TYPE: PRT
<213> ORGANISM: Artificial Sequence
<220> FEATURE:
<223> OTHER INFORMATION: 4D11 Light Chain Variable Region

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg
            100                 105

<210> SEQ ID NO 23
<211> LENGTH: 357
<212> TYPE: DNA
<213> ORGANISM: Artificial Sequence
<220> FEATURE:
<223> OTHER INFORMATION: 4D11 Heavy Chain Variable Region

<400> SEQUENCE: 23
gaggtgcagc tgttggagtc tgggggaggc ttggtacagc ctggggggtc cctgagactc     60
```

```
tcctgtgcag cctctggatt cacctttagc agctatgcca tgagctgggt ccgccaggct    120
ccagggaagg ggctggagtg ggtgtcaagt attgacccgg aaggtcggca gacatattac    180
gcagactccg tgaagggccg gttcaccatc tccagagaca attccaagaa cacgctgtat    240
ctgcaaatga acagcctgag agccgaggac acggccgtat attactgtgc gaaagacatc    300
ggcggcaggt cggcctttga ctactggggc cagggaaccc tggtcaccgt ctcctca       357
```

```
<210> SEQ ID NO 24
<211> LENGTH: 119
<212> TYPE: PRT
<213> ORGANISM: Artificial Sequence
<220> FEATURE:
<223> OTHER INFORMATION: 4D11 Heavy Chain Variable Region

<400> SEQUENCE: 24
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115
```

```
<210> SEQ ID NO 25
<211> LENGTH: 642
<212> TYPE: DNA
<213> ORGANISM: Artificial Sequence
<220> FEATURE:
<223> OTHER INFORMATION: 4D11 Light Chain

<400> SEQUENCE: 25
```

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgcg gcatccagtt tgcaaagtgg ggtcccatca    180
aggttcagtg gcagtggatc tgggacagat ttcactctca ccatcagcag tctgcaacct    240
gaagattttg caacttacta ctgtcaacag acggttgtgg cgcctccgtt attcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacctgacg    540 ctgagcaaag cagactacga gaaacacaaa gtctacgcct gcgaagtcac ccatcagggc    600
ctgagctcgc ccgtcacaaa gagcttcaac aggggagagt gt                       642
```

```
<210> SEQ ID NO 26
```

<211> LENGTH: 214
<212> TYPE: PRT
<213> ORGANISM: Artificial Sequence
<220> FEATURE:
<223> OTHER INFORMATION: 4D11 Light Chain

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 27
<211> LENGTH: 1338
<212> TYPE: DNA
<213> ORGANISM: Artificial Sequence
<220> FEATURE:
<223> OTHER INFORMATION: 4D11 Heavy Chain

<400> SEQUENCE: 27

| | | | | | |
|---|---|---|---|---|---|
| gaggtgcagc | tgttggagtc | tgggggaggc | ttggtacagc | ctggggggtc | cctgagactc | 60 |
| tcctgtgcag | cctctggatt | cacctttagc | agctatgcca | tgagctgggt | ccgccaggct | 120 |
| ccagggaagg | ggctggagtg | ggtgtcaagt | attgaagaga | tggttggca | gacaaagtac | 180 |
| gcagactccg | tgaagggccg | gttcaccatc | tccagagaca | attccaagaa | cacgctgtat | 240 |
| ctgcaaatga | acagcctgag | agccgaggac | acggccgtat | attactgtgc | gaaatcggct | 300 |
| gctgcttttg | actactgggg | ccagggaacc | ctggtcaccg | tctcctcagc | tagcaccaag | 360 |
| ggcccatcgg | tcttccccct | ggcaccctcc | tccaagagca | cctctggggg | cacagcggcc | 420 |
| ctgggctgcc | tggtcaagga | ctacttcccc | gaaccggtga | cggtgtcgtg | gaactcaggc | 480 |
| gccctgacca | gcggcgtgca | caccttcccg | gctgtcctac | agtcctcagg | actctactcc | 540 |
| ctcagcagcg | tggtgaccgt | gccctccagc | agcttgggca | cccagaccta | catctgcaac | 600 |

```
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 28
<211> LENGTH: 449
<212> TYPE: PRT
<213> ORGANISM: Artificial Sequence
<220> FEATURE:
<223> OTHER INFORMATION: 4D11 Heavy Chain

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 29
<211> LENGTH: 774
<212> TYPE: DNA
<213> ORGANISM: Artificial Sequence
<220> FEATURE:
<223> OTHER INFORMATION: 5342-1204-4D11 Light Chain

<400> SEQUENCE: 29

```
caaggccagt ctggccagtg caatatttgg ctcgtaggtg gtgattgcag gggctggcag      60
gggggctcga gcgtggcag cggtggctct ggtggtctga gcggccgttc cgataatcat     120
ggcggcggtt ctgacatcca gatgacccag tctccatcct ccctgtctgc atctgtagga    180
gacagagtca ccatcacttg ccgggcaagt cagagcatta gcagctattt aaattggtat    240
cagcagaaac cagggaaagc ccctaagctc ctgatctatg cggcatccag tttgcaaagt    300
ggggtcccat caaggttcag tggcagtgga tctgggacag atttcactct caccatcagc    360
agtctgcaac ctgaagattt tgcaacttac tactgtcaac agcggttgt ggcgcctccg    420 ttattcggcc aagggaccaa ggtggaaatc aaacgtacgg tggctgcacc atctgtcttc    480
atcttcccgc catctgatga gcagttgaaa tctggaactg cctctgttgt gtgcctgctg    540
aataacttct atcccagaga ggccaaagta cagtggaagg tggataacgc cctccaatcg    600
ggtaactccc aggagagtgt cacagagcag gacagcaagg acagcaccta cagcctcagc    660
agcaccctga cgctgagcaa agcagactac gagaaacaca agtctacgc ctgcgaagtc    720 acccatcagg gcctgagctc gcccgtcaca aagagcttca caggggaga gtgt           774
```

```
<210> SEQ ID NO 30
<211> LENGTH: 258
<212> TYPE: PRT
<213> ORGANISM: Artificial Sequence
<220> FEATURE:
<223> OTHER INFORMATION: 5342-1204-4D11 Light Chain
<220> FEATURE:
<221> NAME/KEY: misc_feature
<222> LOCATION: (126)..(126)
<223> OTHER INFORMATION: Xaa can be any naturally occurring amino acid

<400> SEQUENCE: 30
```

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly Ser Gly Gly
            20                  25                  30

Leu Ser Gly Arg Ser Asp Asn His Gly Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Xaa Phe Ala
        115                 120                 125

Thr Tyr Tyr Cys Gln Gln Thr Val Val Ala Pro Pro Leu Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

```
<210> SEQ ID NO 31
<211> LENGTH: 774
<212> TYPE: DNA
<213> ORGANISM: Artificial Sequence
<220> FEATURE:
<223> OTHER INFORMATION: 5342-PLGL-4D11 Light Chain

<400> SEQUENCE: 31
```
caaggccagt ctggccagtg caatatttgg ctcgtaggtg gtgattgcag gggctggcag      60
gggggctcga gcggtggcag cggtggctct ggtggctcag gtggaggctc gccactgggc     120

| | |
|---|---|
| ctgggcggtt ctgacatcca gatgacccag tctccatcct ccctgtctgc atctgtagga | 180 |
| gacagagtca ccatcacttg ccgggcaagt cagagcatta gcagctattt aaattggtat | 240 |
| cagcagaaac cagggaaagc ccctaagctc ctgatctatg cggcatccag tttgcaaagt | 300 |
| ggggtcccat caaggttcag tggcagtgga tctgggacag atttcactct caccatcagc | 360 |
| agtctgcaac tgaagatttt gcaacttac tactgtcaac agacggttgt ggcgcctccg | 420 |
| ttattcggcc aagggaccaa ggtggaaatc aaacgtacgg tggctgcacc atctgtcttc | 480 |
| atcttcccgc catctgatga gcagttgaaa tctggaactg cctctgttgt gtgcctgctg | 540 |
| aataacttct atcccagaga ggccaaagta cagtggaagg tggataacgc cctccaatcg | 600 |
| ggtaactccc aggagagtgt cacagagcag gacagcaagg acagcaccta cagcctcagc | 660 |
| agcaccctga cgctgagcaa agcagactac gagaaacaca agtctacgc ctgcgaagtc | 720 |
| acccatcagg gcctgagctc gcccgtcaca aagagcttca caggggagag tgt | 774 |

<210> SEQ ID NO 32
<211> LENGTH: 258
<212> TYPE: PRT
<213> ORGANISM: Artificial Sequence
<220> FEATURE:
<223> OTHER INFORMATION: 5342-PLGL-4D11 Light Chain

<400> SEQUENCE: 32

```
Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly Ser Gly Gly
            20                  25                  30

Ser Gly Gly Gly Ser Pro Leu Gly Leu Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Thr Val Val Ala Pro Pro Leu Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255
```

Glu Cys

<210> SEQ ID NO 33
<211> LENGTH: 5
<212> TYPE: PRT
<213> ORGANISM: Artificial Sequence
<220> FEATURE:
<223> OTHER INFORMATION: linking peptide
<220> FEATURE:
<221> NAME/KEY: REPEAT
<222> LOCATION: (1)..(5)
<223> OTHER INFORMATION: May be repeated

<400> SEQUENCE: 33

Gly Ser Gly Gly Ser
1               5

<210> SEQ ID NO 34
<211> LENGTH: 4
<212> TYPE: PRT
<213> ORGANISM: Artificial Sequence
<220> FEATURE:
<223> OTHER INFORMATION: linking peptide
<220> FEATURE:
<221> NAME/KEY: REPEAT
<222> LOCATION: (1)..(4)
<223> OTHER INFORMATION: May be repeated

<400> SEQUENCE: 34

Gly Gly Gly Ser
1

<210> SEQ ID NO 35
<211> LENGTH: 4
<212> TYPE: PRT
<213> ORGANISM: Artificial Sequence
<220> FEATURE:
<223> OTHER INFORMATION: linking peptide

<400> SEQUENCE: 35

Gly Gly Ser Gly
1

<210> SEQ ID NO 36
<211> LENGTH: 5
<212> TYPE: PRT
<213> ORGANISM: Artificial Sequence
<220> FEATURE:
<223> OTHER INFORMATION: linking peptide

<400> SEQUENCE: 36

Gly Gly Ser Gly Gly
1               5

<210> SEQ ID NO 37
<211> LENGTH: 5
<212> TYPE: PRT
<213> ORGANISM: Artificial Sequence
<220> FEATURE:
<223> OTHER INFORMATION: linking peptide

<400> SEQUENCE: 37

Gly Ser Gly Ser Gly
1               5

<210> SEQ ID NO 38
<211> LENGTH: 5

```
<212> TYPE: PRT
<213> ORGANISM: Artificial Sequence
<220> FEATURE:
<223> OTHER INFORMATION: linking peptide

<400> SEQUENCE: 38

Gly Ser Gly Gly Gly
1               5

<210> SEQ ID NO 39
<211> LENGTH: 5
<212> TYPE: PRT
<213> ORGANISM: Artificial Sequence
<220> FEATURE:
<223> OTHER INFORMATION: linking peptide

<400> SEQUENCE: 39

Gly Gly Gly Ser Gly
1               5

<210> SEQ ID NO 40
<211> LENGTH: 5
<212> TYPE: PRT
<213> ORGANISM: Artificial Sequence
<220> FEATURE:
<223> OTHER INFORMATION: linking peptide

<400> SEQUENCE: 40

Gly Ser Ser Ser Gly
1               5

<210> SEQ ID NO 41
<211> LENGTH: 4
<212> TYPE: PRT
<213> ORGANISM: Artificial Sequence
<220> FEATURE:
<223> OTHER INFORMATION: linking peptide

<400> SEQUENCE: 41

Gly Ser Ser Gly
1

<210> SEQ ID NO 42

<400> SEQUENCE: 42

000

<210> SEQ ID NO 43
<211> LENGTH: 6
<212> TYPE: PRT
<213> ORGANISM: Artificial Sequence
<220> FEATURE:
<223> OTHER INFORMATION: masking moiety

<400> SEQUENCE: 43

Cys Ile Ser Pro Arg Gly
1               5

<210> SEQ ID NO 44
<211> LENGTH: 8
<212> TYPE: PRT
<213> ORGANISM: Artificial Sequence
<220> FEATURE:
<223> OTHER INFORMATION: masking moiety

<400> SEQUENCE: 44
```

Cys Ile Ser Pro Arg Gly Cys Gly
1               5

<210> SEQ ID NO 45
<211> LENGTH: 14
<212> TYPE: PRT
<213> ORGANISM: Artificial Sequence
<220> FEATURE:
<223> OTHER INFORMATION: masking moiety

<400> SEQUENCE: 45

Cys Ile Ser Pro Arg Gly Cys Pro Asp Gly Pro Tyr Val Met
1               5                   10

<210> SEQ ID NO 46
<211> LENGTH: 15
<212> TYPE: PRT
<213> ORGANISM: Artificial Sequence
<220> FEATURE:
<223> OTHER INFORMATION: masking moiety

<400> SEQUENCE: 46

Cys Ile Ser Pro Arg Gly Cys Glu Pro Gly Thr Tyr Val Pro Thr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: masking moiety

<400> SEQUENCE: 47

Cys Ile Ser Pro Arg Gly Cys Pro Gly Gln Ile Trp His Pro Pro
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: masking moiety

<400> SEQUENCE: 48

Gly Ser His Cys Leu Ile Pro Ile Asn Met Gly Ala Pro Ser Cys
1               5                   10                  15

<210> SEQ ID NO 49
<211> LENGTH: 32
<212> TYPE: PRT
<213> ORGANISM: Artificial Sequence
<220> FEATURE:
<223> OTHER INFORMATION: masking moiety

<400> SEQUENCE: 49

Cys Ile Ser Pro Arg Gly Cys Gly Gly Ser Ser Ala Ser Gln Ser Gly
1               5                   10                  15

Gln Gly Ser His Cys Leu Ile Pro Ile Asn Met Gly Ala Pro Ser Cys
            20                  25                  30

<210> SEQ ID NO 50
<211> LENGTH: 19
<212> TYPE: PRT
<213> ORGANISM: Artificial Sequence
<220> FEATURE:
<223> OTHER INFORMATION: masking moiety -continued

```
<400> SEQUENCE: 50

Cys Asn His His Tyr Phe Tyr Thr Cys Gly Cys Ile Ser Pro Arg Gly
1               5                   10                  15

Cys Pro Gly

<210> SEQ ID NO 51
<211> LENGTH: 19
<212> TYPE: PRT
<213> ORGANISM: Artificial Sequence
<220> FEATURE:
<223> OTHER INFORMATION: masking moiety

<400> SEQUENCE: 51

Ala Asp His Val Phe Trp Gly Ser Tyr Gly Cys Ile Ser Pro Arg Gly
1               5                   10                  15

Cys Pro Gly

<210> SEQ ID NO 52
<211> LENGTH: 19
<212> TYPE: PRT
<213> ORGANISM: Artificial Sequence
<220> FEATURE:
<223> OTHER INFORMATION: masking moiety

<400> SEQUENCE: 52

Cys His His Val Tyr Trp Gly His Cys Gly Cys Ile Ser Pro Arg Gly
1               5                   10                  15

Cys Pro Gly

<210> SEQ ID NO 53
<211> LENGTH: 19
<212> TYPE: PRT
<213> ORGANISM: Artificial Sequence
<220> FEATURE:
<223> OTHER INFORMATION: masking moiety

<400> SEQUENCE: 53

Cys Pro His Phe Thr Thr Thr Ser Cys Gly Cys Ile Ser Pro Arg Gly
1               5                   10                  15

Cys Pro Gly

<210> SEQ ID NO 54
<211> LENGTH: 19
<212> TYPE: PRT
<213> ORGANISM: Artificial Sequence
<220> FEATURE:
<223> OTHER INFORMATION: masking moiety

<400> SEQUENCE: 54

Cys Asn His His Tyr His Tyr Tyr Cys Gly Cys Ile Ser Pro Arg Gly
1               5                   10                  15

Cys Pro Gly

<210> SEQ ID NO 55
<211> LENGTH: 19
<212> TYPE: PRT
<213> ORGANISM: Artificial Sequence
<220> FEATURE:
<223> OTHER INFORMATION: masking moiety

<400> SEQUENCE: 55

Cys Pro His Val Ser Phe Gly Ser Cys Gly Cys Ile Ser Pro Arg Gly
1               5                   10                  15
```

Cys Pro Gly

<210> SEQ ID NO 56
<211> LENGTH: 19
<212> TYPE: PRT
<213> ORGANISM: Artificial Sequence
<220> FEATURE:
<223> OTHER INFORMATION: masking moiety

<400> SEQUENCE: 56

Cys Pro Tyr Tyr Thr Leu Ser Tyr Cys Gly Cys Ile Ser Pro Arg Gly
1               5                   10                  15

Cys Pro Gly

<210> SEQ ID NO 57
<211> LENGTH: 19
<212> TYPE: PRT
<213> ORGANISM: Artificial Sequence
<220> FEATURE:
<223> OTHER INFORMATION: masking moiety

<400> SEQUENCE: 57

Cys Asn His Val Tyr Phe Gly Thr Cys Gly Cys Ile Ser Pro Arg Gly
1               5                   10                  15

Cys Pro Gly

<210> SEQ ID NO 58
<211> LENGTH: 19
<212> TYPE: PRT
<213> ORGANISM: Artificial Sequence
<220> FEATURE:
<223> OTHER INFORMATION: masking moiety

<400> SEQUENCE: 58

Cys Asn His Phe Thr Leu Thr Thr Cys Gly Cys Ile Ser Pro Arg Gly
1               5                   10                  15

Cys Pro Gly

<210> SEQ ID NO 59
<211> LENGTH: 19
<212> TYPE: PRT
<213> ORGANISM: Artificial Sequence
<220> FEATURE:
<223> OTHER INFORMATION: masking moiety

<400> SEQUENCE: 59

Cys His His Phe Thr Leu Thr Thr Cys Gly Cys Ile Ser Pro Arg Gly
1               5                   10                  15

Cys Pro Gly

<210> SEQ ID NO 60
<211> LENGTH: 18
<212> TYPE: PRT
<213> ORGANISM: Artificial Sequence
<220> FEATURE:
<223> OTHER INFORMATION: masking moiety

<400> SEQUENCE: 60

Tyr Asn Pro Cys Ala Thr Pro Met Cys Cys Ile Ser Pro Arg Gly Cys
1               5                   10                  15

Pro Gly

```
<210> SEQ ID NO 61
<211> LENGTH: 18
<212> TYPE: PRT
<213> ORGANISM: Artificial Sequence
<220> FEATURE:
<223> OTHER INFORMATION: masking moiety

<400> SEQUENCE: 61

Cys Asn His His Tyr Phe Tyr Thr Cys Gly Cys Ile Ser Pro Arg Gly
1               5                   10                  15

Cys Gly

<210> SEQ ID NO 62
<211> LENGTH: 18
<212> TYPE: PRT
<213> ORGANISM: Artificial Sequence
<220> FEATURE:
<223> OTHER INFORMATION: masking moiety

<400> SEQUENCE: 62

Cys Asn His His Tyr His Tyr Tyr Cys Gly Cys Ile Ser Pro Arg Gly
1               5                   10                  15

Cys Gly

<210> SEQ ID NO 63
<211> LENGTH: 18
<212> TYPE: PRT
<213> ORGANISM: Artificial Sequence
<220> FEATURE:
<223> OTHER INFORMATION: masking moiety

<400> SEQUENCE: 63

Cys Asn His Val Tyr Phe Gly Thr Cys Gly Cys Ile Ser Pro Arg Gly
1               5                   10                  15

Cys Gly

<210> SEQ ID NO 64
<211> LENGTH: 18
<212> TYPE: PRT
<213> ORGANISM: Artificial Sequence
<220> FEATURE:
<223> OTHER INFORMATION: masking moiety

<400> SEQUENCE: 64

Cys His His Val Tyr Trp Gly His Cys Gly Cys Ile Ser Pro Arg Gly
1               5                   10                  15

Cys Gly

<210> SEQ ID NO 65
<211> LENGTH: 18
<212> TYPE: PRT
<213> ORGANISM: Artificial Sequence
<220> FEATURE:
<223> OTHER INFORMATION: masking moiety

<400> SEQUENCE: 65

Cys Pro His Phe Thr Thr Thr Ser Cys Gly Cys Ile Ser Pro Arg Gly
1               5                   10                  15

Cys Gly

<210> SEQ ID NO 66
<211> LENGTH: 18
<212> TYPE: PRT
<213> ORGANISM: Artificial Sequence
```

```
<220> FEATURE:
<223> OTHER INFORMATION: masking moiety

<400> SEQUENCE: 66

Cys Asn His Phe Thr Leu Thr Thr Cys Gly Cys Ile Ser Pro Arg Gly
1               5                   10                  15

Cys Gly

<210> SEQ ID NO 67
<211> LENGTH: 18
<212> TYPE: PRT
<213> ORGANISM: Artificial Sequence
<220> FEATURE:
<223> OTHER INFORMATION: masking moiety

<400> SEQUENCE: 67

Cys His His Phe Thr Leu Thr Thr Cys Gly Cys Ile Ser Pro Arg Gly
1               5                   10                  15

Cys Gly

<210> SEQ ID NO 68
<211> LENGTH: 18
<212> TYPE: PRT
<213> ORGANISM: Artificial Sequence
<220> FEATURE:
<223> OTHER INFORMATION: masking moiety

<400> SEQUENCE: 68

Cys Pro Tyr Tyr Thr Leu Ser Tyr Cys Gly Cys Ile Ser Pro Arg Gly
1               5                   10                  15

Cys Gly

<210> SEQ ID NO 69
<211> LENGTH: 18
<212> TYPE: PRT
<213> ORGANISM: Artificial Sequence
<220> FEATURE:
<223> OTHER INFORMATION: masking moiety

<400> SEQUENCE: 69

Cys Pro His Val Ser Phe Gly Ser Cys Gly Cys Ile Ser Pro Arg Gly
1               5                   10                  15

Cys Gly

<210> SEQ ID NO 70
<211> LENGTH: 18
<212> TYPE: PRT
<213> ORGANISM: Artificial Sequence
<220> FEATURE:
<223> OTHER INFORMATION: masking moiety

<400> SEQUENCE: 70

Ala Asp His Val Phe Trp Gly Ser Tyr Gly Cys Ile Ser Pro Arg Gly
1               5                   10                  15

Cys Gly

<210> SEQ ID NO 71
<211> LENGTH: 17
<212> TYPE: PRT
<213> ORGANISM: Artificial Sequence
<220> FEATURE:
<223> OTHER INFORMATION: masking moiety

<400> SEQUENCE: 71
```

```
Tyr Asn Pro Cys Ala Thr Pro Met Cys Cys Ile Ser Pro Arg Gly Cys
1               5                   10                  15

Gly

<210> SEQ ID NO 72
<211> LENGTH: 18
<212> TYPE: PRT
<213> ORGANISM: Artificial Sequence
<220> FEATURE:
<223> OTHER INFORMATION: masking moiety

<400> SEQUENCE: 72

Cys His His Val Tyr Trp Gly His Cys Gly Cys Ile Ser Pro Arg Gly
1               5                   10                  15

Cys Gly

<210> SEQ ID NO 73
<211> LENGTH: 18
<212> TYPE: PRT
<213> ORGANISM: Artificial Sequence
<220> FEATURE:
<223> OTHER INFORMATION: masking moiety
<220> FEATURE:
<221> NAME/KEY: misc_feature
<222> LOCATION: (2)..(2)
<223> OTHER INFORMATION: Xaa may be Asn or Pro
<220> FEATURE:
<221> NAME/KEY: misc_feature
<222> LOCATION: (4)..(4)
<223> OTHER INFORMATION: Xaa may be His, Val or Phe
<220> FEATURE:
<221> NAME/KEY: misc_feature
<222> LOCATION: (5)..(5)
<223> OTHER INFORMATION: Xaa may be Tyr or Thr
<220> FEATURE:
<221> NAME/KEY: misc_feature
<222> LOCATION: (6)..(6)
<223> OTHER INFORMATION: Xaa may be Phe, Trp, Thr or Leu
<220> FEATURE:
<221> NAME/KEY: misc_feature
<222> LOCATION: (7)..(7)
<223> OTHER INFORMATION: Xaa may be Tyr, Gly, Thr or Ser
<220> FEATURE:
<221> NAME/KEY: misc_feature
<222> LOCATION: (8)..(8)
<223> OTHER INFORMATION: Xaa may be Thr, Ser, Tyr or His

<400> SEQUENCE: 73

Cys Xaa His Xaa Xaa Xaa Xaa Xaa Cys Gly Cys Ile Ser Pro Arg Gly
1               5                   10                  15

Cys Gly

<210> SEQ ID NO 74
<211> LENGTH: 15
<212> TYPE: PRT
<213> ORGANISM: Artificial Sequence
<220> FEATURE:
<223> OTHER INFORMATION: masking moiety

<400> SEQUENCE: 74

Cys Ile Ser Pro Arg Gly Cys Gly Gln Pro Ile Pro Ser Val Lys
1               5                   10                  15

<210> SEQ ID NO 75
<211> LENGTH: 15
<212> TYPE: PRT
<213> ORGANISM: Artificial Sequence
<220> FEATURE:
```

```
<223> OTHER INFORMATION: masking moiety

<400> SEQUENCE: 75

Cys Ile Ser Pro Arg Gly Cys Thr Gln Pro Tyr His Val Ser Arg
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: masking moiety

<400> SEQUENCE: 76

Cys Ile Ser Pro Arg Gly Cys Asn Ala Val Ser Gly Leu Gly Ser
1               5                   10                  15

<210> SEQ ID NO 77
<211> LENGTH: 26
<212> TYPE: PRT
<213> ORGANISM: Artificial Sequence
<220> FEATURE:
<223> OTHER INFORMATION: masking moiety

<400> SEQUENCE: 77

Gln Gly Gln Ser Gly Gln Gly Gln Gln Trp Cys Asn Ile Trp Ile
1               5                   10                  15

Asn Gly Gly Asp Cys Arg Gly Trp Asn Gly
            20                  25

<210> SEQ ID NO 78
<211> LENGTH: 15
<212> TYPE: PRT
<213> ORGANISM: Artificial Sequence
<220> FEATURE:
<223> OTHER INFORMATION: masking moiety

<400> SEQUENCE: 78

Pro Trp Cys Met Gln Arg Gln Asp Phe Leu Arg Cys Pro Gln Pro
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: masking moiety

<400> SEQUENCE: 79

Gln Leu Gly Leu Pro Ala Tyr Met Cys Thr Phe Glu Cys Leu Arg
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: masking moiety

<400> SEQUENCE: 80

Cys Asn Leu Trp Val Ser Gly Gly Asp Cys Gly Gly Leu Gln Gly
1               5                   10                  15

<210> SEQ ID NO 81
<211> LENGTH: 15
<212> TYPE: PRT
```

```
<213> ORGANISM: Artificial Sequence
<220> FEATURE:
<223> OTHER INFORMATION: masking moiety

<400> SEQUENCE: 81

Ser Cys Ser Leu Trp Thr Ser Gly Ser Cys Leu Pro His Ser Pro
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: masking moiety

<400> SEQUENCE: 82

Tyr Cys Leu Gln Leu Pro His Tyr Met Gln Ala Met Cys Gly Arg
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: masking moiety

<400> SEQUENCE: 83

Cys Phe Leu Tyr Ser Cys Thr Asp Val Ser Tyr Trp Asn Asn Thr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: masking moiety

<400> SEQUENCE: 84

Pro Trp Cys Met Gln Arg Gln Asp Tyr Leu Arg Cys Pro Gln Pro
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: masking moiety

<400> SEQUENCE: 85

Cys Asn Leu Trp Ile Ser Gly Gly Asp Cys Arg Gly Leu Ala Gly
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: masking moiety

<400> SEQUENCE: 86

Cys Asn Leu Trp Val Ser Gly Gly Asp Cys Arg Gly Val Gln Gly
1               5                   10                  15

<210> SEQ ID NO 87
<211> LENGTH: 15
<212> TYPE: PRT
<213> ORGANISM: Artificial Sequence
```

```
<220> FEATURE:
<223> OTHER INFORMATION: masking moiety

<400> SEQUENCE: 87

Cys Asn Leu Trp Val Ser Gly Gly Asp Cys Arg Gly Leu Arg Gly
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: masking moiety

<400> SEQUENCE: 88

Cys Asn Leu Trp Ile Ser Gly Gly Asp Cys Arg Gly Leu Pro Gly
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: masking moiety

<400> SEQUENCE: 89

Cys Asn Leu Trp Val Ser Gly Gly Asp Cys Arg Asp Ala Pro Trp
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: masking moiety

<400> SEQUENCE: 90

Cys Asn Leu Trp Val Ser Gly Gly Asp Cys Arg Asp Leu Leu Gly
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: masking moiety

<400> SEQUENCE: 91

Cys Asn Leu Trp Val Ser Gly Gly Asp Cys Arg Gly Leu Gln Gly
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: masking moiety

<400> SEQUENCE: 92

Cys Asn Leu Trp Leu His Gly Gly Asp Cys Arg Gly Trp Gln Gly
1               5                   10                  15

<210> SEQ ID NO 93
<211> LENGTH: 15
<212> TYPE: PRT
<213> ORGANISM: Artificial Sequence
<220> FEATURE:
```

<223> OTHER INFORMATION: masking moiety

<400> SEQUENCE: 93

Cys Asn Ile Trp Leu Val Gly Gly Asp Cys Arg Gly Trp Gln Gly
1 5 10 15

<210> SEQ ID NO 94
<211> LENGTH: 15
<212> TYPE: PRT
<213> ORGANISM: Artificial Sequence
<220> FEATURE:
<223> OTHER INFORMATION: masking moiety

<400> SEQUENCE: 94

Cys Thr Thr Trp Phe Cys Gly Gly Asp Cys Gly Val Met Arg Gly
1 5 10 15

<210> SEQ ID NO 95
<211> LENGTH: 15
<212> TYPE: PRT
<213> ORGANISM: Artificial Sequence
<220> FEATURE:
<223> OTHER INFORMATION: masking moiety

<400> SEQUENCE: 95

Cys Asn Ile Trp Gly Pro Ser Val Asp Cys Gly Ala Leu Leu Gly
1 5 10 15

<210> SEQ ID NO 96
<211> LENGTH: 15
<212> TYPE: PRT
<213> ORGANISM: Artificial Sequence
<220> FEATURE:
<223> OTHER INFORMATION: masking moiety

<400> SEQUENCE: 96

Cys Asn Ile Trp Val Asn Gly Gly Asp Cys Arg Ser Phe Glu Gly
1 5 10 15

<210> SEQ ID NO 97
<211> LENGTH: 15
<212> TYPE: PRT
<213> ORGANISM: Artificial Sequence
<220> FEATURE:
<223> OTHER INFORMATION: masking moiety

<400> SEQUENCE: 97

Tyr Cys Leu Asn Leu Pro Arg Tyr Met Gln Asp Met Cys Trp Ala
1 5 10 15

<210> SEQ ID NO 98
<211> LENGTH: 15
<212> TYPE: PRT
<213> ORGANISM: Artificial Sequence
<220> FEATURE:
<223> OTHER INFORMATION: masking moiety

<400> SEQUENCE: 98

Tyr Cys Leu Ala Leu Pro His Tyr Met Gln Ala Asp Cys Ala Arg
1 5 10 15

<210> SEQ ID NO 99
<211> LENGTH: 15
<212> TYPE: PRT
<213> ORGANISM: Artificial Sequence
<220> FEATURE:
<223> OTHER INFORMATION: masking moiety

<400> SEQUENCE: 99

Cys Phe Leu Tyr Ser Cys Gly Asp Val Ser Tyr Trp Gly Ser Ala
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: masking moiety

<400> SEQUENCE: 100

Cys Tyr Leu Tyr Ser Cys Thr Asp Ser Ala Phe Trp Asn Asn Arg
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: masking moiety

<400> SEQUENCE: 101

Cys Tyr Leu Tyr Ser Cys Asn Asp Val Ser Tyr Trp Ser Asn Thr
1               5                   10                  15

<210> SEQ ID NO 102
<211> LENGTH: 12
<212> TYPE: PRT
<213> ORGANISM: Artificial Sequence
<220> FEATURE:
<223> OTHER INFORMATION: masking moiety

<400> SEQUENCE: 102

Cys Phe Leu Tyr Ser Cys Thr Asp Val Ser Tyr Trp
1               5                   10

<210> SEQ ID NO 103
<211> LENGTH: 15
<212> TYPE: PRT
<213> ORGANISM: Artificial Sequence
<220> FEATURE:
<223> OTHER INFORMATION: masking moiety

<400> SEQUENCE: 103

Cys Phe Leu Tyr Ser Cys Thr Asp Val Ala Tyr Trp Asn Ser Ala
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: masking moiety

<400> SEQUENCE: 104

Cys Phe Leu Tyr Ser Cys Thr Asp Val Ser Tyr Trp Gly Asp Thr
1               5                   10                  15

<210> SEQ ID NO 105
<211> LENGTH: 15
<212> TYPE: PRT
<213> ORGANISM: Artificial Sequence
<220> FEATURE

```
<400> SEQUENCE: 105

Cys Phe Leu Tyr Ser Cys Thr Asp Val Ser Tyr Trp Gly Asn Ser
1               5                  10                  15

<210> SEQ ID NO 106
<211> LENGTH: 15
<212> TYPE: PRT
<213> ORGANISM: Artificial Sequence
<220> FEATURE:
<223> OTHER INFORMATION: masking moiety

<400> SEQUENCE: 106

Cys Phe Leu Tyr Ser Cys Thr Asp Val Ala Tyr Trp Asn Asn Thr
1               5                  10                  15

<210> SEQ ID NO 107
<211> LENGTH: 18
<212> TYPE: PRT
<213> ORGANISM: Artificial Sequence
<220> FEATURE:
<223> OTHER INFORMATION: masking moiety

<400> SEQUENCE: 107

Cys Phe Leu Tyr Ser Cys Gly Asp Val Ser Tyr Trp Gly Asn Pro Gly
1               5                  10                  15

Leu Ser

<210> SEQ ID NO 108
<211> LENGTH: 15
<212> TYPE: PRT
<213> ORGANISM: Artificial Sequence
<220> FEATURE:
<223> OTHER INFORMATION: masking moiety

<400> SEQUENCE: 108

Cys Phe Leu Tyr Ser Cys Thr Asp Val Ala Tyr Trp Ser Gly Leu
1               5                  10                  15

<210> SEQ ID NO 109
<211> LENGTH: 15
<212> TYPE: PRT
<213> ORGANISM: Artificial Sequence
<220> FEATURE:
<223> OTHER INFORMATION: masking moiety

<400> SEQUENCE: 109

Cys Tyr Leu Tyr Ser Cys Thr Asp Gly Ser Tyr Trp Asn Ser Thr
1               5                  10                  15

<210> SEQ ID NO 110
<211> LENGTH: 15
<212> TYPE: PRT
<213> ORGANISM: Artificial Sequence
<220> FEATURE:
<223> OTHER INFORMATION: masking moiety

<400> SEQUENCE: 110

Cys Phe Leu Tyr Ser Cys Ser Asp Val Ser Tyr Trp Gly Asn Ile
1               5                  10                  15

<210> SEQ ID NO 111
<211> LENGTH: 12
<212> TYPE: PRT
<213> ORGANISM: Artificial Sequence
<220> FEATURE:
<223> OTHER INFORMATION: masking moiety
```

<400> SEQUENCE: 111

Cys Phe Leu Tyr Ser Cys Thr Asp Val Ala Tyr Trp
1               5                   10

<210> SEQ ID NO 112
<211> LENGTH: 15
<212> TYPE: PRT
<213> ORGANISM: Artificial Sequence
<220> FEATURE:
<223> OTHER INFORMATION: masking moiety

<400> SEQUENCE: 112

Cys Phe Leu Tyr Ser Cys Thr Asp Val Ser Tyr Trp Gly Ser Thr
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: masking moiety

<400> SEQUENCE: 113

Cys Phe Leu Tyr Ser Cys Thr Asp Val Ala Tyr Trp Gly Asp Thr
1               5                   10                  15

<210> SEQ ID NO 114
<211> LENGTH: 20
<212> TYPE: PRT
<213> ORGANISM: Artificial Sequence
<220> FEATURE:
<223> OTHER INFORMATION: masking moiety

<400> SEQUENCE: 114

Gly Cys Asn Ile Trp Leu Asn Gly Gly Asp Cys Arg Gly Trp Val Asp
1               5                   10                  15

Pro Leu Gln Gly
            20

<210> SEQ ID NO 115
<211> LENGTH: 20
<212> TYPE: PRT
<213> ORGANISM: Artificial Sequence
<220> FEATURE:
<223> OTHER INFORMATION: masking moiety

<400> SEQUENCE: 115

Gly Cys Asn Ile Trp Leu Val Gly Gly Asp Cys Arg Gly Trp Ile Gly
1               5                   10                  15

Asp Thr Asn Gly
            20

<210> SEQ ID NO 116
<211> LENGTH: 20
<212> TYPE: PRT
<213> ORGANISM: Artificial Sequence
<220> FEATURE:
<223> OTHER INFORMATION: masking moiety

<400> SEQUENCE: 116

Gly Cys Asn Ile Trp Leu Val Gly Gly Asp Cys Arg Gly Trp Ile Glu
1               5                   10                  15

Asp Ser Asn Gly
            20

```
<210> SEQ ID NO 117
<211> LENGTH: 20
<212> TYPE: PRT
<213> ORGANISM: Artificial Sequence
<220> FEATURE:
<223> OTHER INFORMATION: masking moiety

<400> SEQUENCE: 117

Gly Cys Asn Ile Trp Ala Asn Gly Gly Asp Cys Arg Gly Trp Ile Asp
1               5                   10                  15

Asn Ile Asp Gly
            20

<210> SEQ ID NO 118
<211> LENGTH: 20
<212> TYPE: PRT
<213> ORGANISM: Artificial Sequence
<220> FEATURE:
<223> OTHER INFORMATION: masking moiety

<400> SEQUENCE: 118

Gly Cys Asn Ile Trp Leu Val Gly Gly Asp Cys Arg Gly Trp Leu Gly
1               5                   10                  15

Glu Ala Val Gly
            20

<210> SEQ ID NO 119
<211> LENGTH: 20
<212> TYPE: PRT
<213> ORGANISM: Artificial Sequence
<220> FEATURE:
<223> OTHER INFORMATION: masking moiety

<400> SEQUENCE: 119

Gly Cys Asn Ile Trp Leu Val Gly Gly Asp Cys Arg Gly Trp Leu Glu
1               5                   10                  15

Glu Ala Val Gly
            20

<210> SEQ ID NO 120
<211> LENGTH: 20
<212> TYPE: PRT
<213> ORGANISM: Artificial Sequence
<220> FEATURE:
<223> OTHER INFORMATION: masking moiety

<400> SEQUENCE: 120

Gly Gly Pro Ala Leu Cys Asn Ile Trp Leu Asn Gly Gly Asp Cys Arg
1               5                   10                  15

Gly Trp Ser Gly
            20

<210> SEQ ID NO 121
<211> LENGTH: 20
<212> TYPE: PRT
<213> ORGANISM: Artificial Sequence
<220> FEATURE:
<223> OTHER INFORMATION: masking moiety

<400> SEQUENCE: 121

Gly Ala Pro Val Phe Cys Asn Ile Trp Leu Asn Gly Gly Asp Cys Arg
1               5                   10                  15

Gly Trp Met Gly
```

```
<210> SEQ ID NO 122
<211> LENGTH: 20
<212> TYPE: PRT
<213> ORGANISM: Artificial Sequence
<220> FEATURE:
<223> OTHER INFORMATION: masking moiety

<400> SEQUENCE: 122

Gly Gln Gln Gln Trp Cys Asn Ile Trp Ile Asn Gly Gly Asp Cys Arg
1               5                   10                  15

Gly Trp Asn Gly
            20

<210> SEQ ID NO 123
<211> LENGTH: 20
<212> TYPE: PRT
<213> ORGANISM: Artificial Sequence
<220> FEATURE:
<223> OTHER INFORMATION: masking moiety

<400> SEQUENCE: 123

Gly Lys Ser Glu Phe Cys Asn Ile Trp Leu Asn Gly Gly Asp Cys Arg
1               5                   10                  15

Gly Trp Ile Gly
            20

<210> SEQ ID NO 124
<211> LENGTH: 20
<212> TYPE: PRT
<213> ORGANISM: Artificial Sequence
<220> FEATURE:
<223> OTHER INFORMATION: masking moiety

<400> SEQUENCE: 124

Gly Thr Pro Gly Gly Cys Asn Ile Trp Ala Asn Gly Gly Asp Cys Arg
1               5                   10                  15

Gly Trp Glu Gly
            20

<210> SEQ ID NO 125
<211> LENGTH: 20
<212> TYPE: PRT
<213> ORGANISM: Artificial Sequence
<220> FEATURE:
<223> OTHER INFORMATION: masking moiety

<400> SEQUENCE: 125

Gly Ala Ser Gln Tyr Cys Asn Leu Trp Ile Asn Gly Gly Asp Cys Arg
1               5                   10                  15

Gly Trp Arg Gly
            20

<210> SEQ ID NO 126
<211> LENGTH: 18
<212> TYPE: PRT
<213> ORGANISM: Artificial Sequence
<220> FEATURE:
<223> OTHER INFORMATION: masking moiety

<400> SEQUENCE: 126

Gly Cys Asn Ile Trp Leu Val Gly Gly Asp Cys Arg Pro Trp Val Glu
1               5                   10                  15
```

Gly Gly

<210> SEQ ID NO 127
<211> LENGTH: 18
<212> TYPE: PRT
<213> ORGANISM: Artificial Sequence
<220> FEATURE:
<223> OTHER INFORMATION: masking moiety

<400> SEQUENCE: 127

Gly Cys Asn Ile Trp Ala Val Gly Gly Asp Cys Arg Pro Phe Val Asp
1               5                   10                  15

Gly Gly

<210> SEQ ID NO 128
<211> LENGTH: 18
<212> TYPE: PRT
<213> ORGANISM: Artificial Sequence
<220> FEATURE:
<223> OTHER INFORMATION: masking moiety

<400> SEQUENCE: 128

Gly Cys Asn Ile Trp Leu Asn Gly Gly Asp Cys Arg Ala Trp Val Asp
1               5                   10                  15

Thr Gly

<210> SEQ ID NO 129
<211> LENGTH: 18
<212> TYPE: PRT
<213> ORGANISM: Artificial Sequence
<220> FEATURE:
<223> OTHER INFORMATION: masking moiety

<400> SEQUENCE: 129

Gly Cys Asn Ile Trp Ile Val Gly Gly Asp Cys Arg Pro Phe Ile Asn
1               5                   10                  15

Asp Gly

<210> SEQ ID NO 130
<211> LENGTH: 18
<212> TYPE: PRT
<213> ORGANISM: Artificial Sequence
<220> FEATURE:
<223> OTHER INFORMATION: masking moiety

<400> SEQUENCE: 130

Gly Cys Asn Ile Trp Leu Asn Gly Gly Asp Cys Arg Pro Val Val Phe
1               5                   10                  15

Gly Gly

<210> SEQ ID NO 131
<211> LENGTH: 18
<212> TYPE: PRT
<213> ORGANISM: Artificial Sequence
<220> FEATURE:
<223> OTHER INFORMATION: masking moiety

<400> SEQUENCE: 131

Gly Cys Asn Ile Trp Leu Ser Gly Gly Asp Cys Arg Met Phe Met Asn
1               5                   10                  15

Glu Gly

<210> SEQ ID NO 132

```
<211> LENGTH: 18
<212> TYPE: PRT
<213> ORGANISM: Artificial Sequence
<220> FEATURE:
<223> OTHER INFORMATION: masking moiety

<400> SEQUENCE: 132

Gly Cys Asn Ile Trp Val Asn Gly Gly Asp Cys Arg Ser Phe Val Tyr
1               5                   10                  15

Ser Gly

<210> SEQ ID NO 133
<211> LENGTH: 18
<212> TYPE: PRT
<213> ORGANISM: Artificial Sequence
<220> FEATURE:
<223> OTHER INFORMATION: masking moiety

<400> SEQUENCE: 133

Gly Cys Asn Ile Trp Leu Asn Gly Gly Asp Cys Arg Gly Trp Glu Ala
1               5                   10                  15

Ser Gly

<210> SEQ ID NO 134
<211> LENGTH: 18
<212> TYPE: PRT
<213> ORGANISM: Artificial Sequence
<220> FEATURE:
<223> OTHER INFORMATION: masking moiety

<400> SEQUENCE: 134

Gly Cys Asn Ile Trp Ala His Gly Gly Asp Cys Arg Gly Phe Ile Glu
1               5                   10                  15

Pro Gly

<210> SEQ ID NO 135
<211> LENGTH: 18
<212> TYPE: PRT
<213> ORGANISM: Artificial Sequence
<220> FEATURE:
<223> OTHER INFORMATION: masking moiety

<400> SEQUENCE: 135

Gly Cys Asn Ile Trp Leu Asn Gly Gly Asp Cys Arg Thr Phe Val Ala
1               5                   10                  15

Ser Gly

<210> SEQ ID NO 136
<211> LENGTH: 18
<212> TYPE: PRT
<213> ORGANISM: Artificial Sequence
<220> FEATURE:
<223> OTHER INFORMATION: masking moiety

<400> SEQUENCE: 136

Gly Cys Asn Ile Trp Ala His Gly Gly Asp Cys Arg Gly Phe Ile Glu
1               5                   10                  15

Pro Gly

<210> SEQ ID NO 137
<211> LENGTH: 18
<212> TYPE: PRT
<213> ORGANISM: Artificial Sequence
<220> FEATURE:
```

```
<223> OTHER INFORMATION: masking moiety

<400> SEQUENCE: 137

Gly Phe Leu Glu Asn Cys Asn Ile Trp Leu Asn Gly Gly Asp Cys Arg
1               5                   10                  15

Thr Gly

<210> SEQ ID NO 138
<211> LENGTH: 18
<212> TYPE: PRT
<213> ORGANISM: Artificial Sequence
<220> FEATURE:
<223> OTHER INFORMATION: masking moiety

<400> SEQUENCE: 138

Gly Ile Tyr Glu Asn Cys Asn Ile Trp Leu Asn Gly Gly Asp Cys Arg
1               5                   10                  15

Met Gly

<210> SEQ ID NO 139
<211> LENGTH: 18
<212> TYPE: PRT
<213> ORGANISM: Artificial Sequence
<220> FEATURE:
<223> OTHER INFORMATION: masking moiety

<400> SEQUENCE: 139

Gly Ile Pro Asp Asn Cys Asn Ile Trp Ile Asn Gly Gly Asp Cys Arg
1               5                   10                  15

Tyr Gly

<210> SEQ ID NO 140
<211> LENGTH: 21
<212> TYPE: PRT
<213> ORGANISM: Artificial Sequence
<220> FEATURE:
<223> OTHER INFORMATION: masking moiety

<400> SEQUENCE: 140

Gln Gly Gln Ser Gly Gln Tyr Gly Ser Cys Ser Trp Asn Tyr Val His
1               5                   10                  15

Ile Phe Met Asp Cys
            20

<210> SEQ ID NO 141
<211> LENGTH: 21
<212> TYPE: PRT
<213> ORGANISM: Artificial Sequence
<220> FEATURE:
<223> OTHER INFORMATION: masking moiety

<400> SEQUENCE: 141

Gln Gly Gln Ser Gly Gln Gly Asp Phe Asp Ile Pro Phe Pro Ala His
1               5                   10                  15

Trp Val Pro Ile Thr
            20

<210> SEQ ID NO 142
<211> LENGTH: 24
<212> TYPE: PRT
<213> ORGANISM: Artificial Sequence
<220> FEATURE:
<223> OTHER INFORMATION: masking moiety
```

```
<400> SEQUENCE: 142

Gln Gly Gln Ser Gly Gln Met Gly Val Pro Ala Gly Cys Val Trp Asn
1               5                   10                  15

Tyr Ala His Ile Phe Met Asp Cys
            20

<210> SEQ ID NO 143
<211> LENGTH: 15
<212> TYPE: PRT
<213> ORGANISM: Artificial Sequence
<220> FEATURE:
<223> OTHER INFORMATION: masking moiety

<400> SEQUENCE: 143

Tyr Arg Ser Cys Asn Trp Asn Tyr Val Ser Ile Phe Leu Asp Cys
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: masking moiety

<400> SEQUENCE: 144

Pro Gly Ala Phe Asp Ile Pro Phe Pro Ala His Trp Val Pro Asn Thr
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: masking moiety

<400> SEQUENCE: 145

Glu Ser Ser Cys Val Trp Asn Tyr Val His Ile Tyr Met Asp Cys
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: masking moiety

<400> SEQUENCE: 146

Tyr Pro Gly Cys Lys Trp Asn Tyr Asp Arg Ile Phe Leu Asp Cys
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: masking moiety

<400> SEQUENCE: 147

Tyr Arg Thr Cys Ser Trp Asn Tyr Val Gly Ile Phe Leu Asp Cys
1               5                   10                  15

<210> SEQ ID NO 148
<211> LENGTH: 15
<212> TYPE: PRT
<213> ORGANISM: Artificial Sequence
<220> FEATURE:
```

<223> OTHER INFORMATION: masking moiety

<400> SEQUENCE: 148

Tyr Gly Ser Cys Ser Trp Asn Tyr Val His Ile Phe Met Asp Cys
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: masking moiety

<400> SEQUENCE: 149

Tyr Gly Ser Cys Ser Trp Asn Tyr Val His Ile Phe Leu Asp Cys
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: masking moiety

<400> SEQUENCE: 150

Tyr Gly Ser Cys Asn Trp Asn Tyr Val His Ile Phe Leu Asp Cys
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: masking moiety

<400> SEQUENCE: 151

Tyr Thr Ser Cys Asn Trp Asn Tyr Val His Ile Phe Met Asp Cys
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: masking moiety

<400> SEQUENCE: 152

Tyr Pro Gly Cys Lys Trp Asn Tyr Asp Arg Ile Phe Leu Asp Cys
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: masking moiety

<400> SEQUENCE: 153

Trp Arg Ser Cys Asn Trp Asn Tyr Ala His Ile Phe Leu Asp Cys
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: masking moiety

<400> SEQUENCE: 154

Trp Ser Asn Cys His Trp Asn Tyr Val His Ile Phe Leu Asp Cys
1               5                  10                  15

<210> SEQ ID NO 155
<211> LENGTH: 15
<212> TYPE: PRT
<213> ORGANISM: Artificial Sequence
<220> FEATURE:
<223> OTHER INFORMATION: masking moiety

<400> SEQUENCE: 155

Asp Arg Ser Cys Thr Trp Asn Tyr Val Arg Ile Ser Tyr Asp Cys
1               5                  10                  15

<210> SEQ ID NO 156
<211> LENGTH: 15
<212> TYPE: PRT
<213> ORGANISM: Artificial Sequence
<220> FEATURE:
<223> OTHER INFORMATION: masking moiety

<400> SEQUENCE: 156

Ser Gly Ser Cys Lys Trp Asp Tyr Val His Ile Phe Leu Asp Cys
1               5                  10                  15

<210> SEQ ID NO 157
<211> LENGTH: 15
<212> TYPE: PRT
<213> ORGANISM: Artificial Sequence
<220> FEATURE:
<223> OTHER INFORMATION: masking moiety

<400> SEQUENCE: 157

Ser Arg Ser Cys Ile Trp Asn Tyr Ala His Ile His Leu Asp Cys
1               5                  10                  15

<210> SEQ ID NO 158
<211> LENGTH: 15
<212> TYPE: PRT
<213> ORGANISM: Artificial Sequence
<220> FEATURE:
<223> OTHER INFORMATION: masking moiety

<400> SEQUENCE: 158

Ser Met Ser Cys Tyr Trp Gln Tyr Glu Arg Ile Phe Leu Asp Cys
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: masking moiety

<400> SEQUENCE: 159

Tyr Arg Ser Cys Asn Trp Asn Tyr Val Ser Ile Phe Leu Asp Cys
1 5 10 15

<210> SEQ ID NO 160
<211> LENGTH: 15
<212> TYPE: PRT
<213> ORGANISM: Artificial Sequence
<220> FEATURE:
<223> OTHER INFORMATION: masking moiety

```
<400> SEQUENCE: 160

Tyr Gly Ser Cys Ser Trp Asn Tyr Val His Ile Phe Met Asp Cys
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: masking moiety

<400> SEQUENCE: 161

Ser Gly Ser Cys Lys Trp Asp Tyr Val His Ile Phe Leu Asp Cys
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: masking moiety

<400> SEQUENCE: 162

Tyr Lys Ser Cys His Trp Asp Tyr Val His Ile Phe Leu Asp Cys
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: masking moiety

<400> SEQUENCE: 163

Tyr Gly Ser Cys Thr Trp Asn Tyr Val His Ile Phe Met Glu Cys
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: masking moiety

<400> SEQUENCE: 164

Phe Ser Ser Cys Asn Trp Asn Tyr Val His Ile Phe Leu Asp Cys
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: masking moiety

<400> SEQUENCE: 165

Trp Arg Ser Cys Asn Trp Asn Tyr Ala His Ile Phe Leu Asp Cys
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: masking moiety

<400> SEQUENCE: 166
```

Tyr Gly Ser Cys Gln Trp Asn Tyr Val His Ile Phe Leu Asp Cys
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: masking moiety

<400> SEQUENCE: 167

Tyr Arg Ser Cys Asn Trp Asn Tyr Val His Ile Phe Leu Asp Cys
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: masking moiety

<400> SEQUENCE: 168

Asn Met Ser Cys His Trp Asp Tyr Val His Ile Phe Leu Asp Cys
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: masking moiety

<400> SEQUENCE: 169

Phe Gly Pro Cys Thr Trp Asn Tyr Ala Arg Ile Ser Trp Asp Cys
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: masking moiety
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 170

Xaa Xaa Ser Cys Xaa Trp Xaa Tyr Val His Ile Phe Xaa Asp Cys
1               5                   10                  15

<210> SEQ ID NO 171
<211> LENGTH: 18
<212> TYPE: PRT
<213> ORGANISM: Artificial Sequence
<220> FEATURE:
<223> OTHER INFORMATION: masking moiety

<400> SEQUENCE: 171

Met Gly Val Pro Ala Gly Cys Val Trp Asn Tyr Ala His Ile Phe Met
1               5                   10                  15

Asp Cys

<210> SEQ ID NO 172
<211> LENGTH: 18
<212> TYPE: PRT
<213> ORGANISM: Artificial Sequence
<220> FEATURE:
<223> OTHER INFORMATION: masking moiety

<400> SEQUENCE: 172

Arg Asp Thr Gly Gly Gln Cys Arg Trp Asp Tyr Val His Ile Phe Met
1               5                   10                  15

Asp Cys

<210> SEQ ID NO 173
<211> LENGTH: 18
<212> TYPE: PRT
<213> ORGANISM: Artificial Sequence
<220> FEATURE:
<223> OTHER INFORMATION: masking moiety

<400> SEQUENCE: 173

Ala Gly Val Pro Ala Gly Cys Thr Trp Asn Tyr Val His Ile Phe Met
1               5                   10                  15

Glu Cys

<210> SEQ ID NO 174
<211> LENGTH: 18
<212> TYPE: PRT
<213> ORGANISM: Artificial Sequence
<220> FEATURE:
<223> OTHER INFORMATION: masking moiety

<400> SEQUENCE: 174

Val Gly Val Pro Asn Gly Cys Val Trp Asn Tyr Ala His Ile Phe Met
1               5                   10                  15

Glu Cys

<210> SEQ ID NO 175
<211> LENGTH: 18
<212> TYPE: PRT
<213> ORGANISM: Artificial Sequence
<220> FEATURE:
<223> OTHER INFORMATION: masking moiety

<400> SEQUENCE: 175

Asp Gly Gly Pro Ala Gly Cys Ser Trp Asn Tyr Val His Ile Phe Met
1               5                   10                  15

Glu Cys

<210> SEQ ID NO 176
<211> LENGTH: 18
<212> TYPE: PRT
<213> ORGANISM: Artificial Sequence
<220> FEATURE:
<223> OTHER INFORMATION: masking moiety

<400> SEQUENCE: 176

Ala Val Gly Pro Ala Gly Cys Trp Trp Asn Tyr Val His Ile Phe Met

```
1               5                   10                  15

Glu Cys

<210> SEQ ID NO 177
<211> LENGTH: 18
<212> TYPE: PRT
<213> ORGANISM: Artificial Sequence
<220> FEATURE:
<223> OTHER INFORMATION: masking moiety

<400> SEQUENCE: 177

Cys Thr Trp Asn Tyr Val His Ile Phe Met Asp Cys Gly Glu Gly Glu
1               5                   10                  15

Gly Pro

<210> SEQ ID NO 178
<211> LENGTH: 18
<212> TYPE: PRT
<213> ORGANISM: Artificial Sequence
<220> FEATURE:
<223> OTHER INFORMATION: masking moiety

<400> SEQUENCE: 178

Ala Glu Val Pro Ala Gly Cys Trp Trp Asn Tyr Val His Ile Phe Met
1               5                   10                  15

Glu Cys

<210> SEQ ID NO 179
<211> LENGTH: 18
<212> TYPE: PRT
<213> ORGANISM: Artificial Sequence
<220> FEATURE:
<223> OTHER INFORMATION: masking moiety

<400> SEQUENCE: 179

Gly Gly Val Pro Glu Gly Cys Thr Trp Asn Tyr Ala His Ile Phe Met
1               5                   10                  15

Glu Cys

<210> SEQ ID NO 180
<211> LENGTH: 18
<212> TYPE: PRT
<213> ORGANISM: Artificial Sequence
<220> FEATURE:
<223> OTHER INFORMATION: masking moiety

<400> SEQUENCE: 180

Ala Gly Val Pro Ala Gly Cys Thr Trp Asn Tyr Val His Ile Phe Met
1               5                   10                  15

Glu Cys

<210> SEQ ID NO 181
<211> LENGTH: 18
<212> TYPE: PRT
<213> ORGANISM: Artificial Sequence
<220> FEATURE:
<223> OTHER INFORMATION: masking moiety

<400> SEQUENCE: 181

Ser Gly Ala Ser Gly Gly Cys Lys Trp Asn Tyr Val His Ile Phe Met
1               5                   10                  15

Asp Cys
```

<210> SEQ ID NO 182
<211> LENGTH: 18
<212> TYPE: PRT
<213> ORGANISM: Artificial Sequence
<220> FEATURE:
<223> OTHER INFORMATION: masking moiety

<400> SEQUENCE: 182

Met Gly Val Pro Ala Gly Cys Val Trp Asn Tyr Ala His Ile Phe Met
1               5                   10                  15

Asp Cys

<210> SEQ ID NO 183
<211> LENGTH: 18
<212> TYPE: PRT
<213> ORGANISM: Artificial Sequence
<220> FEATURE:
<223> OTHER INFORMATION: masking moiety

<400> SEQUENCE: 183

Thr Pro Gly Cys Arg Trp Asn Tyr Val His Ile Phe Met Glu Cys Glu
1               5                   10                  15

Ala Leu

<210> SEQ ID NO 184
<211> LENGTH: 18
<212> TYPE: PRT
<213> ORGANISM: Artificial Sequence
<220> FEATURE:
<223> OTHER INFORMATION: masking moiety

<400> SEQUENCE: 184

Val Gly Val Pro Asn Gly Cys Val Trp Asn Tyr Ala His Ile Phe Met
1               5                   10                  15

Glu Cys

<210> SEQ ID NO 185
<211> LENGTH: 16
<212> TYPE: PRT
<213> ORGANISM: Artificial Sequence
<220> FEATURE:
<223> OTHER INFORMATION: masking moiety

<400> SEQUENCE: 185

Pro Gly Ala Phe Asp Ile Pro Phe Pro Ala His Trp Val Pro Asn Thr
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: masking moiety

<400> SEQUENCE: 186

Arg Gly Ala Cys Asp Ile Pro Phe Pro Ala His Trp Ile Pro Asn Thr
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: masking moiety

```
<400> SEQUENCE: 187

Gln Gly Asp Phe Asp Ile Pro Phe Pro Ala His Trp Val Pro Ile Thr
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: masking moiety
<220> FEATURE:
<221> NAME/KEY: misc_feature
<222> LOCATION: (1)..(1)
<223> OTHER INFORMATION: Xaa can be any naturally occurring amino acid

<400> SEQUENCE: 188

Xaa Gly Ala Phe Asp Ile Pro Phe Pro Ala His Trp Val Pro Asn Thr
1               5                   10                  15

<210> SEQ ID NO 189
<211> LENGTH: 19
<212> TYPE: PRT
<213> ORGANISM: Artificial Sequence
<220> FEATURE:
<223> OTHER INFORMATION: masking moiety

<400> SEQUENCE: 189

Arg Gly Asp Gly Asn Asp Ser Asp Ile Pro Phe Pro Ala His Trp Val
1               5                   10                  15

Pro Arg Thr

<210> SEQ ID NO 190
<211> LENGTH: 19
<212> TYPE: PRT
<213> ORGANISM: Artificial Sequence
<220> FEATURE:
<223> OTHER INFORMATION: masking moiety

<400> SEQUENCE: 190

Ser Gly Val Gly Arg Asp Arg Asp Ile Pro Phe Pro Ala His Trp Val
1               5                   10                  15

Pro Arg Thr

<210> SEQ ID NO 191
<211> LENGTH: 19
<212> TYPE: PRT
<213> ORGANISM: Artificial Sequence
<220> FEATURE:
<223> OTHER INFORMATION: masking moiety

<400> SEQUENCE: 191

Trp Ala Gly Gly Asn Asp Cys Asp Ile Pro Phe Pro Ala His Trp Ile
1               5                   10                  15

Pro Asn Thr

<210> SEQ ID NO 192
<211> LENGTH: 19
<212> TYPE: PRT
<213> ORGANISM: Artificial Sequence
<220> FEATURE:
<223> OTHER INFORMATION: masking moiety

<400> SEQUENCE: 192

Trp Gly Asp Gly Met Asp Val Asp Ile Pro Phe Pro Ala His Trp Val
1               5                   10                  15
```

Pro Val Thr

<210> SEQ ID NO 193
<211> LENGTH: 19
<212> TYPE: PRT
<213> ORGANISM: Artificial Sequence
<220> FEATURE:
<223> OTHER INFORMATION: masking moiety

<400> SEQUENCE: 193

Ala Gly Ser Gly Asn Asp Ser Asp Ile Pro Phe Pro Ala His Trp Val
1               5                   10                  15

Pro Arg Thr

<210> SEQ ID NO 194
<211> LENGTH: 19
<212> TYPE: PRT
<213> ORGANISM: Artificial Sequence
<220> FEATURE:
<223> OTHER INFORMATION: masking moiety

<400> SEQUENCE: 194

Glu Ser Arg Ser Gly Tyr Ala Asp Ile Pro Phe Pro Ala His Trp Val
1               5                   10                  15

Pro Arg Thr

<210> SEQ ID NO 195
<211> LENGTH: 19
<212> TYPE: PRT
<213> ORGANISM: Artificial Sequence
<220> FEATURE:
<223> OTHER INFORMATION: masking moiety

<400> SEQUENCE: 195

Arg Glu Cys Gly Arg Cys Gly Asp Ile Pro Phe Pro Ala His Trp Val
1               5                   10                  15

Pro Arg Thr

<210> SEQ ID NO 196
<211> LENGTH: 8
<212> TYPE: PRT
<213> ORGANISM: Artificial Sequence
<220> FEATURE:
<223> OTHER INFORMATION: cleavable moiety

<400> SEQUENCE: 196

Thr Gly Arg Gly Pro Ser Trp Val
1               5

<210> SEQ ID NO 197
<211> LENGTH: 8
<212> TYPE: PRT
<213> ORGANISM: Artificial Sequence
<220> FEATURE:
<223> OTHER INFORMATION: cleavable moiety

<400> SEQUENCE: 197

Ser Ala Arg Gly Pro Ser Arg Trp
1               5

<210> SEQ ID NO 198
<211> LENGTH: 8
<212> TYPE: PRT
<213> ORGANISM: Artificial Sequence

```
<220> FEATURE:
<223> OTHER INFORMATION: cleavable moiety

<400> SEQUENCE: 198

Thr Ala Arg Gly Pro Ser Phe Lys
1               5

<210> SEQ ID NO 199
<211> LENGTH: 8
<212> TYPE: PRT
<213> ORGANISM: Artificial Sequence
<220> FEATURE:
<223> OTHER INFORMATION: cleavable moiety

<400> SEQUENCE: 199

Gly Gly Trp His Thr Gly Arg Asn
1               5

<210> SEQ ID NO 200
<211> LENGTH: 8
<212> TYPE: PRT
<213> ORGANISM: Artificial Sequence
<220> FEATURE:
<223> OTHER INFORMATION: cleavable moiety

<400> SEQUENCE: 200

His Thr Gly Arg Ser Gly Ala Leu
1               5

<210> SEQ ID NO 201
<211> LENGTH: 8
<212> TYPE: PRT
<213> ORGANISM: Artificial Sequence
<220> FEATURE:
<223> OTHER INFORMATION: cleavable moiety

<400> SEQUENCE: 201

Pro Leu Thr Gly Arg Ser Gly Gly
1               5

<210> SEQ ID NO 202
<211> LENGTH: 8
<212> TYPE: PRT
<213> ORGANISM: Artificial Sequence
<220> FEATURE:
<223> OTHER INFORMATION: cleavable moiety

<400> SEQUENCE: 202

Ala Ala Arg Gly Pro Ala Ile His
1               5

<210> SEQ ID NO 203
<211> LENGTH: 8
<212> TYPE: PRT
<213> ORGANISM: Artificial Sequence
<220> FEATURE:
<223> OTHER INFORMATION: cleavable moiety

<400> SEQUENCE: 203

Arg Gly Pro Ala Phe Asn Pro Met
1               5

<210> SEQ ID NO 204
<211> LENGTH: 8
<212> TYPE: PRT
<213> ORGANISM: Artificial Sequence
<220> FEATURE:
```

```
<223> OTHER INFORMATION: cleavable moiety

<400> SEQUENCE: 204

Ser Ser Arg Gly Pro Ala Tyr Leu
1               5

<210> SEQ ID NO 205
<211> LENGTH: 8
<212> TYPE: PRT
<213> ORGANISM: Artificial Sequence
<220> FEATURE:
<223> OTHER INFORMATION: cleavable moiety

<400> SEQUENCE: 205

Arg Gly Pro Ala Thr Pro Ile Met
1               5

<210> SEQ ID NO 206
<211> LENGTH: 4
<212> TYPE: PRT
<213> ORGANISM: Artificial Sequence
<220> FEATURE:
<223> OTHER INFORMATION: cleavable moiety

<400> SEQUENCE: 206

Arg Gly Pro Ala
1

<210> SEQ ID NO 207
<211> LENGTH: 10
<212> TYPE: PRT
<213> ORGANISM: Artificial Sequence
<220> FEATURE:
<223> OTHER INFORMATION: cleavable moiety

<400> SEQUENCE: 207

Gly Gly Gln Pro Ser Gly Met Trp Gly Trp
1               5                   10

<210> SEQ ID NO 208
<211> LENGTH: 10
<212> TYPE: PRT
<213> ORGANISM: Artificial Sequence
<220> FEATURE:
<223> OTHER INFORMATION: cleavable moiety

<400> SEQUENCE: 208

Phe Pro Arg Pro Leu Gly Ile Thr Gly Leu
1               5                   10

<210> SEQ ID NO 209
<211> LENGTH: 10
<212> TYPE: PRT
<213> ORGANISM: Artificial Sequence
<220> FEATURE:
<223> OTHER INFORMATION: cleavable moiety

<400> SEQUENCE: 209

Val His Met Pro Leu Gly Phe Leu Gly Pro
1               5                   10

<210> SEQ ID NO 210
<211> LENGTH: 8
<212> TYPE: PRT
<213> ORGANISM: Artificial Sequence
<220> FEATURE:
<223> OTHER INFORMATION: cleavable moiety
```

```
<400> SEQUENCE: 210

Ser Pro Leu Thr Gly Arg Ser Gly
1               5

<210> SEQ ID NO 211
<211> LENGTH: 8
<212> TYPE: PRT
<213> ORGANISM: Artificial Sequence
<220> FEATURE:
<223> OTHER INFORMATION: cleavable moiety

<400> SEQUENCE: 211

Ser Ala Gly Phe Ser Leu Pro Ala
1               5

<210> SEQ ID NO 212
<211> LENGTH: 9
<212> TYPE: PRT
<213> ORGANISM: Artificial Sequence
<220> FEATURE:
<223> OTHER INFORMATION: cleavable moiety

<400> SEQUENCE: 212

Leu Ala Pro Leu Gly Leu Gln Arg Arg
1               5

<210> SEQ ID NO 213
<211> LENGTH: 8
<212> TYPE: PRT
<213> ORGANISM: Artificial Sequence
<220> FEATURE:
<223> OTHER INFORMATION: cleavable moiety

<400> SEQUENCE: 213

Ser Gly Gly Pro Leu Gly Val Arg
1               5

<210> SEQ ID NO 214
<211> LENGTH: 4
<212> TYPE: PRT
<213> ORGANISM: Artificial Sequence
<220> FEATURE:
<223> OTHER INFORMATION: cleavable moiety

<400> SEQUENCE: 214

Pro Leu Gly Leu
1

<210> SEQ ID NO 215
<211> LENGTH: 8
<212> TYPE: PRT
<213> ORGANISM: Artificial Sequence
<220> FEATURE:
<223> OTHER INFORMATION: cleavable moiety

<400> SEQUENCE: 215

Pro Arg Phe Lys Ile Ile Gly Gly
1               5

<210> SEQ ID NO 216
<211> LENGTH: 8
<212> TYPE: PRT
<213> ORGANISM: Artificial Sequence
<220> FEATURE:
<223> OTHER INFORMATION: cleavable moiety
```

```
<400> SEQUENCE: 216

Pro Arg Phe Arg Ile Ile Gly Gly
1               5

<210> SEQ ID NO 217
<211> LENGTH: 9
<212> TYPE: PRT
<213> ORGANISM: Artificial Sequence
<220> FEATURE:
<223> OTHER INFORMATION: cleavable moiety

<400> SEQUENCE: 217

Ser Ser Arg His Arg Arg Ala Leu Asp
1               5

<210> SEQ ID NO 218
<211> LENGTH: 14
<212> TYPE: PRT
<213> ORGANISM: Artificial Sequence
<220> FEATURE:
<223> OTHER INFORMATION: cleavable moiety

<400> SEQUENCE: 218

Arg Lys Ser Ser Ile Ile Ile Arg Met Arg Asp Val Val Leu
1               5                   10

<210> SEQ ID NO 219
<211> LENGTH: 15
<212> TYPE: PRT
<213> ORGANISM: Artificial Sequence
<220> FEATURE:
<223> OTHER INFORMATION: cleavable moiety

<400> SEQUENCE: 219

Ser Ser Ser Phe Asp Lys Gly Lys Tyr Lys Lys Gly Asp Asp Ala
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: cleavable moiety

<400> SEQUENCE: 220

Ser Ser Ser Phe Asp Lys Gly Lys Tyr Lys Arg Gly Asp Asp Ala
1               5                   10                  15

<210> SEQ ID NO 221
<211> LENGTH: 4
<212> TYPE: PRT
<213> ORGANISM: Artificial Sequence
<220> FEATURE:
<223> OTHER INFORMATION: cleavable moiety

<400> SEQUENCE: 221

Ile Glu Gly Arg
1

<210> SEQ ID NO 222
<211> LENGTH: 4
<212> TYPE: PRT
<213> ORGANISM: Artificial Sequence
<220> FEATURE:
<223> OTHER INFORMATION: cleavable moiety

<400> SEQUENCE: 222
```

Ile Asp Gly Arg
1

<210> SEQ ID NO 223
<211> LENGTH: 7
<212> TYPE: PRT
<213> ORGANISM: Artificial Sequence
<220> FEATURE:
<223> OTHER INFORMATION: cleavable moiety

<400> SEQUENCE: 223

Gly Gly Ser Ile Asp Gly Arg
1               5

<210> SEQ ID NO 224
<211> LENGTH: 7
<212> TYPE: PRT
<213> ORGANISM: Artificial Sequence
<220> FEATURE:
<223> OTHER INFORMATION: cleavable moiety

<400> SEQUENCE: 224

Ala Pro Leu Gly Leu Trp Ala
1               5

<210> SEQ ID NO 225
<211> LENGTH: 8
<212> TYPE: PRT
<213> ORGANISM: Artificial Sequence
<220> FEATURE:
<223> OTHER INFORMATION: cleavable moiety

<400> SEQUENCE: 225

Gly Pro Gln Gly Ile Ala Gly Gln
1               5

<210> SEQ ID NO 226
<211> LENGTH: 8
<212> TYPE: PRT
<213> ORGANISM: Artificial Sequence
<220> FEATURE:
<223> OTHER INFORMATION: cleavable moiety

<400> SEQUENCE: 226

Gly Pro Gln Gly Leu Leu Gly Ala
1               5

<210> SEQ ID NO 227
<211> LENGTH: 5
<212> TYPE: PRT
<213> ORGANISM: Artificial Sequence
<220> FEATURE:
<223> OTHER INFORMATION: cleavable moiety

<400> SEQUENCE: 227

Gly Ile Ala Gly Gln
1               5

<210> SEQ ID NO 228
<211> LENGTH: 8
<212> TYPE: PRT
<213> ORGANISM: Artificial Sequence
<220> FEATURE:
<223> OTHER INFORMATION: cleavable moiety

<400> SEQUENCE: 228

```
Gly Pro Leu Gly Ile Ala Gly Ile
1               5

<210> SEQ ID NO 229
<211> LENGTH: 8
<212> TYPE: PRT
<213> ORGANISM: Artificial Sequence
<220> FEATURE:
<223> OTHER INFORMATION: cleavable moiety

<400> SEQUENCE: 229

Gly Pro Glu Gly Leu Arg Val Gly
1               5

<210> SEQ ID NO 230
<211> LENGTH: 8
<212> TYPE: PRT
<213> ORGANISM: Artificial Sequence
<220> FEATURE:
<223> OTHER INFORMATION: cleavable moiety

<400> SEQUENCE: 230

Tyr Gly Ala Gly Leu Gly Val Val
1               5

<210> SEQ ID NO 231
<211> LENGTH: 8
<212> TYPE: PRT
<213> ORGANISM: Artificial Sequence
<220> FEATURE:
<223> OTHER INFORMATION: cleavable moiety

<400> SEQUENCE: 231

Ala Gly Leu Gly Val Val Glu Arg
1               5

<210> SEQ ID NO 232
<211> LENGTH: 8
<212> TYPE: PRT
<213> ORGANISM: Artificial Sequence
<220> FEATURE:
<223> OTHER INFORMATION: cleavable moiety

<400> SEQUENCE: 232

Ala Gly Leu Gly Ile Ser Ser Thr
1               5

<210> SEQ ID NO 233
<211> LENGTH: 8
<212> TYPE: PRT
<213> ORGANISM: Artificial Sequence
<220> FEATURE:
<223> OTHER INFORMATION: cleavable moiety

<400> SEQUENCE: 233

Glu Pro Gln Ala Leu Ala Met Ser
1               5

<210> SEQ ID NO 234
<211> LENGTH: 8
<212> TYPE: PRT
<213> ORGANISM: Artificial Sequence
<220> FEATURE:
<223> OTHER INFORMATION: cleavable moiety

<400> SEQUENCE: 234

Gln Ala Leu Ala Met Ser Ala Ile
```

```
1               5

<210> SEQ ID NO 235
<211> LENGTH: 8
<212> TYPE: PRT
<213> ORGANISM: Artificial Sequence
<220> FEATURE:
<223> OTHER INFORMATION: cleavable moiety

<400> SEQUENCE: 235

Ala Ala Tyr His Leu Val Ser Gln
1               5

<210> SEQ ID NO 236
<211> LENGTH: 8
<212> TYPE: PRT
<213> ORGANISM: Artificial Sequence
<220> FEATURE:
<223> OTHER INFORMATION: cleavable moiety

<400> SEQUENCE: 236

Met Asp Ala Phe Leu Glu Ser Ser
1               5

<210> SEQ ID NO 237
<211> LENGTH: 8
<212> TYPE: PRT
<213> ORGANISM: Artificial Sequence
<220> FEATURE:
<223> OTHER INFORMATION: cleavable moiety

<400> SEQUENCE: 237

Glu Ser Leu Pro Val Val Ala Val
1               5

<210> SEQ ID NO 238
<211> LENGTH: 8
<212> TYPE: PRT
<213> ORGANISM: Artificial Sequence
<220> FEATURE:
<223> OTHER INFORMATION: cleavable moiety

<400> SEQUENCE: 238

Ser Ala Pro Ala Val Glu Ser Glu
1               5

<210> SEQ ID NO 239
<211> LENGTH: 8
<212> TYPE: PRT
<213> ORGANISM: Artificial Sequence
<220> FEATURE:
<223> OTHER INFORMATION: cleavable moiety

<400> SEQUENCE: 239

Asp Val Ala Gln Phe Val Leu Thr
1               5

<210> SEQ ID NO 240
<211> LENGTH: 8
<212> TYPE: PRT
<213> ORGANISM: Artificial Sequence
<220> FEATURE:
<223> OTHER INFORMATION: cleavable moiety

<400> SEQUENCE: 240

Val Ala Gln Phe Val Leu Thr Glu
1               5
```

<210> SEQ ID NO 241
<211> LENGTH: 8
<212> TYPE: PRT
<213> ORGANISM: Artificial Sequence
<220> FEATURE:
<223> OTHER INFORMATION: cleavable moiety

<400> SEQUENCE: 241

Ala Gln Phe Val Leu Thr Glu Gly
1               5

<210> SEQ ID NO 242
<211> LENGTH: 8
<212> TYPE: PRT
<213> ORGANISM: Artificial Sequence
<220> FEATURE:
<223> OTHER INFORMATION: cleavable moiety

<400> SEQUENCE: 242

Pro Val Gln Pro Ile Gly Pro Gln
1               5

<210> SEQ ID NO 243
<211> LENGTH: 1350
<212> TYPE: DNA
<213> ORGANISM: Artificial Sequence
<220> FEATURE:
<223> OTHER INFORMATION: 3954-1204-C225v4 Activatable Antibody Heavy
      Chain

<400> SEQUENCE: 243
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag cctggaatg gctgggcgtg atttggagcg gcggcaacac cgattataac     180
accccgttta ccagccgcct gagcattaac aaagataaca gcaaaagcca ggtgtttttt     240
aaaatgaaca gcctgcaaag caacgatacc gcgatttatt attgcgcgcg cgcgctgacc     300
tattatgatt atgaatttgc gtattggggc cagggcaccc tggtgaccgt gagcgcggct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgaactg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260

-continued

```
cagggaacg tcttctcatg ctccgtgatg catgaggctc tgcacaacca ctacacgcag    1320
aagagcctct ccctgtctcc gggtaaatga                                    1350
```

<210> SEQ ID NO 244
<211> LENGTH: 449
<212> TYPE: PRT
<213> ORGANISM: Artificial Sequence
<220> FEATURE:
<223> OTHER INFORMATION: 3954-1204-C225v4 Activatable Antibody Heavy
    Chain

<400> SEQUENCE: 244

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 245
<211> LENGTH: 786
<212> TYPE: DNA
<213> ORGANISM: Artificial Sequence
<220> FEATURE:
<223> OTHER INFORMATION: 3954-1204-C225v4 Activatable Antibody Light
      Chain Nucleotide Sequence

<400> SEQUENCE: 245
caaggccagt ctggccagtg catctcacct cgtggttgtc cggacggccc atacgtcatg      60
tacggctcga gcggtggcag cggtggctct ggtggatccg gtctgagcgg ccgttccgat     120
aatcatggca gtagcggtac ccagatcttg ctgacccaga gcccggtgat tctgagcgtg     180
agcccgggcg aacgtgtgag ctttagctgc cgcgcgagcc agagcattgg caccaacatt     240
cattggtatc agcagcgcac caacggcagc ccgcgcctgc tgattaaata tgcgagcgaa     300
agcattagcg gcattccgag ccgctttagc ggcagcggca gcggcaccga ttttaccctg     360
agcattaaca gcgtggaaag cgaagatatt gcggattatt attgccagca gaacaacaac     420
tggccgacca cctttggcgc gggcaccaaa ctggaactga acgtacggt ggctgcacca     480 tctgtcttca tcttcccgcc atctgatgag cagttgaaat ctggaactgc ctctgttgtg     540
tgcctgctga ataacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                                786

<210> SEQ ID NO 246
<211> LENGTH: 261
<212> TYPE: PRT
<213> ORGANISM: Artificial Sequence
<220> FEATURE:
<223> OTHER INFORMATION: 3954-1204-C225v4 Activatable Antibody Light
      Chain Nucleotide Sequence

<400> SEQUENCE: 246

Gln Gly Gln Ser Gly Gln Cys Ile Ser Pro Arg Gly Cys Pro Asp Gly
1               5                   10                  15

Pro Tyr Val Met Tyr Gly Ser Ser Gly Ser Gly Gly Ser Gly Gly
                20                  25                  30
```

Ser Gly Leu Ser Gly Arg Ser Asp Asn His Gly Ser Gly Thr Gln
            35                  40                  45

Ile Leu Leu Thr Gln Ser Pro Val Ile Leu Ser Val Ser Pro Gly Glu
 50                  55                  60

Arg Val Ser Phe Ser Cys Arg Ala Ser Gln Ser Ile Gly Thr Asn Ile
 65                  70                  75                  80

His Trp Tyr Gln Gln Arg Thr Asn Gly Ser Pro Arg Leu Leu Ile Lys
                 85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
            115                 120                 125

Asp Ile Ala Asp Tyr Tyr Cys Gln Gln Asn Asn Asn Trp Pro Thr Thr
130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
            195                 200                 205

Ser Val Thr Glu Gln Asp Ser Lys Asp Ser Thr Tyr Ser Leu Ser Ser
            210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 247
<211> LENGTH: 645
<212> TYPE: DNA
<213> ORGANISM: Artificial Sequence
<220> FEATURE:
<223> OTHER INFORMATION: 3954-1204-C225v4 Light Chain

<400> SEQUENCE: 247
cagatcttgc tgacccagag cccggtgatt ctgagcgtga gcccgggcga acgtgtgagc      60
tttagctgcc gcgcgagcca gagcattggc accaacattc attggtatca gcagcgcacc    120
aacggcagcc cgcgcctgct gattaaatat gcgagcgaaa gcattagcgg cattccgagc    180
cgctttagcg gcagcggcag cggcaccgat tttaccctga gcattaacag cgtggaaagc    240
gaagatattg cggattatta ttgccagcag aacaacaact ggccgaccac ctttggcgcg    300
ggcaccaaac tggaactgaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 248

<211> LENGTH: 214
<212> TYPE: PRT
<213> ORGANISM: Artificial Sequence
<220> FEATURE:
<223> OTHER INFORMATION: 3954-1204-C225v4 Light Chain

<400> SEQUENCE: 248

```
Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 249
<211> LENGTH: 777
<212> TYPE: DNA
<213> ORGANISM: Artificial Sequence
<220> FEATURE:
<223> OTHER INFORMATION: 3954-NSUB-C225v4 Masked Antibody Light Chain

<400> SEQUENCE: 249

```
caaggccagt ctggccagtg catctcacct cgtggttgtc cggacggccc atacgtcatg      60
tacggctcga gcggtggcag cggtggctct ggtggctcag gtggaggctc gggcggtggg     120
agcggcggtt ctcagatctt gctgacccag agcccggtga ttctgagcgt gagcccgggc     180
gaacgtgtga gctttagctg ccgcgcgagc cagagcattg gcaccaacat tcattggtat     240
cagcagcgca ccaacggcag cccgcgcctg ctgattaaat atgcgagcga aagcattagc     300
ggcattccga gccgctttag cggcagcggc agcggcaccg attttaccct gagcattaac     360
agcgtggaaa gcgaagatat tgcggattat tattgccagc agaacaacaa ctggccgacc     420
acctttggcg cgggcaccaa actggaactg aaacgtacgg tggctgcacc atctgtcttc     480
atcttcccgc catctgatga gcagttgaaa tctggaactg cctctgttgt gtgcctgctg     540
aataacttct atcccagaga ggccaaagta cagtggaagg tggataacgc cctccaatcg     600
```

```
ggtaactccc aggagagtgt cacagagcag gacagcaagg acagcaccta cagcctcagc    660
agcaccctga cgctgagcaa agcagactac gagaaacaca aagtctacgc ctgcgaagtc    720
acccatcagg gcctgagctc gcccgtcaca aagagcttca caggggaga gtgttag       777
```

<210> SEQ ID NO 250
<211> LENGTH: 258
<212> TYPE: PRT
<213> ORGANISM: Artificial Sequence
<220> FEATURE:
<223> OTHER INFORMATION: 3954-NSUB-C225v4 Masked Antibody Light Chain
<400> SEQUENCE: 250

```
Gln Gly Gln Ser Gly Gln Cys Ile Ser Pro Arg Gly Cys Pro Asp Gly
1               5                   10                  15

Pro Tyr Val Met Tyr Gly Ser Ser Gly Ser Gly Ser Gly Ser Gly Gly
                20                  25                  30

Ser Gly Gly Gly Ser Gly Gly Gly Ser Gly Gly Ser Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
                100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
    130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
                180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys
```

<210> SEQ ID NO 251
<211> LENGTH: 10
<212> TYPE: PRT
<213> ORGANISM: Artificial Sequence
<220> FEATURE:
<223> OTHER INFORMATION: cleavable moiety
<400> SEQUENCE: 251

```
Ser Leu Ala Pro Leu Gly Leu Gln Arg Arg
1               5                   10
```

<210> SEQ ID NO 252
<211> LENGTH: 6
<212> TYPE: PRT
<213> ORGANISM: Artificial Sequence
<220> FEATURE:
<223> OTHER INFORMATION: cleavable moiety

<400> SEQUENCE: 252

Arg Arg Ala Leu Ala Leu
1               5

<210> SEQ ID NO 253
<211> LENGTH: 449
<212> TYPE: PRT
<213> ORGANISM: Artificial Sequence
<220> FEATURE:
<223> OTHER INFORMATION: C225v6 Antibody Heavy Chain

<400> SEQUENCE: 253

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 254
<211> LENGTH: 449
<212> TYPE: PRT
<213> ORGANISM: Artificial Sequence
<220> FEATURE:
<223> OTHER INFORMATION: Av1 Antibody Heavy Chain

<400> SEQUENCE: 254

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
                35                  40                  45

Ile Gly Tyr Ile Ser Tyr Ser Gly Ile Thr Thr Tyr Asn Pro Ser Leu
50                  55                  60

Lys Ser Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205
```

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 255
<211> LENGTH: 214
<212> TYPE: PRT
<213> ORGANISM: Artificial Sequence
<220> FEATURE:
<223> OTHER INFORMATION: Av1 Antibody Light Chain

<400> SEQUENCE: 255

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 256
<211> LENGTH: 449
<212> TYPE: PRT
<213> ORGANISM: Artificial Sequence
<220> FEATURE:
<223> OTHER INFORMATION: 4D11v2 Heavy Chain

<400> SEQUENCE: 256

Glu Val His Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 257
<211> LENGTH: 214
<212> TYPE: PRT
<213> ORGANISM: Artificial Sequence
<220> FEATURE:
<223> OTHER INFORMATION: 4D11v2 Light Chain
<220> FEATURE:
<221> NAME/KEY: misc_feature
<222> LOCATION: (182)..(182)
<223> OTHER INFORMATION: Xaa can be any naturally occurring amino acid

<400> SEQUENCE: 257

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Xaa Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 258
<211> LENGTH: 108
<212> TYPE: PRT
<213> ORGANISM: Artificial Sequence
<220> FEATURE:
<223> OTHER INFORMATION: Variable Light Chain Amino Sequence Lc4

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 259
<211> LENGTH: 119
<212> TYPE: PRT
<213> ORGANISM: Artificial Sequence
<220> FEATURE:
<223> OTHER INFORMATION: Variable Heavy Chain Amino Sequence Hc4

<400> SEQUENCE: 259

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
            115
```

<210> SEQ ID NO 260
<211> LENGTH: 108
<212> TYPE: PRT
<213> ORGANISM: Artificial Sequence
<220> FEATURE:
<223> OTHER INFORMATION: Variable Light Chain Amino Sequence Lc5

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 261
<211> LENGTH: 119
<212> TYPE: PRT
<213> ORGANISM: Artificial Sequence
<220> FEATURE:
<223> OTHER INFORMATION: Variable Heavy Chain Amino Sequence Hc5

<400> SEQUENCE: 261

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr His Gly Gln Phe Asp Tyr Trp Gly Gln Gly
            100                 105                 110

Thr Leu Val Thr Val Ser Ser
        115

<210> SEQ ID NO 262
<211> LENGTH: 108
<212> TYPE: PRT
<213> ORGANISM: Artificial Sequence
<220> FEATURE:
<223> OTHER INFORMATION: Variable Light Chain Amino Sequence Lc7

<400> SEQUENCE: 262

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
            85                  90                  95

Thr Phe Gly Gln Gly Thr Lys Val Glu Ile Lys Arg
            100                 105

<210> SEQ ID NO 263
<211> LENGTH: 119
<212> TYPE: PRT
<213> ORGANISM: Artificial Sequence
<220> FEATURE:
<223> OTHER INFORMATION: Variable Heavy Chain Amino Sequence Hc7

<400> SEQUENCE: 263

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Pro Pro Phe Phe Gly Gln Phe Asp Tyr Trp Gly Gln Gly
            100                 105                 110

Thr Leu Val Thr Val Ser Ser
        115

<210> SEQ ID NO 264
<211> LENGTH: 108
<212> TYPE: PRT
<213> ORGANISM: Artificial Sequence
<220> FEATURE:
<223> OTHER INFORMATION: Variable Light Chain Amino Sequence Lc8

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
            85                  90                  95

Thr Phe Gly Gln Gly Thr Lys Val Glu Ile Lys Arg
            100                 105

<210> SEQ ID NO 265
<211> LENGTH: 119
<212> TYPE: PRT
<213> ORGANISM: Artificial Sequence
<220> FEATURE:
<223> OTHER INFORMATION: Variable Heavy Chain Amino Sequence Hc8

<400> SEQUENCE: 265

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Ile Gly Arg Thr Asn Pro Phe Asp Tyr Trp Gly Gln Gly
            100                 105                 110

Thr Leu Val Thr Val Ser Ser
        115

<210> SEQ ID NO 266
<211> LENGTH: 108
<212> TYPE: PRT
<213> ORGANISM: Artificial Sequence
<220> FEATURE:
<223> OTHER INFORMATION: Variable Light Chain Amino Sequence Lc13

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 267
<211> LENGTH: 116
<212> TYPE: PRT
<213> ORGANISM: Artificial Sequence
<220> FEATURE:
<223> OTHER INFORMATION: Variable Heavy Chain Amino Sequence Hc13

<400> SEQUENCE: 267

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
            115
```

<210> SEQ ID NO 268
<211> LENGTH: 108
<212> TYPE: PRT
<213> ORGANISM: Artificial Sequence
<220> FEATURE:
<223> OTHER INFORMATION: Variable Light Chain Amino Sequence Lc16

<400> SEQUENCE: 268

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 269
<211> LENGTH: 119
<212> TYPE: PRT
<213> ORGANISM: Artificial Sequence
<220> FEATURE:
<223> OTHER INFORMATION: Variable Heavy Chain Amino Sequence Hc16

<400> SEQUENCE: 269

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Ser Pro Pro Tyr Tyr Gly Gln Phe Asp Tyr Trp Gly Gln Gly
            100                 105                 110

Thr Leu Val Thr Val Ser Ser
        115

<210> SEQ ID NO 270
<211> LENGTH: 108
<212> TYPE: PRT
<213> ORGANISM: Artificial Sequence
<220> FEATURE:
<223> OTHER INFORMATION: Variable Light Chain Amino Sequence Lc19

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 271
<211> LENGTH: 119
<212> TYPE: PRT
<213> ORGANISM: Artificial Sequence
<220> FEATURE:
<223> OTHER INFORMATION: Variable Heavy Chain Amino Sequence Hc19

<400> SEQUENCE: 271

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115

<210> SEQ ID NO 272
<211> LENGTH: 108
<212> TYPE: PRT
```

```
<213> ORGANISM: Artificial Sequence
<220> FEATURE:
<223> OTHER INFORMATION: Variable Light Chain Amino Sequence Lc21

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 273
<211> LENGTH: 119
<212> TYPE: PRT
<213> ORGANISM: Artificial Sequence
<220> FEATURE:
<223> OTHER INFORMATION: Variable Heavy Chain Amino Sequence Hc21

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 274
<211> LENGTH: 108
<212> TYPE: PRT
<213> ORGANISM: Artificial Sequence
<220> FEATURE:
<223> OTHER INFORMATION: Variable Light Chain Amino Sequence Lc24

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 275
<211> LENGTH: 116
<212> TYPE: PRT
<213> ORGANISM: Artificial Sequence
<220> FEATURE:
<223> OTHER INFORMATION: Variable Heavy Chain Amino Sequence Hc24

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 276
<211> LENGTH: 108
<212> TYPE: PRT
<213> ORGANISM: Artificial Sequence
<220> FEATURE:
<223> OTHER INFORMATION: Variable Light Chain Amino Sequence Lc26

<400> SEQUENCE: 276

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

```
<210> SEQ ID NO 277
<211> LENGTH: 119
<212> TYPE: PRT
<213> ORGANISM: Artificial Sequence
<220> FEATURE:
<223> OTHER INFORMATION: Variable Heavy Chain Amino Sequence Hc26

<400> SEQUENCE: 277

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 278
<211> LENGTH: 108
<212> TYPE: PRT
<213> ORGANISM: Artificial Sequence
<220> FEATURE:
<223> OTHER INFORMATION: Variable Light Chain Amino Sequence Lc27

<400> SEQUENCE: 278

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 279
<211> LENGTH: 119
<212> TYPE: PRT
<213> ORGANISM: Artificial Sequence
<220> FEATURE:
<223> OTHER INFORMATION: Variable Heavy Chain Amino Sequence Hc27

<400> SEQUENCE: 279

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Tyr Gly Gln Phe Asp Tyr Trp Gly Gln Gly
            100                 105                 110

Thr Leu Val Thr Val Ser Ser
            115

<210> SEQ ID NO 280
<211> LENGTH: 108
<212> TYPE: PRT
<213> ORGANISM: Artificial Sequence
<220> FEATURE:
<223> OTHER INFORMATION: Variable Light Chain Amino Sequence Lc28

<400> SEQUENCE: 280

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 281
<211> LENGTH: 119
<212> TYPE: PRT
<213> ORGANISM: Artificial Sequence
<220> FEATURE:
<223> OTHER INFORMATION: Variable Heavy Chain Amino Sequence Hc28

<400> SEQUENCE: 281

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly

```
                100             105             110
Thr Leu Val Thr Val Ser Ser
            115

<210> SEQ ID NO 282
<211> LENGTH: 108
<212> TYPE: PRT
<213> ORGANISM: Artificial Sequence
<220> FEATURE:
<223> OTHER INFORMATION: Variable Light Chain Amino Sequence Lc30

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 283
<211> LENGTH: 115
<212> TYPE: PRT
<213> ORGANISM: Artificial Sequence
<220> FEATURE:
<223> OTHER INFORMATION: Variable Heavy Chain Amino Sequence Hc30

<400> SEQUENCE: 283

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ala
                85                  90                  95

Lys Ser Ala Ala Ala Phe Asp Tyr Trp Gly Gln Gly Thr Leu Val Thr
            100                 105                 110

Val Ser Ser
        115

<210> SEQ ID NO 284
<211> LENGTH: 108
<212> TYPE: PRT
<213> ORGANISM: Artificial Sequence
<220> FEATURE:
<223> OTHER INFORMATION: Variable Light Chain Amino Sequence Lc31

<400> SEQUENCE: 284
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 285
<211> LENGTH: 119
<212> TYPE: PRT
<213> ORGANISM: Artificial Sequence
<220> FEATURE:
<223> OTHER INFORMATION: Variable Heavy Chain Amino Sequence Hc31

<400> SEQUENCE: 285

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115
```

<210> SEQ ID NO 286
<211> LENGTH: 108
<212> TYPE: PRT
<213> ORGANISM: Artificial Sequence
<220> FEATURE:
<223> OTHER INFORMATION: Variable Light Chain Amino Sequence Lc32

<400> SEQUENCE: 286

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Val Val Ala Pro Leu
                    85                  90                  95

Thr Phe Gly Gln Gly Thr Lys Val Glu Ile Lys Arg
                    100                 105
```

<210> SEQ ID NO 287
<211> LENGTH: 116
<212> TYPE: PRT
<213> ORGANISM: Artificial Sequence
<220> FEATURE:
<223> OTHER INFORMATION: Variable Heavy Chain Amino Sequence Hc32

<400> SEQUENCE: 287

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ser Ile Asp Pro Glu Gly Trp Gln Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
                100                 105                 110

Thr Val Ser Ser
        115
```

<210> SEQ ID NO 288
<211> LENGTH: 108
<212> TYPE: PRT
<213> ORGANISM: Artificial Sequence
<220> FEATURE:
<223> OTHER INFORMATION: Variable Light Chain Amino Sequence Lc37

<400> SEQUENCE: 288

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
                100                 105
```

<210> SEQ ID NO 289
<211> LENGTH: 119
<212> TYPE: PRT
<213> ORGANISM: Artificial Sequence
<220> FEATURE:

<223> OTHER INFORMATION: Variable Heavy Chain Amino Sequence Hc37

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro His Asn Gly Gln Phe Asp Tyr Trp Gly Gln Gly
            100                 105                 110

Thr Leu Val Thr Val Ser Ser
            115

<210> SEQ ID NO 290
<211> LENGTH: 108
<212> TYPE: PRT
<213> ORGANISM: Artificial Sequence
<220> FEATURE:
<223> OTHER INFORMATION: Variable Light Chain Amino Sequence Lc39

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 291
<211> LENGTH: 116
<212> TYPE: PRT
<213> ORGANISM: Artificial Sequence
<220> FEATURE:
<223> OTHER INFORMATION: Variable Heavy Chain Amino Sequence Hc39

<400> SEQUENCE: 291

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Glu Tyr Ala Asp Ser Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ala Ala Ala Phe Asp Tyr Trp Gly Gln Gly Thr Leu Val
            100                 105                 110

Thr Val Ser Ser
       115

<210> SEQ ID NO 292
<211> LENGTH: 108
<212> TYPE: PRT
<213> ORGANISM: Artificial Sequence
<220> FEATURE:
<223> OTHER INFORMATION: Variable Light Chain Amino Sequence Lc40

<400> SEQUENCE: 292

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
            100                 105

<210> SEQ ID NO 293
<211> LENGTH: 119
<212> TYPE: PRT
<213> ORGANISM: Artificial Sequence
<220> FEATURE:
<223> OTHER INFORMATION: Heavy Chain Amino Sequence Hc40

<400> SEQUENCE: 293

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Pro Pro Phe Phe Gly Gln Phe Asp Tyr Trp Gly Gln Gly
            100                 105                 110

Thr Leu Val Thr Val Ser Ser
       115
```

<210> SEQ ID NO 294
<211> LENGTH: 108
<212> TYPE: PRT
<213> ORGANISM: Artificial Sequence
<220> FEATURE:
<223> OTHER INFORMATION: Variable Light Chain Amino Sequence Lc47

<400> SEQUENCE: 294

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 295
<211> LENGTH: 116
<212> TYPE: PRT
<213> ORGANISM: Artificial Sequence
<220> FEATURE:
<223> OTHER INFORMATION: Variable Heavy Chain Amino Sequence Hc47

<400> SEQUENCE: 295

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Glu Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 296
<211> LENGTH: 108
<212> TYPE: PRT
<213> ORGANISM: Artificial Sequence
<220> FEATURE:
<223> OTHER INFORMATION: Variable 4B2 Light Chain

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr

```
                    20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Leu Asp Ala Pro Pro
                85                  90                  95

Gln Phe Gly Gln Gly Thr Lys Val Glu Ile Lys Arg
            100                 105
```

<210> SEQ ID NO 297
<211> LENGTH: 119
<212> TYPE: PRT
<213> ORGANISM: Artificial Sequence
<220> FEATURE:
<223> OTHER INFORMATION: Variable 4B2 Heavy Chain

<400> SEQUENCE: 297

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115
```

<210> SEQ ID NO 298
<211> LENGTH: 108
<212> TYPE: PRT
<213> ORGANISM: Artificial Sequence
<220> FEATURE:
<223> OTHER INFORMATION: Variable 4E7 Light Chain

<400> SEQUENCE: 298

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Val Ala Pro Leu
                85                  90                  95
```

Thr Phe Gly Gln Gly Thr Lys Val Glu Ile Lys Arg
            100                 105

<210> SEQ ID NO 299
<211> LENGTH: 116
<212> TYPE: PRT
<213> ORGANISM: Artificial Sequence
<220> FEATURE:
<223> OTHER INFORMATION: Variable 4E7 Heavy Chain

<400> SEQUENCE: 299

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 300
<211> LENGTH: 108
<212> TYPE: PRT
<213> ORGANISM: Artificial Sequence
<220> FEATURE:
<223> OTHER INFORMATION: Variable 4E11 Light Chain

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Asp Ala Pro Leu
                85                  90                  95

Met Phe Gly Gln Gly Thr Lys Val Glu Ile Lys Arg
            100                 105

<210> SEQ ID NO 301
<211> LENGTH: 119
<212> TYPE: PRT
<213> ORGANISM: Artificial Sequence
<220> FEATURE:
<223> OTHER INFORMATION: Variable 4E11 Heavy Chain

<400> SEQUENCE: 301

Glu Val Gln Leu Leu Glu Ser Gly Gly Gly Leu Val Gln Pro Gly Gly

```
                1               5                   10                  15
        Ser Leu Arg Leu Ser Cys Ala Ala Ser Gly Phe Thr Phe Ser Ser Tyr
                        20                  25                  30

Ala Met Ser Trp Val Arg Gln Ala Pro Gly Lys Gly Leu Glu Trp Val
                        35                  40                  45

Ser Ser Ile Glu Pro Met Gly Gln Leu Thr Glu Tyr Ala Asp Ser Val
                        50                  55                  60

Lys Gly Arg Phe Thr Ile Ser Arg Asp Asn Ser Lys Asn Thr Leu Tyr
         65                  70                  75                  80

Leu Gln Met Asn Ser Leu Arg Ala Glu Asp Thr Ala Val Tyr Tyr Cys
                        85                  90                  95

Ala Lys Asp Ile Gly Gly Arg Ser Ala Phe Asp Tyr Trp Gly Gln Gly
                        100                 105                 110

Thr Leu Val Thr Val Ser Ser
                        115

<210> SEQ ID NO 302
<211> LENGTH: 108
<212> TYPE: PRT
<213> ORGANISM: Artificial Sequence
<220> FEATURE:
<223> OTHER INFORMATION: Variable 6B7 Light Chain

<400> SEQUENCE: 302

Asp Ile Gln Met Thr Gln Ser Pro Ser Ser Leu Ser Ala Ser Val Gly
         1               5                   10                  15

Asp Arg Val Thr Ile Thr Cys Arg Ala Ser Gln Ser Ile Ser Ser Tyr
                        20                  25                  30

Leu Asn Trp Tyr Gln Gln Lys Pro Gly Lys Ala Pro Lys Leu Leu Ile
                        35                  40                  45

Tyr Ala Ala Ser Ser Leu Gln Ser Gly Val Pro Ser Arg Phe Ser Gly
                        50                  55                  60

Ser Gly Ser Gly Thr Asp Phe Thr Leu Thr Ile Ser Ser Leu Gln Pro
         65                  70                  75                  80

Glu Asp Phe Ala Thr Tyr Tyr Cys Gln Gln Ala Leu Val Ala Pro Leu
                        85                  90                  95

Thr Phe Gly Gln Gly Thr Lys Val Glu Ile Lys Arg
                        100                 105

<210> SEQ ID NO 303
<211> LENGTH: 116
<212> TYPE: PRT
<213> ORGANISM: Artificial Sequence
<220> FEATURE:
<223> OTHER INFORMATION: Variable 6B7 Heavy Chain

<400> SEQUENCE: 303

Glu Val Gln Leu Leu Glu Ser Gly Gly Gly Leu Val Gln Pro Gly Gly
         1               5                   10                  15

Ser Leu Arg Leu Ser Cys Ala Ala Ser Gly Phe Thr Phe Ser Ser Tyr
                        20                  25                  30

Ala Met Ser Trp Val Arg Gln Ala Pro Gly Lys Gly Leu Glu Trp Val
                        35                  40                  45

Ser Ser Ile Asp Glu Met Gly Trp Gln Thr Tyr Tyr Ala Asp Ser Val
                        50                  55                  60

Lys Gly Arg Phe Thr Ile Ser Arg Asp Asn Ser Lys Asn Thr Leu Tyr
         65                  70                  75                  80
```

```
Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 304
<211> LENGTH: 108
<212> TYPE: PRT
<213> ORGANISM: Artificial Sequence
<220> FEATURE:
<223> OTHER INFORMATION: Variable 6F8 Light Chain

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Val Ala Pro Leu
                85                  90                  95

Thr Phe Gly Gln Gly Thr Lys Val Glu Ile Lys Arg
            100                 105

<210> SEQ ID NO 305
<211> LENGTH: 116
<212> TYPE: PRT
<213> ORGANISM: Artificial Sequence
<220> FEATURE:
<223> OTHER INFORMATION: Variable 6F8 Heavy Chain

<400> SEQUENCE: 305

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Glu Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 306
<211> LENGTH: 8
<212> TYPE: PRT
<213> ORGANISM: Artificial Sequence
```

```
<220> FEATURE:
<223> OTHER INFORMATION: cleavable moiety

<400> SEQUENCE: 306

Ile Ser Ser Gly Leu Leu Ser Ser
1               5

<210> SEQ ID NO 307
<211> LENGTH: 8
<212> TYPE: PRT
<213> ORGANISM: Artificial Sequence
<220> FEATURE:
<223> OTHER INFORMATION: cleavable moiety

<400> SEQUENCE: 307

Gln Asn Gln Ala Leu Arg Met Ala
1               5

<210> SEQ ID NO 308
<211> LENGTH: 8
<212> TYPE: PRT
<213> ORGANISM: Artificial Sequence
<220> FEATURE:
<223> OTHER INFORMATION: cleavable moiety

<400> SEQUENCE: 308

Ala Gln Asn Leu Leu Gly Met Val
1               5

<210> SEQ ID NO 309
<211> LENGTH: 8
<212> TYPE: PRT
<213> ORGANISM: Artificial Sequence
<220> FEATURE:
<223> OTHER INFORMATION: cleavable moiety

<400> SEQUENCE: 309

Ser Thr Phe Pro Phe Gly Met Phe
1               5

<210> SEQ ID NO 310
<211> LENGTH: 8
<212> TYPE: PRT
<213> ORGANISM: Artificial Sequence
<220> FEATURE:
<223> OTHER INFORMATION: cleavable moiety

<400> SEQUENCE: 310

Pro Val Gly Tyr Thr Ser Ser Leu
1               5

<210> SEQ ID NO 311
<211> LENGTH: 8
<212> TYPE: PRT
<213> ORGANISM: Artificial Sequence
<220> FEATURE:
<223> OTHER INFORMATION: cleavable moiety

<400> SEQUENCE: 311

Asp Trp Leu Tyr Trp Pro Gly Ile
1               5

<210> SEQ ID NO 312
<211> LENGTH: 8
<212> TYPE: PRT
<213> ORGANISM: Artificial Sequence
<220> FEATURE:
```

```
<223> OTHER INFORMATION: cleavable moiety

<400> SEQUENCE: 312

Met Ile Ala Pro Val Ala Tyr Arg
1               5

<210> SEQ ID NO 313
<211> LENGTH: 8
<212> TYPE: PRT
<213> ORGANISM: Artificial Sequence
<220> FEATURE:
<223> OTHER INFORMATION: cleavable moiety

<400> SEQUENCE: 313

Arg Pro Ser Pro Met Trp Ala Tyr
1               5

<210> SEQ ID NO 314
<211> LENGTH: 8
<212> TYPE: PRT
<213> ORGANISM: Artificial Sequence
<220> FEATURE:
<223> OTHER INFORMATION: cleavable moiety

<400> SEQUENCE: 314

Trp Ala Thr Pro Arg Pro Met Arg
1               5

<210> SEQ ID NO 315
<211> LENGTH: 8
<212> TYPE: PRT
<213> ORGANISM: Artificial Sequence
<220> FEATURE:
<223> OTHER INFORMATION: cleavable moiety

<400> SEQUENCE: 315

Phe Arg Leu Leu Asp Trp Gln Trp
1               5

<210> SEQ ID NO 316
<211> LENGTH: 8
<212> TYPE: PRT
<213> ORGANISM: Artificial Sequence
<220> FEATURE:
<223> OTHER INFORMATION: cleavable moiety

<400> SEQUENCE: 316

Leu Lys Ala Ala Pro Arg Trp Ala
1               5

<210> SEQ ID NO 317
<211> LENGTH: 8
<212> TYPE: PRT
<213> ORGANISM: Artificial Sequence
<220> FEATURE:
<223> OTHER INFORMATION: cleavable moiety

<400> SEQUENCE: 317

Gly Pro Ser His Leu Val Leu Thr
1               5

<210> SEQ ID NO 318
<211> LENGTH: 8
<212> TYPE: PRT
<213> ORGANISM: Artificial Sequence
<220> FEATURE:
<223> OTHER INFORMATION: cleavable moiety
```

```
<400> SEQUENCE: 318

Leu Pro Gly Gly Leu Ser Pro Trp
1               5

<210> SEQ ID NO 319
<211> LENGTH: 8
<212> TYPE: PRT
<213> ORGANISM: Artificial Sequence
<220> FEATURE:
<223> OTHER INFORMATION: cleavable moiety

<400> SEQUENCE: 319

Met Gly Leu Phe Ser Glu Ala Gly
1               5

<210> SEQ ID NO 320
<211> LENGTH: 8
<212> TYPE: PRT
<213> ORGANISM: Artificial Sequence
<220> FEATURE:
<223> OTHER INFORMATION: cleavable moiety

<400> SEQUENCE: 320

Ser Pro Leu Pro Leu Arg Val Pro
1               5

<210> SEQ ID NO 321
<211> LENGTH: 8
<212> TYPE: PRT
<213> ORGANISM: Artificial Sequence
<220> FEATURE:
<223> OTHER INFORMATION: cleavable moiety

<400> SEQUENCE: 321

Arg Met His Leu Arg Ser Leu Gly
1               5

<210> SEQ ID NO 322
<211> LENGTH: 8
<212> TYPE: PRT
<213> ORGANISM: Artificial Sequence
<220> FEATURE:
<223> OTHER INFORMATION: cleavable moiety

<400> SEQUENCE: 322

Leu Ala Ala Pro Leu Gly Leu Leu
1               5

<210> SEQ ID NO 323
<211> LENGTH: 8
<212> TYPE: PRT
<213> ORGANISM: Artificial Sequence
<220> FEATURE:
<223> OTHER INFORMATION: cleavable moiety

<400> SEQUENCE: 323

Ala Val Gly Leu Leu Ala Pro Pro
1               5

<210> SEQ ID NO 324
<211> LENGTH: 8
<212> TYPE: PRT
<213> ORGANISM: Artificial Sequence
<220> FEATURE:
<223> OTHER INFORMATION: cleavable moiety
```

-continued

```
<400> SEQUENCE: 324

Leu Leu Ala Pro Ser His Arg Ala
1               5

<210> SEQ ID NO 325
<211> LENGTH: 8
<212> TYPE: PRT
<213> ORGANISM: Artificial Sequence
<220> FEATURE:
<223> OTHER INFORMATION: cleavable moiety

<400> SEQUENCE: 325

Pro Ala Gly Leu Trp Leu Asp Pro
1               5

<210> SEQ ID NO 326
<211> LENGTH: 7
<212> TYPE: PRT
<213> ORGANISM: Artificial Sequence
<220> FEATURE:
<223> OTHER INFORMATION: cleavable moiety

<400> SEQUENCE: 326

Ile Ser Ser Gly Leu Ser Ser
1               5
```